(12) United States Patent
Dominguez et al.

(10) Patent No.: US 12,083,108 B2
(45) Date of Patent: *Sep. 10, 2024

(54) COMPOUNDS FOR TARGETING MUTANT HUNTINGTIN PROTEIN AND USES THEREOF

(71) Applicant: CHDI Foundation, Inc., New York, NY (US)

(72) Inventors: Celia Dominguez, Los Angeles, CA (US); Jonathan Bard, New York, NY (US); Matthew R. Lee, San Diego, CA (US); Longbin Liu, Los Angeles, CA (US); Michael Edward Prime, Swindon (GB); Samuel Coe, Northampton (GB)

(73) Assignee: CHDI Foundation, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/752,683

(22) Filed: May 24, 2022

(65) Prior Publication Data
US 2022/0409600 A1    Dec. 29, 2022

Related U.S. Application Data

(63) Continuation of application No. 16/799,651, filed on Feb. 24, 2020, now Pat. No. 11,389,438.

(60) Provisional application No. 62/810,213, filed on Feb. 25, 2019.

(51) Int. Cl.
| | |
|---|---|
| *A61K 31/454* | (2006.01) |
| *A61K 31/165* | (2006.01) |
| *A61K 31/427* | (2006.01) |
| *A61K 47/54* | (2017.01) |

(52) U.S. Cl.
CPC .......... *A61K 31/454* (2013.01); *A61K 31/165* (2013.01); *A61K 31/427* (2013.01); *A61K 47/555* (2017.08)

(58) Field of Classification Search
CPC ... A61K 31/454; A61K 47/555; A61K 31/165
See application file for complete search history.

(56) References Cited

U.S. PATENT DOCUMENTS

| | | |
|---|---|---|
| 10,137,211 B2 | 11/2018 | Dominguez et al. |
| 10,479,802 B2 | 11/2019 | Dominguez et al. |
| 10,765,764 B2 | 9/2020 | Dominguez et al. |
| 10,907,197 B2 | 2/2021 | Dominguez et al. |
| 2017/0281804 A1 | 10/2017 | Dominguez et al. |
| 2017/0283439 A1 | 10/2017 | Dominguez et al. |
| 2018/0125821 A1 | 5/2018 | Crew et al. |
| 2020/0102328 A1 | 4/2020 | Dominguez et al. |
| 2021/0060187 A1 | 3/2021 | Dominguez et al. |

FOREIGN PATENT DOCUMENTS

| | | |
|---|---|---|
| WO | WO 2015/000867 A1 | 1/2015 |
| WO | WO 2016/197078 A1 | 12/2016 |
| WO | WO 2018/118598 A1 | 6/2018 |
| WO | WO 2018/140809 A1 | 8/2018 |
| WO | WO 2020/176424 A1 | 9/2020 |

OTHER PUBLICATIONS

U.S. Appl. No. 17/558,397, filed Dec. 21, 2021, Dominguez et al.
U.S. Appl. No. 17/881,895, filed Aug. 5, 2022, Dominguez et al.
U.S. Appl. No. 17/125,905, filed Dec. 17, 2020, Liu et al.
U.S. Appl. No. 17/325,038, filed May 19, 2021, Dominguez et al.
U.S. Appl. No. 17/344,582, filed Jun. 10, 2021, Liu et al.
U.S. Appl. No. 17/353,611, filed Jun. 21, 2021, Dominguez et al.
U.S. Appl. No. 17/353,627, filed Jun. 21, 2021, Dominguez et al.
International Search Report and Written Opinion for PCT/US2020/019537, Jun. 15, 2020, 21 pages.
Tomoshige, et al., "Discovery of Small Molecules that Induce the Degradation of Huntingtin", Angewandte Chemie, International Edition, vol. 56, No. 38, Sep. 11, 2017, pp. 11530-11533, XP055694994.
Tomoshige, et al., "Supporting Information, Discovery of Small Molecules that Induce the Degradation of Huntingtin", Jan. 1, 2017, Retrieved from the Internet: URL:https://onlinelibrary.wiley.com/action/downloadSupplement?doi=10.1002/anie.201706529&file=anie201706529-sup-0001-misc_information.pdf, retrieved on May 29, 2020.
Tomoshige, et al., "Degradation of huntingtin mediated by a hybrid molecule composed of IAP antagonist linked to phenyldiazenyl benzothiazole derivative", Bioorganic & Medicinal Chemistry Letters, vol. 28, No. 4, Feb. 1, 2018, pp. 707-710, XP055699376.
Cyrus, Kedra et al., "Impact of linker length on the activity of PROTACs", Molecular BioSystems, vol. 7, No. 2, pp. 359-364 (2011).
Dominguez, U.S. Appl. No. 16/799,651, filed Feb. 24, 2020.

*Primary Examiner* — Kamal A Saeed
(74) *Attorney, Agent, or Firm* — Sheppard Mullin Richter & Hampton LLP

(57) ABSTRACT

The present disclosure relates generally to compounds that simultaneously bind both mutant huntingtin protein (mHTT) and an ubiquitin E3 ligase and their use as therapeutic agents, for example, in treating diseases, such as neurodegenerative disorders caused by aggregation of mHTT.

17 Claims, 3 Drawing Sheets
Specification includes a Sequence Listing.

COMPOUNDS FOR TARGETING MUTANT HUNTINGTIN PROTEIN AND USES THEREOF

CROSS-REFERENCE TO RELATED APPLICATIONS

This application is a continuation of U.S. patent application Ser. No. 16/799,651, filed Feb. 24, 2020, which claims the benefit under 35 U.S.C. § 119(e) of U.S. Provisional Application No. 62/810,213, filed Feb. 25, 2019, which is hereby incorporated by reference in its entirety.

REFERENCE TO A SEQUENCE LISTING

The content of the electronic sequence listing 49DX-292081-US2 SL; date of creation of Jul. 18, 2024, and 4,985 bytes in size, is herein incorporated by reference in its entirety.

FIELD

The present disclosure relates generally to compounds that simultaneously bind both mutant huntingtin protein (mHTT) and an ubiquitin E3 ligase and their use as therapeutic agents, for example, in treating diseases, such as neurodegenerative disorders caused by aggregation of mHTT.

BACKGROUND

Huntington's disease (HD) is an inherited progressive neurodegenerative disorder, characterized by motor, cognitive, and psychiatric deficits as well as neurodegeneration and brain atrophy beginning in the striatum and the cortex and extending to other subcortical brain regions. It belongs to a family of neurodegenerative diseases caused by mutations in which an expanded CAG repeat tract results in long stretches of polyglutamine (polyQ) in the encoded mutant protein. This family also includes dentatorubral-pallidoluysian atrophy (DRPLA), spinal and bulbar muscular atrophy (SBMA) and the spinocerebellar ataxias (SCAs). Apart from their polyQ repeats, the proteins involved are unrelated, and although they are all widely expressed in the central nervous system and peripheral tissues, they lead to characteristic patterns of neurodegeneration.

In HD, the selective neurodegeneration of the γ-aminobutyric acid-releasing spiny-projection neurons of the striatum is predominant, although loss of neurons in many other brain regions has also been reported. In the unaffected population, the number of CAG repeats in the $IT_{15}$ gene that encodes the HD protein huntingtin (HTT protein) varies from 6 to 35. CAG repeats of 36 or more define an HD allele, thereby resulting in translation of a mutant huntingtin protein (mHTT) containing a longer polyQ stretch. This mHTT protein is prone to misfolding and aggregate formation. The length of the CAG expansion is inversely correlated with age of disease onset, with cases of juvenile onset characterized by expansions of more than 60 repeats. HD has a prevalence of 5-10 cases per 100,000 worldwide, which makes it the most common inherited neurodegenerative disorder.

The HTT protein is a 348-kDa multidomain protein that contains a polymorphic glutamine/proline-rich domain at its amino-terminus. The longer polyQ domain of mHTT seems to induce conformational changes in the protein, which causes it to form intracellular aggregates that, in most cases, manifest as nuclear inclusions. However, aggregates can also form outside of the nucleus. mHTT protein is present in the nucleus, cell body, dendrites and nerve terminals of neurons, and is also associated with a number of organelles including the Golgi apparatus, endoplasmic reticulum and mitochondria.

Since HD is caused by expression of mHTT protein, lowering expression of mHTT is a key therapeutic strategy. Reducing the amount of mHTT protein in HD-affected brains is predicted to prevent cellular dysfunction, neurodegeneration, and alleviate symptoms of the disease. There remains a need for compounds that can effectively treat HD.

SUMMARY

Provided herein are heterobifunctional molecules that simultaneously bind both mHTT and an ubiquitin E3 ligase.

Provided herein, in some embodiments, is a compound of formula (I):

$$W\text{-}L\text{-}ULM \qquad (I)$$

or a pharmaceutically acceptable salt, a stereoisomer, a mixture of stereoisomers, or isotopically enriched analog thereof, wherein:
  W is a compound targeting mutant huntingtin protein (mHTT);
  L is a bond or linking moiety optionally substituted with B;
  ULM is a E3 ubiquitin ligase targeting moiety; and
  B is a moiety that crosses the blood brain barrier and/or enhances cell permeability.

Some embodiments provide for pharmaceutical compositions comprising a compound as described herein, or a pharmaceutically acceptable salt, a stereoisomer, a mixture of stereoisomers, or isotopically enriched analog thereof, and a pharmaceutically acceptable excipient or carrier.

Also provided herein are methods for inducing degradation of mHTT comprising administering a therapeutically effective amount of a compound as described herein, or a pharmaceutically acceptable salt, a stereoisomer, a mixture of stereoisomers, or isotopically enriched analog thereof, or a pharmaceutical composition as described herein.

Also provided herein are methods for treating Huntington's disease comprising administering a therapeutically effective amount of a compound as described herein, or a pharmaceutically acceptable salt, a stereoisomer, a mixture of stereoisomers, or isotopically enriched analog thereof, or a pharmaceutical composition as described herein.

DETAILED DESCRIPTION

Definitions

Figure 1A:
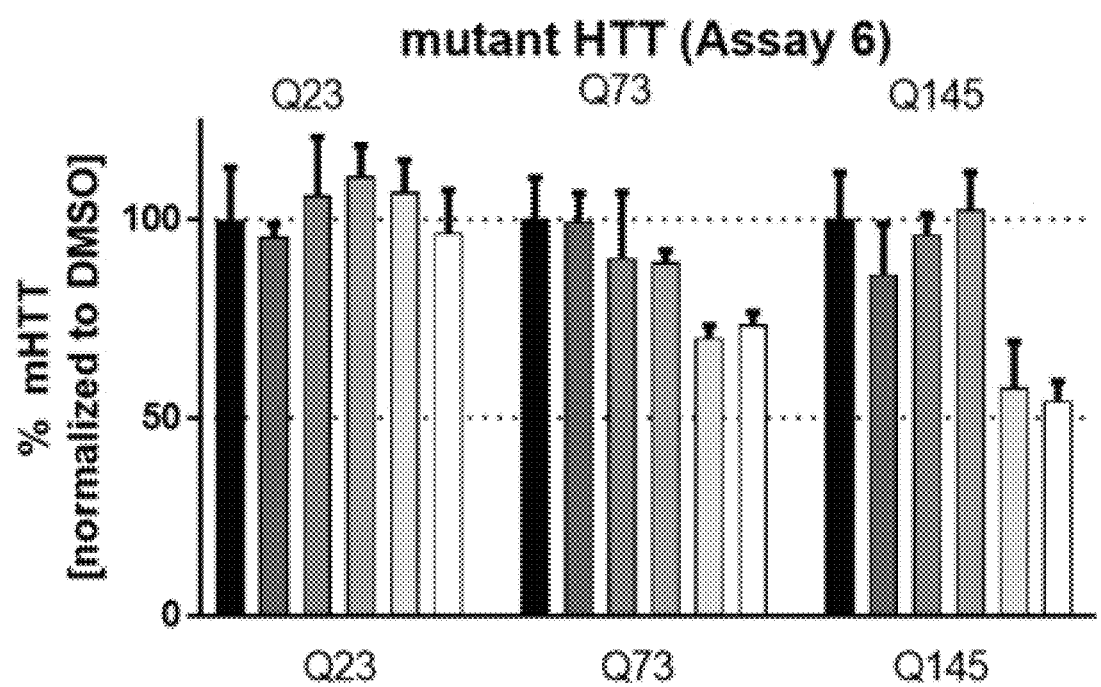
FIG. 1A and FIG. 1B depict HTT degradation of mHTT with compound 1 in HeLa cells transfected with various Exon1-Qn-EGFP constructs. Analysis by MSD assays for soluble mHTT (FIG. 1A) and aggregated HTT (FIG. 1B).

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom.

As used herein the terms "group," "radical" or "fragment" refer to a functional group or fragment of a molecule attachable to a bond or other fragments of molecules.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

When a moiety is defined as being optionally substituted, it may be substituted as itself or as part of another moiety. For example, if $R^x$ is defined as "$C_{1-6}$ alkyl or $OC_{1-6}$ alkyl, wherein $C_{1-6}$ alkyl is optionally substituted with halogen", then both the $C_{1-6}$ alkyl group alone and the $C_{1-6}$ alkyl that makes up part of the $OC_{1-6}$ alkyl group may be substituted with halogen.

The term "alkyl" encompasses straight chain and branched chain moieties having the indicated number of carbon atoms, usually from 1 to 20 carbon atoms, for example 1 to 8 carbon atoms, such as 1 to 6 carbon atoms. For example, $C_1$-$C_6$ alkyl encompasses both straight and branched chain alkyl of from 1 to 6 carbon atoms. Examples of $C_1$-$C_6$ alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. When an alkyl residue having a specific number of carbons is named, all geometric isomers having that number of carbons are intended to be encompassed; thus, for example, "butyl" is meant to include n-butyl, sec-butyl, isobutyl and tert-butyl; "propyl" includes n-propyl and isopropyl. "Lower alkyl" refers to alkyl groups having 1 to 6 carbons.

"Alkylene" refers to a divalent alkyl group as defined above. As used herein, alkylene has 1 to 10 carbon atoms (i.e., $C_{1-10}$ alkylene), 1 to 8 carbon atoms (i.e., $C_{1-8}$ alkylene), 1 to 6 carbon atoms (i.e., ($C_{1-6}$ alkylene), or 1 to 4 carbon atoms (i.e., ($C_{1-4}$ alkylene).

"Heteroalkylene" refers to an alkylene group in which one or more of the carbon atoms (and any associated hydrogen atoms) are each independently replaced with the same or different heteroatomic group. The term "heteroalkylene" includes unbranched or branched saturated chain having carbon and heteroatoms. By way of example, 1, 2 or 3 carbon atoms may be independently replaced with the same or different heteroatomic group. Heteroatomic groups include, but are not limited to, —NH—, —O—, —S—, —S(O)—, —S(O)$_2$—, and the like. As used herein, heteroalkylene includes 1 to 8 carbon atoms, or 1 to 4 carbon atoms; and 1 to 3 heteroatoms, 1 to 2 heteroatoms, or 1 heteroatom.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to alkoxy groups having 1 to 6 carbons. By "cycloalkoxy" is meant a cycloalkyl group that is likewise attached through an oxygen bridge.

"Alkenyl" refers to an unsaturated branched or straight-chain alkyl group having the indicated number of carbon atoms (e.g., 2 to 8 or 2 to 6 carbon atoms) and at least one carbon-carbon double bond derived by the removal of one molecule of hydrogen from adjacent carbon atoms of the corresponding alkyl. Alkenyl groups include, but are not limited to, ethenyl, propenyl (e.g., prop-1-en-1-yl, prop-2-en-1-yl) and butenyl (e.g., but-1-en-1-yl, but-1-en-3-yl, but-3-en-1-yl). "Lower alkenyl" refers to alkenyl groups having 2 to 6 carbons.

"Alkenylene" refers to an alkylene group containing at least one carbon-carbon double bond and having from 2 to 8 carbon atoms (i.e., $C_{2-8}$ alkenylene), 2 to 6 carbon atoms (i.e., $C_{2-6}$ alkenylene), or 2 to 4 carbon atoms (i.e., $C_{2-4}$ alkenylene).

"Heteroalkenylene" refers to a heteroalkylene group containing at least one carbon-carbon double bond and having from 2 to 8 carbon atoms, 2 to 6 carbon atoms, or 2 to 4 carbon atoms; and 1 to 3 heteroatoms, 1 to 2 heteroatoms, or 1 heteroatom.

The term, "alkenyloxy," refers to the group —O-alkenyl, wherein the alkenyl is as described herein.

"Alkynyl" refers to an unsaturated branched or straight-chain alkyl group having the indicated number of carbon atoms (e.g., 2 to 8 or 2 to 6 carbon atoms) and at least one carbon-carbon triple bond derived by the removal of two molecules of hydrogen from adjacent carbon atoms of the corresponding alkyl. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl). "Lower alkynyl" refers to alkynyl groups having 2 to 6 carbons.

"Alkynylene" refers to an alkylene group containing at least one carbon-carbon triple bond and having from 2 to 8 carbon atoms (i.e., $C_{2-8}$ alkynylene), 2 to 6 carbon atoms (i.e., $C_{2-6}$ alkynylene), or 2 to 4 carbon atoms (i.e., $C_{2-4}$ alkynylene). The term "alkynyl" also includes those groups having one triple bond and one double bond.

"Heteroalkynylene" refers to a heteroalkylene group containing at least one carbon-carbon triple bond and having from 2 to 8 carbon atoms, 2 to 6 carbon atoms, or 2 to 4 carbon atoms; and 1 to 3 heteroatoms, 1 to 2 heteroatoms, or 1 heteroatom. The term "alkynyl" also includes those groups having one triple bond and one double bond.

The term, "alkynyloxy," refers to the group —O-alkynyl, wherein the alkynyl is as described herein.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl" regardless of the point of attachment (e.g., both quinolin-5-yl and quinolin-2-yl are heteroaryl groups). In some instances, aryl is phenyl or naphthyl. In certain instances, aryl is phenyl.

"Aralkyl" refers to "-alkylene-aryl."

"Arylene" refers to a divalent aryl group as defined above.

Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentenyl and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Cycloalkylene" refers to a divalent cycloalkyl group as defined above.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond derived by the removal of one molecule of hydrogen from adjacent carbon atoms of the corresponding cycloalkyl. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group. Examples of polycyclic cycloalkenyl groups consisting of a cycloalkenyl group fused to an aromatic ring are described below.

The term "cycloalkoxy" refers to —O-cycloalkyl, wherein cycloalkyl is as described herein.

The term "cyano" refers to —CN.

The term "halo" includes fluoro, chloro, bromo, and iodo, and the term "halogen" includes fluorine, chlorine, bromine, and iodine.

"Haloalkyl" includes straight and branched carbon chains having the indicated number of carbon atoms (e.g., 1 to 6 carbon atoms) substituted with at least one halogen atom. In instances wherein the haloalkyl group contains more than one halogen atom, the halogens may be the same (e.g., dichloromethyl) or different (e.g., chlorofluoromethyl). Examples of haloalkyl groups include, but are not limited to, chloromethyl, dichloromethyl, trichloromethyl, fluoromethyl, difluoromethyl, trifluoromethyl, chlorofluoromethyl, 2-fluoroethyl, 2,2-difluoroethyl, 2,2,2-trifluoroethyl, 1,2-difluoroethyl, 2-chloroethyl, 2,2-dichloroethyl, 2,2,2-trichloroethyl, 1,2-dichloroethyl, pentachloroethyl, and pentafluoroethyl.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

"Heteroaralkyl" refers to the group "-alkylene-heteroaryl."

"Heteroarylene" refers to a divalent heteroaryl group as defined above.

"Heteroaryloxy" refers to "—O-heteroaryl."

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic).

Examples of monocyclic heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl.

When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide.

In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group.

"Heterocycloalkylene" refers to a divalent heterocycloalkyl group as defined above.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic).

When nitrogen is present in a heterocycloalkenyl ring, it may, where the nature of the adjacent atoms and groups permits, exist in an oxidized state (i.e., $N^+$—$O^-$).

Additionally, when sulfur is present in a heterocycloalkenyl ring, it may, where the nature of the adjacent atoms and groups permits, exist in an oxidized state (i.e., $S^+$—$O^-$ or —$SO_2$—). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group.

The term "hydroxy" or "hydroxyl" refers to —OH.

"(Lower alkyl)thio" refers to the group "lower alkyl-S—".

"Oxo" refers to the group (=O) or (O).

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable.

The term "substituted," as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation $C_1$-$C_4$ alkyl), cycloalkyl, cycloalkenyl, aryl, heterocycloalkyl, heterocycloalkenyl, and heteroaryl, unless otherwise expressly defined, refer respectively to alkyl, cycloalkyl, cycloalkenyl, aryl, heterocycloalkyl, heterocycloalkenyl, and heteroaryl, wherein one or more (such as up to 5, for example, up to 3) hydrogen atoms are replaced by a substituent independently chosen from:

—$R^a$, —$OR^b$, —O($C_1$-$C_2$ alkyl)O— (e.g., methylenedioxy-), —$SR^b$, guanidine (—NHC(=NH)NH$_2$), guanidine wherein one or more of the guanidine hydrogens are replaced with a $C_1$-$C_4$alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from $C_1$-$C_6$ alkyl, cycloalkyl, aryl, heterocycloalkyl, and heteroaryl;

$R^b$ is chosen from H, $C_1$-$C_6$ alkyl, aryl, and heteroaryl; and $R^c$ is chosen from hydrogen and $C_1$-$C_4$ alkyl; or $R^b$ and $R_c$, and the nitrogen to which they are attached, form a heterocycloalkyl group; and where each $C_1$-$C_6$ alkyl, cycloalkyl, aryl, heterocycloalkyl, and heteroaryl is optionally substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —N($C_1$-$C_4$ alkyl)($C_1$-$C_4$ alkylheteroaryl), —NH($C_1$-$C_4$ alkylphenyl), cyano, nitro, oxo (as a substitutent for heteroaryl), —CO$_2$H, —C(O)OC$_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(aryl), —SO$_2$(heteroaryl), —SO$_2$($C_1$-$C_4$ haloalkyl), —SO$_2$NH$_2$, —SO$_2$NH($C_1$-$C_4$ alkyl), —SO$_2$NH(aryl), —SO$_2$NH(heteroaryl), —SO$_2$(aryl), —NHSO$_2$($C_1$-$C_4$ alkyl), —NHSO$_2$(phenyl), —NHSO$_2$(aryl), —NHSO$_2$(heteroaryl), and —NHSO$_2$($C_1$-$C_4$ haloalkyl).

The term "amino" refers to the group —NH$_2$.

The term "(alkyl)amino" refers to the group —NH(alkyl), wherein alkyl is as described herein.

The term "di(alkyl)amino" refers to the group —N(alkyl)(alkyl), wherein alkyl is as described herein.

The term "substituted amino" refers to the group —NHR$^d$ or —NR$^dR^d$ where each R$^d$ is independently chosen from: optionally substituted alkyl, optionally substituted cycloalkyl, optionally substituted acyl, optionally substituted aryl, optionally substituted heteroaryl, optionally substituted heterocycloalkyl, alkoxycarbonyl, sulfinyl and sulfonyl, wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, —O($C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NRCONR^bR^c$, —$CO_2R^b$, —$CONR^bR^c$, —$NR^cCOR^b$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl;

where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylene-aryl, —$OC_1$-$C_4$ alkylene-heteroaryl, —$C_1$-$C_4$ alkyl-OH, —$OC_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylenearyl), —N($C_1$-$C_4$ alkyl)($C_1$-$C_4$ alkyleneheteroaryl), —N($C_1$-$C_4$ alkyl)($C_1$-$C_4$ alkylheteroaryl), —NH($C_1$-$C_4$ alkylphenyl), cyano, nitro, oxo (as a substitutent for heteroaryl), —CO$_2$H, —C(O)OC$_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(aryl), —NHC(O)(heteroaryl), —N($C_1$-$C_4$ alkyl)C(O)($C_1$-$C_4$ alkyl), —N($C_1$-$C_4$ alkyl)C(O)(aryl), —N($C_1$-$C_4$ alkyl)C(O)(heteroaryl), —C(O)$C_1$-$C_4$ alkyl, —C(O)$C_1$-$C_6$ aryl, —C(O)heteroaryl, —C(O)$C_1$-$C_4$ haloalkyl, —OC(O)$C_1$-$C_4$ alkyl, —SO$_2$($C_1$-$C_4$ alkyl), —SO$_2$(aryl), —SO$_2$(heteroaryl), —SO$_2$($C_1$-$C_4$ haloalkyl), —SO$_2$NH$_2$, —SO$_2$NH($C_1$-$C_4$ alkyl), —SO$_2$NH(aryl), —SO$_2$NH(heteroaryl), —NHSO$_2$($C_1$-$C_4$ alkyl), —NHSO$_2$(aryl), —NHSO$_2$(heteroaryl), and —NHSO$_2$($C_1$-$C_4$ haloalkyl).

The term "substituted amino" also refers to the group —NR$^e$R$^f$ wherein R$^e$ and R$^f$, together with the nitrogen to which they are bound, form an optionally substituted 5- to 7-membered nitrogen-containing, non-aromatic, heterocycle which optionally contains 1 or 2 additional heteroatoms chosen from nitrogen, oxygen, and sulfur.

"Aminocarbonyl" encompasses a group of the formula —(C=O)(optionally substituted amino) wherein substituted amino is as described herein.

"Alkylaminocarbonyl" refers to —C(=O)((alkyl)amino), wherein (alkyl)amino is as described herein.

"Di(alkyl)aminocarbonyl" refers to —C(=O)(di(alkyl)amino), wherein di(alkyl)amino is as described herein.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. The term "isomers" refers to different compounds that have the same molecular formula. The term "stereoisomers" refers to isomers that differ only in the way the atoms are arranged in space. The term "enantiomers" refers to stereoisomers that are non-superimposable mirror images of each other. A 1:1 mixture of a pair of enantiomers is a "racemic" mixture. The symbol "(±)" may be used to designate a racemic mixture where appropriate. The term "diastereoisomers" refers to stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either R or S. Resolved compounds whose absolute configuration is unknown can be designated (+) or (-) depending on the direction (dextro- or levorotatory) which they rotate plane polarized light at the wavelength of the sodium D line.

Where compounds described herein exist in various tautomeric forms, the term "compound" includes all tautomeric forms of the compound. Such compounds also include crystal forms including polymorphs and clathrates. Similarly, the term "salt" includes all tautomeric forms and crystal forms of the compound. The term "tautomers" refers to structurally distinct isomers that interconvert by tautomerization. Tautomerization is a form of isomerization and includes prototropic or proton-shift tautomerization, which is considered a subset of acid-base chemistry. Prototropic tautomerization or proton-shift tautomerization involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Pharmaceutically acceptable forms of the compounds recited herein include pharmaceutically acceptable salts, and mixtures thereof. In some embodiments, the compounds described herein are in the form of pharmaceutically acceptable salts.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, haloalkanoate such as trifluoroacetate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

Any compound or structure given herein is intended to represent unlabeled forms as well as "isotopically enriched analogs" of the compounds. Isotopically enriched forms of compounds may also be referred to as "labeled." Isotopically enriched analogs have structures depicted herein, except that one or more atoms are enriched in an isotope having a selected atomic mass or mass number. Examples of isotopes that can be incorporated into the compounds described herein include isotopes of hydrogen, carbon, nitrogen, oxygen, phosphorous, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$ and $^{125}$I, respectively. Generally, an isotopically enriched analog includes compounds having any isotopic enrichment above the natural abundance of the isotope (e.g., at Earth's surface). Various isotopically labeled compounds are included in the present disclosure, for example, those into which radioactive isotopes such as $^3$H, $^{18}$F, $^{11}$C, $^{13}$C and $^{14}$C are incorporated. Compounds labeled with $^{18}$F, $^3$H, or $^{11}$C may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds may exhibit increased resistance to metabolism and are thus may be useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. Isotopically labeled compounds of this disclosure can generally be prepared by carrying out the procedures disclosed in the schemes or in the examples and preparations described below by substituting a readily available isotopically labeled reagent for a non-isotopically labeled reagent. Where a compound is described as a deuterated analog, the compound may be drawn with deuterium as a substituent.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen and its isotopes at their natural abundances.

The term "huntingtin protein" or "HTT protein," as "β-amyloid aggregate used herein, refers to the protein encoded by the human huntingtin gene (HTT gene) located on the short (p) arm of chromosome 4 at position 16.3. More precisely, the $IT_{15}$ gene coding for the HTT protein is located from base pair 3,076,407 to base pair 3,245,686 on chromosome 4.

The term "β-amyloid aggregate" as used herein refers to an insoluble fibrous amyloid comprising mis-folded β-amyloid protein molecules.

The term "HTT protein aggregate" as used herein refers to an insoluble fibrous amyloid comprising mis-folded HTT protein molecules.

The term "mutant huntingtin protein" or "mHTT protein" refers to polyglutamine-expanded versions of HTT protein produced due to an expansion of CAG repeats in the hutingtin gene. This mutant form of HTT protein is prone to misfolding and aggregate formation.

The term "compound targeting mutant huntintin protein" refers to a compound that can bind to mHTT.

The term "ubiquitin ligase" refers to a family of proteins that facilitate the transfer of ubiquitin to a specific substrate protein and thereby targeting the substrate protein for degradation. E3 ubiquitin ligase, alone or in complex with an E2 ubiquitin conjugating enzyme, is responsible for the transfer of ubiquitin to targeted proteins. In general, the ubiquitin ligase is involved in polyubiquitination (which marks proteins for degradation by the proteasome) such that a second ubiquitin is attached to the first; a third is attached to the second, and so forth.

The term "E3 ubiquitin ligase targeting moiety" refers to a molecule that can bind and/or recruit an E3 ubiquitin ligase.

The term "VHL ligase targeting moiety" refers to a molecule that can bind and/or recruit von Hippel-Lindau (VHL).

The term "cereblon ligase targeting moiety" refers to a molecule that can bind and/or recruit cereblon (CRBN).

The term "cellular inhibitor of apoptosis protein 1 targeting moiety" refers to a molecule that can bind and/or recruit cellular inhibitor of apoptosis protein 1 (cIAP1).

The term "blood brain barrier" or "BBB" refers to the physiological barrier between the peripheral circulation and the brain and spinal cord that restricts the transport of molecules into the brain. The blood brain barrier within the brain, the blood spinal cord barrier within the spinal cord, and the blood retinal barrier within the retina are contiguous capillary barriers within the central nervous system, and are herein collectively referred to as the blood brain barrier or BBB. The BBB also encompasses the blood-CSF barrier (choroid plexus) where the barrier is comprised of ependymal cells rather than capillary endothelial cells.

The term "moiety that crosses the blood brain barrier and/or enhances cell permeability" refers to a molecule or macromolecule that is capable of being transported across the BBB and/or exhibits an increased ability to cross a cell membrane. Transport across the BBB may be accomplished via a variety of mechanisms known in the art (such as transmembrane diffusion, saturable transporters, adsorptive endocytosis, and extracellular pathways). Transport across cell membranes are also known in the art (such as active or passive transport mechanisms). In some embodiments, the molecule or macromolecule can assist in the delivery of an active agent across the BBB and/or cell membrane. Non-limiting examples of a moiety that crosses the blood brain barrier and/or enhances cell permeability are as described herein.

The term "substitutable atom" refers to an atom that may be further substituted with a group or moiety as described herein, and in some embodiments, such substitution allows a compound described herein to retain activity. It will be understood by those skilled in the art that such groups or moieties are not intended to introduce any substitution or substitution patterns that are sterically impractical, synthetically non-feasible, and/or inherently unstable.

Compounds

Provided herein are compounds that simultaneously bind both mHTT and an ubiquitin E3 ligase. It is contemplated that such compounds promote the ubiquination and degradation of mHTT.

It is contemplated that, in some embodiments, the simultaneous binding of compounds described herein to both mHTT and an ubiquitin E3 ligase produces a ternary complex formation, which then leads to the transfer of multiple ubiquitin molecules to mHTT; after dissociation or degradation of the complex, the polyubiquitinated mHTT is recognized by the proteasome and degraded.

Some embodiments provide for a compound of formula (I):

W-L-ULM     (I)

or a pharmaceutically acceptable salt, a stereoisomer, or a mixture of stereoisomers thereof, wherein:
  W is a compound targeting mutant huntingtin protein (mHTT);
  L is a bond or linking moiety optionally substituted with B;
  ULM is a E3 ubiquitin ligase targeting moiety; and
  B is a moiety that crosses the blood brain barrier and/or enhances cell permeability.

Some embodiments provide for a compound of formula (I):

W-L-ULM     (I)

or a pharmaceutically acceptable salt, a stereoisomer, a mixture of stereoisomers, or isotopically enriched analog thereof, wherein:
  W is a compound targeting mutant huntingtin protein (mHTT);
  L is a bond or linking moiety optionally substituted with B;
  ULM is a E3 ubiquitin ligase targeting moiety; and
  B is a moiety that crosses the blood brain barrier and/or enhances cell permeability.

In some embodiments, a compound of formula (I) is not:

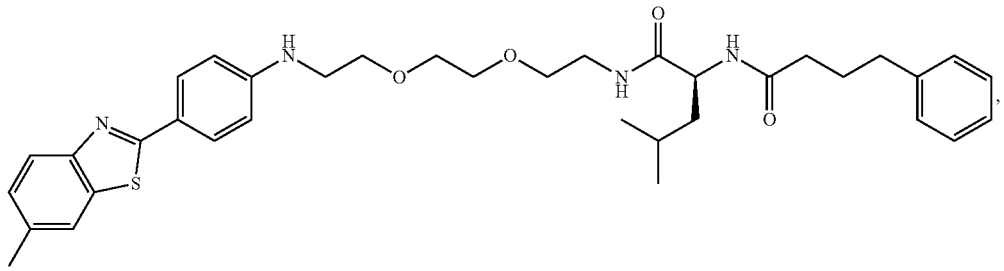

-continued

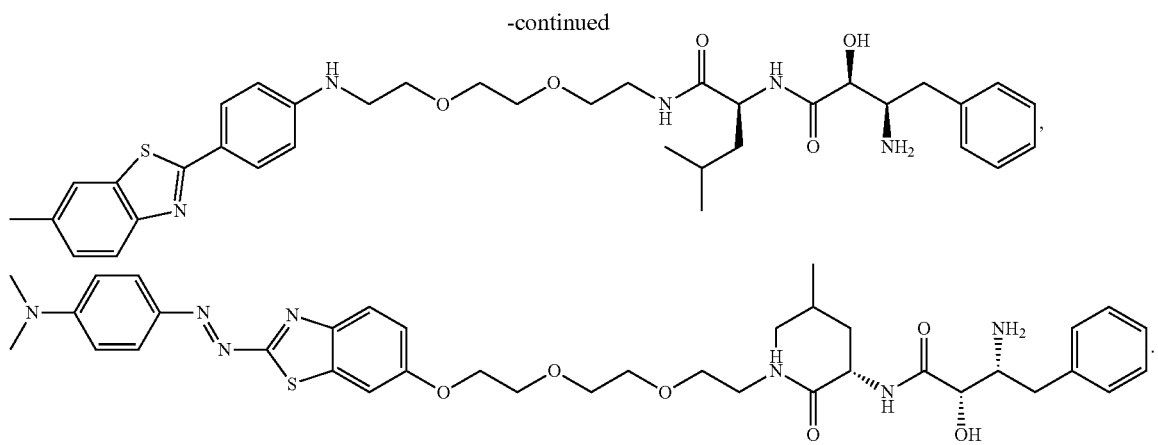

In some embodiments, a compound of formula (I) comprises 1 linking moiety optionally substituted with B.

Some embodiments provide for a deuterated analog of a compound of formula (I).

In some embodiments, each of W, L, and ULM of compounds of formula (I) may be attached at any possible substituent to form a compound of formula (I). In some embodiments, a substitutable atom of W is attached (e.g. covalently bonded) to substitutable atom of L. In some embodiments, a substitutable atom of L is attached (e.g. covalently bonded) to substitutable atom of ULM.

In some embodiments, provided herein are compounds of formula (I):

W-L-ULM  (I)

or a pharmaceutically acceptable salt, a stereoisomer, a mixture of stereoisomers, or isotopically enriched analog thereof, wherein:

L is a linking moiety optionally substituted with B;
ULM is:

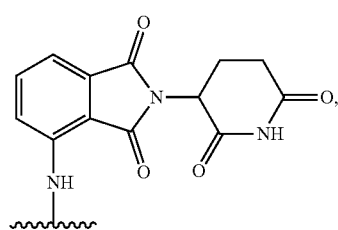 (II)

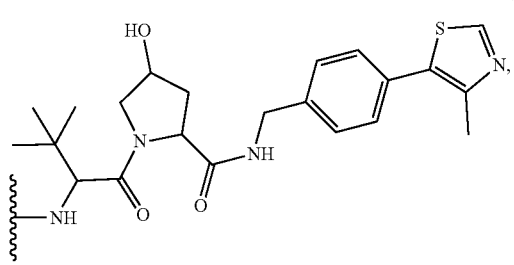 (III)

-continued

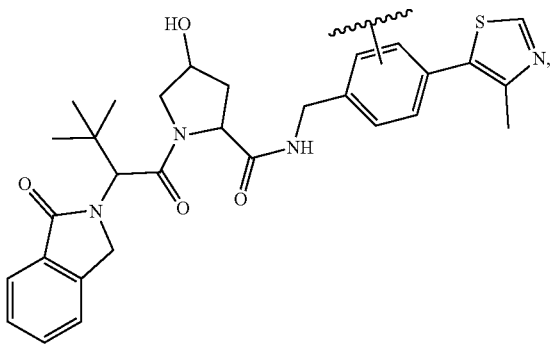 (IV)

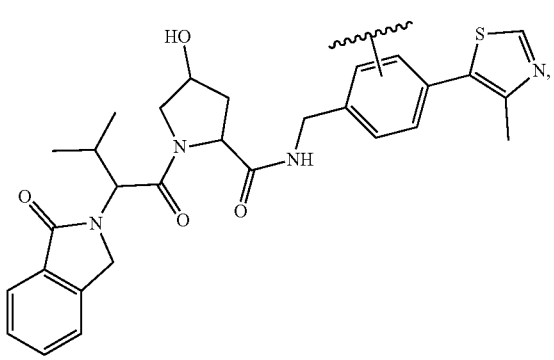 (V)

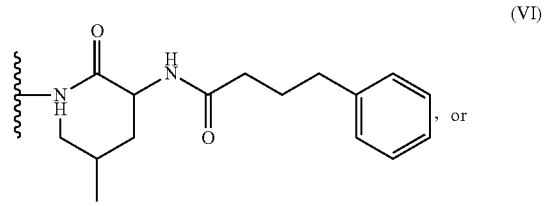 (VI), or

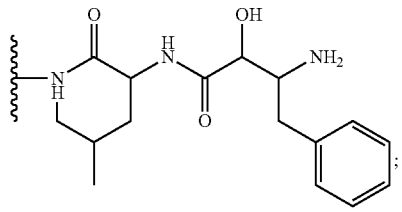

(VII)

W is:
(i) a compound of formula (A):

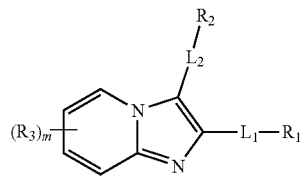

(A)

wherein the point of attachment of W to L-ULM is at any substitutable atom of formula (A);
(ii) a compound of formula (B):

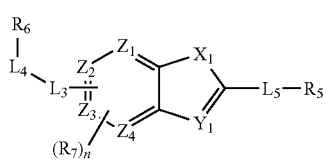

(B)

wherein the point of attachment of W to L-ULM is at any substitutable atom of formula (B);
or (iii) a compound of formula (E):

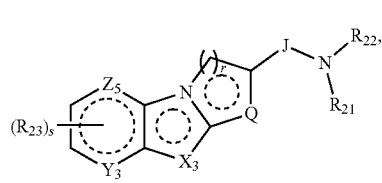

(E)

wherein the point of attachment of W to L-ULM is at any substitutable atom of formula (E);
and the variables of formula (A), (B), and (E) are as described herein.

Exemplary W Moieties

In some embodiments, W is a compound that binds to mutant huntingtin protein (mHTT).

It is contemplated that, even after W is conjugated to L-ULM, the compound of formula (I) retains activity and is able to bind to mHTT. In some embodiments, even after W is conjugated to L-ULM, the compound of formula (I) retains at least 50% activity, at least 60% activity, at least 70% activity, at least 80% activity, at least 90% activity, or at least 95% activity as compared to W before its conjugation to L-ULM.

In some embodiments, W is a compound of formula (A):

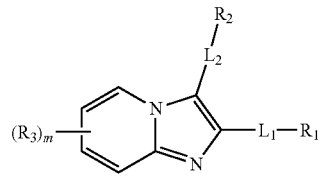

(A)

wherein:
the point of attachment of W to L-ULM is at any substitutable atom of formula (A);
$L_1$ is —CH=CH— or $L_1$ is absent;
$R_1$ is chosen from phenyl or heteroaryl, each of which is optionally substituted with one, two, or three groups independently selected from:
  cyano,
  halo,
  heteroaryl,
  lower alkyl,
  lower alkyl substituted with one or two substituents independently selected from: lower alkoxy substituted with heteroaryl,
  —C(O)O-lower alkyl,
  hydroxyl,
  lower alkynyloxy,
  lower alkoxy, and
  lower alkoxy substituted with one or two substituents independently selected from:
    halo,
    heterocycloalkyl,
    heteroaryl,
    heteroaryl substituted with lower alkoxy,
    optionally substituted amino,
    alkyl substituted with heteroaryl, and
    alkyl substituted with heteroaryl substituted with lower alkoxy;
or
$R_1$ is phenyl substituted with two groups, which taken together with the carbon atoms to which they are bonded form a heterocycloalkenyl ring wherein said phenyl is further optionally substituted with a substituent selected from:
  halo,
  heteroaryl, and
  optionally substituted amino;
$L_2$ is —N($R_4$)— or $L_2$ is absent;
$R_2$ is selected from:
  hydrogen,
  lower alkyl, and
  lower alkyl substituted with lower alkoxy, amino, (alkyl)amino, (dialkyl)amino, or hydroxy;
for each occurrence, $R_3$ is independently selected from:
  halo,
  cyano,
  lower alkoxy,
  lower alkyl optionally substituted with amino, (alkyl)amino, or di(alkyl)amino, and
  ethynyl optionally substituted with tri(alkyl)silyl;
$R_4$ is hydrogen or lower alkyl; and
m is 0, 1, or 2.

In some embodiments, W is a compound of formula (B):

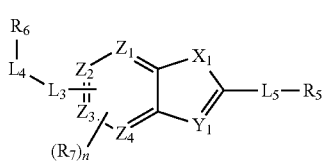

(B)

wherein:
the point of attachment of W to L-ULM is at any substitutable atom of formula (B);
$Z_1$, $Z_2$, $Z_3$, and $Z_4$ are independently selected from CH and N, provided that at least two of $Z_1$, $Z_2$, $Z_3$, and $Z_4$ are CH;
$R_5$ is heteroaryl, heterocycloalkenyl, or heterocycloalkyl, each of which is optionally substituted with one or two groups independently selected from cyano, halo, lower alkyl optionally substituted with amino, alkylamino, or di(alkyl)amino, lower alkoxy optionally substituted with lower alkoxy, optionally substituted amino, haloalkyl, di(alkyl)aminocarbonyl, alkylaminocarbonyl, and aminocarbonyl, or
$R_5$ is phenyl optionally substituted with one or two groups independently selected from cyano, heteroaryl, halo, phenoxy, benzyloxy, heteroaryl, lower alkyl optionally substituted with amino, (alkyl)amino, or di(alkyl)amino, lower alkoxy, optionally substituted amino, di(alkyl)aminocarbonyl, alkylaminocarbonyl, and aminocarbonyl;
$L_3$ is —O— and $L_4$ is —(CR$_8$R$_9$)$_p$— or —(CR$_8$R$_9$)$_p$O—; or
$L_3$ is —NR$_{10}$— and $L_4$ is —C(O)— or —(R$_8$R$_9$)$_p$—; or
$L_3$ is —NR$_{10}$— and $L_4$ is —C(O)(O)(R$_8$R$_9$)$_p$—; or
$L_3$ is —NR$_{10}$— and $L_4$ is —C(O)(R$_8$R$_9$)$_p$(O)—; or
$L_3$ is —NR$_{10}$— and $L_4$ is —C(O)(R$_8$R$_9$)$_p$—; or
$L_3$ is —NR$_{10}$— and $L_4$ is —C(O)CR$_8$═CR$_9$—; or
$L_3$ is —C(O)— and $L_4$ is NR$_{10}$—; or
$L_3$ is —(R$_8$R$_9$)$_p$— and $L_4$ is —NR$_{10}$—, —C(O)— or —O—; or
$L_3$ is absent and $L_4$ is absent; or
$L_3$ taken together with $L_4$ is —CH═CH—, —C≡C—, or heterocyclylene;
$L_5$ is —CH═CH—, or $L_5$ is absent;
$R_6$ is selected from heterocycloalkyl, aryl and heteroaryl, each of which is optionally substituted with one or two groups selected from
—OC(O)—R$_{11}$,
—C(O)O—R$_{11}$,
amino,
halo,
haloalkyl,
phenyl,
heteroaryl,
cyano,
(lower alkyl)thio,
phenoxy,
phenoxymethyl,
heteroaryloxy,
heteroaryloxy substituted with lower alkyl,
hydroxyl,
lower alkenyloxy,
lower alkoxy,
lower alkoxy substituted with lower alkoxy, amino, (alkyl)amino, (dialkyl)amino, heterocycloalkyl, heteroaryl, or halo,
lower alkyl, and
lower alkyl substituted with amino, (alkyl)amino, (dialkyl)amino, hydroxyl or lower alkoxy;
$X_1$ is NR$_{12}$, O, or S;
$Y_1$ is CR$_{12}$ or N;
$R_{10}$ is hydrogen or lower alkyl;
$R_{12}$ is hydrogen, halo, cyano, or lower alkyl;
each $R_7$ is independently selected from lower alkyl, lower alkoxy, and halo;
$R_{11}$ is lower alkyl;
each $R_8$ is independently selected from hydrogen, hydroxyl, trifluoromethyl, and lower alkyl;
each $R_9$ is independently selected from hydrogen and lower alkyl;
n is 0 or 1; and
p is 0, 1, or 2.

In some embodiments, W is a compound of formula (B)(i):

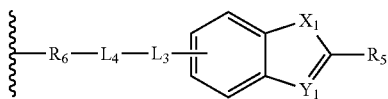

(B)(i)

wherein the wavy line indicates the point of attachment to L of L-ULM.

In some embodiments, W is a compound of formula (B)(i)(a):

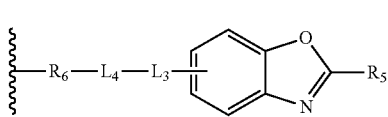

(B)(i)(a)

wherein the wavy line indicates the point of attachment to L of L-ULM.

In some embodiments, W is a compound of formula (B)(ii):

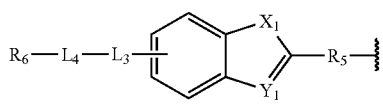

(B)(ii)

wherein the wavy line indicates the point of attachment to L of L-ULM.

In some embodiments, W is a compound of formula (B)(ii)(a):

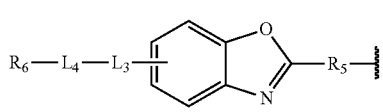

(B)(ii)(a)

wherein the wavy line indicates the point of attachment to L of L-ULM.

In some embodiments, $R_5$ is heteroaryl optionally substituted with one or two groups independently selected from cyano, halo, lower alkyl optionally substituted with amino, alkylamino, or di(alkyl)amino, lower alkoxy optionally substituted with lower alkoxy, optionally substituted amino, haloalkyl, di(alkyl)aminocarbonyl, alkylaminocarbonyl, and aminocarbonyl.

In some embodiments, $R_5$ is heterocycloalkenyl optionally substituted with one or two groups independently selected from cyano, halo, lower alkyl optionally substituted with amino, alkylamino, or di(alkyl)amino, lower alkoxy optionally substituted with lower alkoxy, optionally substituted amino, haloalkyl, di(alkyl)aminocarbonyl, alkylaminocarbonyl, and aminocarbonyl.

In some embodiments, $R_5$ is heterocycloalkyl optionally substituted with one or two groups independently selected from cyano, halo, lower alkyl optionally substituted with amino, alkylamino, or di(alkyl)amino, lower alkoxy optionally substituted with lower alkoxy, optionally substituted amino, haloalkyl, di(alkyl)aminocarbonyl, alkylaminocarbonyl, and aminocarbonyl.

In some embodiments, $R_6$ is 5-6 membered heteroaryl, each of which is optionally substituted with one or two groups selected from: halo; lower alkoxy; lower alkoxy substituted with lower alkoxy, amino, (alkyl)amino, (dialkyl)amino, heterocycloalkyl, heteroaryl, or halo; lower alkyl, and lower alkyl substituted with amino, (alkyl)amino, (dialkyl)amino, hydroxyl or lower alkoxy.

In some embodiments, W is a compound of formula (C):

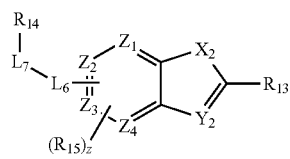

wherein:
wherein the point of attachment of W to L-ULM is at any substitutable atom of formula (C);
$X_2$ is ($CR_{16}$=$CR_{16}$), O, NH, or S;
$Y2$ is $CR_{16}$ or N;
each $R_{16}$ is independently selected from hydrogen, halo, cyano, and lower alkyl;
$Z_1$, $Z_2$, $Z_3$, and $Z_4$ are independently selected from CH and N, provided that at least two of $Z_1$, $Z_2$, $Z_3$, and $Z_4$ are CH;
$R_{13}$ is aryl, heteroaryl, or heterocycloalkyl, each of which is optionally substituted with one or two groups independently selected from alkynyl, heteroaryl, cyano, optionally substituted amino, halo, and lower alkyl optionally substituted with optionally substituted amino;
$L_6$ is absent, C(O)O, O, or $NR_{17}$;
$R_{17}$ is hydrogen or lower alkyl;
$L_7$ is $(CH_2)_q$;
$R_{14}$ is hydrogen, hydroxyl, lower alkyl, lower haloalkyl, halo, or lower alkoxy,
each $R_{15}$ is selected from lower alkyl, lower alkoxy, and halo; or
$R_{14}$ and $R_{15}$, taken together with any intervening atoms forms a 5- to 7-membered heterocycloalkyl ring;
z is 0 or 1; and
q is 0, 1, or 2.

In some embodiments, W is a compound of formula (D):

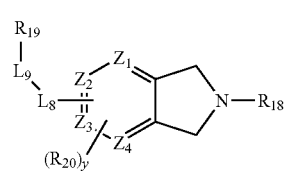

wherein:
the point of attachment of W to L-ULM is at any substitutable atom of formula (D);
$Z_1$, $Z_2$, $Z_3$, and $Z_4$ are independently selected from CH and N, provided that at least two of $Z_1$, $Z_2$, $Z_3$, and $Z_4$ are CH;
$R_{18}$ is aryl, heteroaryl, or heterocycloalkenyl, each of which is optionally substituted with one or two groups independently selected from alkynyl, heteroaryl, cyano, optionally substituted amino, halo, lower alkyl, and lower alkyl substituted with optionally substituted amino;
$L_8$ is O or $NR_{21}$;
$R_{21}$ is hydrogen or lower alkyl;
$L_9$ is $(CH_2)_x$;
$R_{19}$ is hydrogen, aryl, aryl substituted with hydroxyl or lower alkoxy, heteroaryl, and heteroaryl substituted with hydroxyl or lower alkoxy;
each $R_{20}$ is independently selected from lower alkyl, lower alkoxy, halo, and oxo (as a substituent on the heterocycloalkyl ring);
x is 0, 1, or 2; and
y is 0 or 1.

In some embodiments, W is a compound of formula (E):

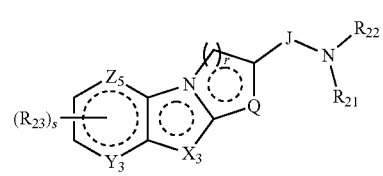

wherein:
the point of attachment of W to L-ULM is at any substitutable atom of formula (E);
J is C(=O) or —$CH_2$—;
$X_3$ is S or N;
$Y_3$ is CH or N;
$Z_5$ is CH or N;
Q is N or S;
for each occurrence, $R_{23}$ is independently selected from halo, lower alkoxy, hydroxy, aryl, heteroaryl, cycloalkoxy, and lower alkyl, wherein the lower alkoxy, cycloalkoxy, lower alkyl, aryl, or heteroaryl are each optionally substituted with one, two, or three groups independently selected from lower alkoxy, alkenyl, —$NR_{24}R_{25}$, halo, and heteroaryl optionally substituted with one to three lower alkoxy;
$R_{21}$ is hydrogen or lower alkyl; and
$R_{22}$ is alkyl, aryl, aralkyl, heterocycloalkyl, heterocycloalkenyl, heteroaryl, or heteroaralkyl, each of which is optionally substituted with one, two, or three groups independently selected from hydroxy, lower alkoxy optionally substituted with lower alkoxy or halo, lower alkyl optionally substituted with halo, halo, heteroaryl, —(CH$_2$)$_r$NR$_{24}$R$_{25}$, oxo, cyano, and —C(O)—NR$_{24}$R$_{25}$, or R$_{21}$ and R$_{22}$ taken together with the nitrogen to which they are bound form a heterocycloalkyl ring, optionally substituted with one, two, or three groups independently selected from hydroxy, lower alkoxy, lower alkyl, halo, and —C(O)—NR$_{24}$R$_{25}$;

t is 0, 1, or 2;

each R$_{24}$ is independently selected from hydrogen or lower alkyl;

each R$_{25}$ is independently selected from hydrogen or lower alkyl; or

R$_{24}$ and R$_{25}$ taken together with the nitrogen to which they are bound form a heterocycloalkyl ring, optionally substituted with one, two, or three groups independently selected from hydroxy, lower alkoxy, lower alkyl, halo, or —C(O)—NR$_{26}$R$_{27}$;

each R$_{26}$ is independently hydrogen or lower alkyl;

each R$_{27}$ is independently hydrogen or lower alkyl;

s is 0, 1, or 2; and r is 1 or 2.

In some embodiments, W is a compound of formula (E)(i):

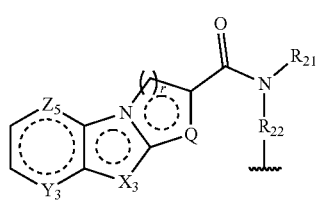

(E)(i)

wherein the wavy line indicates the point of attachment to L of L-ULM.

In some embodiments, R$_{21}$ is hydrogen and R$_{22}$ is aryl, aralkyl, heterocycloalkyl, heterocycloalkenyl, heteroaryl, or heteroaralkyl, each of which is optionally substituted with one, two, or three groups independently selected from hydroxy, lower alkoxy optionally substituted with lower alkoxy or halo, lower alkyl optionally substituted with halo, halo, heteroaryl, —(CH$_2$)$_r$NR$_{24}$R$_{25}$, oxo, cyano, and —C(O)—NR$_{24}$R$_{25}$.

In some embodiments, W is a compound of formula (F):

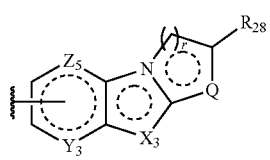

(F)

wherein:

X$_3$ is S or N;

Y3 is CH or N;

Z$_5$ is CH or N;

Q is N or S;

R$_{28}$ is heteroaryl optionally substituted with one, two, or three groups independently selected from cyano, lower alkoxy, lower alkenyl, —NR$_{24}$R$_{25}$, halo, and heteroaryl optionally substituted with one to three lower alkoxy;

each R$_{24}$ is independently selected from hydrogen or lower alkyl;

each R$_{25}$ is independently selected from hydrogen or lower alkyl; or

R$_{24}$ and R$_{25}$ taken together with the nitrogen to which they are bound form a heterocycloalkyl ring, optionally substituted with one, two, or three groups independently selected from hydroxy, lower alkoxy, lower alkyl, halo, or —C(O)—NR$_{26}$R$_{27}$;

each R$_{26}$ is independently hydrogen or lower alkyl;

each R$_{27}$ is independently hydrogen or lower alkyl; and wherein the wavy line indicates the point of attachment of W to L of L-ULM.

In some embodiments, R$_{28}$ is bicyclic heteroaryl optionally substituted with one, two, or three groups independently selected from cyano, lower alkoxy, lower alkenyl, —NR$_{24}$R$_{25}$, halo, and heteroaryl optionally substituted with one to three lower alkoxy.

In some embodiments, R$_{28}$ is bicyclic heteroaryl optionally substituted with one or two groups independently selected from cyano and —NR$_{24}$R$_{25}$.

In some embodiments, W is attached to L of L-ULM via any substitutable atom and is a compound selected from:

2-(5-fluoro-1-benzofuran-2-yl)-N-methylimidazo[1,2-a]pyridin-3-amine;

2-(5-methoxy-1-benzofuran-2-yl)-N-methylimidazo[1,2-a]pyridin-3-amine;

6-fluoro-2-(5-methoxy-1-benzofuran-2-yl)-N-methylimidazo[1,2-a]pyridin-3-amine;

7-fluoro-2-(5-methoxy-1-benzofuran-2-yl)-N-methylimidazo[1,2-a]pyridin-3-amine;

2-(5-methoxy-1-benzofuran-2-yl)-3-(methylamino)imidazo[1,2-a]pyridine-7-carbonitrile;

2-[6-fluoro-3-(methylamino)imidazo[1,2-a]pyridin-2-yl]-1-benzofuran-5-ol;

2-(5-methoxy-1-benzofuran-2-yl)-N-(2-methoxyethyl)imidazo[1,2-a]pyridin-3-amine;

2-[7-fluoro-3-(methylamino)imidazo[1,2-a]pyridin-2-yl]-1-benzofuran-5-ol;

2-{3-[(2-hydroxyethyl)amino]imidazo[1,2-a]pyridin-2-yl}-1-benzofuran-5-ol;

2-(5-hydroxy-1-benzofuran-2-yl)-3-(methylamino)imidazo[1,2-a]pyridine-7-carbonitrile;

2-[5-(2-fluoroethoxy)-1-benzofuran-2-yl]-3-(methylamino)imidazo[1,2-a]pyridine-7-carbonitrile;

2-(4-methoxyphenyl)-3-(methylamino)imidazo[1,2-a]pyridine-7-carbonitrile;

2-(6-methoxy-1-benzofuran-2-yl)-3-(methylamino)imidazo[1,2-a]pyridine-7-carbonitrile;

7-methoxy-2-(5-methoxy-1-benzofuran-2-yl)-N-methylimidazo[1,2-a]pyridin-3-amine;

3-(methylamino)-2-[3-(pyridin-3-ylmethoxy)phenyl]imidazo[1,2-a]pyridine-7-carbonitrile;

3-(methylamino)-2-[4-(pyridin-3-ylmethoxy)phenyl]imidazo[1,2-a]pyridine-7-carbonitrile;

7-chloro-2-(5-methoxy-1-benzofuran-2-yl)-N-methylimidazo[1,2-a]pyridin-3-amine;

7-bromo-2-(5-methoxy-1-benzofuran-2-yl)-N-methylimidazo[1,2-a]pyridin-3-amine;

2-(5-methoxy-1-benzofuran-2-yl)-3-(methylamino)imidazo[1,2-a]pyridine-6-carbonitrile;

2-(5-bromo-1-benzofuran-2-yl)-3-(methylamino)imidazo[1,2-a]pyridine-7-carbonitrile;

3-(methylamino)-2-[3-(pyrazin-2-yl)phenyl]imidazo[1,2-a]pyridine-7-carbonitrile;

3-(methylamino)-2-[4-(pyrazin-2-yl)phenyl]imidazo[1,2-a]pyridine-7-carbonitrile;

2-[(E)-2-(4-methoxyphenyl)ethenyl]-3-(methylamino)imidazo[1,2-a]pyridine-7-carbonitrile;
2-(5-methoxy-1-benzofuran-2-yl)-3-[(2-methoxyethyl)amino]imidazo[1,2-a]pyridine-7-carbonitrile;
2-(2,3-dihydro-1,4-benzodioxin-6-yl)-3-(methylamino)imidazo[1,2-a]pyridine-7-carbonitrile;
2-(5-bromofuran-2-yl)-3-(methylamino)imidazo[1,2-a]pyridine-7-carbonitrile;
2-(4-cyanophenyl)-3-(methylamino)imidazo[1,2-a]pyridine-7-carbonitrile;
2-(1-benzofuran-5-yl)-3-(methylamino)imidazo[1,2-a]pyridine-7-carbonitrile;
3-(methylamino)-2-[4-(prop-2-yn-1-yloxy)phenyl]imidazo[1,2-a]pyridine-7-carbonitrile;
2-(5-fluoro-1-benzofuran-2-yl)-3-(methylamino)imidazo[1,2-a]pyridine-7-carbonitrile;
2-{3-[(5-methoxypyrazin-2-yl)methoxy]phenyl}-3-(methylamino)imidazo[1,2-a]pyridine-7-carbonitrile;
2-{5-[(5-methoxypyrazin-2-yl)methoxy]pyridin-2-yl}-3-(methylamino)imidazo[1,2-a]pyridine-7-carbonitrile;
3-(dimethylamino)-2-(5-methoxy-1-benzofuran-2-yl)imidazo[1,2-a]pyridine-7-carbonitrile;
2-(5-methoxy-1-methyl-1H-1,3-benzodiazol-2-yl)-3-(methylamino)imidazo[1,2-a]pyridine-7-carbonitrile;
2-(6-methoxy-1,3-benzothiazol-2-yl)-3-(methylamino)imidazo[1,2-a]pyridine-7-carbonitrile;
2-(5-methoxy-1,3-benzoxazol-2-yl)-3-(methylamino)imidazo[1,2-a]pyridine-7-carbonitrile;
2-(5-methoxy-1H-1,3-benzodiazol-2-yl)-3-(methylamino)imidazo[1,2-a]pyridine-7-carbonitrile;
2-(5-methoxy-1-benzofuran-2-yl)imidazo[1,2-a]pyridine-7-carbonitrile;
2-(6-methoxy-1-methyl-1H-1,3-benzodiazol-2-yl)-3-(methylamino)imidazo[1,2-a]pyridine-7-carbonitrile;
3-(methylamino)-2-[5-(pyridin-3-ylmethoxy)-1-benzofuran-2-yl]imidazo[1,2-a]pyridine-7-carbonitrile;
3-amino-2-[5-(2-fluoroethoxy)-1-benzofuran-2-yl]imidazo[1,2-a]pyridine-7-carbonitrile;
3-amino-2-(5-methoxy-1-benzofuran-2-yl)imidazo[1,2-a]pyridine-7-carbonitrile;
2-(5-methoxy-1-benzofuran-2-yl)-3-(methoxymethyl)imidazo[1,2-a]pyridine-7-carbonitrile;
3-[(dimethylamino)methyl]-2-(5-methoxy-1-benzofuran-2-yl)imidazo[1,2-a]pyridine-7-carbonitrile;
2-{5-[2-(dimethylamino)ethoxy]-1-benzofuran-2-yl}-3-(methylamino)imidazo[1,2-a]pyridine-7-carbonitrile;
3-(methylamino)-2-{4-[(pyridin-3-ylmethoxy)methyl]phenyl}imidazo[1,2-a]pyridine-7-carbonitrile;
3-{[2-(dimethylamino)ethyl]amino}-2-(5-methoxy-1-benzofuran-2-yl)imidazo[1,2-a]pyridine-7-carbonitrile
tert-butyl 2-[7-cyano-3-(methylamino)imidazo[1,2-a]pyridin-2-yl]-4H,5H,6H,7H-furo[3,2-c]pyridine-5-carboxylate;
7-(aminomethyl)-2-(5-methoxy-1-benzofuran-2-yl)-N-methylimidazo[1,2-a]pyridin-3-amine;
3-(methylamino)-2-{3-[(pyridin-3-ylmethoxy)methyl]phenyl}imidazo[1,2-a]pyridine-7-carbonitrile;
2-{4-[(5-methoxypyrazin-2-yl)methoxy]phenyl}-3-(methylamino)imidazo[1,2-a]pyridine-7-carbonitrile;
2-{6-[(5-methoxypyrazin-2-yl)methoxy]pyridin-3-yl}-3-(methylamino)imidazo[1,2-a]pyridine-7-carbonitrile;
2-(5-methoxy-1-benzofuran-2-yl)-N-methyl-7-[2-(trimethylsilyl)ethynyl]imidazo[1,2-a]pyridin-3-amine;
7-ethynyl-2-(5-methoxy-1-benzofuran-2-yl)-N-methylimidazo[1,2-a]pyridin-3-amine;
2-(4-{[(5-methoxypyridin-2-yl)methyl]amino}phenyl)-3-(methylamino)imidazo[1,2-a]pyridine-7-carbonitrile;
2-(4-{5H,6H-imidazo[2,1-b][1,3]thiazol-3-ylmethoxy}phenyl)-3-(methylamino)imidazo[1,2-a]pyridine-7-carbonitrile;
2-{10-methoxy-7-thia-2,5-diazatricyclo[6.4.0.0$^{2,6}$]dodeca-1(12),3,5,8,10-pentaen-4-yl}-3-(methylamino)imidazo[1,2-a]pyridine-7-carbonitrile;
2-{11-methoxy-7-thia-2,5-diazatricyclo[6.4.0.0$^{2,6}$]dodeca-1(12),3,5,8,10-pentaen-4-yl}-3-(methylamino)imidazo[1,2-a]pyridine-7-carbonitrile; and
2-{5-[(5-methoxypyridin-2-yl)methoxy]pyrazin-2-yl}-3-(methylamino)imidazo[1,2-a]pyridine-7-carbonitrile.

In some embodiments, W is attached to L of L-ULM via any substitutable atom and is a compound selected from:

tert-butyl 4-[2-(pyridin-3-yl)-1,3-benzoxazol-5-yl]piperazine-1-carboxylate;
4-methoxy-N-[2-(pyridin-3-yl)-1,3-benzoxazol-5-yl]benzamide;
4-methoxy-N-[2-(pyridin-4-yl)-1,3-benzoxazol-5-yl]benzamide;
N-[(4-methoxyphenyl)methyl]-2-(pyridin-3-yl)-1,3-benzoxazol-5-amine;
2-(3-bromopyridin-4-yl)-6-[2-(morpholin-4-yl)ethoxy]-1,3-benzothiazole;
5-methoxy-N-[2-(3-methylphenyl)-1,3-benzoxazol-5-yl]pyridine-2-carboxamide;
6-methoxy-N-[2-(3-methylphenyl)-1,3-benzoxazol-5-yl]pyridine-3-carboxamide;
2-methoxy-N-[2-(3-methylphenyl)-1,3-benzoxazol-5-yl]pyrimidine-5-carboxamide;
5-methoxy-N-[2-(3-methylphenyl)-1,3-benzoxazol-5-yl]pyrazine-2-carboxamide;
4-methoxy-N-[2-(3-methylphenyl)-[1,3]oxazolo[5,4-b]pyridin-6-yl]benzamide;
5-(4-methoxyphenyl)-2-(pyridin-3-yl)-1,3-benzoxazole;
N-(4-methoxyphenyl)-2-(pyridin-3-yl)-1,3-benzoxazol-5-amine;
2-(pyridin-3-yl)-N-{[1,2,4]triazolo[4,3-a]pyridin-3-yl}-1,3-benzoxazol-5-amine;
2-(pyridin-3-yl)-N-(pyrimidin-4-yl)-1,3-benzoxazol-5-amine;
2-(pyridin-3-yl)-N-(pyrimidin-2-yl)-1,3-benzoxazol-5-amine;
5-(5-methoxypyridin-2-yl)-2-(pyridin-3-yl)-1,3-benzoxazole;
5-(2-methoxypyrimidin-5-yl)-2-(pyridin-3-yl)-1,3-benzoxazole;
5-(5-methoxypyrimidin-2-yl)-2-(pyridin-3-yl)-1,3-benzoxazole;
5-(6-methoxypyridazin-3-yl)-2-(pyridin-3-yl)-1,3-benzoxazole;
5-(5-methoxypyrazin-2-yl)-2-(pyridin-3-yl)-1,3-benzoxazole;
1-methyl-4-[5-(pyrimidin-5-ylmethoxy)-1-benzofuran-2-yl]-1H-pyrazole-3-carbonitrile;
4-[5-(pyrimidin-5-ylmethoxy)-1-benzofuran-2-yl]pyridine-3-carbonitrile;
4-{5-[(5-methoxypyridin-2-yl)methoxy]-1-benzofuran-2-yl}pyridine-3-carbonitrile;
4-{5-[(5-methoxypyridin-2-yl)methoxy]-1-benzofuran-2-yl}pyridine;
4-{5-[(1-methyl-1H-imidazol-4-yl)methoxy]-1-benzofuran-2-yl}pyridine-3-carbonitrile;
4-{5-[(1-methyl-1H-imidazol-2-yl)methoxy]-1-benzofuran-2-yl}pyridine-3-carbonitrile;
5-methoxy-2-[2-(pyridin-3-yl)-1,3-benzoxazol-5-yl]-2,3-dihydro-1H-isoindol-1-one;

3-{6-[(E)-2-(4-methoxyphenyl)ethenyl]-[1,3]oxazolo[5,4-b]pyridin-2-yl}pyridine;
4-[5-(pyridin-3-yloxy)-1-benzofuran-2-yl]pyridine-3-carbonitrile;
6-methoxy-2-[2-(pyridin-3-yl)-1,3-benzoxazol-5-yl]-1,2,3,4-tetrahydroisoquinolin-1-one;
dimethyl({3-[4-({[2-(pyridin-3-yl)-1,3-benzoxazol-5-yl]oxy}methyl)phenoxy]propyl})amine;
5-[(1-methyl-1H-pyrazol-4-yl)methoxy]-2-(pyridin-3-yl)-1,3-benzoxazole;
5-[(4-methoxyphenyl)methoxy]-2-(pyridin-3-yl)-1,3-benzoxazole;
5-[(3-methoxyphenyl)methoxy]-2-(pyridin-3-yl)-1,3-benzoxazole;
5-[(5-methoxypyridin-2-yl)methoxy]-2-(pyridin-3-yl)-1,3-benzoxazole;
2-(pyridin-3-yl)-5-(pyridin-3-ylmethoxy)-1,3-benzoxazole;
5-{5H,6H-imidazo[2,1-b][1,3]thiazol-3-ylmethoxy}-2-(pyridin-3-yl)-1,3-benzoxazole;
1-(pyridin-2-yl)-2-[2-(pyridin-3-yl)-1,3-benzoxazol-5-yl]ethan-1-ol;
1-(pyridin-2-yl)-2-[2-(pyridin-3-yl)-1,3-benzoxazol-5-yl]ethan-1-one;
6-methoxy-2-[2-(pyridin-3-yl)-1,3-benzoxazol-5-yl]-1,2-dihydroisoquinolin-1-one;
2-(pyridin-3-yl)-N-[2,2,2-trifluoro-1-(4-methoxyphenyl)ethyl]-[1,3]oxazolo[5,4-b]pyridin-6-amine;
3-{6-[2-(4-methoxyphenyl)ethynyl]-[1,3]oxazolo[5,4-b]pyridin-2-yl}pyridine;
3-{6-[(Z)-2-(4-methoxyphenyl)ethenyl]-[1,3]oxazolo[5,4-b]pyridin-2-yl}pyridine;
5-methoxy-2-[2-(pyridin-3-yl)-[1,3]oxazolo[5,4-b]pyridin-6-yl]-2,3-dihydro-1H-isoindol-1-one;
5-[(5-methoxypyrazin-2-yl)methoxy]-2-(pyridin-3-yl)-1,3-benzoxazole;
3-methoxy-6-[2-(pyridin-3-yl)-1,3-benzoxazol-5-yl]-5H,6H,7H-pyrrolo[3,4-b]pyridin-7-one;
2-(pyridin-3-yl)-6-(pyridin-3-ylmethoxy)-1,3-benzoxazole;
3-{6-[2-(pyridin-3-yl)ethynyl]-[1,3]oxazolo[5,4-b]pyridin-2-yl}pyridine;
5-{[(5-methoxypyridin-2-yl)oxy]methyl}-2-(pyridin-3-yl)-1,3-benzoxazole;
4-[5-(pyridin-3-ylmethoxy)-1-benzofuran-2-yl]pyridine-3-carbonitrile;
4-{5-[(1-methyl-1H-pyrazol-4-yl)methoxy]-1-benzofuran-2-yl}pyridine-3-carbonitrile;
3-[5-(pyridin-3-ylmethoxy)-1-benzofuran-2-yl]pyridine-4-carbonitrile;
3-{5-[(1-methyl-1H-pyrazol-4-yl)methoxy]-1-benzofuran-2-yl}pyridine-4-carbonitrile;
3-{6-[1-(5-methoxypyridin-2-yl)ethoxy]-[1,3]oxazolo[5,4-b]pyridin-2-yl}pyridine;
4-{5-[(5-methoxypyrazin-2-yl)methoxy]-1-benzofuran-2-yl}pyridine-3-carbonitrile;
6-({[2-(pyridin-3-yl)-1,3-benzoxazol-5-yl]oxy}methyl)pyridin-3-ol;
5-{[5-(prop-2-en-1-yloxy)pyrazin-2-yl]methoxy}-2-(pyridin-3-yl)-1,3-benzoxazole;
5-({[2-(pyridin-3-yl)-1,3-benzoxazol-5-yl]oxy}methyl)-1,2-dihydropyrazin-2-one;
1-methyl-5-({[2-(pyridin-3-yl)-1,3-benzoxazol-5-yl]oxy}methyl)-1,2-dihydropyrazin-2-one;
5-[4-(5-methoxypyrimidin-2-yl)piperazin-1-yl]-2-(pyridin-3-yl)-1,3-benzoxazole;
3-{6-[(5-methoxypyridin-2-yl)methoxy]-[1,3]oxazolo[5,4-b]pyridin-2-yl}pyridine;
5-(1-methyl-1H-pyrazol-4-yl)-2-(pyridin-3-yl)-1,3-benzoxazole;
3-{6-[(6-methoxypyridin-3-yl)methoxy]-[1,3]oxazolo[5,4-b]pyridin-2-yl}pyridine;
5-[(5-methoxypyridin-2-yl)methoxy]-2-(pyridin-4-yl)-1,3-benzoxazole;
[(3-{5-[(5-methoxypyridin-2-yl)methoxy]-1,3-benzoxazol-2-yl}phenyl)methyl]dimethylamine;
5-[(5-methoxypyridin-2-yl)methoxy]-2-(1-methyl-1H-pyrazol-4-yl)-1,3-benzoxazole;
5-[(5-methoxypyridin-2-yl)methoxy]-2-(pyrazin-2-yl)-1,3-benzoxazole;
5-[(5-methoxypyridin-2-yl)methoxy]-2-(1-methylpiperidin-4-yl)-1,3-benzoxazole;
5-[(5-methoxypyridin-2-yl)methoxy]-2-(1,3-thiazol-5-yl)-1,3-benzoxazole;
5-[2-(pyridin-2-yloxy)ethoxy]-2-(pyridin-3-yl)-1,3-benzoxazole;
4-[5-(1H-pyrazol-4-ylmethoxy)-1-benzofuran-2-yl]pyridine-3-carbonitrile;
3-{[(2-{5H,6H-imidazo[2,1-b][1,3]thiazol-3-yl}-1-benzofuran-5-yl)oxy]methyl}pyridine;
2-(3-fluoroazetidin-1-yl)-5-[(5-methoxypyridin-2-yl)methoxy]-1,3-benzoxazole;
2-{3H,4H,5H,6H,7H-imidazo[4,5-c]pyridin-5-yl}-5-[(5-methoxypyridin-2-yl)methoxy]-1,3-benzoxazole;
5-[(5-methoxypyridin-2-yl)methoxy]-2-{2H,4H,5H,6H,7H-pyrazolo[4,3-c]pyridin-5-yl}-1,3-benzoxazole;
2-{5H,6H,7H,8H-imidazo[1,5-a]pyrazin-7-yl}-5-[(5-methoxypyridin-2-yl)methoxy]-1,3-benzoxazole;
5-[(5-methoxypyridin-2-yl)methoxy]-2-{5H,6H,7H-pyrrolo[3,4-b]pyridin-6-yl}-1,3-benzoxazole;
7-{5-[(5-methoxypyridin-2-yl)methoxy]-1,3-benzoxazol-2-yl}-5,6,7,8-tetrahydro-1,7-naphthyridine;
2-(1H-imidazol-1-yl)-5-[(5-methoxypyridin-2-yl)methoxy]-1,3-benzoxazole;
2-{5H,6H,7H,8H-imidazo[1,2-a]pyrazin-7-yl}-5-[(5-methoxypyridin-2-yl)methoxy]-1,3-benzoxazole;
4-(5-{[1-(2-methoxyethyl)-1H-pyrazol-4-yl]methoxy}-1-benzofuran-2-yl)pyridine-3-carbonitrile;
2-[5-(2-methoxyethoxy)pyridin-3-yl]-5-[(5-methoxypyridin-2-yl)methoxy]-1,3-benzoxazole;
N-(5-{5-[(5-methoxypyridin-2-yl)methoxy]-1,3-benzoxazol-2-yl}pyridin-2-yl)acetamide;
5-{5-[(5-methoxypyridin-2-yl)methoxy]-1,3-benzoxazol-2-yl}pyridin-2-amine;
methyl({[4-({[2-(pyridin-3-yl)-1,3-benzoxazol-5-yl]oxy}methyl)phenyl]methyl})amine;
4-(5-{[1-(2-hydroxyethyl)-1H-pyrazol-4-yl]methoxy}-1-benzofuran-2-yl)pyridine-3-carbonitrile;
dimethyl({2-[4-({[2-(pyridin-3-yl)-1,3-benzoxazol-5-yl]oxy}methyl)phenoxy]ethyl})amine;
5-{[5-(2-methoxyethoxy)pyridin-2-yl]methoxy}-2-(pyridin-3-yl)-1,3-benzoxazole;
4-[5-({1-[2-(dimethylamino)ethyl]-1H-pyrazol-4-yl}methoxy)-1-benzofuran-2-yl]pyridine-3-carbonitrile;
5-{5-[(5-methoxypyridin-2-yl)methoxy]-1,3-benzoxazol-2-yl}-N-methylpyridin-2-amine;
3-{[(2-{2-bromo-5H,6H-imidazo[2,1-b][1,3]thiazol-3-yl}-1-benzofuran-5-yl)oxy]methyl}pyridine;
5-[(5-methoxypyrazin-2-yl)methoxy]-1-methyl-2-(pyridin-3-yl)-1H-1,3-benzodiazole;
6-[(5-methoxypyrazin-2-yl)methoxy]-1-methyl-2-(pyridin-3-yl)-1H-1,3-benzodiazole;
5-[(5-methoxypyrazin-2-yl)methoxy]-2-(pyridin-3-yl)-1H-1,3-benzodiazole;

5-[(5-methoxypyridin-2-yl)methoxy]-2-(piperazin-1-yl)-1,3-benzoxazole;
N-methyl-6-({[2-(pyridin-3-yl)-1,3-benzoxazol-5-yl]oxy}methyl)pyridin-3-amine;
3-[5-(pyridin-3-ylmethoxy)-1-benzofuran-2-yl]-5H,6H-imidazo[2,1-b][1,3]thiazole-2-carbonitrile;
5-{5-[(5-methoxypyridin-2-yl)methoxy]-1,3-benzoxazol-2-yl}-N-methylpyridine-2-carboxamide;
5-[(5-methoxypyridin-2-yl)methoxy]-2-(1-methyl-1H-imidazol-4-yl)-1,3-benzoxazole;
5-methoxy-N-{[2-(pyridin-3-yl)-1,3-benzoxazol-5-yl]methyl}pyridin-2-amine;
4-(5-{5H,6H-imidazo[2,1-b][1,3]thiazol-3-ylmethoxy}-1-benzofuran-2-yl)pyridine-3-carbonitrile;
5-({5-[2-(morpholin-4-yl)ethoxy]pyridin-2-yl}methoxy)-2-(pyridin-3-yl)-1,3-benzoxazole;
2-bromo-6-{5-[(5-methoxypyridin-2-yl)methoxy]-1-benzofuran-2-yl}benzonitrile;
4-{[2-(4-chlorophenyl)-1,3-benzoxazol-5-yl]carbamoyl}phenyl acetate;
N-(2-phenyl-1,3-benzoxazol-5-yl)benzamide;
4-methoxy-N-[2-(3-methylphenyl)-1,3-benzoxazol-5-yl]benzamide;
2-methoxy-N-[2-(4-methoxyphenyl)-1,3-benzoxazol-5-yl]benzamide;
4-methoxy-N-[2-(4-methoxyphenyl)-1,3-benzoxazol-5-yl]benzamide;
3-methoxy-N-[2-(4-methoxyphenyl)-1,3-benzoxazol-5-yl]benzamide;
3-{5-[(5-methoxypyridin-2-yl)methoxy]-1,3-benzoxazol-2-yl}pyridin-1-ium-1-olate;
2-phenoxy-N-[2-(pyridin-3-yl)-1,3-benzoxazol-5-yl]acetamide;
N-[2-(pyridin-3-yl)-1,3-benzoxazol-5-yl]-1-benzofuran-2-carboxamide;
N-[2-(pyridin-3-yl)-1,3-benzoxazol-5-yl]-6-(trifluoromethyl)pyridine-3-carboxamide;
N-[2-(pyridin-3-yl)-1,3-benzoxazol-5-yl]quinoxaline-2-carboxamide;
6-phenoxy-N-[2-(pyridin-3-yl)-1,3-benzoxazol-5-yl]pyridine-3-carboxamide;
N-[2-(pyridin-3-yl)-1,3-benzoxazol-5-yl]-2H-1,3-benzodioxole-5-carboxamide;
3-(benzyloxy)-N-[2-(pyridin-3-yl)-1,3-benzoxazol-5-yl]benzamide;
3-phenoxy-N-[2-(pyridin-3-yl)-1,3-benzoxazol-5-yl]benzamide;
N-[2-(pyridin-3-yl)-1,3-benzoxazol-5-yl]quinoline-2-carboxamide;
N-[2-(pyridin-3-yl)-1,3-benzoxazol-5-yl]-2,3-dihydro-1-benzofuran-2-carboxamide;
5-methyl-N-[2-(pyridin-3-yl)-1,3-benzoxazol-5-yl]pyridine-3-carboxamide;
N-[2-(pyridin-3-yl)-1,3-benzoxazol-5-yl]quinoxaline-6-carboxamide;
(2E)-3-(4-methoxyphenyl)-N-[2-(pyridin-3-yl)-1,3-benzoxazol-5-yl]prop-2-enamide;
5-methoxy-N-[2-(pyridin-3-yl)-1,3-benzoxazol-5-yl]pyridine-2-carboxamide;
3-cyano-N-[2-(pyridin-3-yl)-1,3-benzoxazol-5-yl]benzamide;
4-(methylsulfanyl)-N-[2-(pyridin-3-yl)-1,3-benzoxazol-5-yl]benzamide;
benzyl N-[2-(pyridin-3-yl)-1,3-benzoxazol-5-yl]carbamate;
5-[2-(pyridin-3-yl)-1,3-benzoxazol-5-yl]pyrazin-2-ol;
5-[(5-methoxypyridin-2-yl)methoxy]-2-(pyrimidin-5-yl)-1,3-benzoxazole;
2-(2,3-dihydro-1-benzofuran-2-yl)-5-[(5-methoxypyridin-2-yl)methoxy]-1,3-benzoxazole;
2-[(2R)-2,3-dihydro-1-benzofuran-2-yl]-5-[(5-methoxypyridin-2-yl)methoxy]-1,3-benzoxazole;
2-[(2S)-2,3-dihydro-1-benzofuran-2-yl]-5-[(5-methoxypyridin-2-yl)methoxy]-1,3-benzoxazole;
5-[5-(2-methoxyethoxy)pyrimidin-2-yl]-2-(pyridin-3-yl)-1,3-benzoxazole;
5-[(5-methoxypyridin-2-yl)methoxy]-2-(5-methylpyridin-3-yl)-1,3-benzoxazole;
5-[(5-methoxypyridin-2-yl)methoxy]-2-(2-methylpyridin-4-yl)-1,3-benzoxazole;
5-[(5-methoxypyridin-2-yl)methoxy]-2-(3-phenoxyphenyl)-1,3-benzoxazole;
6-{5-[(5-methoxypyridin-2-yl)methoxy]-1,3-benzoxazol-2-yl}-2-methyl-2,3-dihydropyridazin-3-one;
5-[(5-methoxypyridin-2-yl)methoxy]-2-(pyridazin-3-yl)-1,3-benzoxazole;
5-[(5-methoxypyridin-2-yl)methoxy]-2-(pyridazin-4-yl)-1,3-benzoxazole;
5-{5-[(5-methoxypyridin-2-yl)methoxy]-1,3-benzoxazol-2-yl}-1,2-dihydropyridin-2-one;
5-{5-[(5-methoxypyridin-2-yl)methoxy]-1,3-benzoxazol-2-yl}-1-methyl-1,2-dihydropyridin-2-one;
5-phenyl-N-[2-(pyridin-3-yl)-1,3-benzoxazol-5-yl]-1,3,4-oxadiazole-2-carboxamide;
5-[(5-methoxypyridin-2-yl)methoxy]-2-(pyrimidin-4-yl)-1,3-benzoxazole;
5-[(5-bromopyridin-2-yl)methoxy]-2-(pyridin-3-yl)-1,3-benzoxazole;
5-(pyridin-2-ylmethoxy)-2-(pyridin-3-yl)-1,3-benzoxazole;
N-[2-(pyridin-3-yl)-1,3-benzoxazol-5-yl]-1-benzofuran-5-carboxamide;
2-phenyl-N-[2-(pyridin-3-yl)-1,3-benzoxazol-5-yl]pyrimidine-5-carboxamide;
N-[2-(pyridin-3-yl)-1,3-benzoxazol-5-yl]-4-(pyrimidin-2-yl)benzamide;
1-methyl-N-[2-(pyridin-3-yl)-1,3-benzoxazol-5-yl]-1H-pyrazole-4-carboxamide;
4-[(6-methylpyrazin-2-yl)oxy]-N-[2-(pyridin-3-yl)-1,3-benzoxazol-5-yl]benzamide;
4-(phenoxymethyl)-N-[2-(pyridin-3-yl)-1,3-benzoxazol-5-yl]benzamide;
2-phenoxy-N-[2-(pyridin-3-yl)-1,3-benzoxazol-5-yl]pyridine-3-carboxamide;
4-cyano-N-[2-(pyridin-3-yl)-1,3-benzoxazol-5-yl]benzamide;
6-methoxy-N-[2-(pyridin-3-yl)-1,3-benzoxazol-5-yl]pyridine-2-carboxamide;
2-methyl-N-[2-(pyridin-3-yl)-1,3-benzoxazol-5-yl]pyridine-4-carboxamide;
3-methoxy-N-[2-(pyridin-3-yl)-1,3-benzoxazol-5-yl]pyridine-2-carboxamide;
4-methoxy-N-[2-(pyridin-3-yl)-1,3-benzoxazol-5-yl]pyridine-2-carboxamide;
4-hydroxy-N-[2-(pyridin-3-yl)-1,3-benzoxazol-5-yl]pyridine-2-carboxamide;
3-methoxy-N-[2-(pyridin-3-yl)-1,3-benzoxazol-5-yl]-1,2-oxazole-5-carboxamide;
5-methoxy-N-[2-(pyridin-3-yl)-1,3-benzoxazol-5-yl]pyridine-3-carboxamide;
6-({[2-(1-methyl-1H-pyrazol-4-yl)-1,3-benzoxazol-5-yl]oxy}methyl)pyridin-3-ol;
5-[(5-methoxypyrazin-2-yl)methoxy]-2-(1-methyl-1H-pyrazol-4-yl)-1,3-benzoxazole;
2-methoxy-5-({[2-(1-methyl-1H-pyrazol-4-yl)-[1,3]oxazolo[5,4-b]pyridin-6-yl]oxy}methyl)pyrazine;

3-{6-[(5-bromopyridin-2-yl)methoxy]-[1,3]oxazolo[5,4-b]pyridin-2-yl}pyridine;
3-methoxy-6-({[2-(pyridin-3-yl)-[1,3]oxazolo[5,4-b]pyridin-6-yl]oxy}methyl)pyridazine;
3-{5-[(5-methoxypyridin-2-yl)methoxy]-1,3-benzoxazol-2-yl}benzonitrile;
4-{5-[(5-methoxypyridin-2-yl)methoxy]-1,3-benzoxazol-2-yl}benzonitrile;
5-(1-methyl-1H-pyrazol-4-yl)-2-({[2-(pyridin-3-yl)-[1,3]oxazolo[5,4-b]pyridin-6-yl]oxy}methyl)pyridine;
3-methoxy-5-({[2-(pyridin-3-yl)-[1,3]oxazolo[5,4-b]pyridin-6-yl]oxy}methyl)pyridine;
4-methoxy-2-({[2-(pyridin-3-yl)-[1,3]oxazolo[5,4-b]pyridin-6-yl]oxy}methyl)pyridine;
2-({[2-(1-methyl-1H-pyrazol-4-yl)-[1,3]oxazolo[5,4-b]pyridin-6-yl]oxy}methyl)pyrazine;
[(3-{5-[(5-methoxypyridin-2-yl)methoxy]-1,3-benzoxazol-2-yl}phenyl)methyl](methyl)amine;
(5-methoxypyridin-2-yl)methyl N-[2-(pyridin-3-yl)-1,3-benzoxazol-5-yl]carbamate;
2-(5-methoxypyridin-2-yl)-5-[(5-methoxypyridin-2-yl)methoxy]-1,3-benzoxazole;
2-(1-benzofuran-2-yl)-5-[(5-methoxypyridin-2-yl)methoxy]-1,3-benzoxazole;
5-[(5-methoxypyridin-2-yl)methoxy]-2-[6-(trifluoromethyl)pyridin-3-yl]-1,3-benzoxazole;
2-(1-benzofuran-5-yl)-5-[(5-methoxypyridin-2-yl)methoxy]-1,3-benzoxazole;
2-{5-[(5-methoxypyridin-2-yl)methoxy]-1,3-benzoxazol-2-yl}quinoline;
2-[3-(benzyloxy)phenyl]-5-[(5-methoxypyridin-2-yl)methoxy]-1,3-benzoxazole;
5-[(5-methoxypyridin-2-yl)methoxy]-2-[4-(pyrimidin-2-yl)phenyl]-1,3-benzoxazole;
2-[(E)-2-(4-Methoxyphenyl)ethenyl]-5-[(5-methoxypyridin-2-yl)methoxy]-1,3-benzoxazole;
5-methoxy-2-({[2-(pyridin-3-yl)-[1,3]oxazolo[5,4-b]pyridin-6-yl]oxy}methyl)pyrimidine;
6-({[2-(1-methyl-1H-pyrazol-4-yl)-[1,3]oxazolo[5,4-b]pyridin-6-yl]oxy}methyl)pyridin-3-amine;
5-{5-[(5-hydroxypyridin-2-yl)methoxy]-1,3-benzoxazol-2-yl}-N-methylpyridine-2-carboxamide;
6-{6-[(5-methoxypyridin-2-yl)methoxy]-[1,3]oxazolo[5,4-b]pyridin-2-yl}-2-methyl-2,3-dihydropyridazin-3-one;
2-methyl-6-({[2-(pyridin-3-yl)-[1,3]oxazolo[5,4-b]pyridin-6-yl]oxy}methyl)-2,3-dihydropyridazin-3-one;
2-{6-[(5-methoxypyridin-2-yl)methoxy]-[1,3]oxazolo[5,4-b]pyridin-2-yl}pyrazine;
5-{6-[(5-methoxypyridin-2-yl)methoxy]-[1,3]oxazolo[5,4-b]pyridin-2-yl}-N-methylpyridine-2-carboxamide;
5-{5-[(5-methoxypyridin-2-yl)methoxy]-1,3-benzoxazol-2-yl}-1-methyl-1,2-dihydropyrazin-2-one;
6-(6-{[5-(2-fluoroethoxy)pyridin-2-yl]methoxy}-[1,3]oxazolo[5,4-b]pyridin-2-yl)-2-methyl-2,3-dihydropyridazin-3-one;
5-methoxy-2-({[2-(pyridin-3-yl)-[1,3]oxazolo[5,4-b]pyridin-6-yl]oxy}methyl)pyridin-1-ium-1-olate;
3-{6-[(5-methoxy-1-oxidopyridin-1-ium-2-yl)methoxy]-[1,3]oxazolo[5,4-b]pyridin-2-yl}pyridin-1-ium-1-olate;
5-{5-[(5-methoxypyridin-2-yl)methoxy]-1,3-benzoxazol-2-yl}-2-(methylcarbamoyl)pyridin-1-ium-1-olate;
(5-hydroxypyridin-2-yl)methyl N-[2-(pyridin-3-yl)-1,3-benzoxazol-5-yl]carbamate;
5-methoxy-N-[2-(1-methyl-6-oxo-1,6-dihydropyridazin-3-yl)-1,3-benzoxazol-5-yl]pyridine-2-carboxamide;
5-methoxy-N-[2-(1-methyl-6-oxo-1,6-dihydropyridazin-3-yl)-1,3-benzoxazol-5-yl]pyridine-3-carboxamide;
4-methoxy-N-[2-(1-methyl-6-oxo-1,6-dihydropyridazin-3-yl)-1,3-benzoxazol-5-yl]pyridine-2-carboxamide;
1-methyl-N-[2-(1-methyl-6-oxo-1,6-dihydropyridazin-3-yl)-1,3-benzoxazol-5-yl]-6-oxo-1,6-dihydropyridazine-3-carboxamide;
[(5-{5-[(5-methoxypyridin-2-yl)methoxy]-1,3-benzoxazol-2-yl}pyridin-3-yl)methyl](methyl)amine;
6-{5-[(5-hydroxypyridin-2-yl)methoxy]-1,3-benzoxazol-2-yl}-2-methyl-2,3-dihydropyridazin-3-one; and
N-(5-Methoxypyridin-3-yl)-2-(pyridin-3-yl)-1,3-benzoxazole-5-carboxamide.

In some embodiments, W is attached to L of L-ULM via any substitutable atom and is a compound selected from:
6-methoxy-2-(pyridin-3-yl)-1,3-benzoxazole;
[2-(pyridin-3-yl)-1,3-benzoxazol-5-yl]methanol;
4-[5-(methoxymethoxy)-1-benzofuran-2-yl]-1-methyl-1H-pyrazole-3-carbonitrile;
4-(5-methoxy-1-benzofuran-2-yl)-3-methylpyridine;
3-iodo-4-(5-methoxy-1-benzofuran-2-yl)pyridine;
2-[(dimethylamino)methyl]-6-(5-methoxy-1-benzofuran-2-yl)benzonitrile;
2-bromo-6-(5-methoxy-1-benzofuran-2-yl)benzonitrile;
5-bromo-2-(5-methoxy-1-benzofuran-2-yl)benzonitrile;
4-iodo-6-(5-methoxy-1-benzofuran-2-yl)pyrimidine-5-carbonitrile;
3-(5-hydroxy-1-benzofuran-2-yl)-5H,6H-imidazo[2,1-b][1,3]thiazole-2-carbonitrile;
4-(6-methoxynaphthalen-2-yl)pyridine-3-carbonitrile;
6-methoxy-2-(2-methoxyphenyl)-1,3-benzothiazole;
4-(6-methoxy-1,3-benzothiazol-2-yl)benzonitrile;
4-(6-methoxy-1H-1,3-benzodiazol-2-yl)pyridine-3-carbonitrile;
6-methoxy-2-[3-(1H-pyrazol-5-yl)pyridin-4-yl]-1,3-benzothiazole;
4-(6-methoxy-1,3-benzothiazol-2-yl)-N-methylpyridin-3-amine;
4-(6-methoxyquinolin-2-yl)pyridine-3-carbonitrile;
4-(6-methoxy-1,3-benzothiazol-2-yl)pyridine-3-carbonitrile;
4-(5-methoxy-1-benzofuran-2-yl)pyridine-3-carbonitrile;
N-[6-(5-methoxy-1-benzofuran-2-yl)pyridin-2-yl]acetamide;
6-(5-methoxy-1-benzofuran-2-yl)pyridine-3-carbonitrile;
4-(1,3-benzothiazol-2-yl)pyridine-3-carbonitrile;
2-(6-methoxy-1,3-benzothiazol-2-yl)benzonitrile;
2-(3-bromopyridin-4-yl)-6-methoxy-1,3-benzothiazole;
2-(3-bromopyridin-4-yl)-1,3-benzothiazol-6-ol;
2-(3-bromopyridin-2-yl)-6-methoxy-1,3-benzothiazole;
2-(6-methoxy-1,3-benzothiazol-2-yl)pyridine-3-carbonitrile;
2-(3-fluoropyridin-4-yl)-6-methoxy-1,3-benzothiazole;
4-[6-(dimethylamino)-1,3-benzothiazol-2-yl]pyridine-3-carbonitrile;
4-(6-methoxy-1,3-benzothiazol-2-yl)pyridine-2-carbonitrile;
2-(6-methoxy-1,3-benzoxazol-2-yl)benzonitrile;
N-[4-(6-methoxy-1,3-benzothiazol-2-yl)pyridin-3-yl]acetamide;
2-(3-bromopyridin-4-yl)-6-(2-fluoroethoxy)-1,3-benzothiazole;
4-[6-(2-fluoroethoxy)-1,3-benzothiazol-2-yl]pyridine-3-carbonitrile;
4-(5-methoxy-1,3-benzothiazol-2-yl)pyridine-3-carbonitrile;
4-[6-(trifluoromethyl)-1,3-benzothiazol-2-yl]pyridine-3-carbonitrile;

4-[5-(2-fluoroethoxy)-1-benzofuran-2-yl]pyridine-3-carbonitrile;
3-(6-methoxy-1,3-benzothiazol-2-yl)pyridine-4-carbonitrile;
5-bromo-3-{5-bromofuro[2,3-b]pyridin-2-yl}-1,2-dihydropyridin-2-one;
2-{5-methoxyfuro[2,3-c]pyridin-2-yl}benzonitrile;
2-{5-bromofuro[2,3-b]pyridin-2-yl}benzonitrile;
2-{5-methoxyfuro[2,3-b]pyridin-2-yl}benzonitrile;
4-(5-methoxy-1-benzofuran-2-yl)-1H-indazole;
7-(5-methoxy-1-benzofuran-2-yl)-1H-indazole;
4-[5-(methoxymethoxy)-1-benzofuran-2-yl]pyridine-3-carbonitrile;
4-(5-hydroxy-1-benzofuran-2-yl)pyridine-3-carbonitrile;
4-[5-(2-methoxyethoxy)-1-benzofuran-2-yl]pyridine-3-carbonitrile;
2-(5-methoxy-1-benzofuran-2-yl)pyridine-3-carbonitrile;
4-{5-methoxyfuro[2,3-c]pyridin-2-yl}pyridine-3-carbonitrile;
4-{6-methoxyfuro[3,2-b]pyridin-2-yl}pyridine-3-carbonitrile;
4-(3-bromo-5-methoxy-1-benzofuran-2-yl)pyridine;
5-methoxy-2-(pyridin-4-yl)-1-benzofuran-3-carbonitrile;
4-[5-(2-hydroxyethoxy)-1-benzofuran-2-yl]pyridine-3-carbonitrile;
2-{4,6,10-trioxa-12-azatricyclo[7.3.0.0$^{3,7}$]dodeca-1(9),2,7,11-tetraen-11-yl}benzonitrile;
4-{5-[(2-hydroxyethyl)(methyl)amino]-1-benzofuran-2-yl}pyridine-3-carbonitrile;
2-{2-methoxyfuro[2,3-d]pyrimidin-6-yl}benzonitrile;
4-(6-methoxy-1,3-benzoxazol-2-yl)pyridine-3-carbonitrile;
3-(5-methoxy-1-benzofuran-2-yl)-5H,6H-imidazo[2,1-b][1,3]thiazole-2-carbonitrile;
3-ethynyl-4-(5-methoxy-1-benzofuran-2-yl)pyridine;
4-(5-methoxy-3-methyl-1-benzofuran-2-yl)pyridine-3-carbonitrile;
4-[(dimethylamino)methyl]-2-(5-methoxy-1-benzofuran-2-yl)benzonitrile;
2-(3-Methylphenyl)-1,3-benzoxazol-5-amine;
2-(Pyridin-3-yl)-1,3-benzoxazol-5-amine;
2-(Pyridin-4-yl)-1,3-benzoxazol-5-amine; and
2-(3-Methylphenyl)-[1,3]oxazolo[5,4-b]pyridin-6-amine.

In some embodiments, W is attached to L of L-ULM via any substitutable atom and is a compound selected from:
2-(5-methoxy-2,3-dihydro-1H-isoindol-2-yl)pyridine-3-carbonitrile;
2-{5-[(5-methoxypyridin-2-yl)methoxy]-2,3-dihydro-1H-isoindol-2-yl}pyridine-3-carbonitrile;
2-[5-(pyrimidin-5-ylmethoxy)-2,3-dihydro-1H-isoindol-2-yl]pyridine-3-carbonitrile;
4-{5-[(5-methoxypyridin-2-yl)methoxy]-2,3-dihydro-1H-isoindol-2-yl}pyridine-3-carbonitrile;
4-(5-methoxy-2,3-dihydro-1H-isoindol-2-yl)pyrimidine-5-carbonitrile;
4-{5-[(5-methoxypyridin-2-yl)methoxy]-2,3-dihydro-1H-isoindol-2-yl}pyrimidine-5-carbonitrile;
4-{5-[(5-hydroxypyridin-2-yl)methoxy]-2,3-dihydro-1H-isoindol-2-yl}pyridine-3-carbonitrile;
4-(5-methoxy-2,3-dihydro-1H-isoindol-2-yl)pyridine-3-carbonitrile;
4-[5-(pyrimidin-5-ylmethoxy)-2,3-dihydro-1H-isoindol-2-yl]pyridine-3-carbonitrile;
5-[(5-methoxypyrazin-2-yl)methoxy]-2-(pyridin-4-yl)-2,3-dihydro-1H-isoindole;
4-[5-(benzyloxy)-2,3-dihydro-1H-isoindol-2-yl]pyrimidine-5-carbonitrile;
4-{5-[(5-hydroxypyridin-2-yl)methoxy]-2,3-dihydro-1H-isoindol-2-yl}pyrimidine-5-carbonitrile;
6-{5-[(5-methoxypyridin-2-yl)methoxy]-2,3-dihydro-1H-isoindol-2-yl}-2-methyl-2,3-dihydropyridazin-3-one; and
5-[(5-methoxypyridin-2-yl)methoxy]-2-(pyridin-4-yl)-2,3-dihydro-1H-isoindol-1-one.

In some embodiments, W is attached to L of L-ULM via any substitutable atom and is a compound selected from:
10-methoxy-N-(pyridin-3-yl)-7-thia-2,5-diazatricyclo[6.4.0.0$^{2,6}$]dodeca-1(12),3,5,8,10-pentaene-4-carboxamide;
10-methoxy-N-(6-methoxypyridin-3-yl)-7-thia-2,5-diazatricyclo[6.4.0.0$^{2,6}$]dodeca-1(12),3,5,8,10-pentaene-4-carboxamide;
10-methoxy-N-(pyridin-3-ylmethyl)-7-thia-2,5-diazatricyclo[6.4.0.0$^{2,6}$]dodeca-1(12),3,5,8,10-pentaene-4-carboxamide;
10-methoxy-N-methyl-N-(pyridin-3-yl)-7-thia-2,5-diazatricyclo[6.4.0.0$^{2,6}$]dodeca-1(12),3,5,8,10-pentaene-4-carboxamide;
N-(1-benzofuran-5-yl)-10-methoxy-7-thia-2,5-diazatricyclo[6.4.0.0$^{2,6}$]dodeca-1(12),3,5,8,10-pentaene-4-carboxamide;
10-hydroxy-N-(6-methoxypyridin-3-yl)-7-thia-2,5-diazatricyclo[6.4.0.0$^{2,6}$]dodeca-1(12),3,5,8,10-pentaene-4-carboxamide;
N-(6-methoxypyridin-3-yl)-1,8,10-triazatricyclo[7.4.0.0$^{2,7}$]trideca-2(7),3,5,8,10,12-hexaene-11-carboxamide;
N-(6-fluoropyridin-3-yl)-1,8,10-triazatricyclo[7.4.0.0$^{2,7}$]trideca-2(7),3,5,8,10,12-hexaene-11-carboxamide;
10-hydroxy-N-(pyridin-3-yl)-7-thia-2,5-diazatricyclo[6.4.0.0$^{2,6}$]dodeca-1(12),3,5,8,10-pentaene-4-carboxamide;
10-methoxy-N-(5-methoxypyridin-3-yl)-7-thia-2,5-diazatricyclo[6.4.0.0$^{2,6}$]dodeca-1(12),3,5,8,10-pentaene-4-carboxamide;
10-methoxy-N-(1-methyl-1H-pyrazol-4-yl)-7-thia-2,5-diazatricyclo[6.4.0.0$^{2,6}$]dodeca-1(12),3,5,8,10-pentaene-4-carboxamide;
N-(6-fluoropyridin-3-yl)-10-methoxy-7-thia-2,5-diazatricyclo[6.4.0.0$^{2,6}$]dodeca-1(12),3,5,8,10-pentaene-4-carboxamide;
10-methoxy-N-(pyridin-3-yl)-7-thia-2,5,9-triazatricyclo[6.4.0.0$^{2,6}$]dodeca-1(12),3,5,8,10-pentaene-4-carboxamide;
10-methoxy-N-(5-methoxypyridin-3-yl)-7-thia-2,5,9-triazatricyclo[6.4.0.0$^{2,6}$]dodeca-1(12),3,5,8,10-pentaene-4-carboxamide;
10-methoxy-N-[6-(methylcarbamoyl)pyridin-3-yl]-7-thia-2,5-diazatricyclo[6.4.0.0$^{2,6}$]dodeca-1(12),3,5,8,10-pentaene-4-carboxamide;
10-methoxy-4-{1H,2H,3H-pyrrolo[2,3-c]pyridine-1-carbonyl}-7-thia-2,5-diazatricyclo[6.4.0.0$^{2,6}$]dodeca-1(12),3,5,8,10-pentaene;
10-methoxy-N-(6-methylpyridin-3-yl)-7-thia-2,5-diazatricyclo[6.4.0.0$^{2,6}$]dodeca-1(12),3,5,8,10-pentaene-4-carboxamide;
10-methoxy-4-{1-methyl-1H,4H,5H,6H-pyrrolo[3,4-c]pyrazole-5-carbonyl}-7-thia-2,5-diazatricyclo[6.4.0.0$^{2,6}$]dodeca-1(12),3,5,8,10-pentaene;
10-methoxy-N-(1-methyl-6-oxo-1,6-dihydropyridazin-3-yl)-7-thia-2,5-diazatricyclo[6.4.0.0$^{2,6}$]dodeca-1(12),3,5,8,10-pentaene-4-carboxamide;
10-methoxy-N-(2-methylpyrimidin-5-yl)-7-thia-2,5-diazatricyclo[6.4.0.0$^{2,6}$]dodeca-1(12),3,5,8,10-pentaene-4-carboxamide;

N-[6-(1H-imidazol-1-yl)pyridin-3-yl]-10-methoxy-7-thia-2,5-diazatricyclo[6.4.0.0$^{2,6}$]dodeca-1(12),3,5,8,10-pentaene-4-carboxamide;

10-methoxy-N-(pyrimidin-5-yl)-7-thia-2,5-diazatricyclo[6.4.0.0$^{2,6}$]dodeca-1(12),3,5,8,10-pentaene-4-carboxamide;

N-[2-(dimethylamino)ethyl]-10-methoxy-7-thia-2,5-diazatricyclo[6.4.0.0$^{2,6}$]dodeca-1(12),3,5,8,10-pentaene-4-carboxamide;

10-methoxy-N-(2-methoxyethyl)-7-thia-2,5-diazatricyclo[6.4.0.0$^{2,6}$]dodeca-1(12),3,5,8,10-pentaene-4-carboxamide;

10-methoxy-N-(6-oxo-1,6-dihydropyridin-3-yl)-7-thia-2,5-diazatricyclo[6.4.0.0$^{2,6}$]dodeca-1(12),3,5,8,10-pentaene-4-carboxamide;

10-methoxy-N-[5-(pyridin-3-yl)pyridin-2-yl]-7-thia-2,5-diazatricyclo[6.4.0.0$^{2,6}$]dodeca-1(12),3,5,8,10-pentaene-4-carboxamide;

10-methoxy-N-(6-oxo-1,6-dihydropyridazin-3-yl)-7-thia-2,5-diazatricyclo[6.4.0.0$^{2,6}$]dodeca-1(12),3,5,8,10-pentaene-4-carboxamide;

5-methoxy-N-(pyridin-3-yl)-1,8,10-triazatricyclo[7.4.0.0$^{2,7}$]trideca-2(7),3,5,8,10,12-hexaene-11-carboxamide;

N-[6-(methylcarbamoyl)pyridin-3-yl]-1,8,10-triazatricyclo[7.4.0.0$^{2,7}$]trideca-2(7),3,5,8,10,12-hexaene-11-carboxamide;

N-(5-methoxypyridin-3-yl)-1,8,10-triazatricyclo[7.4.0.0$^{2,7}$]trideca-2(7),3,5,8,10,12-hexaene-11-carboxamide;

N-(1-methyl-6-oxo-1,6-dihydropyridazin-3-yl)-1,8,10-triazatricyclo[7.4.0.0$^{2,7}$]trideca-2(7),3,5,8,10,12-hexaene-11-carboxamide;

N-(6-oxo-1,6-dihydropyridin-3-yl)-1,8,10-triazatricyclo[7.4.0.0$^{2,7}$]trideca-2(7),3,5,8,10,12-hexaene-11-carboxamide;

N-(pyridin-3-yl)-1,8,10-triazatricyclo[7.4.0.0$^{2,7}$]trideca-2(7),3,5,8,10,12-hexaene-11-carboxamide;

N-(3-cyanopyridin-4-yl)-1,8,10-triazatricyclo[7.4.0.0$^{2,7}$]trideca-2(7),3,5,8,10,12-hexaene-11-carboxamide;

N-(2-methoxypyridin-4-yl)-1,8,10-triazatricyclo[7.4.0.0$^{2,7}$]trideca-2(7),3,5,8,10,12-hexaene-11-carboxamide;

N-(5,6-dimethoxypyridin-3-yl)-1,8,10-triazatricyclo[7.4.0.0$^{2,7}$]trideca-2(7),3,5,8,10,12-hexaene-11-carboxamide;

5-methoxy-N-(1-methyl-6-oxo-1,6-dihydropyridazin-3-yl)-1,8,10-triazatricyclo[7.4.0.0$^{2,7}$]trideca-2(7),3,5,8,10,12-hexaene-11-carboxamide;

5-methoxy-11-{1-methyl-1H,4H,5H,6H-pyrrolo[3,4-c]pyrazole-5-carbonyl}-1,8,10-triazatricyclo[7.4.0.0$^{2,7}$]trideca-2(7),3,5,8,10,12-hexaene;

4-methoxy-N-(5-methoxypyridin-3-yl)-1,8,10-triazatricyclo[7.4.0.0$^{2,7}$]trideca-2(7),3,5,8,10,12-hexaene-11-carboxamide;

5-methoxy-N-(5-methoxypyridin-3-yl)-1,8,10-triazatricyclo[7.4.0.0$^{2,7}$]trideca-2(7),3,5,8,10,12-hexaene-11-carboxamide;

N-[6-(1H-imidazol-1-yl)pyridin-3-yl]-5-methoxy-1,8,10-triazatricyclo[7.4.0.0$^{2,7}$]trideca-2(7),3,5,8,10,12-hexaene-11-carboxamide;

N-(3-cyanopyridin-4-yl)-5-methoxy-1,8,10-triazatricyclo[7.4.0.0$^{2,7}$]trideca-2(7),3,5,8,10,12-hexaene-11-carboxamide;

N-(6-oxo-1,6-dihydropyridazin-3-yl)-1,8,10-triazatricyclo[7.4.0.0$^{2,7}$]trideca-2(7),3,5,8,10,12-hexaene-11-carboxamide;

N-(3-cyano-2-methoxypyridin-4-yl)-1,8,10-triazatricyclo[7.4.0.0$^{2,7}$]trideca-2(7),3,5,8,10,12-hexaene-11-carboxamide;

5-methoxy-N-(6-methoxypyridin-3-yl)-1,8,10-triazatricyclo[7.4.0.0$^{2,7}$]trideca-2(7),3,5,8,10,12-hexaene-11-carboxamide;

10-methoxy-N-(5-methoxypyridin-2-yl)-7-thia-2,5-diazatricyclo[6.4.0.0$^{2,6}$]dodeca-1(12),3,5,8,10-pentaene-4-carboxamide;

N-(5-methoxypyridin-3-yl)-7-thia-2,5-diazatricyclo[6.4.0.0$^{2,6}$]dodeca-1(12),3,5,8,10-pentaene-4-carboxamide;

10-methoxy-N-(pyridin-4-yl)-7-thia-2,5-diazatricyclo[6.4.0.0$^{2,6}$]dodeca-1(12),3,5,8,10-pentaene-4-carboxamide;

10-methoxy-N-(pyrazin-2-yl)-7-thia-2,5-diazatricyclo[6.4.0.0$^{2,6}$]dodeca-1(12),3,5,8,10-pentaene-4-carboxamide;

3-{10-methoxy-7-thia-2,5-diazatricyclo[6.4.0.0$^{2,6}$]dodeca-1(12),3,5,8,10-pentaene-4-amido}pyridin-1-ium-1-olate;

10-(2-fluoroethoxy)-N-(pyridin-3-yl)-7-thia-2,5-diazatricyclo[6.4.0.0$^{2,6}$]dodeca-1(8),3,5,9,11-pentaene-4-carboxamide;

N-({10-methoxy-7-thia-2,5-diazatricyclo[6.4.0.0$^{2,6}$]dodeca-1(12),3,5,8,10-pentaen-4-yl}methyl)pyridin-3-amine;

10-[(5-methoxypyridin-2-yl)methoxy]-N-(5-methoxypyridin-3-yl)-7-thia-2,5-diazatricyclo[6.4.0.0$^{2,6}$]dodeca-1(12),3,5,8,10-pentaene-4-carboxamide;

N-(1-methyl-6-oxo-1,6-dihydropyridin-3-yl)-1,8,10-triazatricyclo[7.4.0.0$^{2,7}$]trideca-2(7),3,5,8,10,12-hexaene-11-carboxamide;

11-bromo-N-(5-methoxypyridin-3-yl)-7-thia-2,5,9-triazatricyclo[6.4.0.0$^{2,6}$]dodeca-1(12),3,5,8,10-pentaene-4-carboxamide;

N-(1-methyl-6-oxo-1,6-dihydropyridazin-3-yl)-10-(prop-2-en-1-yloxy)-7-thia-2,5-diazatricyclo[6.4.0.0$^{2,6}$]dodeca-1(12),3,5,8,10-pentaene-4-carboxamide;

10-methoxy-N-(5-methoxypyridin-3-yl)-5-thia-2,7-diazatricyclo[6.4.0.0$^{2,6}$]dodeca-1(12),3,6,8,10-pentaene-4-carboxamide;

10-methoxy-N-(1-methyl-6-oxo-1,6-dihydropyridazin-3-yl)-5-thia-2,7-diazatricyclo[6.4.0.0$^{2,6}$]dodeca-1(12),3,6,8,10-pentaene-4-carboxamide;

10-methoxy-N-(2-methylpyrimidin-5-yl)-5-thia-2,7-diazatricyclo[6.4.0.0$^{2,6}$]dodeca-1(8),3,6,9,11-pentaene-4-carboxamide;

N-(1-methyl-2-oxo-1,2-dihydropyrimidin-5-yl)-1,8,10-triazatricyclo[7.4.0.0$^{2,7}$]trideca-2(7),3,5,8,10,12-hexaene-11-carboxamide;

11-methoxy-N-(5-methoxypyridin-3-yl)-7-thia-2,5,9-triazatricyclo[6.4.0.0$^{2,6}$]dodeca-1(12),3,5,8,10-pentaene-4-carboxamide;

11-methoxy-N-(1-methyl-6-oxo-1,6-dihydropyridazin-3-yl)-7-thia-2,5,9-triazatricyclo[6.4.0.0$^{2,6}$]dodeca-1(12),3,5,8,10-pentaene-4-carboxamide;

10-methoxy-N-{3-[(methylamino)methyl]phenyl}-7-thia-2,5-diazatricyclo[6.4.0.0$^{2,6}$]dodeca-1(8),3,5,9,11-pentaene-4-carboxamide;

10-[(dimethylamino)methyl]-N-(5-methoxypyridin-3-yl)-7-thia-2,5-diazatricyclo[6.4.0.0$^{2,6}$]dodeca-1(12),3,5,8,10-pentaene-4-carboxamide;

N-(5-methoxypyridin-3-yl)-10-phenyl-7-thia-2,5-diazatricyclo[6.4.0.0$^{2,6}$]dodeca-1(12),3,5,8,10-pentaene-4-carboxamide;

N,5-bis(5-methoxypyridin-3-yl)-1,8,10-triazatricyclo[7.4.0.0$^{2,7}$]trideca-2(7),3,5,8,10,12-hexaene-11-carboxamide;

N,4-bis(5-methoxypyridin-3-yl)-1,8,10-triazatricyclo[7.4.0.0$^{2,7}$]trideca-2(7),3,5,8,10,12-hexaene-11-carboxamide;

N-[5-(2-methoxyethoxy)pyridin-3-yl]-1,8,10-triazatricyclo[7.4.0.0²,⁷]trideca-2(7),3,5,8,10,12-hexaene-11-carboxamide; and N-[6-(2-methoxyethoxy)pyridin-3-yl]-1,8,10-triazatricyclo[7.4.0.0²,⁷]trideca-2(7),3,5,8,10,12-hexaene-11-carboxamide.

In some embodiments, W is selected from:

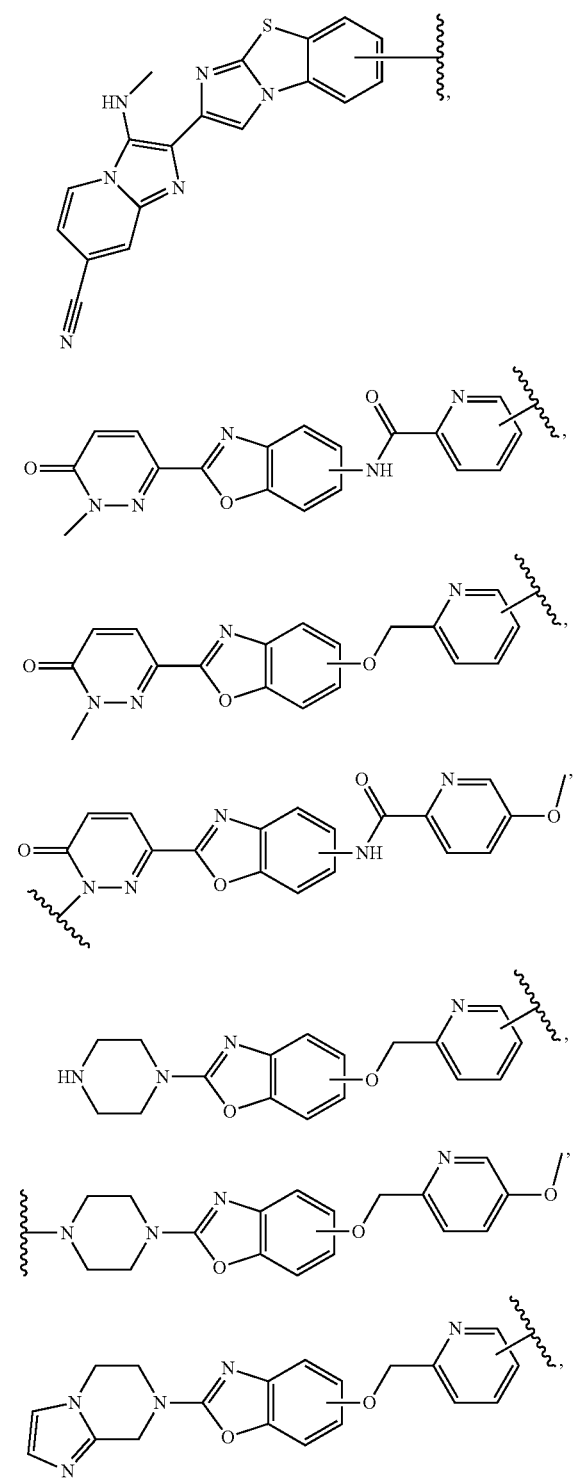

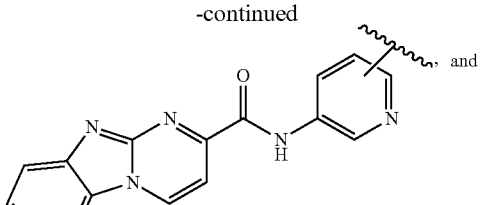
, and

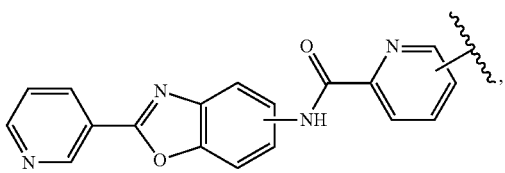

wherein the wavy line indicates the point of attachment to L of L-ULM.

Exemplary ULM Moieties

In some embodiments, ULM is a moiety that recognizes an ubiquitin pathway protein. In some embodiments, the ubiquitin pathway protein is an E3 ubiquitin ligase. In some embodiments, ULM is a moiety that binds to an E3 ubiquitin ligase. In some embodiments, ULM is a E3 ligase ubiquitin recruiter that targets a E3 ubiquitin ligase.

Exemplary ULM are known in the art (such as, for example, WO 2018/102067, which is hereby incorporated by reference in its entirety).

In some embodiments, ULM is a molecule that binds to mouse double minute two homolog (MDM2), cellular inhibitor of apoptosis protein 1 (cIAP1), cerebrlon (CRBN), or von Hippel-Lindau (VHL). Such exemplary molecules are known in the art (such as Gu et al., *BioEssays*, 2018 April; 40(4):e170024, which is hereby incorporated by reference in its entirety).

In some embodiments, ULM is a compound of formula (VIII):

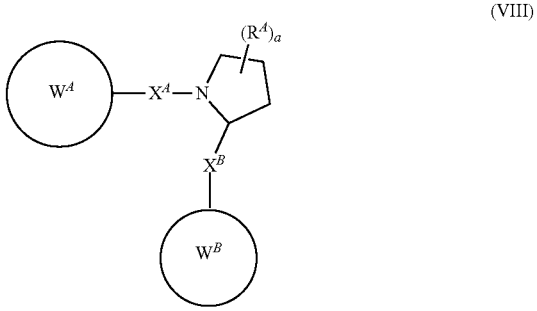

(VIII)

a is 1, 2, or 3;

$X^A$ and $X^B$ are each independently selected from a bond, O, $NR^B$, $CR^BR^C$, C=O, C=S, SO, and $SO_2$;

$R^B$ and $R^C$ and each independently selected from hydrogen, $C_{1-6}$alkyl, $C_{1-6}$haloalkyl, and $C_{1-6}$alkoxy;

each $R^A$ is independently selected from H, halo, OH, and $C_{1-3}$alkyl;

$W^A$ is -T($NR^{D1}R^{D2}$), an optionally substituted -T($NR^{D1}R^{D2}$)$X^C$, -T-aryl, an optionally substituted T-heteroaryl, an optionally substituted -T-heterocycle, an optionally substituted —$NR^D$-T-aryl, an optionally substituted —$NR^D$-T-heteroaryl, or an —$NR^D$-T-heterocycle, wherein T is covalently bonded to $X^A$;

$X^C$ is C=O, $R^D$, $R^{D1}$, or $R^{D2}$;

$R^D$, $R^{D1}$, and $R^{D2}$ are each independently selected from hydrogen, $C_{1-6}$alkyl optionally substituted with 1-3 halo or OH, $R^BC$=O, $R^BC$=S, $R^BSO$, $R^BSO_2$, $N(R^BR^C)C$=O, $N(R^BR^C)C$=S, $N(R^BR^C)SO$, and $N(R^BR^C)SO_2$;

T is a bond or $C_{1-12}$alkyl optionally substituted with 1-5 halo or OH groups or an optionally substituted amino acid side chain;

$W^B$ is optionally substituted —$NR^{D4}$-T-aryl, optionally substituted —$NR^{D4}$-T-heteroaryl, or —$NR^{D4}$-T-heterocycle, wherein —$NR^{D4}$ is covalently bonded to $X^B$; and $R^{D4}$ is hydrogen or $C_{1-3}$alkyl.

wherein ULM is attached to W-L at any substitutable atom of ULM and L.

In some embodiments, ULM is a compound of formula:

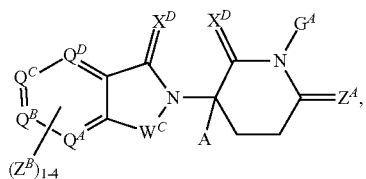

(IX)

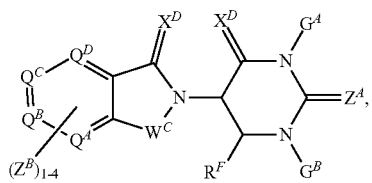

(X)

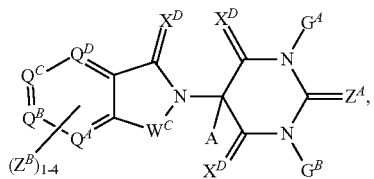

(XI)

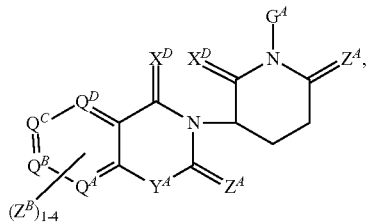

(XII)

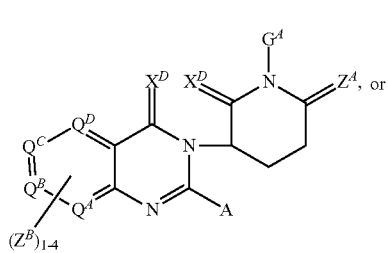

(XIII)

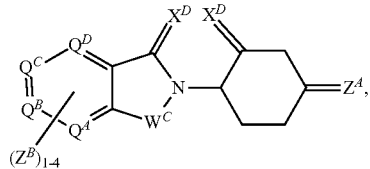

(XIV)

$W^C$ is $CH_2$, $CHR^E$, C=O, $SO_2$, NH, or N-alkyl;

each $X^D$ is independently selected from O, S, and $H_2$;

$Y^A$ is $CH_2$, —C=$CR^F$, NH, N-alkyl, N-aryl, N-heteroaryl, N-cycloalkyl, N-heterocyclyl, O, or S;

$Z^A$ is O, S, or $H_2$, provided that both $X^D$ and $Z^A$ cannot be $H_2$;

$G^A$ and $G^B$ are each independently selected from H, alkyl optionally substituted with $R^F$, OH, $R^FOCOOR^E$, $R^FOCONR^ER^G$, —$CH_2$-heterocyclyl optionally substituted with $R^F$, and benzyl optionally substituted with $R^F$;

$Q^A$, $Q^B$, $Q^C$ and $Q^D$ are each independently $CR^F$, N, or N-oxide;

A is H, alkyl, cycloalkyl, Cl, or F;

$R^E$ is —$CONR^FR^G$, —$OR^F$, —$NR^FR^G$, —$SR^F$, —$SO_2R^F$, —$SO_2NR^FR^G$, —$CR^FR^G$, —$CR^FNR^FR^G$, aryl, heteroaryl, optionally substituted alkyl, cycloalkyl, heterocycloalkyl, —P(O)($OR^F$)($R^G$), —P(O)$R^FR^G$, —OP(O)($OR^F$)($R^G$), —OP(O)$R^FR^G$, halo, —$CF_3$, —CN, —$NR^FSO_2NR^FR^G$, —$NR^FCONR^FR^G$, —$CONR^FCOR^G$, —$NR^FC$(=N—CN)$NR^FR^G$, —C(=N—CN)$NR^FR^G$, —$NR^FC$(=N—CN)$R^G$, —$NR^FC$(=C—$NO_2$)$NR^FR^G$, —$SO_2NR^FCOR^G$, —$NO_2$, —$CO_2R^F$, —C(C=N—$OR^F$)$R^G$, —$CR^F$=$CR^FR^G$, —$CCR^F$, —S(C=O)(C=N—$R^F$)$R^G$, —$SF_5$, or —$OCF_3$;

$R^F$ and $R^G$ are each independently selected from a bond, H, N, N-oxide, alkyl, cycloalkyl, aryl, heteroaryl, heterocyclyl, or —C(O)$R^H$, wherein the alkyl, cycloalkyl, aryl, heteroaryl, or heterocyclyl are optionally substituted;

$R^H$ is hydrogen, alkyl, aryl, heteroaryl, cycloalkyl, or heterocycloalkyl; and $Z^B$ is a functional group or atom, and optionally one of which is modified to be covalently joined to the remainder of a compound of formula (I).

In some embodiments, $Z^B$ is a bond connecting ULM to W-L of formula (I).

In some embodiments, ULM is a moiety that targets mouse double minute two homolog (MDM2), cellular inhibitor of apoptosis protein 1 (cIAP1), cerebrlon (CRBN), or von Hippel-Lindau (VHL).

In some embodiments, ULM is a VHL ligase targeting moiety.

In some embodiments, ULM is a cereblon ligase targeting moiety.

In some embodiments, ULM is a cellular inhibitor of apoptosis protein 1 (cIAP1) targeting moiety.

In some embodiments, ULM is selected from:
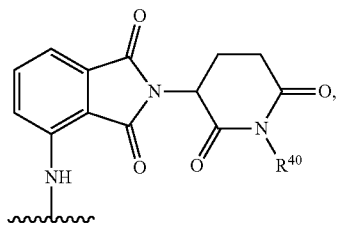
(II)
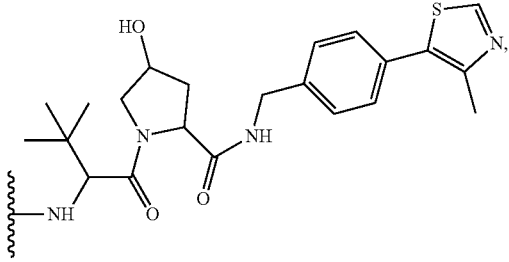
(III)
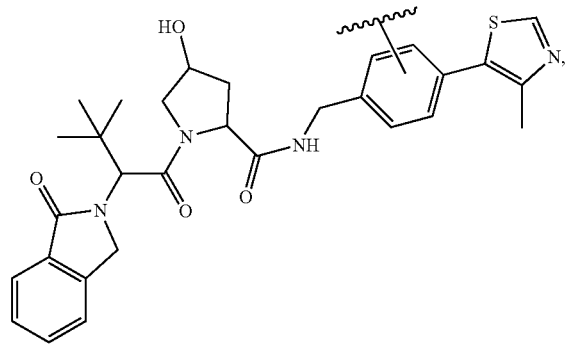
(IV)
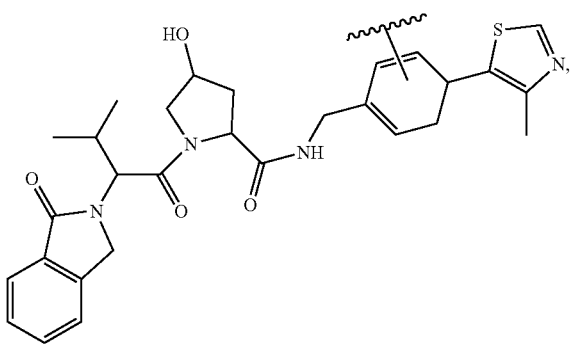
(V)
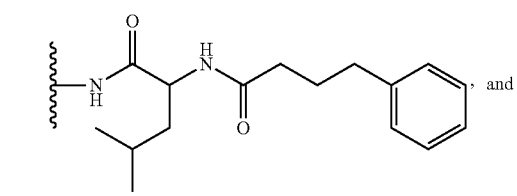
(VI)
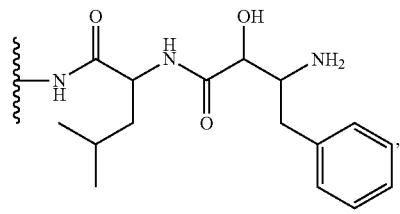
(VII)
wherein $R^{40}$ is hydrogen or $C_{1-6}$ alkyl.
In some embodiments, $R^{40}$ is hydrogen.
In some embodiments, ULM is:
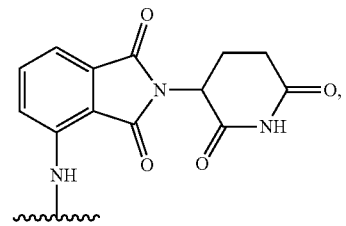
(II)(i)
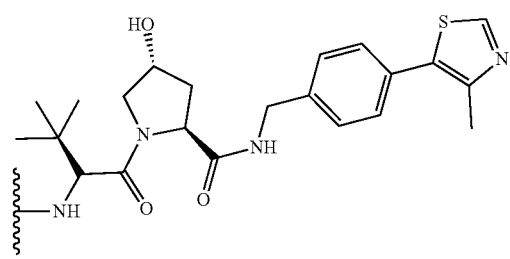
(III)(i)
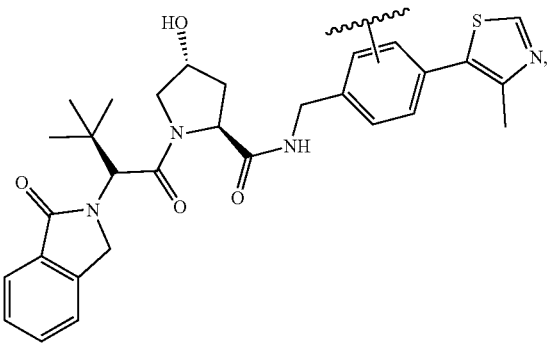
(IV)(i)
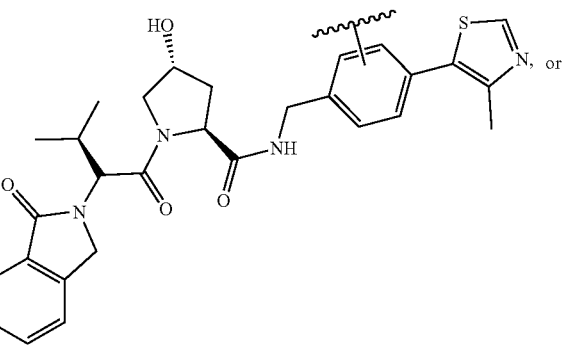
(V)(i), or -continued

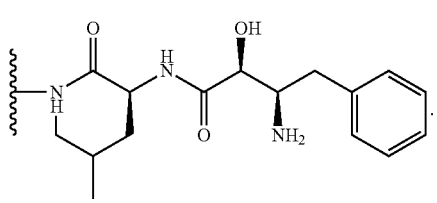

(VII)(i)

Exemplary L Moieties

In some embodiments, L is a bond.

In some embodiments, L is a linking moiety optionally substituted with B.

In some embodiments, wherein the linking moiety is alkylene, heteroalkylene, alkenylene, heteroalkenylene, alkynylene, heteroalkynylene, arylene, heteroarylene, cycloalkylene or heterocycloalkylene;
  wherein each alkylene, heteroalkylene, alkenylene, heteroalkenylene, alkynylene, heteroalkynylene, may optionally comprise an arylene, heteroarylene, cycloalkylene or heterocycloalkylene; and
  further wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl.

In some embodiments, the linking moiety is of the formula:

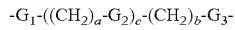
-$G_1$-((CH$_2$)$_a$-$G_2$)$_c$-(CH$_2$)$_b$-$G_3$- wherein:
  each of $G_1$, $G_2$, and $G_3$ are independently a bond, —NR$_{28}$—, —O—, —S(O)$_{0-2}$—, —NR$_{28}$C(O)—, —C(O)NR$_{28}$—, —NR$_{28}$S(O)$_2$—, —S(O)$_2$NR$_{28}$—, —CR$_{29}$=N—NR$_{28}$—, —NR$_{28}$—N=CR$_{29}$—, or —C(O)—, alkylene, heteroalkylene, alkenylene, heteroalkenylene, alkynylene, heteroalkynylene, arylene, heteroarylene, cycloalkylene or heterocycloalkylene;
  wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl;
  each R$_{28}$ is independently hydrogen, $C_{1-4}$ alkyl, $C_{1-4}$ haloalkyl, aryl, heteroaryl, cycloalkyl or heterocyclyl;
  R$_{29}$ is $C_{1-4}$ alkyl, $C_{1-4}$ haloalkyl, aryl, heteroaryl, cycloalkyl or heterocyclyl; and a and b are each independently 0, 1, 2, 3, 4, 5, 6, 7, or 8;
  c is an integer between 0-20;
and wherein the linking moiety is optionally substituted, on a substitutable atom, with:

(-$G_4$-(CH$_2$)$_d$-$G_5$-)$_e$-B each of G$^4$ and G$^5$ are independently a bond, —NR$_{28}$—, —O—, —S(O)$_{0-2}$—, —NR$_{28}$C(O)—, —C(O)NR$_{28}$—, —NR$_{28}$S(O)$_2$—, —S(O)$_2$NR$_{28}$—, —CR$_{29}$=N—NR$_{28}$—, —NR$_{28}$—N=CR$_{29}$—, or —C(O)—, alkylene, heteroalkylene, alkenylene, heteroalkenylene, alkynylene, heteroalkynylene, arylene, heteroarylene, cycloalkylene or heterocycloalkylene;
  wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl; and d and e are each independently 0, 1, 2, 3, 4, 5, 6, 7, or 8.

In some embodiments, the linking moiety is of the formula:

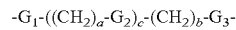
-$G_1$-((CH$_2$)$_a$-$G_2$)$_c$-(CH$_2$)$_b$-$G_3$- wherein:
  each of $G_1$, $G_2$, and $G_3$ are independently a bond, —NR$_{28}$—, —O—, —S(O)$_{0-2}$—, —NR$_{28}$C(O)—, —C(O)NR$_{28}$—, —NR$_{28}$S(O)$_2$—, —S(O)$_2$NR$_{28}$—, —CR$_{29}$=N—NR$_{28}$—, —NR$_{28}$—N=CR$_{29}$—, or —C(O)—, alkylene, heteroalkylene, alkenylene, heteroalkenylene, alkynylene, heteroalkynylene, arylene, heteroarylene, cycloalkylene or heterocycloalkylene;
  wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl;
  each R$_{28}$ is independently hydrogen, $C_{1-4}$ alkyl, $C_{1-4}$ haloalkyl, aryl, heteroaryl, cycloalkyl or heterocyclyl;
  R$_{29}$ is $C_{1-4}$ alkyl, $C_{1-4}$ haloalkyl, aryl, heteroaryl, cycloalkyl or heterocyclyl; and
  a and b are each independently 0, 1, 2, 3, 4, 5, 6, 7, or 8; and
  c is an integer between 0-20.

In some embodiments, the linking moiety is of the formula:

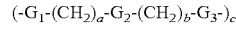
(-$G_1$-(CH$_2$)$_a$-$G_2$-(CH$_2$)$_b$-$G_3$-)$_c$ wherein:
  each of $G_1$, $G_2$, and $G_3$ are independently a bond, —NR$_{28}$—, —O—, —S(O)$_{0-2}$—, —NR$_{28}$C(O)—, —C(O)NR$_{28}$—, —NR$_{28}$S(O)$_2$—, —S(O)$_2$NR$_{28}$—, —CR$_{29}$=N—NR$_{28}$—, —NR$_{28}$—N=CR$_{29}$—, or —C(O)—, alkylene, heteroalkylene, alkenylene, heteroalkenylene, alkynylene, heteroalkynylene, arylene, heteroarylene, cycloalkylene or heterocycloalkylene;
  wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl;
  each R$_{28}$ is independently $C_{1-4}$ alkyl, $C_{1-4}$ haloalkyl, aryl, heteroaryl, cycloalkyl or heterocyclyl;
  R$_{29}$ is $C_{1-4}$ alkyl, $C_{1-4}$ haloalkyl, aryl, heteroaryl, cycloalkyl or heterocyclyl; and
  a, b, and c are each independently 0, 1, 2, 3, 4, 5, 6, 7, or 8;
and wherein the linking moiety is optionally substituted, on a substitutable atom, with:

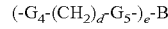
(-$G_4$-(CH$_2$)$_d$-$G_5$-)$_e$-B each of G$^4$ and G$^5$ are independently a bond, —NR$_{28}$—, —O—, —S(O)$_{0-2}$—, —NR$_{28}$C(O)—, —C(O)NR$_{28}$—, —NR$_{28}$S(O)$_2$—, —S(O)$_2$NR$_{28}$—, —CR$_{29}$=N—NR$_{28}$—, —NR$_{28}$—N=CR$_{29}$—, or —C(O)—, alkylene, heteroalkylene, alkenylene, heteroalkenylene, alkynylene, heteroalkynylene, arylene, heteroarylene, cycloalkylene or heterocycloalkylene;
  wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl; and d and e are each independently 0, 1, 2, 3, 4, 5, 6, 7, or 8.

In some embodiments, the linking moiety is of the formula:

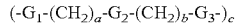

wherein:
- each of $G_1$, $G_2$, and $G_3$ are independently a bond, $-NR_{28}-$, $-O-$, $-S(O)_{0-2}-$, $-NR_{28}C(O)-$, $-C(O)NR_{28}-$, $-NR_{28}S(O)_2-$, $-S(O)_2NR_{28}-$, $-CR_{29}=N-NR_{28}-$, $-NR_{28}-N=CR_{29}-$, or $-C(O)-$, alkylene, heteroalkylene, alkenylene, heteroalkenylene, alkynylene, heteroalkynylene, arylene, heteroarylene, cycloalkylene or heterocycloalkylene; wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl;
- each $R_{28}$ is independently $C_{1-4}$ alkyl, $C_{1-4}$ haloalkyl, aryl, heteroaryl, cycloalkyl or heterocyclyl;
- $R_{29}$ is $C_{1-4}$ alkyl, $C_{1-4}$ haloalkyl, aryl, heteroaryl, cycloalkyl or heterocyclyl; and
- a, b, and c are each independently 0, 1, 2, 3, 4, 5, 6, 7, or 8.

In some embodiments, the linking moiety is of the formula:

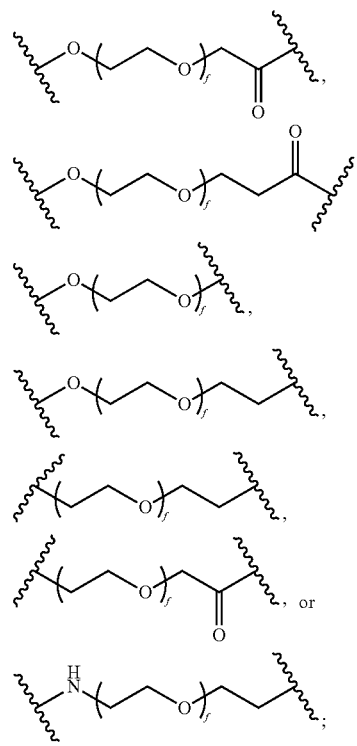

wherein the wavy lines indicate the point of attachment to W and ULM;

f is an integer between 1-20; and wherein any substitutable atom may be further optionally substituted with L-B, wherein L is any linking moiety as described herein.

In some embodiments, the linking moiety is of the formula:

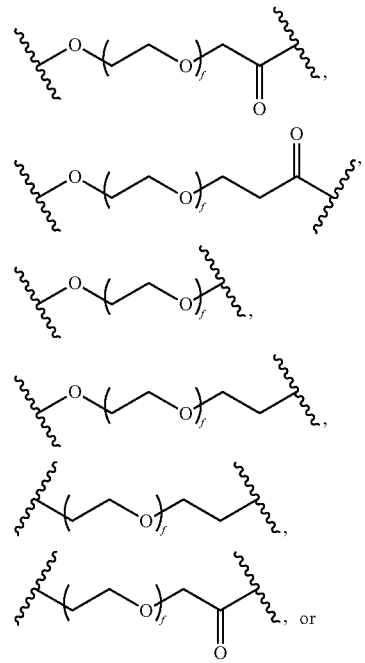

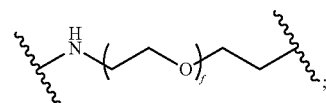

wherein the wavy lines indicate the point of attachment to W and ULM; and f is an integer between 1-20.

Exemplary B Moieties

In some embodiments, L is a linking moiety optionally substituted with B, and B is a moiety that crosses the blood brain barrier.

In some embodiments, a moiety that crosses the blood brain barrier is a molecule or macromolecule that may pass through the blood brain barrier via targeting a receptor for transport through the blood brain barrier. Such moieties include those known in the art.

In some embodiments, B is a carrier peptide, cholesterol, or a carrier peptide conjugated (e.g. via a linking moiety as described herein or covalently bonded) to cholesterol.

In some embodiments, a carrier peptide is a peptide having about 5-35 resides and is capable of crossing cell membranes. Exemplary carrier peptides are known in the art.

In some embodiments, B is Angiopep2, ApoE-I, ApoE-II, ApoB, THR, Peptide-22, L57, TGN, leptin30, RVG29, nipah virus envelope (env.) HR region conjugated to cholesterol, newcastle disease virus conjugated to cholesterol, or measles virus peptide conjugated to cholesterol.

Peptide sequences for exemplary B moities are provided below in Table 1:

TABLE 1

| Peptide | Peptide sequence | SEQ ID NO. |
|---|---|---|
| Angiopep2 | TFFYGGSRGKRNNFKTEEY | 1 |
| ApoE-I | TEELRVRLASHLRKLRKRLLRDA | 2 |
| ApoE-II | Ac-(LRKLRKRLL)2-CONH2 | 3 |
| ApoB | SVIDALQYKLEGTTRLTRKRGLKLATALSLSNKFVEGS | 4 |
| THR | THRPPMWSPVWP-NH2 and retro-inverso | 5 |
| Peptide-22 | Ac-CMPRLRGC (cycle) | 6 |
| L57 | TWPKHFDKHTFYSILKLGKH | 7 |
| TGN | TGNYKALHPHNG | 8 |
| Leptin30 | YQQILTSMPSRNVIQISNDLENLRDLLHVL | 9 |
| RVG29 | YTIWMPENPRPGTPCDIFTNSRGKRASNG-COOH | 10 |
| Nipah Virus Env. HR region +Chol | Ac-VALDPIDISIVLNKIKSDLEESKEWIRRSNKILDSI-PEG4-Cholesterol | 11 |
| Newcastle disease virus peptide conjugated to cholesterol | Ac-VNKKIEEIDKKIEELNKKLEELEKKLEEVNKK-Peg4-Cholesterol | 12 |
| Measles virus peptide and cholesterol | Ac-PPISLERLDVGTNLGNAIAKLEDAKELLESSDQILR-PEG4-Cholesterol | 13 |

Exemplary Compounds

In some embodiments, provided is a compound, or a pharmaceutically acceptable salt, stereoisomer, or mixture of stereoisomers thereof, selected from Table 2. In some embodiments, provided is a compound, or a pharmaceutically acceptable salt, stereoisomer, mixture of stereoisomers, or isotopically enriched analog thereof, selected from Table 2.

TABLE 2

| # | Structure |
|---|---|
| 1 | 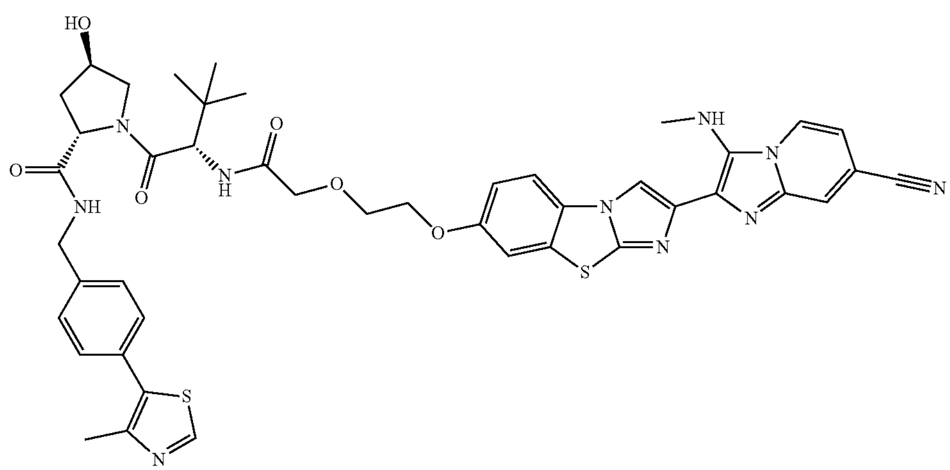 [SMILES: CNc1c(-c2cn3c(n2)sc2cc(OCCOCC(=O)N[C@H](C(=O)N4C[C@H](O)C[C@H]4C(=O)NCc4ccc(-c5scnc5C)cc4)C(C)(C)C)ccc23)nc2cc(C#N)ccn12]  |

TABLE 2-continued

| # | Structure |
|---|---|
| 2 | 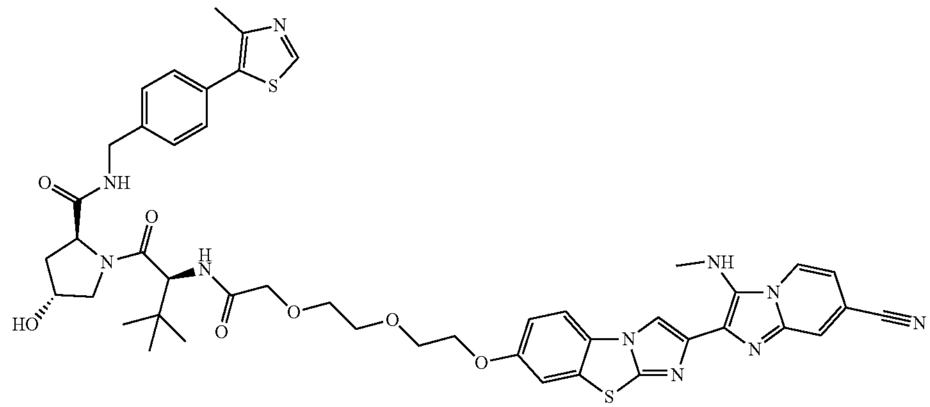 [SMILES: CNc1c(-c2cn3c(n2)sc2cc(OCCOCCOCC(=O)N[C@H](C(=O)N4C[C@H](O)C[C@H]4C(=O)NCc4ccc(-c5scnc5C)cc4)C(C)(C)C)ccc23)nc2cc(C#N)ccn12] |
| 3 | 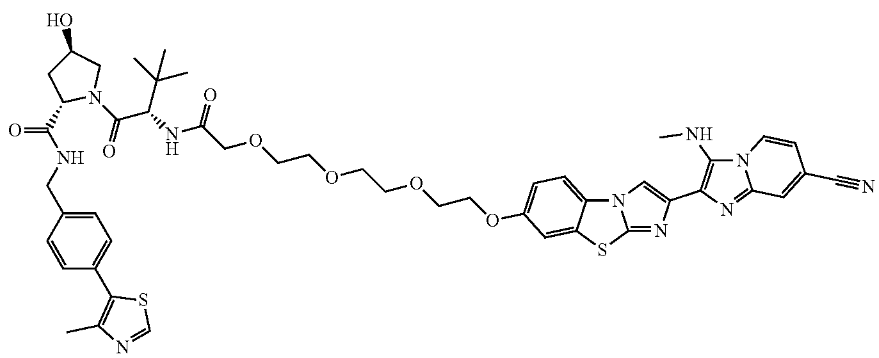 [SMILES: CNc1c(-c2cn3c(n2)sc2cc(OCCOCCOCCOCC(=O)N[C@H](C(=O)N4C[C@H](O)C[C@H]4C(=O)NCc4ccc(-c5scnc5C)cc4)C(C)(C)C)ccc23)nc2cc(C#N)ccn12] |
| 4 | 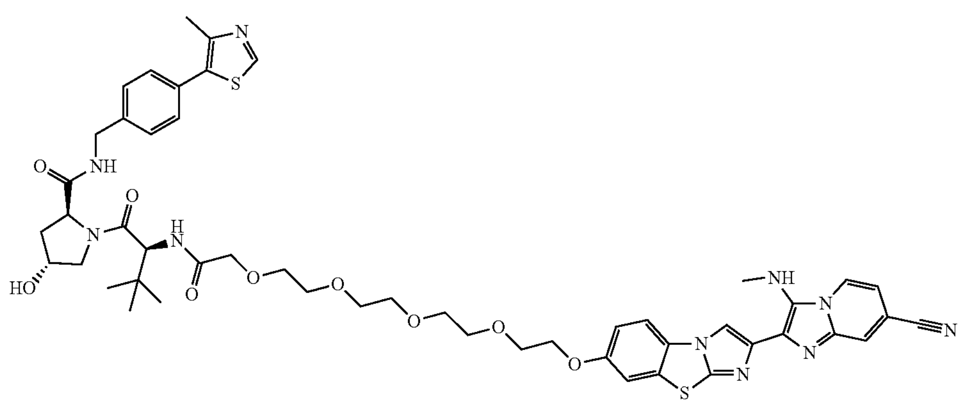 [SMILES: CNc1c(-c2cn3c(n2)sc2cc(OCCOCCOCCOCCOCC(=O)N[C@H](C(=O)N4C[C@H](O)C[C@H]4C(=O)NCc4ccc(-c5scnc5C)cc4)C(C)(C)C)ccc23)nc2cc(C#N)ccn12] |

TABLE 2-continued

| # | Structure |
|---|---|
| 5 | 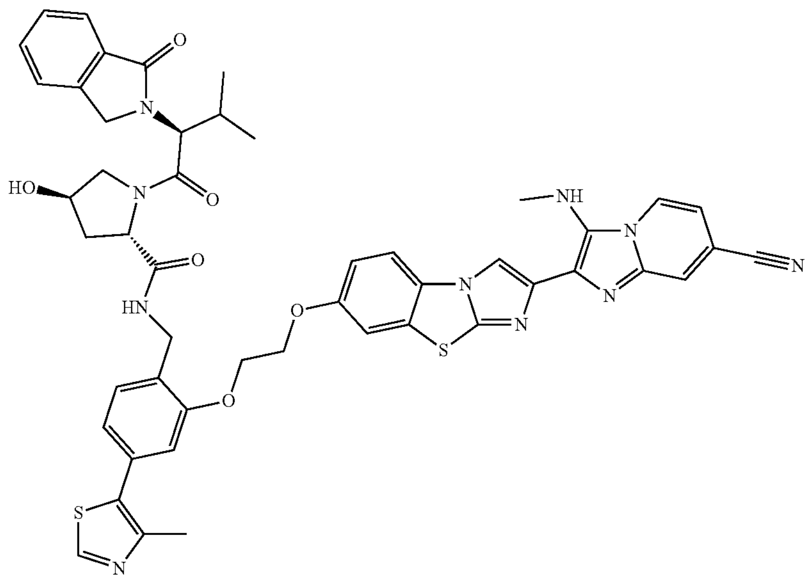 [SMILES: CNc1c(-c2cn3c(n2)sc2cc(OCCOc4cc(-c5scnc5C)ccc4CNC(=O)[C@@H]4C[C@@H](O)CN4C(=O)[C@H](C(C)C)N4Cc5ccccc5C4=O)ccc23)nc2cc(C#N)ccn12] |
| 6 | 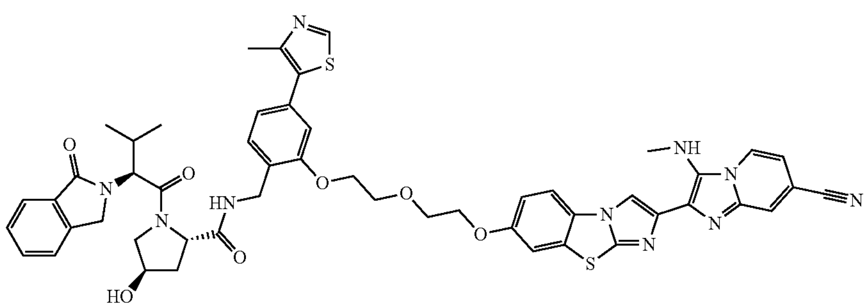 [SMILES: CNc1c(-c2cn3c(n2)sc2cc(OCCOCCOc4cc(-c5scnc5C)ccc4CNC(=O)[C@@H]4C[C@@H](O)CN4C(=O)[C@H](C(C)C)N4Cc5ccccc5C4=O)ccc23)nc2cc(C#N)ccn12] |
| 7 | 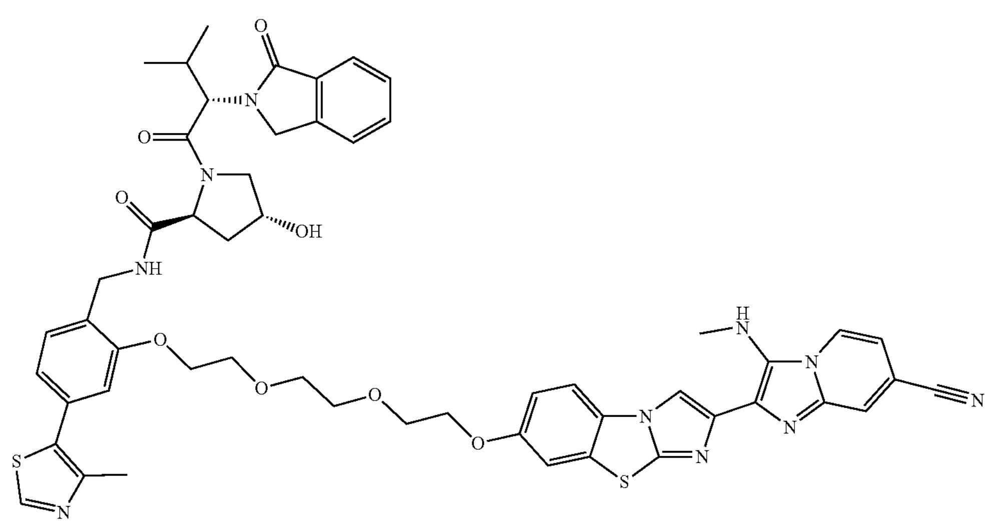 [SMILES: CNc1c(-c2cn3c(n2)sc2cc(OCCOCCOCCOc4cc(-c5scnc5C)ccc4CNC(=O)[C@@H]4C[C@@H](O)CN4C(=O)[C@H](C(C)C)N4Cc5ccccc5C4=O)ccc23)nc2cc(C#N)ccn12] |

TABLE 2-continued

| # | Structure |
|---|---|
| 8 | 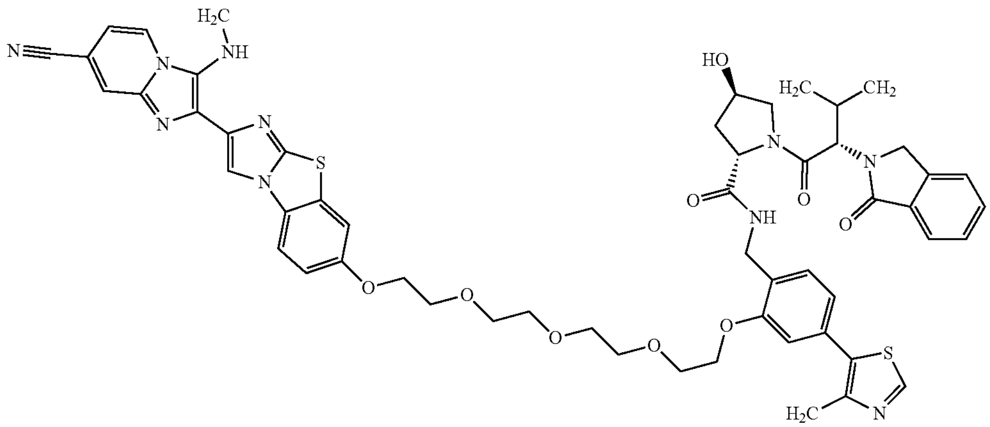 [SMILES: CNc1c(-c2cn3c(n2)sc2cc(OCCOCCOCCOCCOc4cc(-c5scnc5C)ccc4CNC(=O)[C@@H]4C[C@@H](O)CN4C(=O)[C@H](C(C)C)N4Cc5ccccc5C4=O)ccc23)nc2cc(C#N)ccn12] |
| 9 | 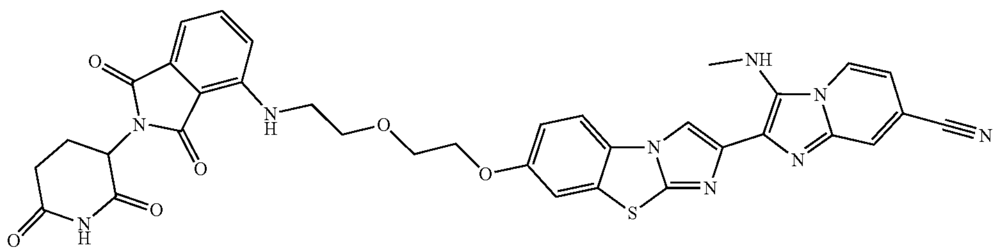 [SMILES: CNc1c(-c2cn3c(n2)sc2cc(OCCOCCNc4cccc5c4C(=O)N(C4CCC(=O)NC4=O)C5=O)ccc23)nc2cc(C#N)ccn12] |
| 10 | 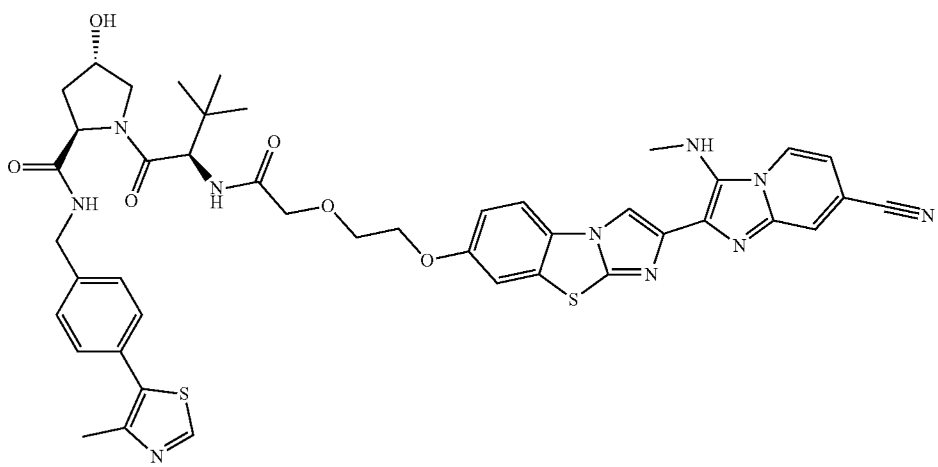 [SMILES: CNc1c(-c2cn3c(n2)sc2cc(OCCOCC(=O)N[C@@H](C(=O)N4C[C@@H](O)C[C@@H]4C(=O)NCc4ccc(-c5scnc5C)cc4)C(C)(C)C)ccc23)nc2cc(C#N)ccn12] |
| 11 | 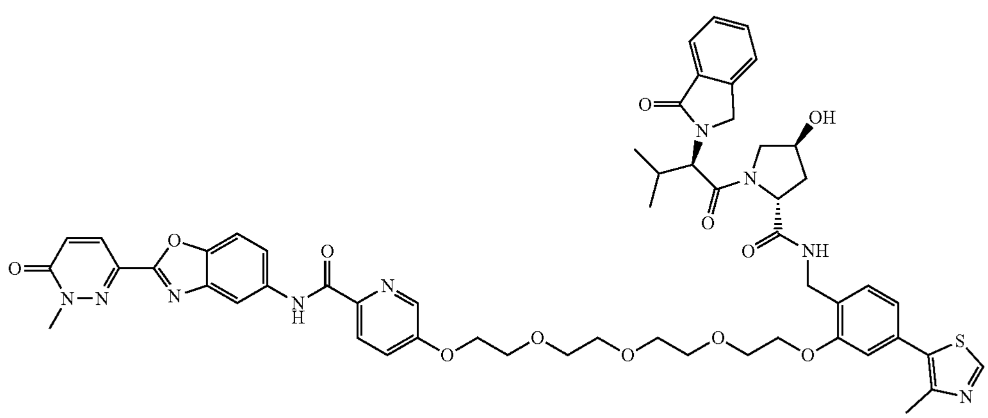 [SMILES: Cc1ncsc1-c1ccc(CNC(=O)[C@H]2C[C@H](O)CN2C(=O)[C@@H](C(C)C)N2Cc3ccccc3C2=O)c(OCCOCCOCCOCCOc2ccc(C(=O)Nc3ccc4oc(-c5ccc(=O)n(C)n5)nc4c3)nc2)c1] |

TABLE 2-continued

| # | Structure |
|---|---|
| 12 | 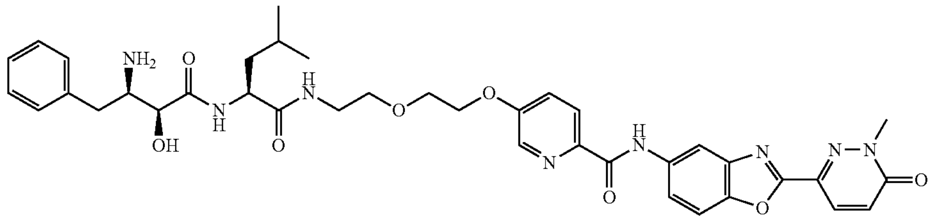 [SMILES: CC(C)C[C@H](NC(=O)[C@@H](O)[C@H](N)Cc1ccccc1)C(=O)NCCOCCOc1ccc(C(=O)Nc2ccc3oc(-c4ccc(=O)n(C)n4)nc3c2)nc1] |
| 13 | 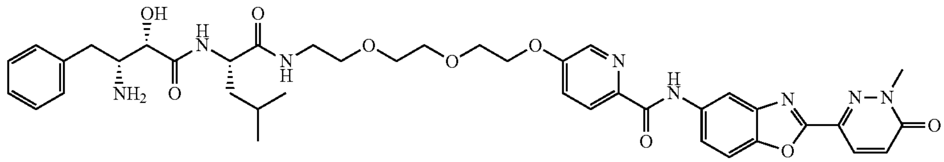 [SMILES: CC(C)C[C@H](NC(=O)[C@@H](O)[C@H](N)Cc1ccccc1)C(=O)NCCOCCOCCOc1ccc(C(=O)Nc2ccc3oc(-c4ccc(=O)n(C)n4)nc3c2)nc1] |
| 14 | 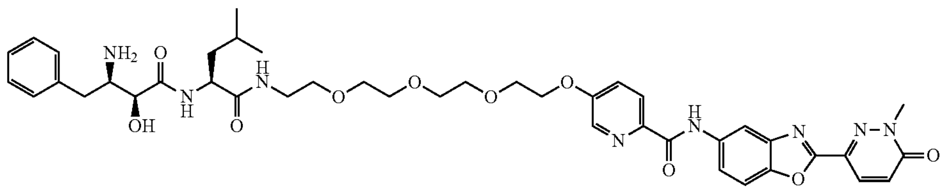 [SMILES: CC(C)C[C@H](NC(=O)[C@@H](O)[C@H](N)Cc1ccccc1)C(=O)NCCOCCOCCOCCOc1ccc(C(=O)Nc2ccc3oc(-c4ccc(=O)n(C)n4)nc3c2)nc1] |
| 15 | 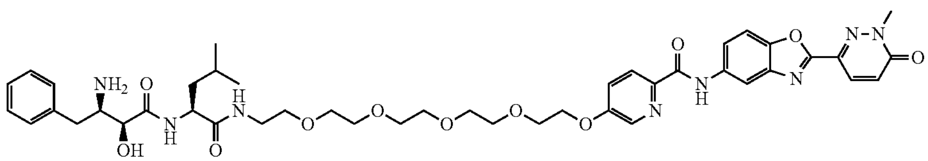 [SMILES: CC(C)C[C@H](NC(=O)[C@@H](O)[C@H](N)Cc1ccccc1)C(=O)NCCOCCOCCOCCOCCOc1ccc(C(=O)Nc2ccc3oc(-c4ccc(=O)n(C)n4)nc3c2)nc1] |
| 16 | 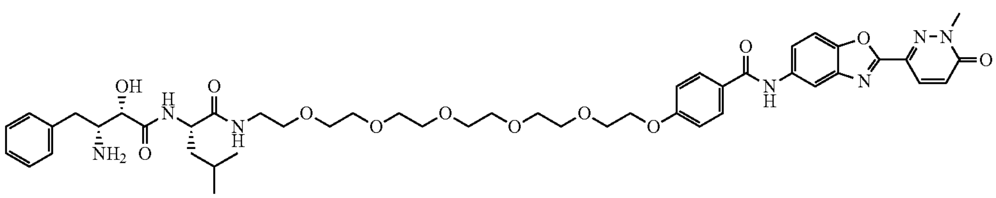 [SMILES: CC(C)C[C@H](NC(=O)[C@@H](O)[C@H](N)Cc1ccccc1)C(=O)NCCOCCOCCOCCOCCOCCOc1ccc(C(=O)Nc2ccc3oc(-c4ccc(=O)n(C)n4)nc3c2)cc1] |
| 17 | 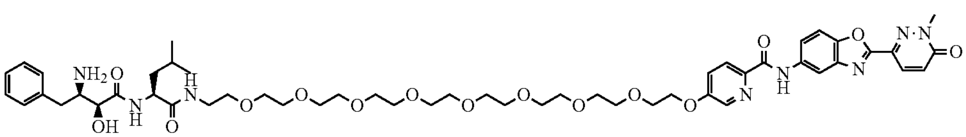 [SMILES: CC(C)C[C@H](NC(=O)[C@@H](O)[C@H](N)Cc1ccccc1)C(=O)NCCOCCOCCOCCOCCOCCOCCOCCOCCOc1ccc(C(=O)Nc2ccc3oc(-c4ccc(=O)n(C)n4)nc3c2)nc1] |
| 18 | 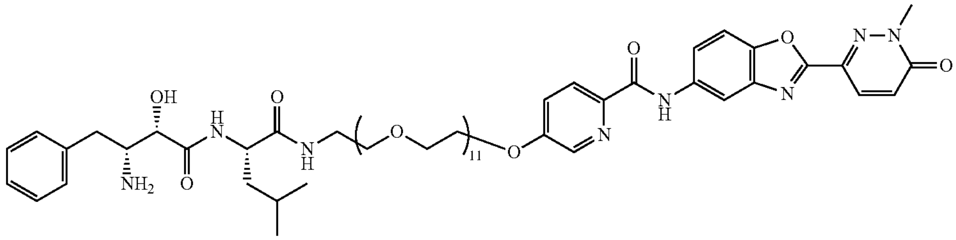 |
| 19 | 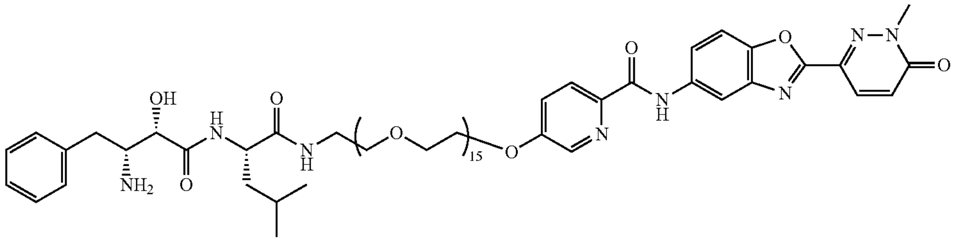 |

TABLE 2-continued
| # | Structure |
|---|---|
| 20 | 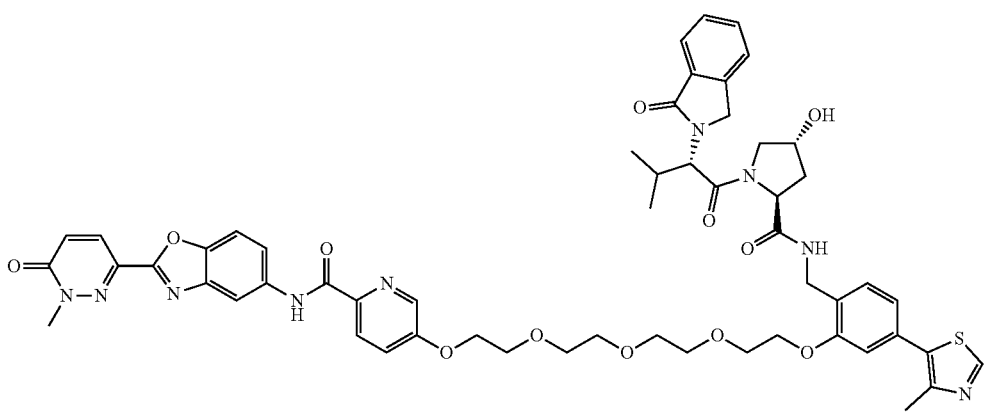 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOCCOc2ccc(C(=O)Nc3ccc4oc(-c5ccc(=O)n(C)n5)nc4c3)nc2)c1] |
| 21 | 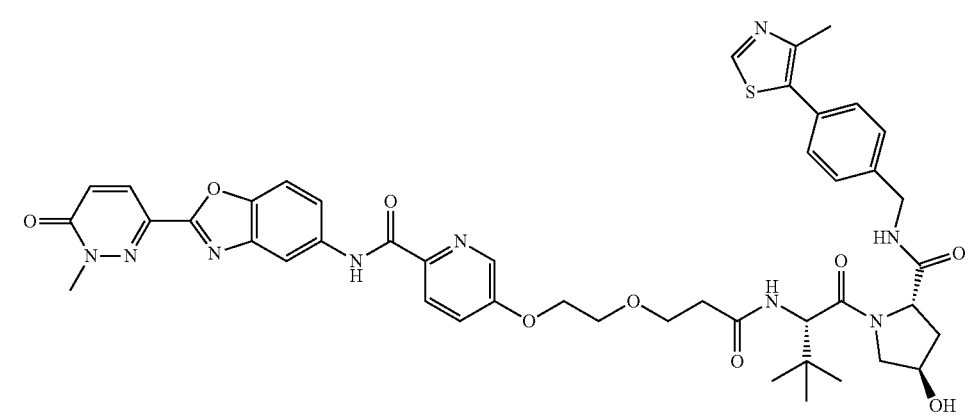 [SMILES: Cc1ncsc1-c1ccc(CNC(=O)[C@@H]2C[C@@H](O)CN2C(=O)[C@@H](NC(=O)CCOCCOc2ccc(C(=O)Nc3ccc4oc(-c5ccc(=O)n(C)n5)nc4c3)nc2)C(C)(C)C)cc1] |
| 22 | 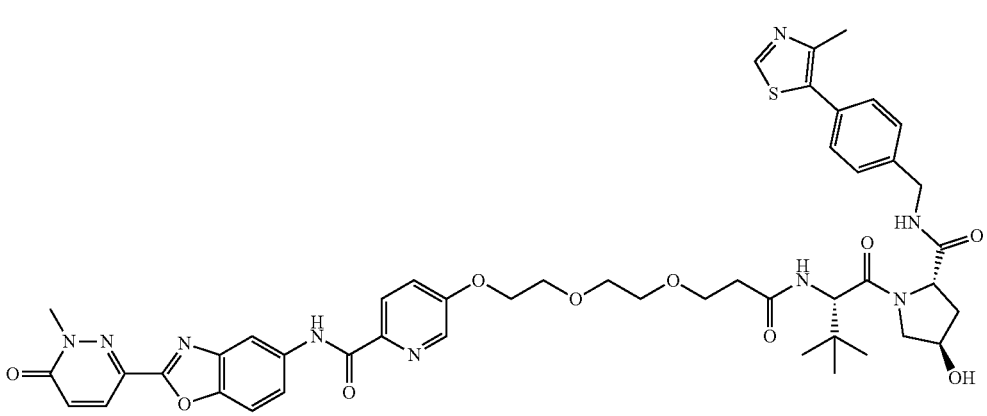 [SMILES: Cc1ncsc1-c1ccc(CNC(=O)[C@@H]2C[C@@H](O)CN2C(=O)[C@@H](NC(=O)CCOCCOCCOc2ccc(C(=O)Nc3ccc4oc(-c5ccc(=O)n(C)n5)nc4c3)nc2)C(C)(C)C)cc1] |
| 23 | 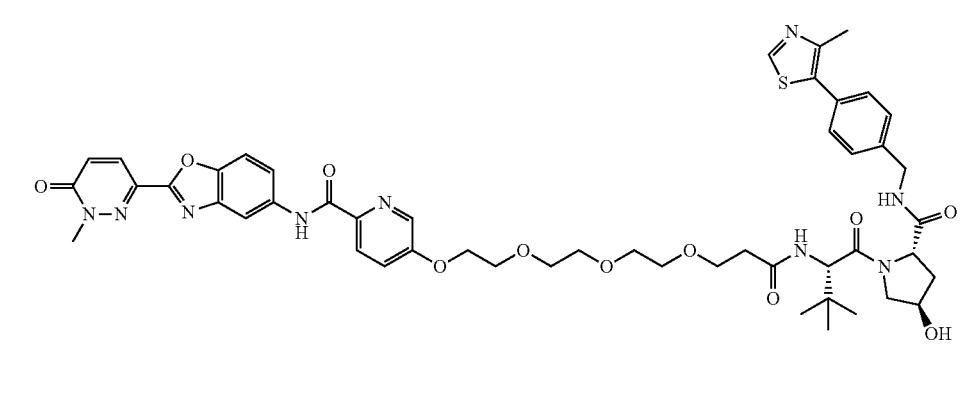 [SMILES: Cc1ncsc1-c1ccc(CNC(=O)[C@@H]2C[C@@H](O)CN2C(=O)[C@@H](NC(=O)CCOCCOCCOCCOc2ccc(C(=O)Nc3ccc4oc(-c5ccc(=O)n(C)n5)nc4c3)nc2)C(C)(C)C)cc1] |

TABLE 2-continued

| # | Structure |
|---|---|
| 24 | 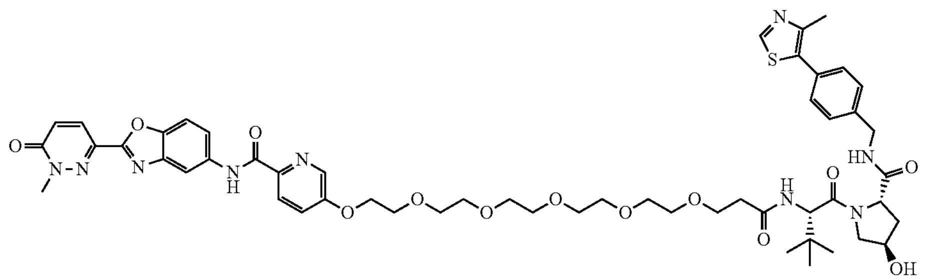 [SMILES: Cc1ncsc1-c1ccc(CNC(=O)[C@@H]2C[C@@H](O)CN2C(=O)[C@@H](NC(=O)CCOCCOCCOCCOCCOCCOc2ccc(C(=O)Nc3ccc4oc(-c5ccc(=O)n(C)n5)nc4c3)nc2)C(C)(C)C)cc1] |
| 25 | 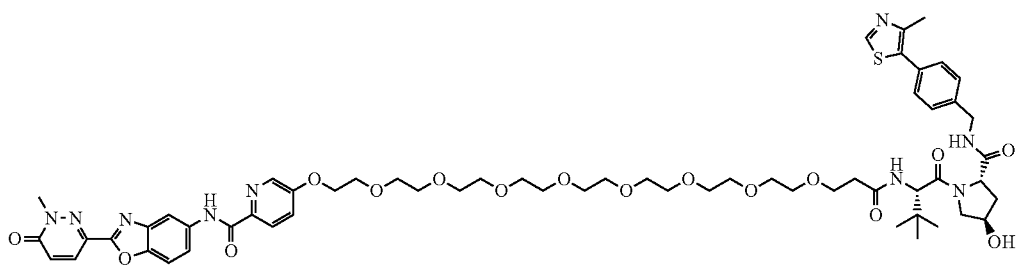 [SMILES: Cc1ncsc1-c1ccc(CNC(=O)[C@@H]2C[C@@H](O)CN2C(=O)[C@@H](NC(=O)CCOCCOCCOCCOCCOCCOCCOCCOCCOc2ccc(C(=O)Nc3ccc4oc(-c5ccc(=O)n(C)n5)nc4c3)nc2)C(C)(C)C)cc1] |
| 26 | 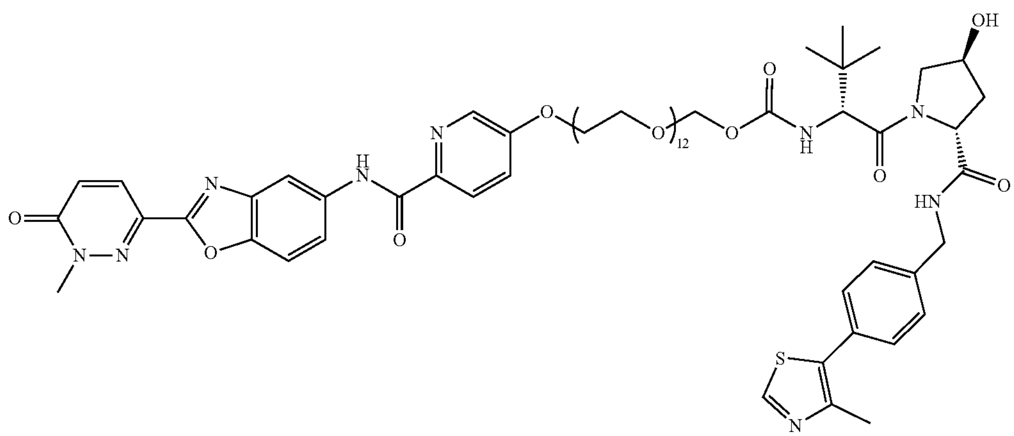 |
| 27 | 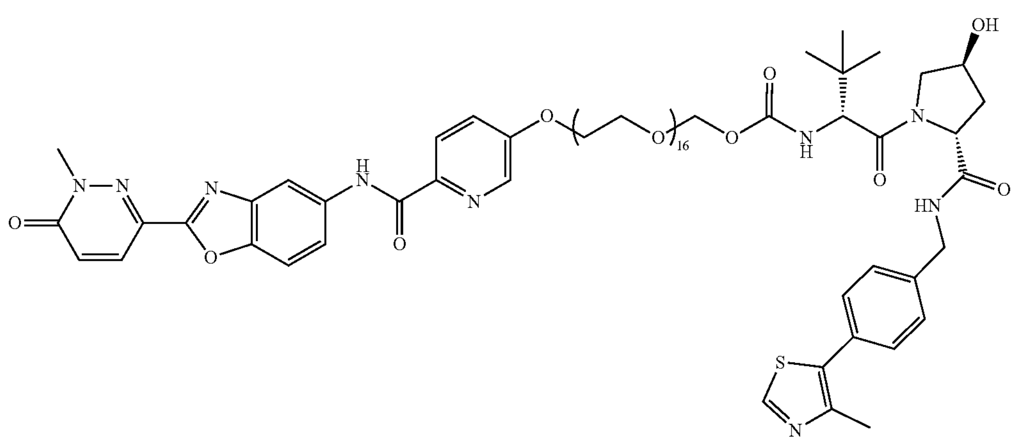 |

TABLE 2-continued
| # | Structure |
|---|---|
| 28 | 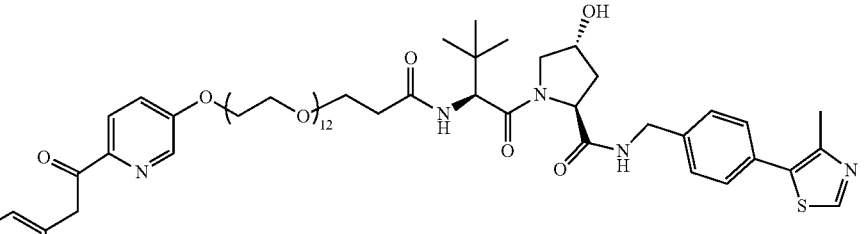 |
| 29 | 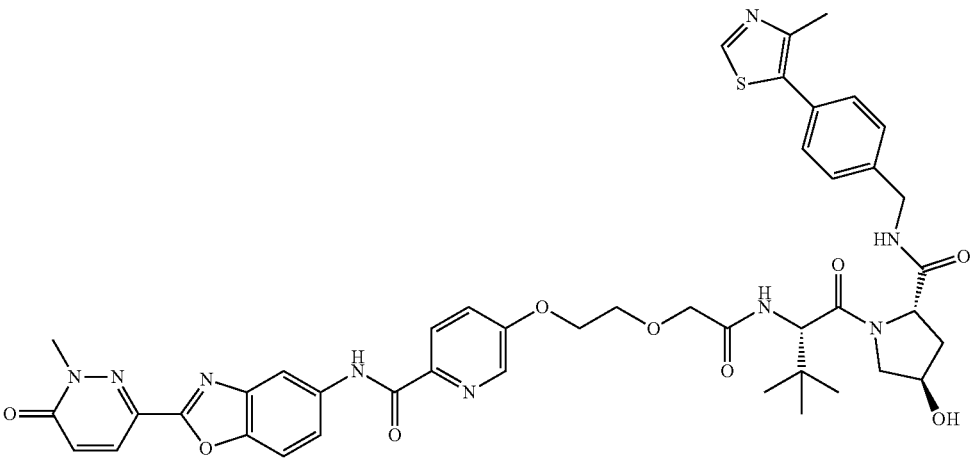 [SMILES: Cc1ncsc1-c1ccc(CNC(=O)[C@@H]2C[C@@H](O)CN2C(=O)[C@@H](NC(=O)COCCOc2ccc(C(=O)Nc3ccc4oc(-c5ccc(=O)n(C)n5)nc4c3)nc2)C(C)(C)C)cc1] |
| 30 | 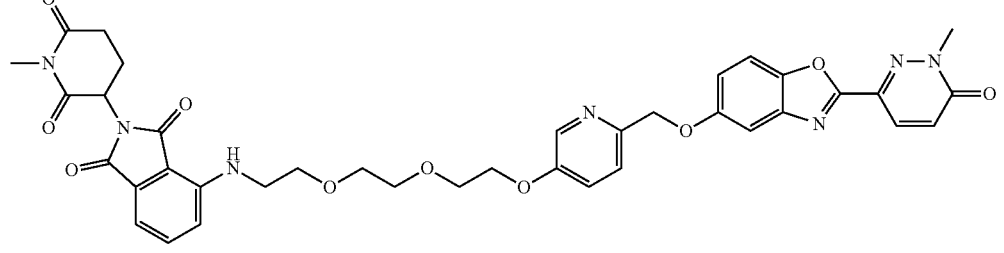 |
| 31 | 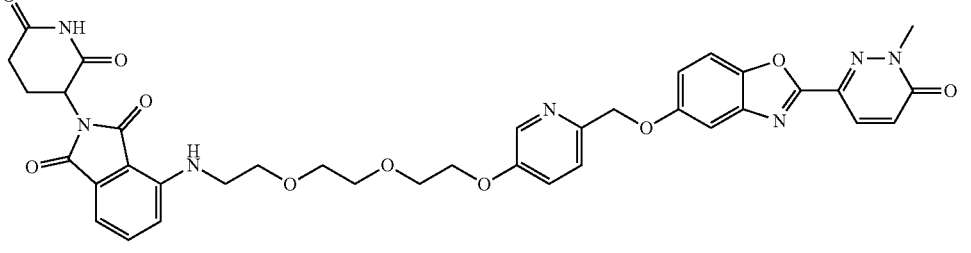 |

TABLE 2-continued
| # | Structure |
|---|---|
| 32 | 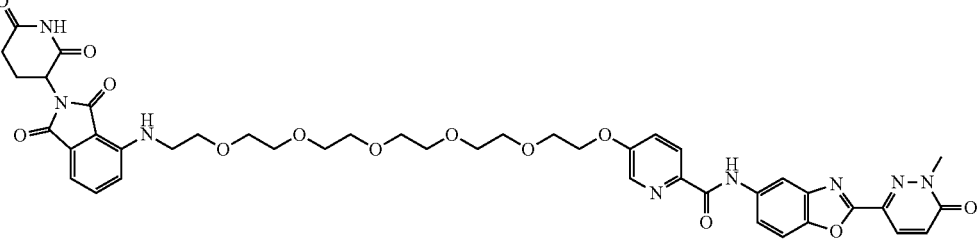 |
| 33 | 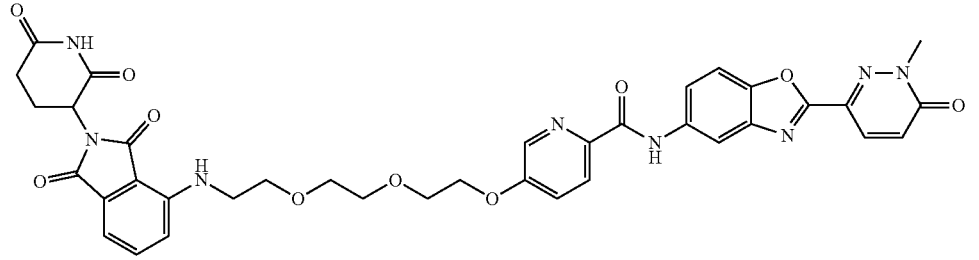 [SMILES: Cn1nc(-c2nc3cc(NC(=O)c4ccc(OCCOCCOCCNc5cccc6c5C(=O)N(C5CCC(=O)NC5=O)C6=O)cn4)ccc3o2)ccc1=O] |
| 34 | 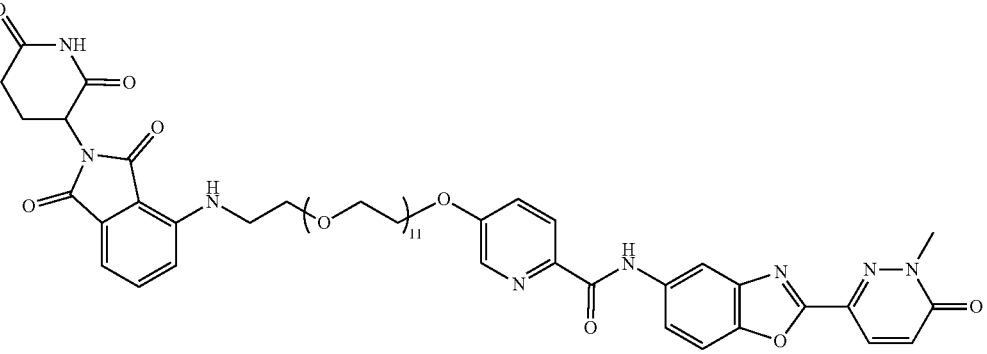 |
| 35 | 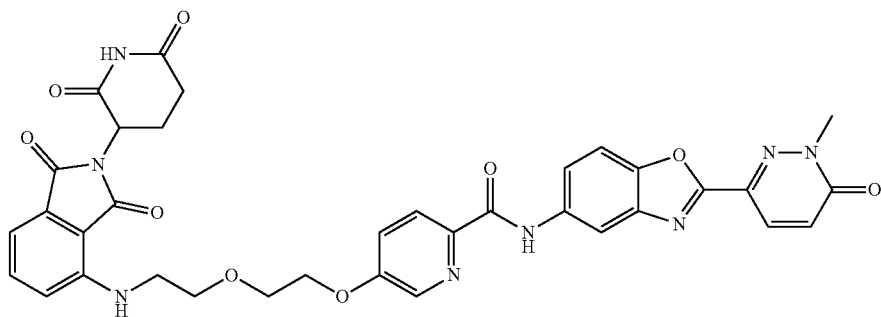 [SMILES: Cn1nc(-c2nc3cc(NC(=O)c4ccc(OCCOCCNc5cccc6c5C(=O)N(C5CCC(=O)NC5=O)C6=O)cn4)ccc3o2)ccc1=O] |
| 36 | 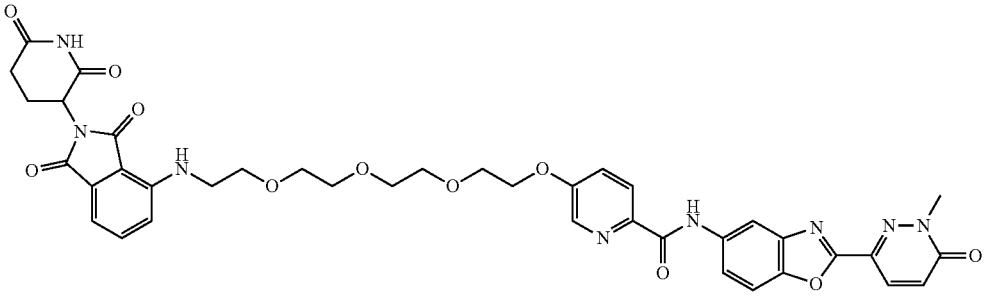 [SMILES: Cn1nc(-c2nc3cc(NC(=O)c4ccc(OCCOCCOCCOCCNc5cccc6c5C(=O)N(C5CCC(=O)NC5=O)C6=O)cn4)ccc3o2)ccc1=O] |

TABLE 2-continued

| # | Structure |
|---|---|
| 37 | 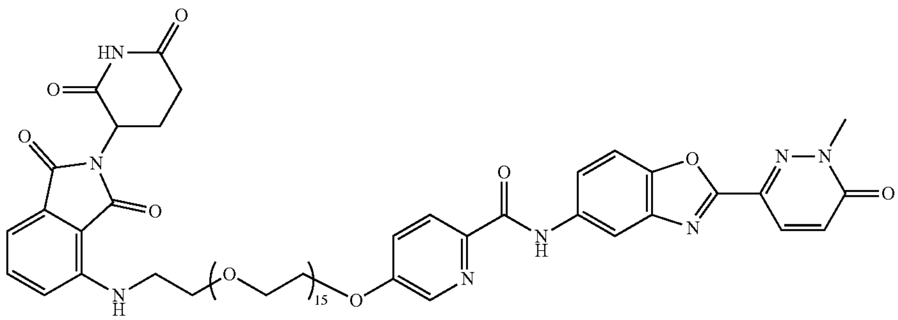 |
| 38 | 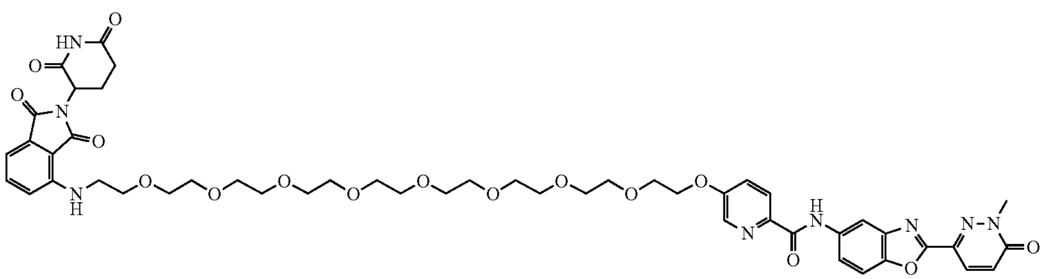 [SMILES: Cn1nc(-c2nc3cc(NC(=O)c4ccc(OCCOCCOCCOCCOCCOCCOCCOCCOCCNc5cccc6c5C(=O)N(C5CCC(=O)NC5=O)C6=O)cn4)ccc3o2)ccc1=O] |
| 39 | 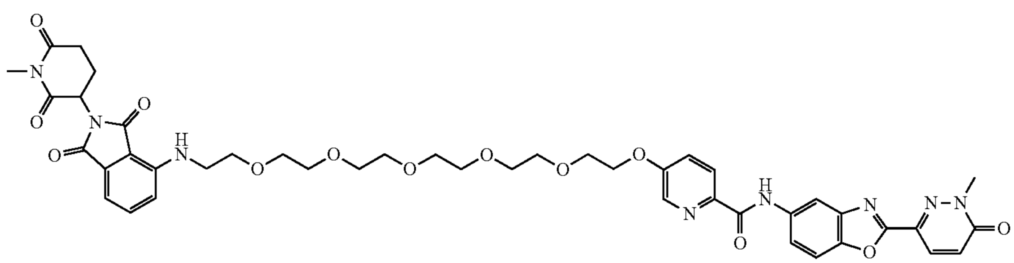 [SMILES: CN1C(=O)CCC(N2C(=O)c3cccc(NCCOCCOCCOCCOCCOCCOc4ccc(C(=O)Nc5ccc6oc(-c7ccc(=O)n(C)n7)nc6c5)nc4)c3C2=O)C1=O] |
| 40 | 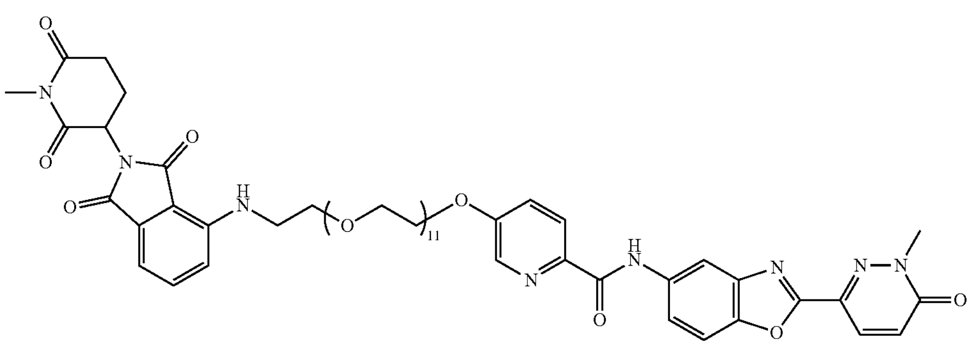 |
| 41 | 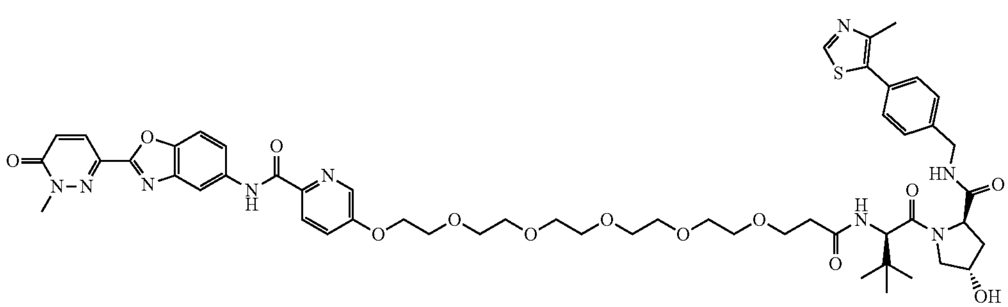 [SMILES: Cc1ncsc1-c1ccc(CNC(=O)[C@H]2C[C@H](O)CN2C(=O)[C@H](NC(=O)CCOCCOCCOCCOCCOCCOc2ccc(C(=O)Nc3ccc4oc(-c5ccc(=O)n(C)n5)nc4c3)nc2)C(C)(C)C)cc1] |

TABLE 2-continued

| # | Structure |
|---|---|
| 42 | 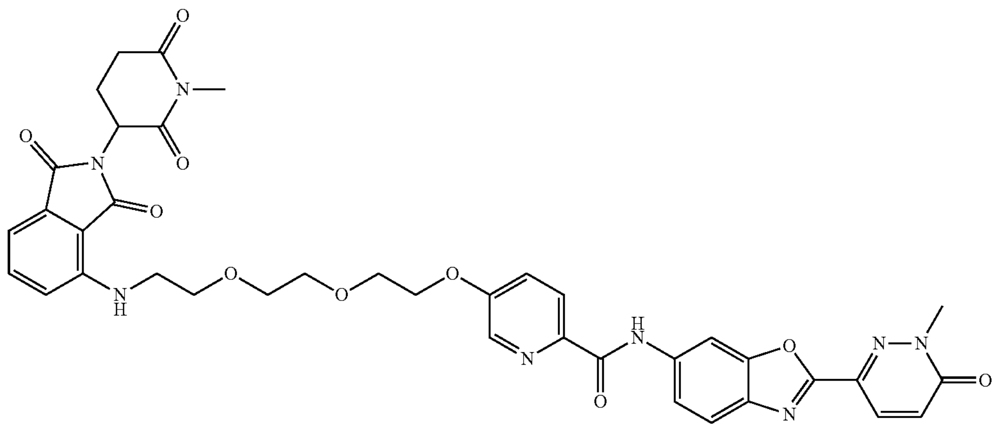 [SMILES: CN1C(=O)CCC(N2C(=O)c3cccc(NCCOCCOCCOc4ccc(C(=O)Nc5ccc6nc(-c7ccc(=O)n(C)n7)oc6c5)nc4)c3C2=O)C1=O] |
| 43 | 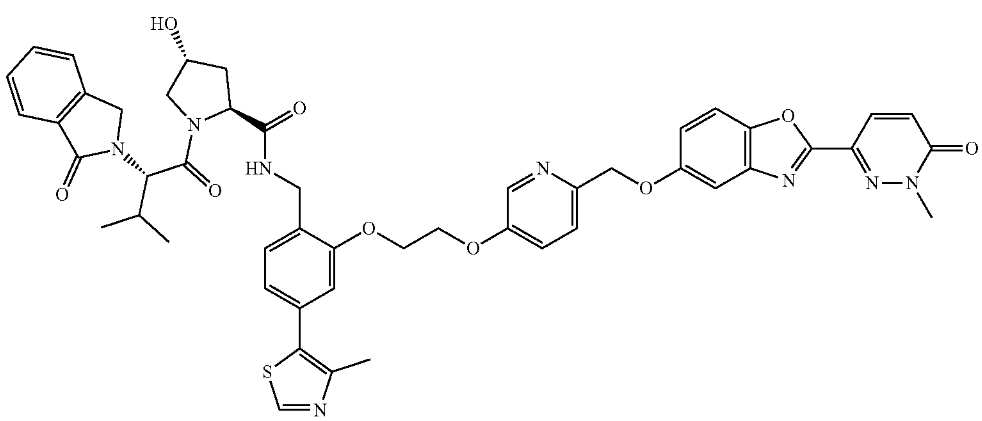 [SMILES: Cc1ncsc1-c1ccc(CNC(=O)[C@@H]2C[C@@H](O)CN2C(=O)[C@H](C(C)C)N2Cc3ccccc3C2=O)c(OCCOc2ccc(COc3ccc4oc(-c5ccc(=O)n(C)n5)nc4c3)nc2)c1] |
| 44 | 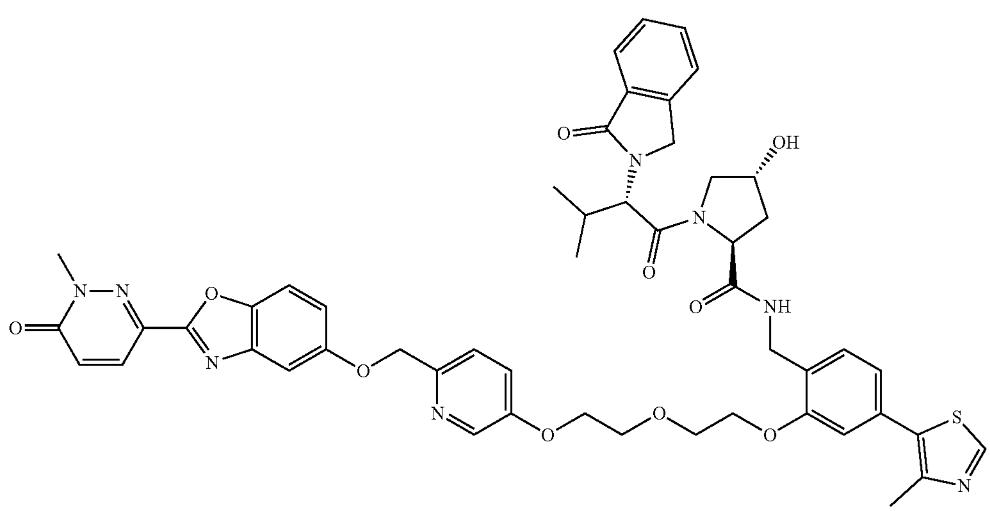 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOc2ccc(COc3ccc4oc(-c5ccc(=O)n(C)n5)nc4c3)nc2)c1] |

| # | Structure |
|---|---|
| 45 | 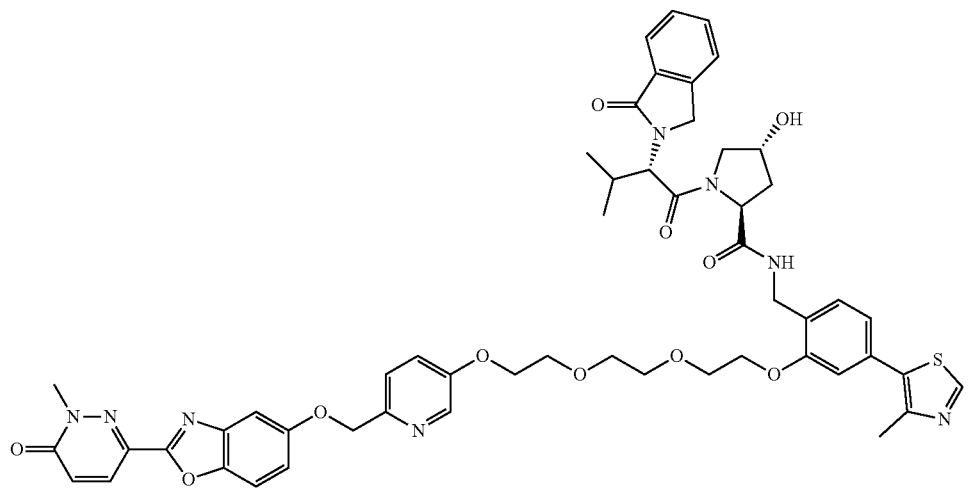 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOc2ccc(COc3ccc4oc(-c5ccc(=O)n(C)n5)nc4c3)nc2)c1] |
| 46 | 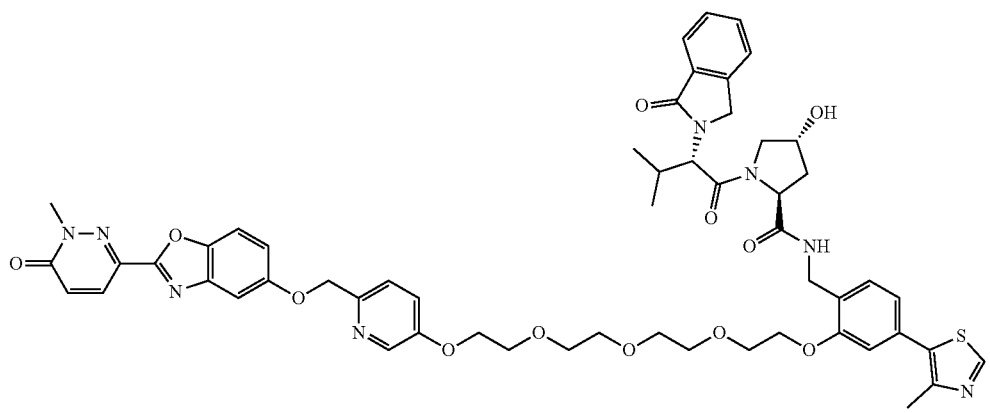 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOCCOc2ccc(COc3ccc4oc(-c5ccc(=O)n(C)n5)nc4c3)nc2)c1] |
| 47 | 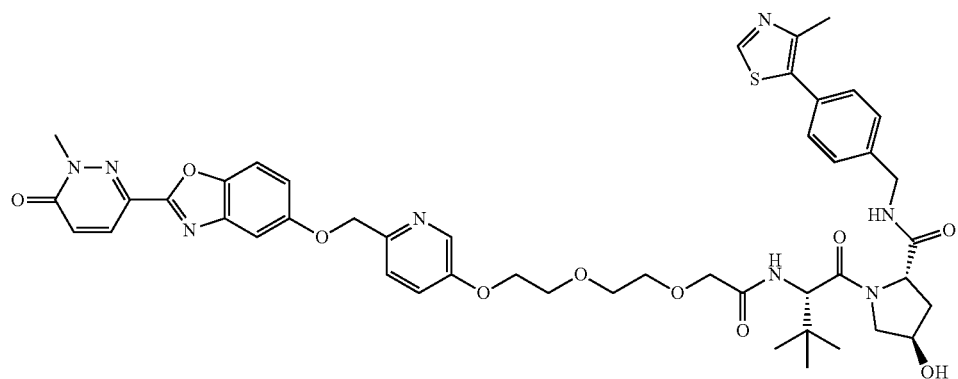 [SMILES: Cc1ncsc1-c1ccc(CNC(=O)[C@@H]2C[C@@H](O)CN2C(=O)[C@@H](NC(=O)COCCOCCOc2ccc(COc3ccc4oc(-c5ccc(=O)n(C)n5)nc4c3)nc2)C(C)(C)C)cc1] |

TABLE 2-continued
| # | Structure |
|---|---|
| 48 | 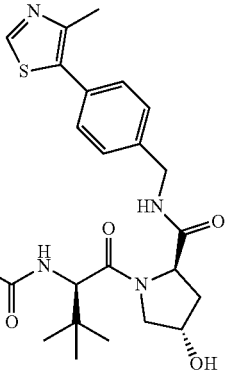 |
| 49 | 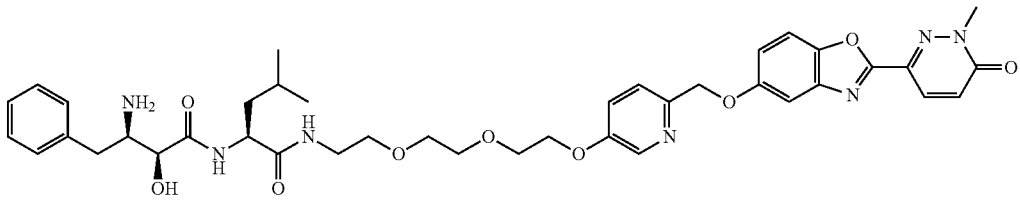 [SMILES: CC(C)C[C@H](NC(=O)[C@@H](O)[C@H](N)Cc1ccccc1)C(=O)NCCOCCOCCOc1ccc(COc2ccc3oc(-c4ccc(=O)n(C)n4)nc3c2)nc1] |
| 50 | 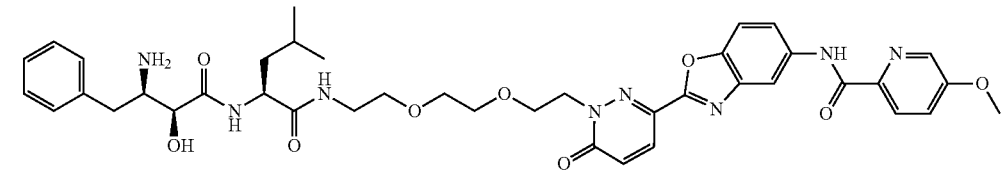 [SMILES: COc1ccc(C(=O)Nc2ccc3oc(-c4ccc(=O)n(CCOCCOCCNC(=O)[C@H](CC(C)C)NC(=O)[C@@H](O)[C@H](N)Cc5ccccc5)n4)nc3c2)nc1] |
| 51 | 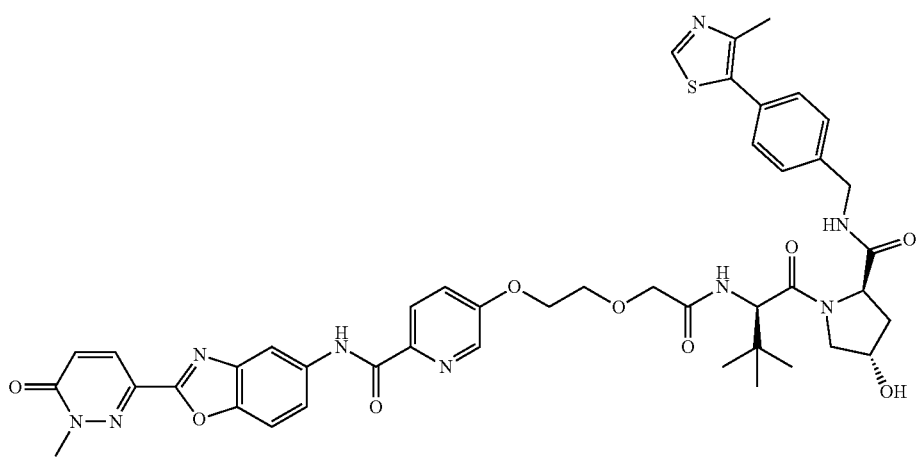 [SMILES: Cc1ncsc1-c1ccc(CNC(=O)[C@H]2C[C@H](O)CN2C(=O)[C@H](NC(=O)COCCOc2ccc(C(=O)Nc3ccc4oc(-c5ccc(=O)n(C)n5)nc4c3)nc2)C(C)(C)C)cc1] |
| 52 | 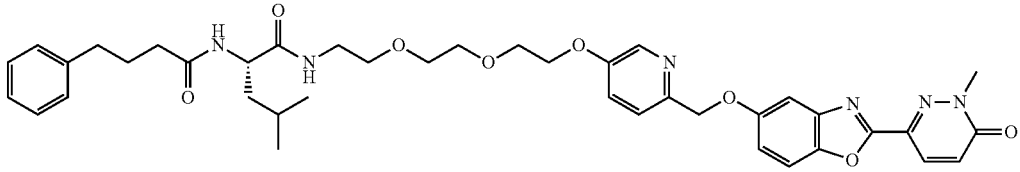 [SMILES: CC(C)C[C@H](NC(=O)CCCc1ccccc1)C(=O)NCCOCCOCCOc1ccc(COc2ccc3oc(-c4ccc(=O)n(C)n4)nc3c2)nc1] |

TABLE 2-continued
| # | Structure |
|---|---|
| 53 | 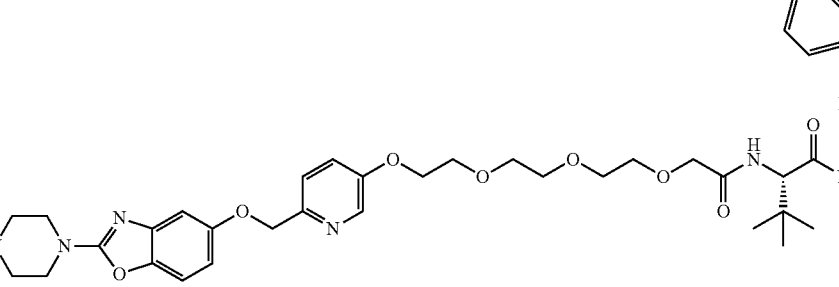 |
| 54 | 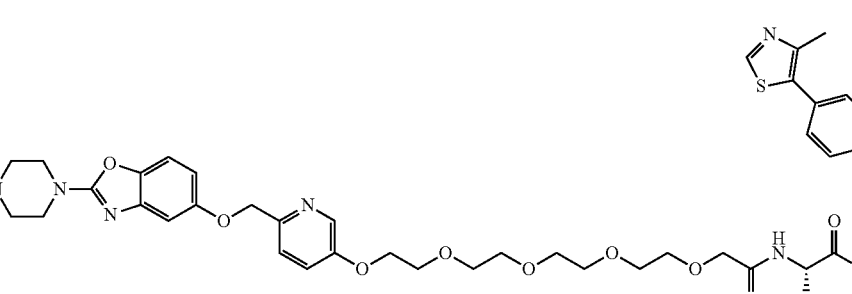 |
| 55 | 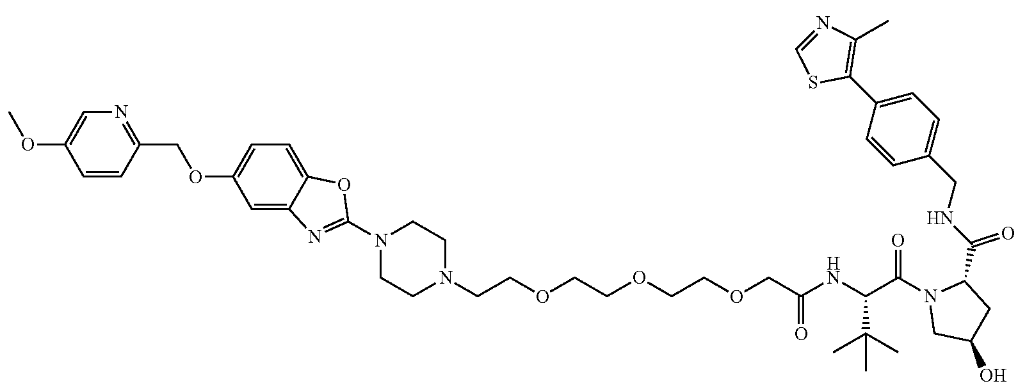 [SMILES: COc1ccc(COc2ccc3oc(N4CCN(CCOCCOCCOCC(=O)N[C@H](C(=O)N5C[C@H](O)C[C@H]5C(=O)NCc5ccc(-c6scnc6C)cc5)C(C)(C)C)CC4)nc3c2)nc1] |
| 56 | 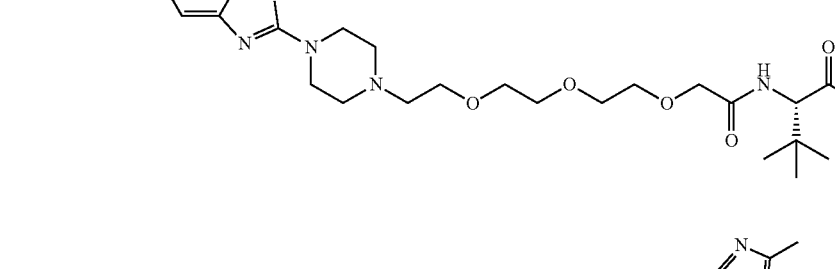 |

TABLE 2-continued

| # | Structure |
|---|---|
| 57 | 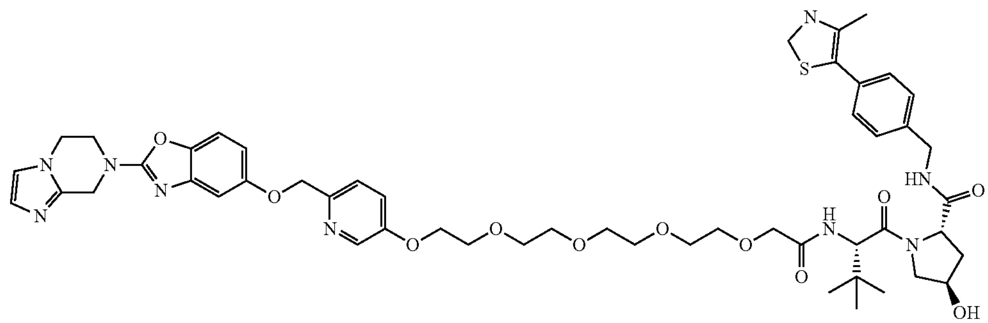 [SMILES: CC1=C(c2ccc(CNC(=O)[C@@H]3C[C@@H](O)CN3C(=O)[C@@H](NC(=O)COCCOCCOCCOCCOc3ccc(COc4ccc5oc(N6CCn7ccnc7C6)nc5c4)nc3)C(C)(C)C)cc2)SCN1] |
| 58 | 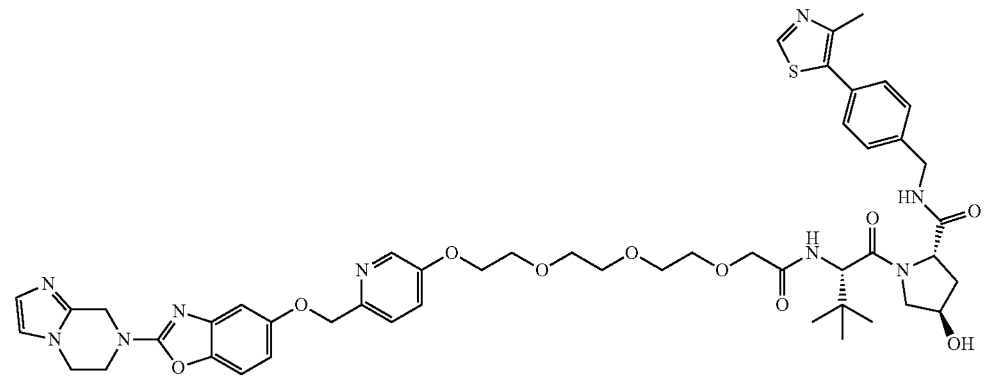 [SMILES: Cc1ncsc1-c1ccc(CNC(=O)[C@@H]2C[C@@H](O)CN2C(=O)[C@@H](NC(=O)COCCOCCOCCOc2ccc(COc3ccc4oc(N5CCn6ccnc6C5)nc4c3)nc2)C(C)(C)C)cc1] |
| 59 | 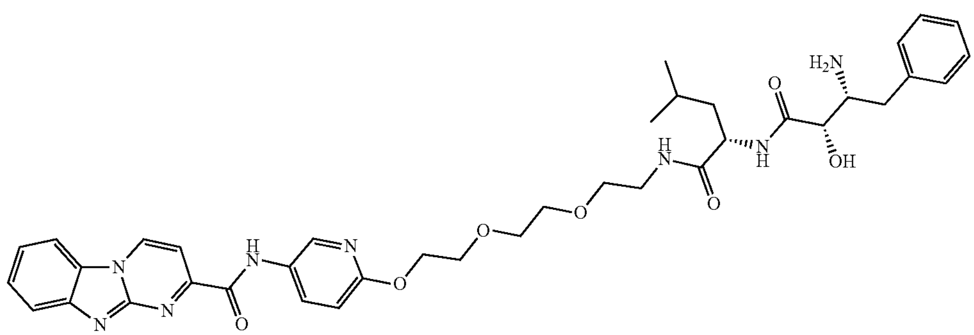 [SMILES: CC(C)C[C@H](NC(=O)[C@@H](O)[C@H](N)Cc1ccccc1)C(=O)NCCOCCOCCOc1ccc(NC(=O)c2ccn3c(n2)nc2ccccc23)cn1] |
| 60 | 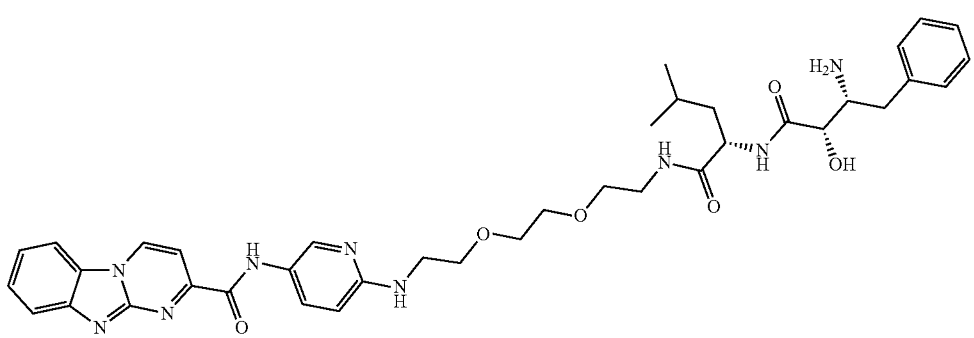 [SMILES: CC(C)C[C@H](NC(=O)[C@@H](O)[C@H](N)Cc1ccccc1)C(=O)NCCOCCOCCNc1ccc(NC(=O)c2ccn3c(n2)nc2ccccc23)cn1] |
| 61 | 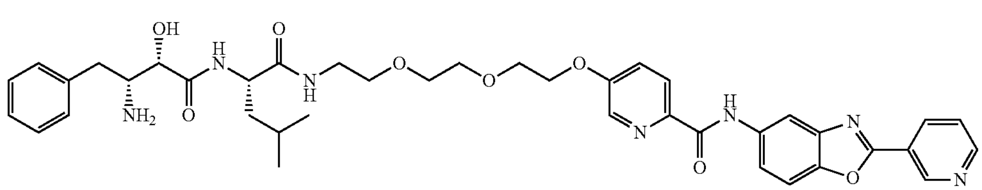 [SMILES: CC(C)C[C@H](NC(=O)[C@@H](O)[C@H](N)Cc1ccccc1)C(=O)NCCOCCOCCOc1ccc(C(=O)Nc2ccc3oc(-c4cccnc4)nc3c2)nc1] |

TABLE 2-continued

| # | Structure |
|---|---|
| 62 | 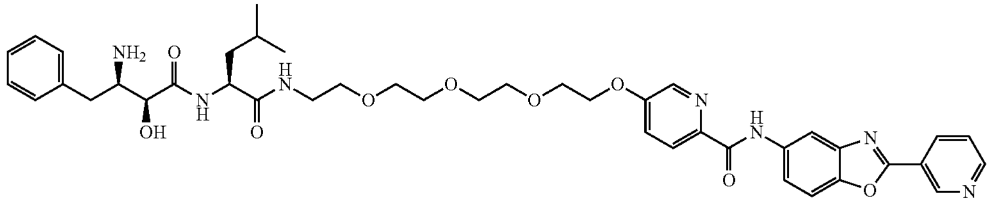 [SMILES: CC(C)C[C@H](NC(=O)[C@@H](O)[C@H](N)Cc1ccccc1)C(=O)NCCOCCOCCOCCOc1ccc(C(=O)Nc2ccc3oc(-c4cccnc4)nc3c2)nc1] |
| 63 | 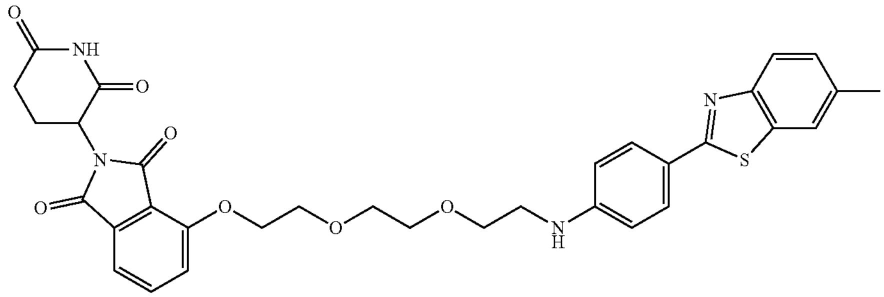 [SMILES: Cc1ccc2nc(-c3ccc(NCCOCCOCCOc4cccc5c4C(=O)N(C4CCC(=O)NC4=O)C5=O)cc3)sc2c1] |
| 64 | 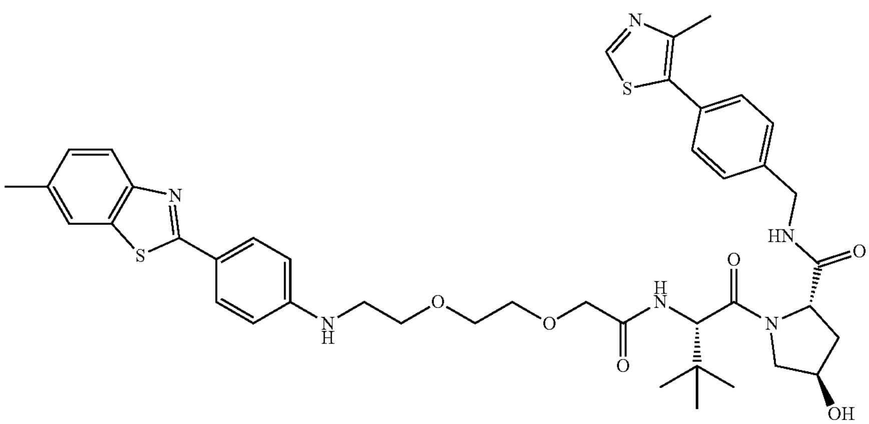 [SMILES: Cc1ccc2nc(-c3ccc(NCCOCCOCC(=O)N[C@H](C(=O)N4C[C@H](O)C[C@H]4C(=O)NCc4ccc(-c5scnc5C)cc4)C(C)(C)C)cc3)sc2c1] |
| 65 | 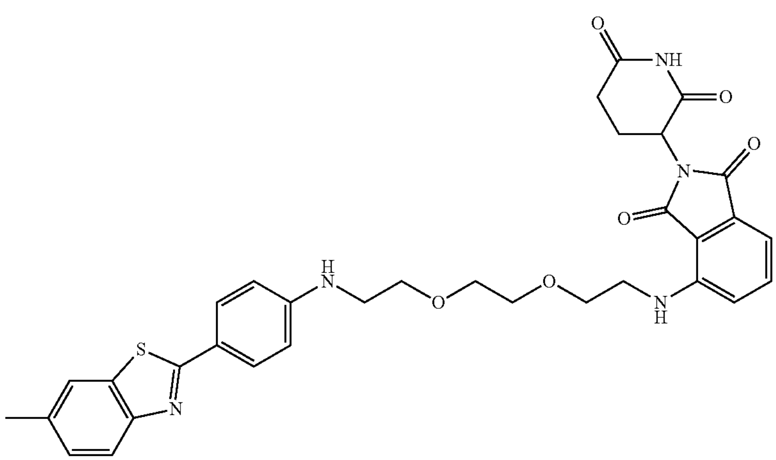 [SMILES: Cc1ccc2nc(-c3ccc(NCCOCCOCCNc4cccc5c4C(=O)N(C4CCC(=O)NC4=O)C5=O)cc3)sc2c1] |
| 66 | 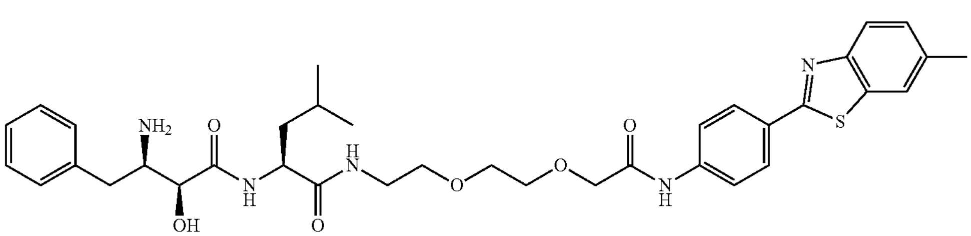 [SMILES: Cc1ccc2nc(-c3ccc(NC(=O)COCCOCCNC(=O)[C@H](CC(C)C)NC(=O)[C@@H](O)[C@H](N)Cc4ccccc4)cc3)sc2c1] |

TABLE 2-continued

| # | Structure |
|---|---|
| 67 | 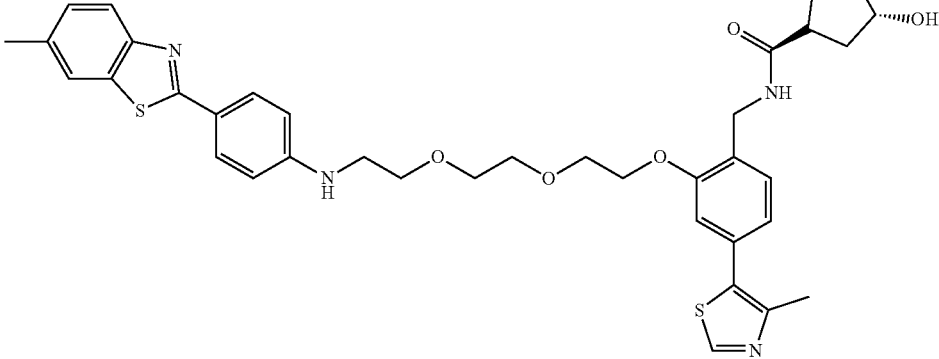 |
| 68 | 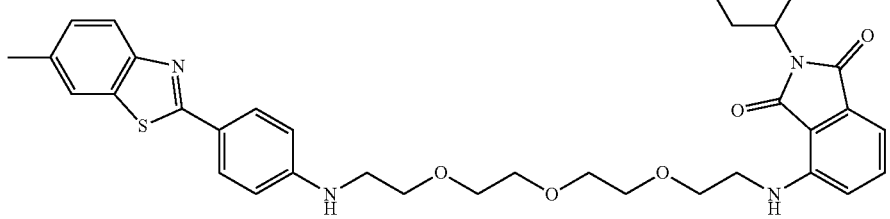 |
| 69 | 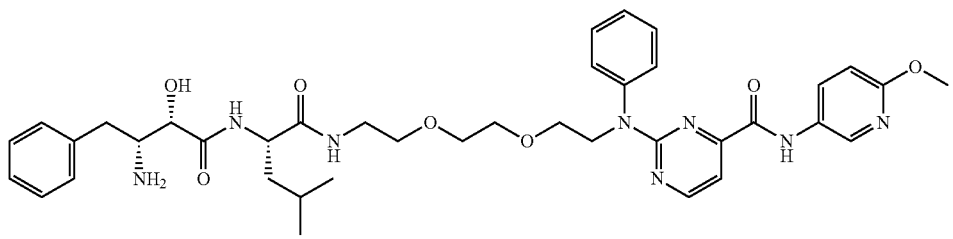 [SMILES: COc1ccc(NC(=O)c2ccnc(N(CCOCCOCCNC(=O)[C@H](CC(C)C)NC(=O)[C@@H](O)[C@H](N)Cc3ccccc3)c3ccccc3)n2)cn1] |
| 70 | 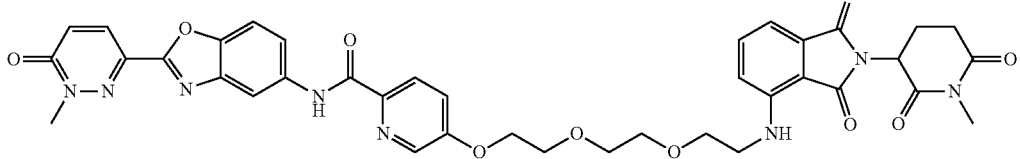 |

Treatment Methods and Uses

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, stereoisomer, or mixture of stereoisomers, thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of HD. The therapeutically effective amount may vary depending on the subject, and disease or condition being treated, the weight and age of the subject, the severity of the disease or condition, and the manner of administering, which can readily be determined by one or ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

In some embodiments, the compounds provided herein bind the target protein, mHTT, and an E3-ubiquitin ligase complex. It is contemplated that this ternary complex formation leads to the transfer of multiple ubiquitin molecules to mHTT. Upon dissociation of the complex, the polyubiquitinated mHTT is recognized by the proteasome and degraded.

Some embodiments provide for a method for inducing degradation of mHTT comprising administering a therapeutically effective amount of a compound described herein or a pharmaceutical composition described herein.

In some embodiments, the degradation of mHTT provides treatment of a disease caused by the aggregation of mHTT.

The compounds disclosed herein are useful for the treatment of neurodegenerative diseases.

In some embodiments, the neurodegenerative disease is caused by aggregates of mHTT.

In some embodiments, the neurodegenerative disease is Huntington's Disease (HD), Alzheimer's disease (AD), Parkinson's disease (PD), or a polyglutamine (polyQ) disease.

In some embodiments, the polyglutamine (polyQ) disease is dentatorubropallidoluysian atrophy (DRPLA), HD, spinal and bulbar muscular atrophy (ABMA), spinocerebellar ataxia Type 1, spinocerebellar ataxia Type 2, spinocerebellar ataxia Type 3, spinocerebellar ataxia Type 6, spinocerebellar ataxia Type 7, or spinocerebellar ataxia Type 17.

Some embodiments provide for a method for treating Huntington's disease comprising administering a therapeutically effective amount of a compound described herein or a pharmaceutical composition described herein.

Combination Therapies

In some embodiments, the compounds disclosed herein may be used in combination with one or more additional therapeutic agent that are being used and/or developed to treat a neurodegenerative disease.

In some embodiments, the compounds disclosed herein may be used in combination with one or more additional therapeutic agent that are being used and/or developed to treat HD.

In some embodiments, the one or more additional therapeutic agent may be a compound that activates an E3 enzymes that otherwise may be down regulated by mHTT.

In some embodiments, the one or more additional therapeutic agent may be an inhibitor, such as P-glycoprotein 1 (pgp) or Breast Cancer Resistance Protein (BCRP) efflux inhibitors, such as Elacridar, to enhance cellular uptake.

Kits

Provided herein are also kits that include a compound of the disclosure, or a pharmaceutically acceptable salt, stereoisomer, or mixture of stereoisomers thereof, and suitable packaging. In some embodiments, a kit further includes instructions for use. In some embodiments, a kit includes a compound of the disclosure, or a pharmaceutically acceptable salt, stereoisomer, or mixture of stereoisomers thereof, and a label and/or instructions for use of the compounds in the treatment of the indications, including the diseases or conditions, described herein.

Provided herein are also articles of manufacture that include a compound described herein or a pharmaceutically acceptable salt, stereoisomer, or mixture of stereoisomers thereof in a suitable container. The container may be a vial, jar, ampoule, preloaded syringe, and intravenous bag.

Pharmaceutical Compositions and Modes of Administration

Compounds provided herein are usually administered in the form of pharmaceutical compositions. Thus, provided herein are also pharmaceutical compositions that contain one or more of the compounds described herein or a pharmaceutically acceptable salt, stereoisomer, or mixture of stereoisomers thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, stereoisomer, or mixture of stereoisomers thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, stereoisomer, or mixture of stereoisomers thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, stereoisomer, or mixture of stereoisomers thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound described herein may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 1,000-2,000 mg/day, between about 10-500 mg/day, between about 50-300 mg/day, between about 75-200 mg/day, or between about 100-150 mg/day.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment.

Treatment cycles may be used, and are frequently alternated with resting periods of about 1 to 28 days, commonly about 7 days or about 14 days, between cycles. The treatment cycles, in other embodiments, may also be continuous.

Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

A compound of formula (I) can be synthesized according to the following exemplary synthetic pathways.

Scheme 1

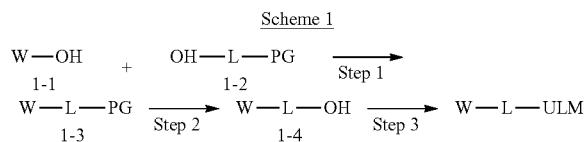

In Scheme 1, PG refers to a protecting group, and W, L, and ULM are as defined herein. As shown in Scheme 1, in some embodiments, a compound 1-1 and compound 1-2 are coupled under appropriate conditions (for example, via a Mitsunobu reaction) to form a compound 1-3. Suitable deprotection of compound 1-3 provides compound 1-4. A compound of formula (I) is produced from coupling compound 1-4 and ULM (for example, in the presence of HATU and a base).

Scheme 2

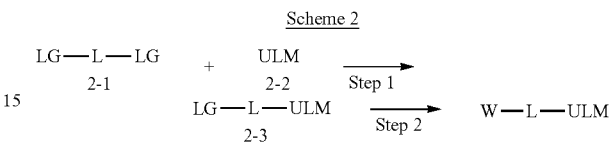

In Scheme 2, LG refers to a leaving group, and W, L, and ULM are as defined herein. As shown in Scheme 2, in some embodiments, a compound 2-1 and compound 2-2 are coupled under appropriate conditions (for example, in the presence of a base) to form a compound 2-3. A compound of formula (I) is produced from coupling compound 2-3 and W (for example, in the presence of a base).

Scheme 3

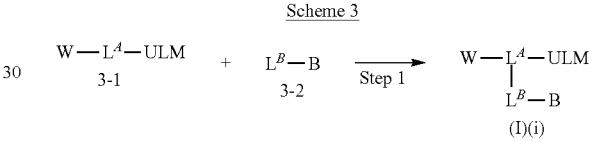

In Scheme 3, $L^A$ and $L^B$ are each independently L as described herein, and W, ULM, and B are as described herein. As shown in Scheme 3, in some embodiments, a compound of formula (I)(i) can be achieved by coupling compound 3-1 and compound 3-2 via standard coupling conditions (for example, via click chemistry between an azido-substituted-$L^A$ of compound 3-1 and alkynyl-substituted-$L^B$ of 3-2).

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

General Synthetic Procedures. Commercially available reagents and solvents (HPLC grade) were used without further purification. $^1$H NMR spectra were recorded on a Bruker DRX 500 MHz spectrometer or Bruker DPX 250 MHz spectrometer in deuterated solvents. Chemical shifts (δ) are in parts per million. Thin-layer chromatography (TLC) analysis was performed with Kieselgel 60 $F_{254}$ (Merck) plates and visualized using UV light.

Analytical HPLC-MS was performed on Shimadzu LCMS-2010EV systems using reverse phase Atlantis dC18 columns (3 μm, 2.1×50 mm), gradient 5-100% B (A=water/ 0.1% formic acid, B=acetonitrile/0.1% formic acid) over 3 min, injection volume 3 μL, flow=1.0 mL/min. UV spectra were recorded at 215 nm using a Waters 2788 dual wavelength UV detector. Mass spectra were obtained over the range m/z 150 to 850 at a sampling rate of 2 scans per second using Waters LCT or analytical HPLC-MS on Shimadzu LCMS-2010EV systems using reverse phase Waters Atlantis dC18 columns (3 μm, 2.1×100 mm), gradient 5-100% B (A=water/0.1% formic acid, B=acetonitrile/0.1% formic acid) over 7 min, injection volume 3 μl, flow=0.6 mL/min. UV spectra were recorded at 215 nm using a Waters 2996 photo diode array. Data were integrated and reported using Shimadzu Psiport software.

Alternatively the following were used: Proton nuclear magnetic resonance spectra were obtained on a Bruker ASCEND 500 spectrometer at 500 MHz. Spectra are given in ppm (δ) and coupling constants, J values, are reported in hertz (Hz). Tetramethylsilane was used as an internal standard for proton nuclear magnetic resonance. Mass spectra and LCMS analyses were obtained using a Varian 1200L single quadrupole mass spectrometer (ESI, HP-LCMS), a Waters Acquity SQD (ESI, UP-LCMS) or a Shimadzu 2020 single quadrupole mass spectrometer (DUIS, UP-LCMS). HPLC analyses were obtained using either a Phenomenex Luna C18(2) column, 5 μm, (4.6×150 mm) with elution as per solvent gradient Method 1 or using a Phenomenex C18 Kinetex column, 5 μm (4.6×150 mm) with elution as per solvent gradient Method 2. Detection was by UV absorbance at 254 nm.

Method 1

| Time (min) | Flow (mL/min) | % A | % B |
|---|---|---|---|
| 0.0 | 2.0 | 95.0 | 5.0 |
| 10.0 | 2.0 | 0.0 | 100.0 |
| 13.0 | 2.0 | 0.0 | 100.0 |

A = Water with 0.1% v/v Trifluoroacetic Acid
B = Acetonitrile with 0.1% v/v Trifluoroacetic Acid Method 2

| Time (min) | Flow (mL/min) | % A | % B |
|---|---|---|---|
| 0.01 | 2.0 | 95.0 | 5.0 |
| 10.0 | 2.0 | 0.0 | 100.0 |
| 13.0 | 2.0 | 0.0 | 100.0 |
| 14.0 | 2.0 | 95.0 | 5.0 |

A = Water with 0.1% v/v Trifluoroacetic Acid
B = Acetonitrile with 0.1% v/v Trifluoroacetic Acid Abbreviations AcOH—Acetic acid
aq—aqueous
Boc—tert-butyloxycarbonyl
CMBP—Cyanomethyltributylphosphorane
DCM—Dichloromethane
DIAD—diisopropyl azodicarboxylate
DIPEA—diisopropylethylamine
DMF—N,N-dimethylformamide
DMSO—dimethyl sulfoxide
EDC—N-Ethyl-N'-(3-dimethylaminopropyl)carbodiimide
ESI—electrospray ionisation
Et—Ethyl
EtOAc—Ethyl acetate
EtOH—Ethanol
FCC—flash column chromatography
h—hour(s)
HATU—1-[Bis(dimethylamino)methylene]-1H-1,2,3-triazolo[4,5-b]pyridinium 3-oxid hexafluorophosphate
HOBT—Hydroxybenzotriazole
HPLC—High performance liquid chromatography
IPA—isopropanol
LCMS—liquid chromatography mass spectrometry
Me—Methyl
MeCN—acetonitrile
MeOH—methanol
min—minute(s)
Ms—methylsulfonyl
m/z—mass to charge ratio
NMR—nuclear magnetic resonance
O/N—over-night
Ph—Phenyl
ppm—part(s) per million
rt—room temperature
sat.—saturated
TBME—tert-Butyl methyl ether
tBu—tert-Butyl
TFA—trifluoroacetic acid
THF—tetrahydrofuran
TLC—thin layer chromatography
Ts—p-toluenesulfonyl
UV—ultraviolet

SYNTHETIC EXAMPLES

Example 1

Scheme for Example 1

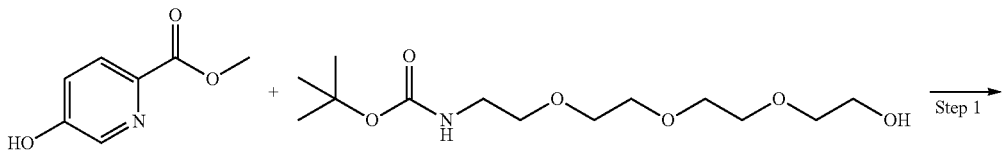

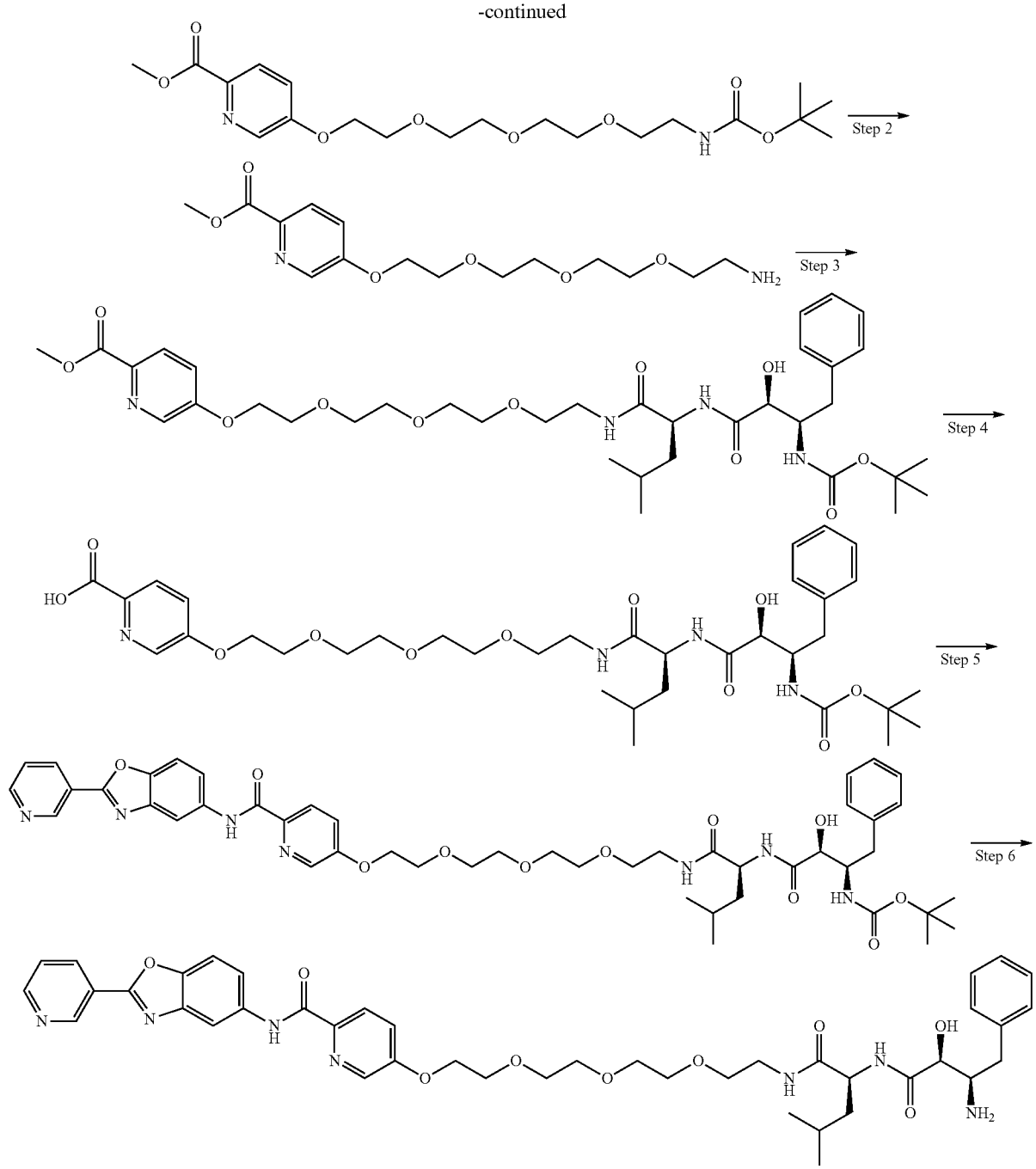

Step 1: Methyl 5-(2-{2-[2-(2-{[(tert-butoxy)carbonyl]amino}ethoxy)ethoxy]ethoxy}ethoxy)pyridine-2-carboxylate A stirred solution of methyl 5-hydroxypyridine-2-carboxylate (100 mg, 0.65 mmol) and tert-butyl N-(2-{2-[2-(2-hydroxyethoxy)ethoxy]ethoxy}ethyl)carbamate (211 mg, 0.72 mmol) in THF (7.5 mL) was cooled to 0° C. and treated with triphenylphosphine (257 mg, 0.98 mmol). The reaction mixture was stirred for 5 min and then treated with a solution of DIAD (192 μL, 0.98 mmol) in THF (2.5 mL) dropwise over 5 min. The mixture was stirred at 0° C. for a further 10 min and then at rt overnight. The reaction mixture was concentrated to a reduced volume then diluted with water (20 mL) and extracted with DCM (4×20 mL). The combined organic extracts were washed with brine (20 mL), dried over MgSO$_4$, filtered and concentrated in vacuo. The crude material was purified by acidic reverse phase chromatography (C-18, 0-100% MeCN/Water+0.100 formic acid) to give the title compound. $^1$H NMR (250 MHz, Chloroform-d) 8.40 (d, J=2.8 Hz, 1H), 8.07 (d, J=8.7 Hz, 1H), 7.37-7.21 (m, 1H), 5.00 (d, J=6.3 Hz, 1H), 4.23 (dd, J=5.7, 3.7 Hz, 2H), 3.95 (s, 3H), 3.90-3.83 (m, 2H), 3.78-3.56 (m, 8H), 3.51 (t, J=5.2 Hz, 2H), 3.27 (q, J=5.4 Hz, 2H), 1.41 (s, 9H). Tr(METCR1410)=1.03 min, (ES$^+$) [M+H]$^+$ 429.

Step 2: Methyl 5-(2-{2-[2-(2-azaniumylethoxy)ethoxy]ethoxy}ethoxy)pyridine-2-carboxylate chloride A mixture of methyl 5-(2-{2-[2-(2-{[(tert-butoxy)carbonyl]amino}ethoxy)ethoxy]ethoxy}ethoxy)pyridine-2-carboxylate (170 mg, 0.38 mmol) in 4N HCl in dioxane (4 mL) was stirred at rt for 3 h. After this time, the reaction was evaporated to dryness to give the title compound. $^1$H NMR (500 MHz, Methanol-d$_4$) δ 8.58 (d, J=2.8 Hz, 1H), 8.39 (d, J=8.9 Hz, 1H), 8.06 (dd, J=8.9, 2.8 Hz, 1H), 4.48-4.42 (m, 2H), 4.05 (s, 3H), 3.98-3.88 (m, 2H), 3.76-3.67 (m, 10H), 3.13 (t, J=5.1 Hz, 2H). Tr(METCR1410)=0.71 min, (ES$^+$) [M+H]$^+$ 329.

Step 3: Methyl 5-{2-[2-(2-{2-[(2S)-2-[(2S,3R)-3-{[(tert-butoxy)carbonyl]amino}-2-hydroxy-4-phenylbutanamido]-4-methylpentanamido]ethoxy}ethoxy)ethoxy]ethoxy}pyridine-2-carboxylate DIPEA (407 μL, 2.34 mmol) was added dropwise to a suspension of methyl 5-(2-{2-[2-(2-azaniumylethoxy)ethoxy]ethoxy}ethoxy)pyridine-2-carboxylate chloride (138 mg, 0.36 mmol), (2S)-2-[[(2S,3R)-3-(tert-butoxycarbonylamino)-2-hydroxy-4-phenyl-butanoyl]amino]-4-methyl-pentanoic acid (160 mg, 0.36 mmol), HOBT (124 mg, 0.81 mmol) and EDC.HCl (276 mg, 1.44 mmol) cooled to 0° C. The mixture was stirred at 0° C. for 15 min then allowed to warm to rt overnight. The reaction was concentrated to dryness and the crude oil was partitioned between water and EtOAc. The aqueous layer was extracted once more then combined extracts were washed with 10% citric acid (aq), sat NaHCO$_3$(aq) and brine. The organic layer was dried over MgSO$_4$, filtered and evaporated to dryness to give the title compound. $^1$H NMR (500 MHz, Chloroform-d) δ 8.45 (d, J=2.9 Hz, 1H), 8.14 (d, J=8.7 Hz, 1H), 7.41 (d, J=8.7 Hz, 1H), 7.34 (dd, J=8.7, 2.9 Hz, 1H), 7.32-7.28 (m, 2H), 7.25-7.21 (m, 2H), 6.82 (t, J=5.6 Hz, 1H), 5.69 (s, 1H), 5.16 (d, J=8.5 Hz, 1H), 4.51 (td, J=9.1, 5.0 Hz, 1H), 4.32-4.27 (m, 2H), 4.19-4.16 (m, 1H), 4.11 (d, J=8.2 Hz, 1H), 4.01 (s, 3H), 3.97-3.93 (m, 2H), 3.81-3.75 (m, 2H), 3.73-3.68 (m, 2H), 3.66-3.59 (m, 4H), 3.56 (t, J=5.4 Hz, 2H), 3.48-3.40 (m, 2H), 3.11-3.02 (m, 2H), 1.79-1.57 (m, 3H), 1.42 (s, 9H), 0.96 (d, J=6.2 Hz, 3H), 0.94 (d, J=6.2 Hz, 3H). Tr(METCR1410)=1.11 min, (ES$^+$) [M+H]$^+$ 719.

Step 4: 5-{2-[2-(2-{2-[(2S)-2-[(2S,3R)-3-{[(tert-Butoxy)carbonyl]amino}-2-hydroxy-4-phenylbutanamido]-4-methylpentanamido]ethoxy}ethoxy)ethoxy]ethoxy}pyridine-2-carboxylic acid A solution of methyl 5-{2-[2-(2-{2-[(2S)-2-[(2S,3R)-3-{[(tert-butoxy)carbonyl]amino}-2-hydroxy-4-phenylbutanamido]-4-methylpentanamido]ethoxy}ethoxy)ethoxy]ethoxy}pyridine-2-carboxylate (250 mg, 0.35 mmol) and K$_2$CO$_3$ (144 mg, 1.04 mmol) in a 2:1 MeOH:water mixture (7.5 mL) was stirred at rt for 24 h. The mixture was concentrated to a reduced volume and then acidified with a 10% citric acid solution until pH 4/5. The aqueous phase was extracted with DCM (4×15 mL) and the combined organic layers were washed with brine, dried over Na$_2$SO$_4$, filtered and evaporated to dryness to afford the title compound. $^1$H NMR (250 MHz, Chloroform-d) δ 8.32 (d, J=2.8 Hz, 1H), 8.15 (d, J=8.7 Hz, 1H), 7.40 (dd, J=8.7, 2.8 Hz, 1H), 7.24 (d, J=8.8 Hz, 5H), 6.86-6.72 (m, 1H), 5.08 (s, 1H), 4.59-4.40 (m, 1H), 4.28 (dd, J=5.6, 3.6 Hz, 2H), 4.15 (d, J=2.6 Hz, 3H), 3.99-3.84 (m, 2H), 3.81-3.34 (m, 10H), 2.95 (s, 2H), 1.80-1.52 (m, 3H), 1.37 (s, 9H), 0.90 (t, J=6.4 Hz, 6H). Tr(METCR1410)=1.10 min, (ES$^+$) [M+H]$^+$ 705.

Step 5: tert-Butyl N-[(1S,2R)-1-hydroxy-1-{[(1S)-3-methyl-1-({2-[2-(2-{2-[(6-{[2-(pyridin-3-yl)-1,3-benzoxazol-5-yl]carbamoyl}pyridin-3-yl)oxy]ethoxy}ethoxy)ethoxy]ethyl}carbamoyl)butyl]carbamoyl}-3-phenylpropan-2-yl]carbamate HATU (71 mg, 0.19 mmol) was added to a solution of DIPEA (82 μL, 0.47 mmol), 5-{2-[2-(2-{2-[(2S)-2-[(2S,3R)-3-{[(tert-butoxy)carbonyl]amino}-2-hydroxy-4-phenylbutanamido]-4-methylpentanamido]ethoxy}ethoxy)ethoxy]ethoxy}pyridine-2-carboxylic acid (110 mg, 0.16 mmol) and 2-(pyridin-3-yl)-1,3-benzoxazol-5-amine (33 mg, 0.16 mmol) in THF (2 mL) cooled to 0° C. After 1.5 h the reaction was evaporated to dryness then partitioned between EtOAc and 10% citric acid. The organic layer was washed with sat NaHCO$_3$(aq) (2×), brine, dried over Na$_2$SO$_4$, filtered and evaporated to dryness to give the title compound. $^1$H NMR (250 MHz, Chloroform-d) δ 9.97 (s, 1H), 9.48-9.38 (m, 1H), 8.74 (dd, J=4.9, 1.7 Hz, 1H), 8.49 (dt, J=8.1, 1.9 Hz, 1H), 8.32-8.18 (m, 3H), 7.74 (dd, J=8.8, 2.1 Hz, 1H), 7.57 (d, J=8.8 Hz, 1H), 7.45 (dd, J=8.0, 4.8 Hz, 1H), 7.36 (dd, J=8.7, 2.9 Hz, 2H), 7.25-7.12 (m, 5H), 6.91-6.79 (m, 1H), 5.72 (s, 1H), 5.19 (d, J=8.5 Hz, 1H), 4.46 (td, J=8.8, 3.4 Hz, 1H), 4.25 (dd, J=5.7, 3.5 Hz, 2H), 4.15-4.04 (m, 2H), 3.89 (dd, J=5.6, 3.5 Hz, 2H), 3.76-3.48 (m, 10H), 3.38 (q, J=5.2 Hz, 2H), 3.03-2.92 (m, 2H), 1.71-1.54 (m, 3H), 1.34 (s, 9H), 0.98-0.83 (m, 6H). Tr(METCR1603)=4.81 min, (ES)$^+$ [M+H]$^+$ 899.

Step 6: 5-{2-[2-(2-{2-[(2S)-2-[(2S,3R)-3-Azaniumyl-2-hydroxy-4-phenylbutanamido]-4-methylpentanamido]ethoxy}ethoxy)ethoxy]ethoxy}-N-[2-(pyridin-3-yl)-1,3-benzoxazol-5-yl]pyridine-2-carboxamide diformate 4N HCl in dioxane (2.0 mL, 8.00 mmol) was added to a solution of tert-butyl N-[(1S,2R)-1-hydroxy-1-{[(1S)-3-methyl-1-({2-[2-(2-{2-[(6-{[2-(pyridin-3-yl)-1,3-benzoxazol-5-yl]carbamoyl}pyridin-3-yl)oxy]ethoxy}ethoxy)ethoxy]ethyl}carbamoyl)butyl]carbamoyl}-3-phenylpropan-2-yl]carbamate (138 mg, 0.15 mmol) in MeOH (1 mL). The reaction was stirred at rt for 1 h then evaporated to dryness. The crude was dissolved in water and extracted with Et$_2$O. The aqueous layer was neutralised with solid NaHCO$_3$ and then extracted with EtOAc (3×20 mL). The combined EtOAc extracts were washed with brine, dried over MgSO$_4$, filtered and evaporated to dryness. The crude residue was purified by acidic reverse phase chromatography (C-18, 0-100% MeCN/water+0.1% formic acid) to give the title compound. $^1$H NMR (500 MHz, Methanol-d$_4$) δ 9.38 (d, J=2.1 Hz, 1H), 8.75 (dd, J=4.9, 1.6 Hz, 1H), 8.62 (dt, J=8.1, 1.9 Hz, 1H), 8.39 (d, J=2.8 Hz, 1H), 8.37 (d, J=2.0 Hz, 1H), 8.29 (s, 2H), 8.18 (d, J=8.7 Hz, 1H), 7.76 (dd, J=8.8, 2.1 Hz, 1H), 7.71 (d, J=8.8 Hz, 1H), 7.66 (dd, J=8.0, 4.9 Hz, 1H), 7.57 (dd, J=8.7, 2.9 Hz, 1H), 7.37-7.26 (m, 5H), 4.38 (dd, J=8.6, 6.3 Hz, 1H), 4.35-4.27 (m, 2H), 4.12 (d, J=3.1 Hz, 1H), 3.94-3.85 (m, 2H), 3.76 (td, J=7.5, 3.1 Hz, 1H), 3.73-3.70 (m, 2H), 3.68-3.65 (m, 2H), 3.64-3.61 (m, 2H), 3.59-3.56 (m, 2H), 3.52 (t, J=5.5 Hz, 2H), 3.44-3.34 (m, 1H), 3.35-3.29 (m, 1H), 3.10 (dd, J=13.9, 7.9 Hz, 1H), 2.91 (dd, J=13.9, 7.1 Hz, 1H), 1.73-1.56 (m, 3H), 0.99-0.92 (m, 6H). Tr(MET-uPLC-AB-101)=2.31 min, (ES$^+$) [M+H]$^+$ 798.

The following compounds were prepared as described above:

| # | Structure | Data |
|---|---|---|
| 62 | 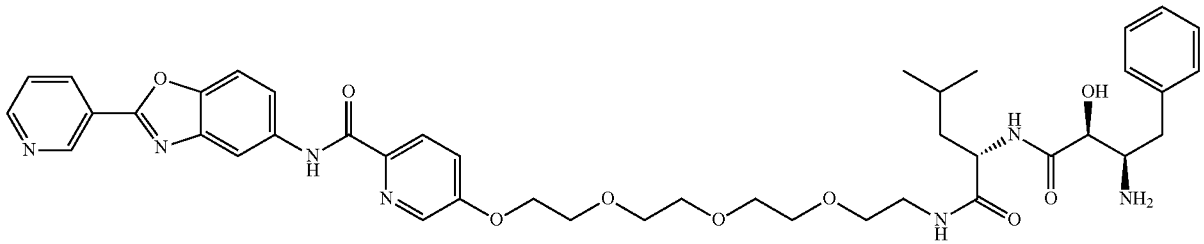 | Tr(MET-uHPLC-AB-101) = 2.31 min, (ES+) (M+H)+ 795 |
| 61 | 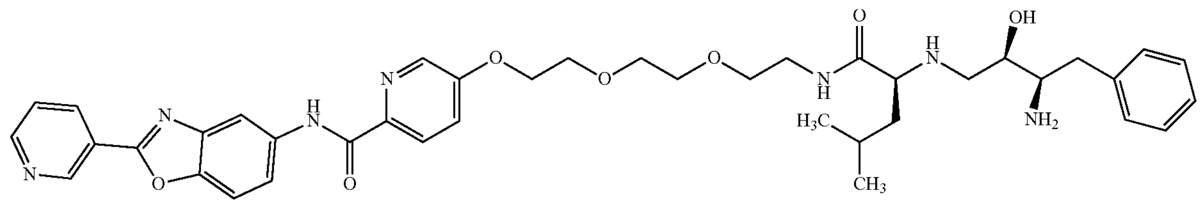 | Tr(MET-uHPLC-AB-101) = 2.24 min, (ES+) (M + H)+ 754 |
| 12 | 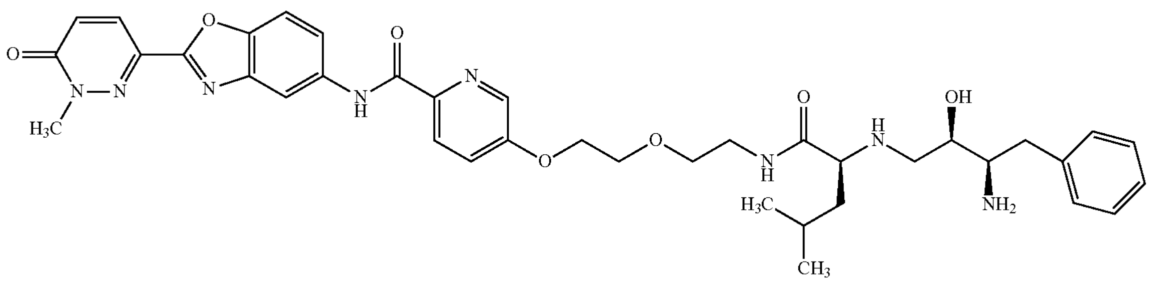 | Tr(MET-uHPLC-AB-101) = 2.16 min, (ES+) (M + H)+ 741 |
| 13 | 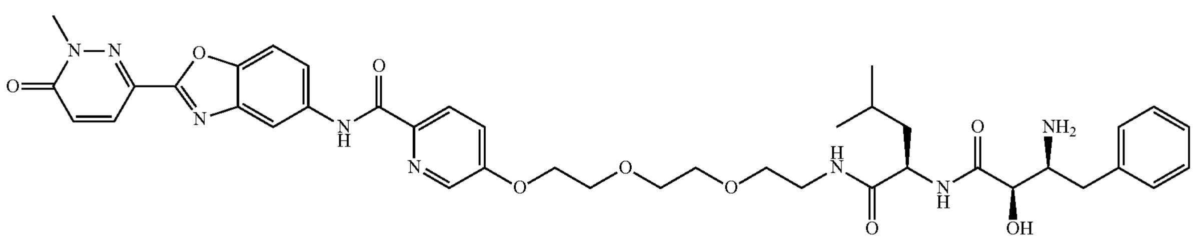 [SMILES: CC(C)C[C@@H](NC(=O)[C@H](O)[C@@H](N)Cc1ccccc1)C(=O)NCCOCCOCCOc1ccc(C(=O)Nc2ccc3oc(-c4ccc(=O)n(C)n4)nc3c2)nc1] | Tr(MET-uHPLC-AB-101) = 2.2 min, (ES+) (M + H)+ 785 |

-continued

| # | Structure | Data |
|---|---|---|
| 14 | 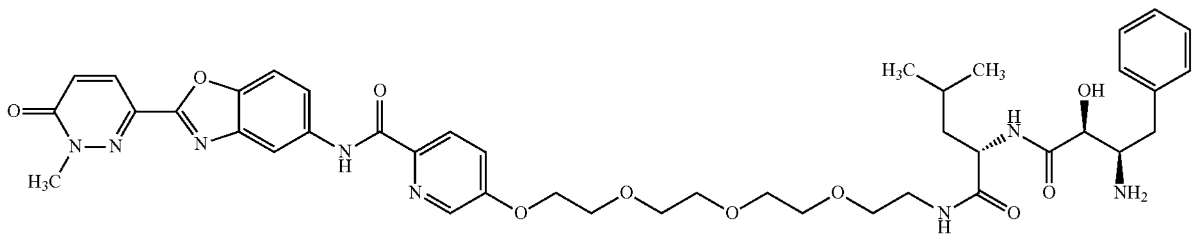 [SMILES: CC(C)C[C@H](NC(=O)[C@@H](O)[C@H](N)Cc1ccccc1)C(=O)NCCOCCOCCOCCOc1ccc(C(=O)Nc2ccc3oc(-c4ccc(=O)n(C)n4)nc3c2)nc1] | Tr(MET-uHPLC-AB-101) = 2.23 min, (ES+) (M + H)+ 829 |
| 15 | 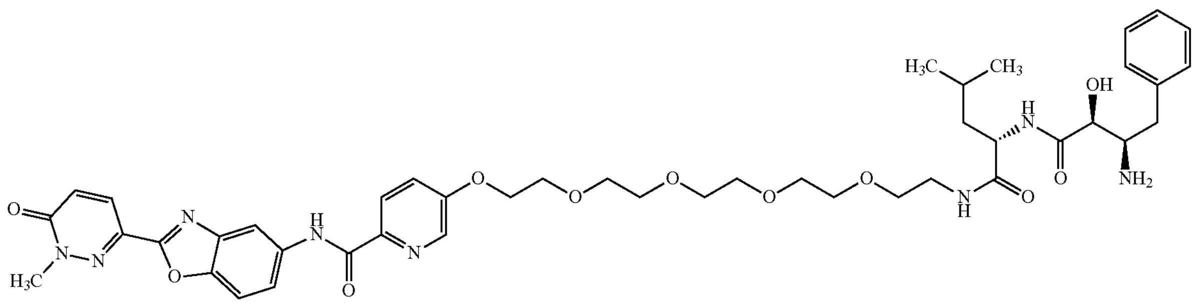 [SMILES: CC(C)C[C@H](NC(=O)[C@@H](O)[C@H](N)Cc1ccccc1)C(=O)NCCOCCOCCOCCOCCOc1ccc(C(=O)Nc2ccc3oc(-c4ccc(=O)n(C)n4)nc3c2)nc1] | Tr(MET-uHPLC-AB-101) = 2.25 min, (ES+) (M + H)+ 873 |
| 16 | 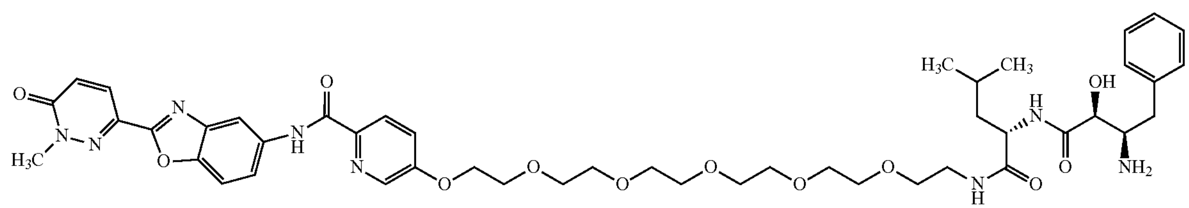 [SMILES: CC(C)C[C@H](NC(=O)[C@@H](O)[C@H](N)Cc1ccccc1)C(=O)NCCOCCOCCOCCOCCOCCOc1ccc(C(=O)Nc2ccc3oc(-c4ccc(=O)n(C)n4)nc3c2)nc1] | Tr(METCR1603 High pH 7 min) = 4.04 min, (ES+) (M + H)+ 918 |

| # | Structure | Data |
|---|---|---|
| 17 | 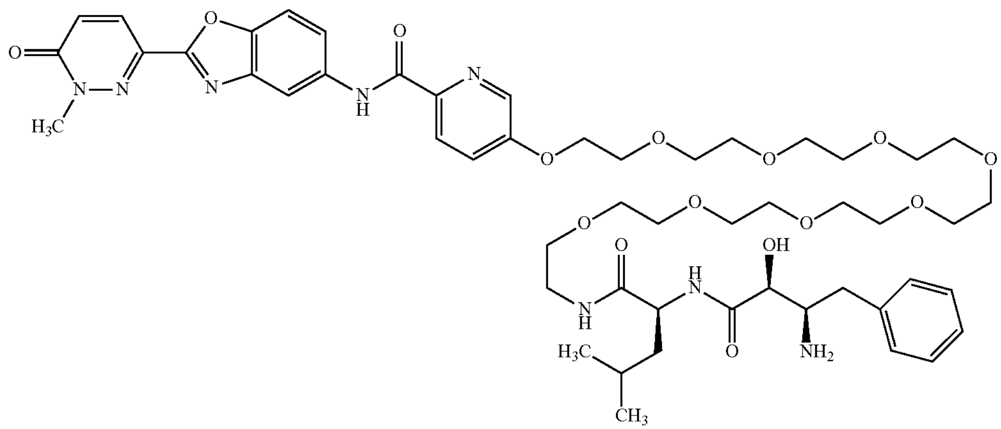 [SMILES: CC(C)C[C@H](NC(=O)[C@@H](O)[C@H](N)Cc1ccccc1)C(=O)NCCOCCOCCOCCOCCOCCOCCOCCOCCOc1ccc(C(=O)Nc2ccc3oc(-c4ccc(=O)n(C)n4)nc3c2)nc1] | Tr(MET-uHPLC-AB-101) = 2.34 min, (ES+) (M + H)+ 1049 |
| 18 | 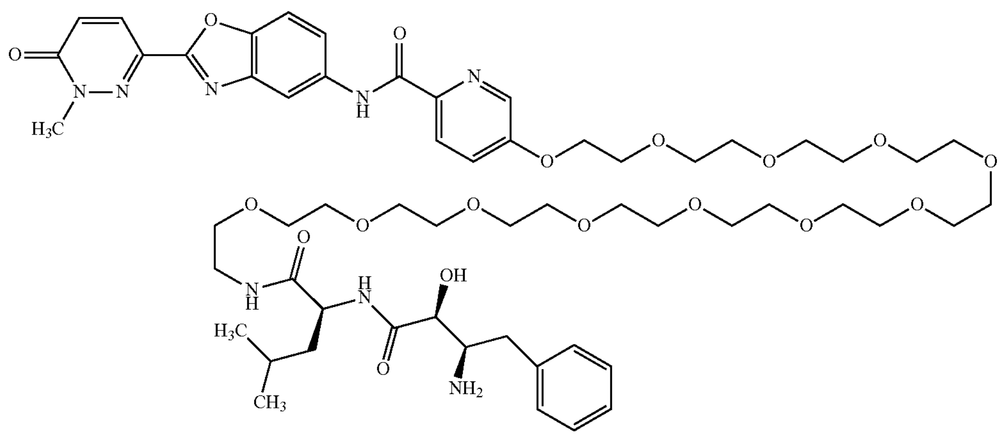 [SMILES: CC(C)C[C@H](NC(=O)[C@@H](O)[C@H](N)Cc1ccccc1)C(=O)NCCOCCOCCOCCOCCOCCOCCOCCOCCOCCOCCOCCOc1ccc(C(=O)Nc2ccc3oc(-c4ccc(=O)n(C)n4)nc3c2)nc1] | Tr(MET-uHPLC-AB-101) = 2.37 min, (ES+) (M)+ 1181 |

| # | Structure | Data |
|---|---|---|
| 19 | 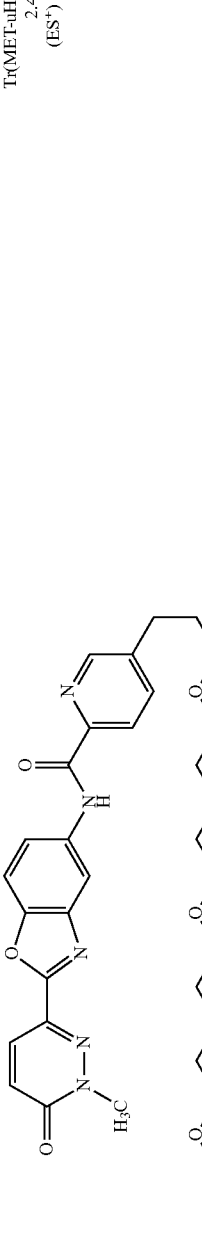 | Tr(MET-uHPLC-AB-101) = 2.43 min, (ES+) (M)+ 1357 |

Example 2

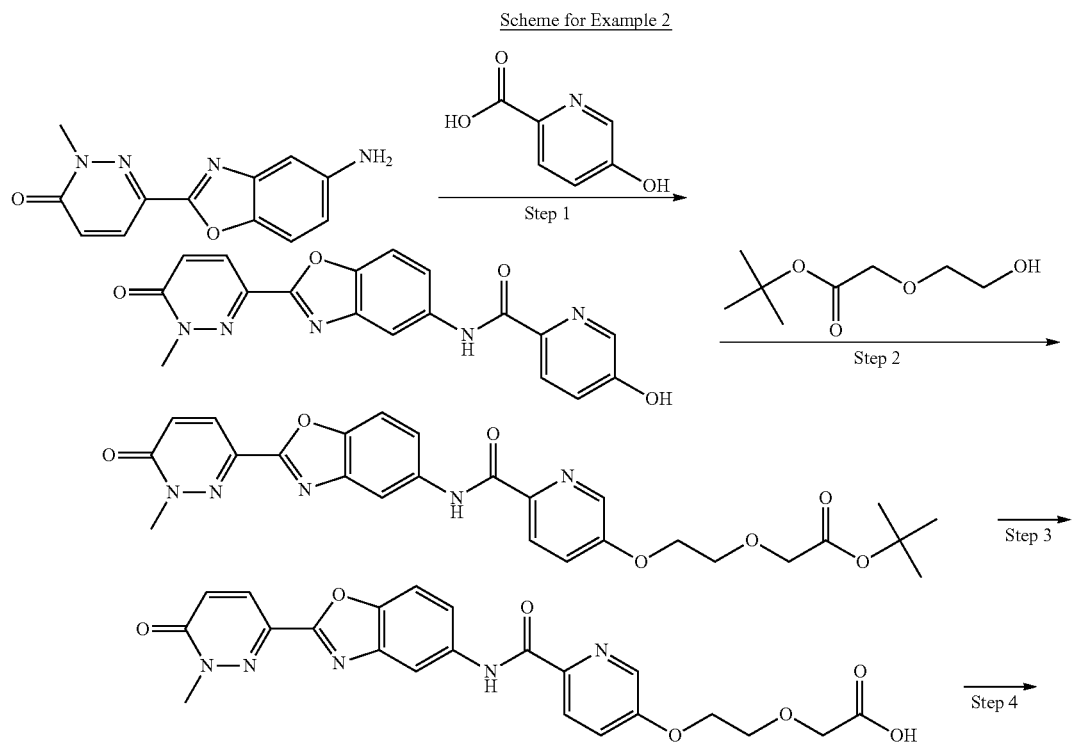

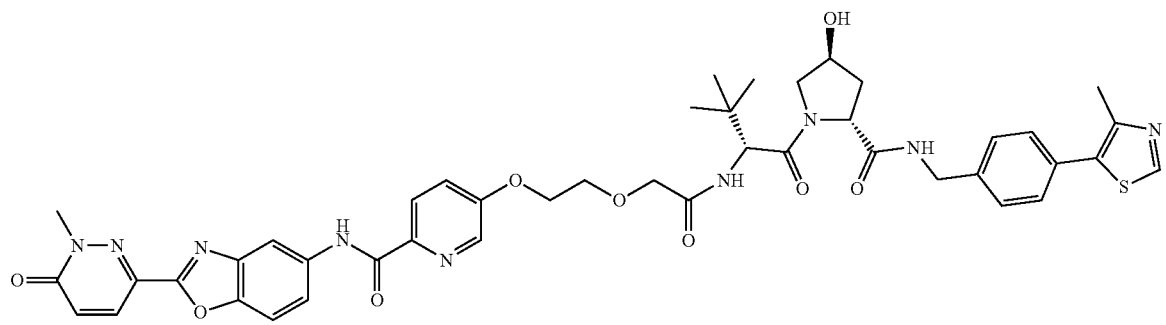

Step 1: 5-Hydroxy-N-[2-(1-methyl-6-oxo-1,6-dihydropyridazin-3-yl)-1,3-benzoxazol-5-yl]pyridine-2-carboxamide 6-(5-Amino-1,3-benzoxazol-2-yl)-2-methyl-pyridazin-3-one (200 mg, 0.83 mmol) and 5-hydroxypyridine-2-carboxylic acid (115 mg, 0.83 mmol) were combined in DMF (5 mL) and cooled to 0° C. N-Ethyl-N-(propan-2-yl)propan-2-amine (160 μL, 0.91 mmol) was added followed by HATU (380 mg, 0.99 mmol). The reaction was allowed to warm to rt overnight. Water was added slowly to induce precipitation. The resulting precipitate was isolated on filter paper and dried under vacuum to give the title compound. $^1$H NMR (500 MHz, DMSO-d6) δ 10.65 (s, 1H), 8.45 (d, J=2.0 Hz, 1H), 8.26 (d, J=2.7 Hz, 1H), 8.19 (d, J=9.7 Hz, 1H), 8.07 (d, J=8.6 Hz, 1H), 7.97 (dd, J=8.9, 2.0 Hz, 1H), 7.81 (d, J=8.9 Hz, 1H), 7.38 (dd, J=8.6, 2.7 Hz, 1H), 7.15 (d, J=9.7 Hz, 1H), 3.82 (s, 3H).

Step 2: tert-Butyl 2-{2-[(6-{[2-(1-methyl-6-oxo-1,6-dihydropyridazin-3-yl)-1,3-benzoxazol-5-yl]carbamoyl}pyridin-3-yl)oxy]ethoxy}acetate 5-Hydroxy-N-[2-(1-methyl-6-oxo-1,6-dihydropyridazin-3-yl)-1,3-benzoxazol-5-yl]pyridine-2-carboxamide (282 mg, 0.78 mmol) and tert-butyl 2-(2-hydroxyethoxy)acetate (140 mg, 0.78 mmol) were suspended in THF (10 mL). Triphenylphosphine (300 mg, 1.16 mmol) was added in one portion and the suspension stirred for 10 min. After this time, DIAD (230 μl, 1.16 mmol) was added and the suspension stirred overnight. The solid was isolated on filter paper to give the title compound. $^1$H NMR (250 MHz, DMSO-d6) δ 10.75 (s, 1H), 8.49-8.41 (m, 2H), 8.22-8.14 (m, 2H), 8.00 (dd, J=9.0, 2.1 Hz, 1H), 7.83 (d, J=8.9 Hz, 1H), 7.66 (dd, J=8.7, 2.9 Hz, 1H), 7.15 (d, J=9.7 Hz, 1H), 4.33 (d, J=4.5 Hz, 2H), 4.09 (s, 2H), 3.88 (s, 2H), 3.82 (s, 3H), 1.44 (s, 8H).

Step 3: 2-{2-[(6-{[2-(1-Methyl-6-oxo-1,6-dihydro-pyridazin-3-yl)-1,3-benzoxazol-5-yl]carbamoyl}pyridin-3-yl)oxy]ethoxy}acetic acid tert-Butyl 2-{2-[(6-{[2-(1-methyl-6-oxo-1,6-dihydro-pyridazin-3-yl)-1,3-benzoxazol-5-yl]carbamoyl}pyridin-3-yl)oxy]ethoxy}acetate (150 mg, 0.29 mmol) was suspended in THF:Water (5 mL:2 mL). K$_2$CO$_3$ (80 mg, 0.58 mmol) was added and the reaction stirred rapidly at rt overnight. No conversion to the desired product was observed. The reaction was concentrated, suspended in DCM (10 mL) and TFA (2 mL) added and the reaction stirred overnight. The reaction was concentrated then purified directly by acidic prep-HPLC to give the title compound. $^1$H NMR (500 MHz, DMSO-d6) δ 10.75 (s, 1H), 8.45 (dd, J=14.4, 2.4 Hz, 2H), 8.18 (dd, J=15.4, 9.2 Hz, 2H), 8.00 (dd, J=8.9, 2.1 Hz, 1H), 7.83 (d, J=8.9 Hz, 1H), 7.66 (dd, J=8.8, 2.9 Hz, 1H), 7.16 (d, J=9.7 Hz, 1H), 4.39-4.30 (m, 2H), 4.11 (s, 2H), 3.89 (dd, J=5.2, 3.6 Hz, 2H), 3.82 (s, 3H).

Step 4: 5-[2-({[(2R)-1-[(2R,4S)-4-Hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethoxy]-N-[2-(1-methyl-6-oxo-1,6-dihydropyridazin-3-yl)-1,3-benzoxazol-5-yl]pyridine-2-carboxamide (Compound 51)

(2R,4S)-1-[(2R)-2-amino-3,3-dimethylbutanoyl]-4-hydroxy-N-{[4-(4-methyl-1,3-thiazol-5-yl)phenyl]methyl}pyrrolidine-2-carboxamide (11 mg, 0.03 mmol) and 2-{2-[(6-{[2-(1-methyl-6-oxo-1,6-dihydropyridazin-3-yl)-1,3-benzoxazol-5-yl]carbamoyl}pyridin-3-yl)oxy]ethoxy}acetic acid (12 mg, 0.03 mmol) were combined in DMF (1 mL). DIPEA (15 μL, 0.08 mmol) was added followed by HATU (12 mg, 0.03 mmol). The reaction was stirred overnight then purified directly by basic prep-HPLC to give the title compound. $^1$H NMR (500 MHz, DMSO-d6) δ 10.67 (s, 1H), 8.94 (s, 1H), 8.59 (t, J=6.0 Hz, 1H), 8.50 (d, J=2.9 Hz, 1H), 8.41 (d, J=2.0 Hz, 1H), 8.19-8.15 (m, 1H), 8.13 (d, J=8.7 Hz, 1H), 7.93 (dd, J=8.9, 2.1 Hz, 1H), 7.79 (d, J=8.9 Hz, 1H), 7.70 (dd, J=8.8, 2.8 Hz, 1H), 7.53 (d, J=9.6 Hz, 1H), 7.42 (d, J=8.3 Hz, 2H), 7.39-7.35 (m, 2H), 7.14 (d, J=9.7 Hz, 1H), 5.17 (d, J=3.5 Hz, 1H), 4.62 (d, J=9.6 Hz, 1H), 4.51-4.26 (m, 6H), 4.09 (s, 2H), 3.92 (t, J=4.4 Hz, 2H), 3.81 (s, 3H), 3.70 (dd, J=10.6, 4.0 Hz, 1H), 3.62 (d, J=10.8 Hz, 1H), 2.40 (s, 3H), 2.12-2.04 (m, 1H), 1.92 (ddd, J=13.0, 8.8, 4.5 Hz, 1H), 0.96 (d, J=9.4 Hz, 9H). Tr(METCR1603 High pH 7 min)=3.82 min, (ES$^+$) (M+H)$^+$ 878.

Example 3

Scheme for Example 3

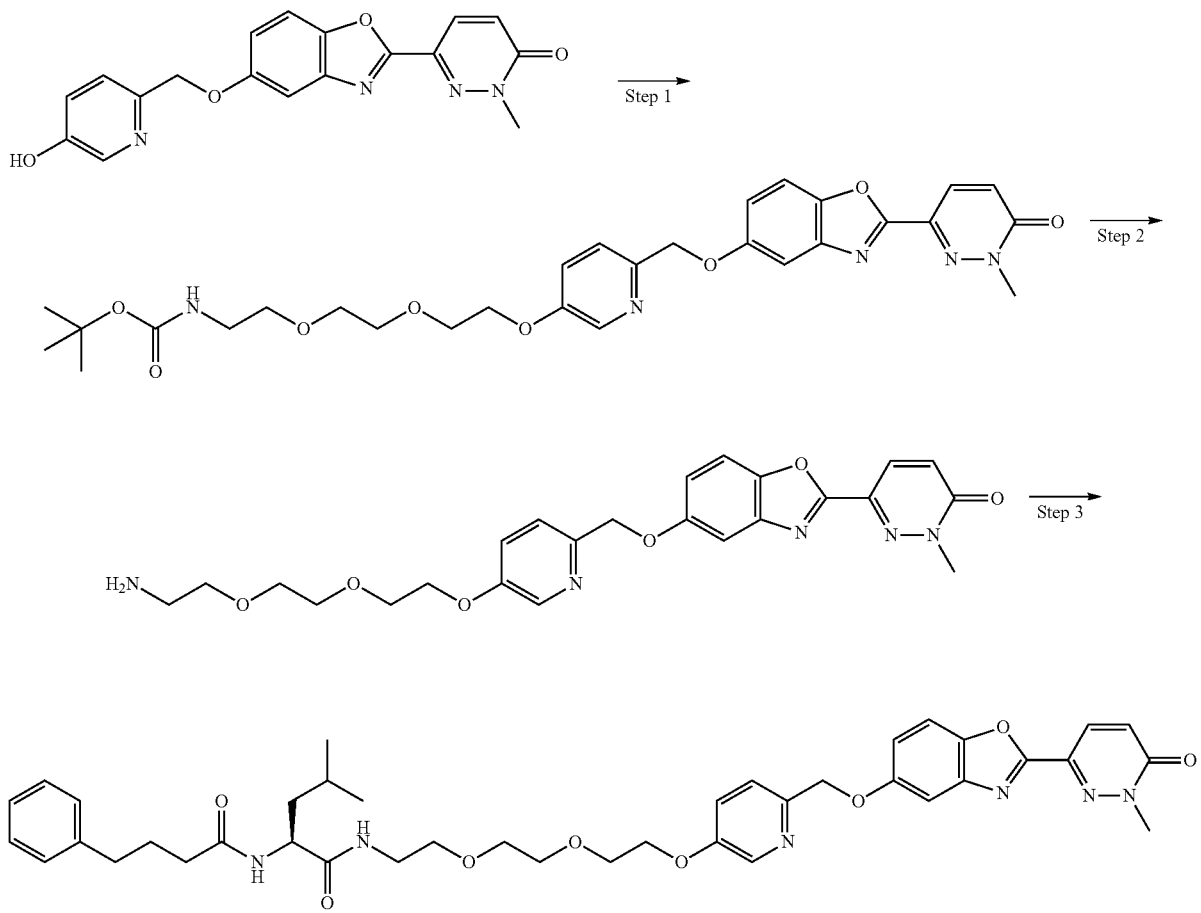

Step 1: tert-Butyl N-{2-[2-(2-{[6-({[2-(1-methyl-6-oxo-1,6-dihydropyridazin-3-yl)-1,3-benzoxazol-5-yl]oxy}methyl)pyridin-3-yl]oxy}ethoxy)ethoxy]ethyl}carbamate DIAD (68 μL, 0.344 mmol) was added to a solution of tert-butyl N-{2-[2-(2-hydroxyethoxy)ethoxy]ethyl}carbamate (57 mg, 0.229 mmol), 6-{5-[(5-hydroxypyridin-2-yl)methoxy]-1,3-benzoxazol-2-yl}-2-methyl-2,3-dihydropyridazin-3-one (110 mg, 0.229 mmol) and Ph₃P (90 mg, 0.344 mmol) in DMF (0.8 mL). The resulting mixture was stirred at rt for 36 h then evaporated to dryness, adsorbed on silica and purified by FCC (silica, 0-10% MeOH in DCM) to give the title compound. ¹H NMR (500 MHz, Chloroform-d) δ 8.34 (d, J=2.8 Hz, 1H), 8.11 (d, J=9.7 Hz, 1H), 7.49-7.41 (m, 2H), 7.33 (d, J=2.5 Hz, 1H), 7.29-7.26 (m, 1H), 7.11 (dd, J=9.0, 2.5 Hz, 1H), 7.06 (d, J=9.7 Hz, 1H), 5.20 (s, 2H), 5.03 (s, 1H), 4.19 (dd, J=5.6, 3.9 Hz, 2H), 3.94 (s, 3H), 3.89-3.83 (m, 2H), 3.77-3.50 (m, 6H), 3.31 (q, J=5.7 Hz, 2H), 1.42 (s, 9H). Tr(METCR1603)=4.13 min, (ES)+[M+H]⁺ 582.

Step 2: 6-{5-[(5-{2-[2-(2-Aminoethoxy)ethoxy]ethoxy}pyridin-2-yl)methoxy]-1,3-benzoxazol-2-yl}-2-methyl-2,3-dihydropyridazin-3-one HCl (4N in dioxane, 1.50 mL, 6.00 mmol) was added to a solution of tert-butyl N-{2-[2-(2-{[6-({[2-(1-methyl-6-oxo-1,6-dihydropyridazin-3-yl)-1,3-benzoxazol-5-yl]oxy}methyl)pyridin-3-yl]oxy}ethoxy)ethoxy]ethyl}carbamate (19%, 256 mg, 0.084 mmol) in MeOH (0.5 mL). The mixture was stirred at rt for 2 h and then partitioned between DCM and 2N HCl (aq). The organic layer was extracted once more with 2N HCl. The combined aqueous layers were neutralized with Na₂CO₃ and then extracted with DCM (3×). The combined organic layers were dried over MgSO₄, filtered and evaporated to dryness to give the title compound. ¹H NMR (250 MHz, Chloroform-d) δ 8.34 (d, J=2.9 Hz, 1H), 8.11 (d, J=9.7 Hz, 1H), 7.52 (d, J=9.0 Hz, 1H), 7.44 (d, J=8.6 Hz, 1H), 7.33 (d, J=2.5 Hz, 1H), 7.31-7.24 (m, 1H), 7.12 (dd, J=9.0, 2.5 Hz, 1H), 7.06 (d, J=9.7 Hz, 1H), 5.20 (s, 2H), 4.27-4.15 (m, 2H), 3.95 (s, 3H), 3.88 (dd, J=5.6, 3.8 Hz, 2H), 3.79-3.50 (m, 6H), 2.94-2.83 (m, 2H). Tr(METCR1410)=0.90 min, (ES)⁺ [M+H]⁺ 482.

Step 3: (2S)-4-Methyl-N-{2-[2-(2-{[6-({[2-(1-methyl-6-oxo-1,6-dihydropyridazin-3-yl)-1,3-benzoxazol-5-yl]oxy}methyl)pyridin-3-yl]oxy}ethoxy)ethoxy]ethyl}-2-(4-phenylbutanamido)pentanamide (Compound 52)

DIPEA (61 μL, 0.351 mmol) was added to a solution of 6-{5-[(5-{2-[2-(2-aminoethoxy)ethoxy]ethoxy}pyridin-2-yl)methoxy]-1,3-benzoxazol-2-yl}-2-methyl-2,3-dihydropyridazin-3-one (65%, 40 mg, 0.054 mmol), N-(4-phenylbutanoyl)-L-leucine (15 mg, 0.054 mmol), EDC.HCl (41 mg, 0.216 mmol) and HOBT (19 mg, 0.121 mmol) cooled to 0° C. The reaction was stirred at rt monitoring by LCMS. After 7 h the reaction was partitioned between water and EtOAc. The organic layer was washed with 10% citric acid solution (aq), sat NaHCO₃(aq) and brine. The organic phase was dried over MgSO₄, filtered and evaporated to dryness. The resulting residue was purified by acidic prep HPLC to give the title compound. ¹H NMR (500 MHz, Methanol-d4) δ 8.28 (d, J=2.8 Hz, 1H), 8.21 (d, J=9.7 Hz, 1H), 7.60 (d, J=9.0 Hz, 1H), 7.55 (d, J=8.6 Hz, 1H), 7.47 (dd, J=8.6, 2.9 Hz, 1H), 7.37 (d, J=2.5 Hz, 1H), 7.27-7.09 (m, 7H), 5.19 (s, 2H), 4.38 (t, J=7.6 Hz, 1H), 4.25-4.20 (m, 2H), 3.91 (s, 3H), 3.86-3.82 (m, 2H), 3.70-3.65 (m, 2H), 3.64-3.57 (m, 2H), 3.52 (t, J=5.5 Hz, 2H), 3.40-3.32 (m, 2H), 2.63-2.53 (m, 2H), 2.24 (t, J=7.5 Hz, 2H), 1.96-1.83 (m, 2H), 1.64 (dp, J=13.3, 6.6 Hz, 1H), 1.54 (dd, J=8.0, 6.6 Hz, 2H), 0.93 (d, J=6.6 Hz, 3H), 0.90 (d, J=6.6 Hz, 3H). Tr(METCR1603)=4.41 min, (ES)⁺ [M+H]⁺ 741.

Example 4

Scheme for Example 4

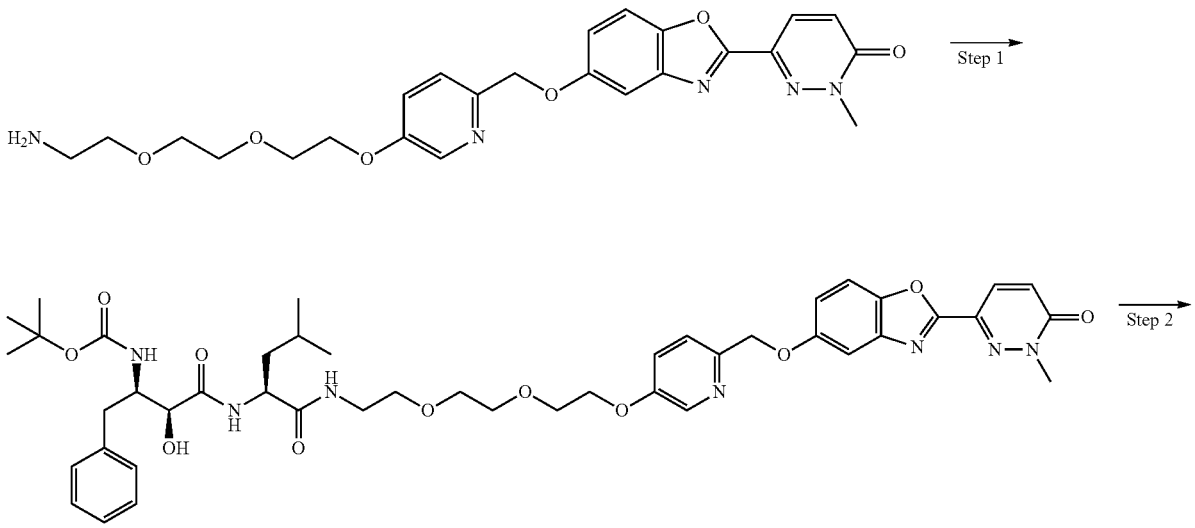

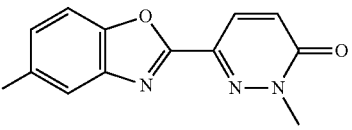

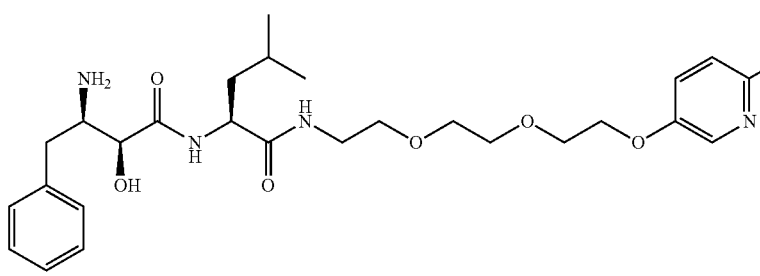

Step 1: (2S)-4-Methyl-N-{2-[2-(2-{[6-({[2-(1-methyl-6-oxo-1,6-dihydropyridazin-3-yl)-1,3-benzoxazol-5-yl]oxy}methyl)pyridin-3-yl]oxy}ethoxy)ethoxy]ethyl}-2-(4-phenylbutanamido)pentanamide DIPEA (61 μL, 0.350 mmol) was added to a solution of 6-{5-[(5-{2-[2-(2-aminoethoxy)ethoxy]ethoxy}pyridin-2-yl)methyl]-1,3-benzoxazol-2-yl}-2-methyl-2,3-dihydropyridazin-3-one (74%, 35 mg, 0.054 mmol), (2S)-2-[[(2S, 3R)-3-(tert-butoxycarbonylamino)-2-hydroxy-4-phenylbutanoyl]amino]-4-methyl-pentanoic acid (23 mg, 0.054 mmol), EDC.HCl (41 mg, 0.215 mmol) and HOBT (19 mg, 0.121 mmol) cooled to 0° C. The solution was then allowed to warm to rt for 18 h. After this time, the reaction mixture was partitioned between water and EtOAc. The organic layer was washed with 10% citric acid solution (aq), sat NaHCO₃(aq) and brine before being dried over MgSO₄, filtered and evaporated to dryness. The crude residue was purified by acidic prep HPLC to give the title compound. ¹H NMR (500 MHz, Chloroform-d) δ 8.37 (d, J=2.8 Hz, 1H), 8.09 (d, J=9.7 Hz, 1H), 7.52 (d, J=8.9 Hz, 1H), 7.44 (d, J=8.6 Hz, 1H), 7.33-7.16 (m, 8H), 7.10 (dd, J=8.9, 2.5 Hz, 1H), 7.05 (d, J=9.7 Hz, 1H), 6.83 (s, 1H), 5.84 (s, 1H), 5.38 (d, J=8.1 Hz, 1H), 5.16 (d, J=12.7 Hz, 1H), 5.12 (d, J=12.7 Hz, 1H), 4.45 (td, J=9.0, 5.2 Hz, 1H), 4.28-4.16 (m, 2H), 4.13 (d, J=2.6 Hz, 1H), 4.03 (d, J=8.3 Hz, 1H), 3.95 (s, 3H), 3.85 (ddt, J=5.0, 4.0, 1.8 Hz, 2H), 3.68 (dd, J=5.2, 3.9 Hz, 2H), 3.65-3.58 (m, 2H), 3.54 (t, J=5.2 Hz, 2H), 3.41 (t, J=5.4 Hz, 2H), 3.16-3.07 (m, 1H), 3.01-2.94 (m, 1H), 1.72-1.53 (m, 3H), 1.36 (s, 9H), 0.90 (d, J=6.2 Hz, 3H), 0.86 (d, J=6.2 Hz, 3H). Tr(MET-uHPLC-AB-101)=3.52 min, (ES)⁺ [M+H]⁺ 872.

Step 2: (2S)-2-[(2S,3R)-3-Azaniumyl-2-hydroxy-4-phenylbutanamido]-4-methyl-N-{2-[2-(2-{[6-({[2-(1-methyl-6-oxo-1,6-dihydropyridazin-3-yl)-1,3-benzoxazol-5-yl]oxy}methyl)pyridin-3-yl]oxy}ethoxy)ethoxy]ethyl}pentanamide formate (Compound 49)

HCl (4N in Dioxane, 200 μL, 0.800 mmol) was added dropwise to a solution of (2S)-4-methyl-N-{2-[2-(2-{[6-({[2-(1-methyl-6-oxo-1,6-dihydropyridazin-3-yl)-1,3-benzoxazol-5-yl]oxy}methyl)pyridin-3-yl]oxy}ethoxy)ethoxy]ethyl}-2-(4-phenylbutanamido)pentanamide (12 mg, 0.014 mmol) in MeOH (0.15 mL) stirred at rt. After 3.5 h the reaction was evaporated to dryness and the residue partitioned between EtOAc and sat NaHCO₃(aq). The aqueous layer was extracted twice with EtOAc. Combined organic layers were dried over MgSO₄, filtered and evaporated to dryness. The crude was purified by acidic prep HPLC to give the title compound. ¹H NMR (500 MHz, Methanol-d4) δ 8.43 (s, 1H), 8.29 (d, J=2.8 Hz, 1H), 8.19 (d, J=9.7 Hz, 1H), 7.59 (d, J=9.0 Hz, 1H), 7.55 (d, J=8.6 Hz, 1H), 7.47 (dd, J=8.6, 2.9 Hz, 1H), 7.38-7.23 (m, 6H), 7.17 (dd, J=9.0, 2.5 Hz, 1H), 7.12 (d, J=9.7 Hz, 1H), 5.18 (s, 2H), 4.37 (dd, J=8.6, 6.3 Hz, 1H), 4.26-4.19 (m, 2H), 4.12 (d, J=3.1 Hz, 1H), 3.90 (s, 3H), 3.85 (dd, J=3.9, 2.3 Hz, 2H), 3.75 (td, J=7.6, 3.1 Hz, 1H), 3.71-3.65 (m, 2H), 3.64-3.57 (m, 2H), 3.52 (t, J=5.5 Hz, 2H), 3.42-3.35 (m, 1H), 3.34-3.31 (m, 1H), 3.09 (dd, J=13.9, 7.9 Hz, 1H), 2.90 (dd, J=13.9, 7.1 Hz, 1H), 1.88-1.47 (m, 3H), 0.94 (d, J=6.3 Hz, 3H), 0.92 (d, J=6.4 Hz, 3H). Tr(METCR1603)=4.01 min, (ES)⁺ [M+H]⁺ 772.

Example 5

Scheme for Example 5

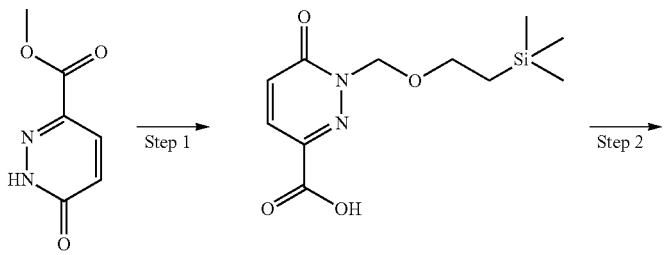

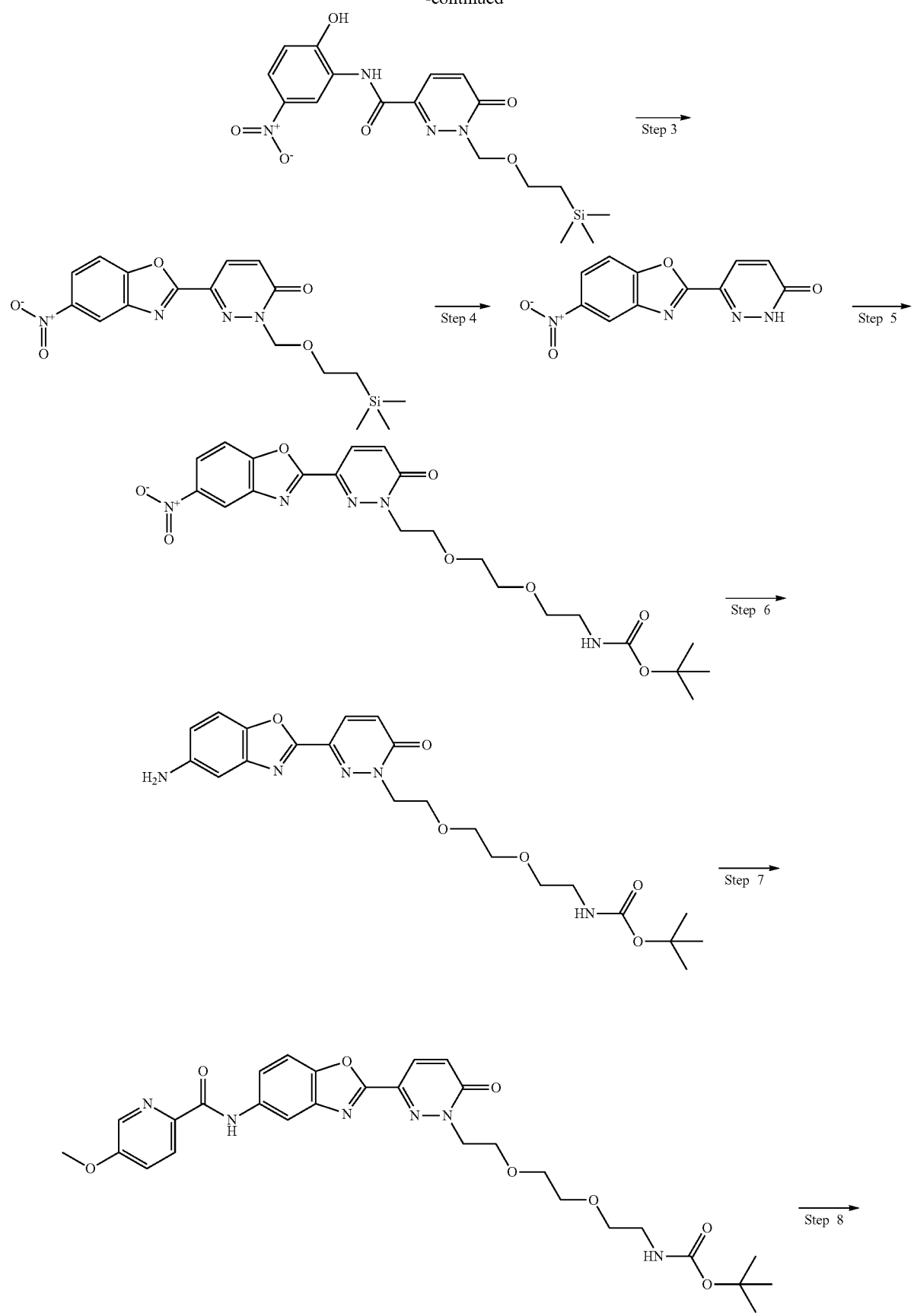

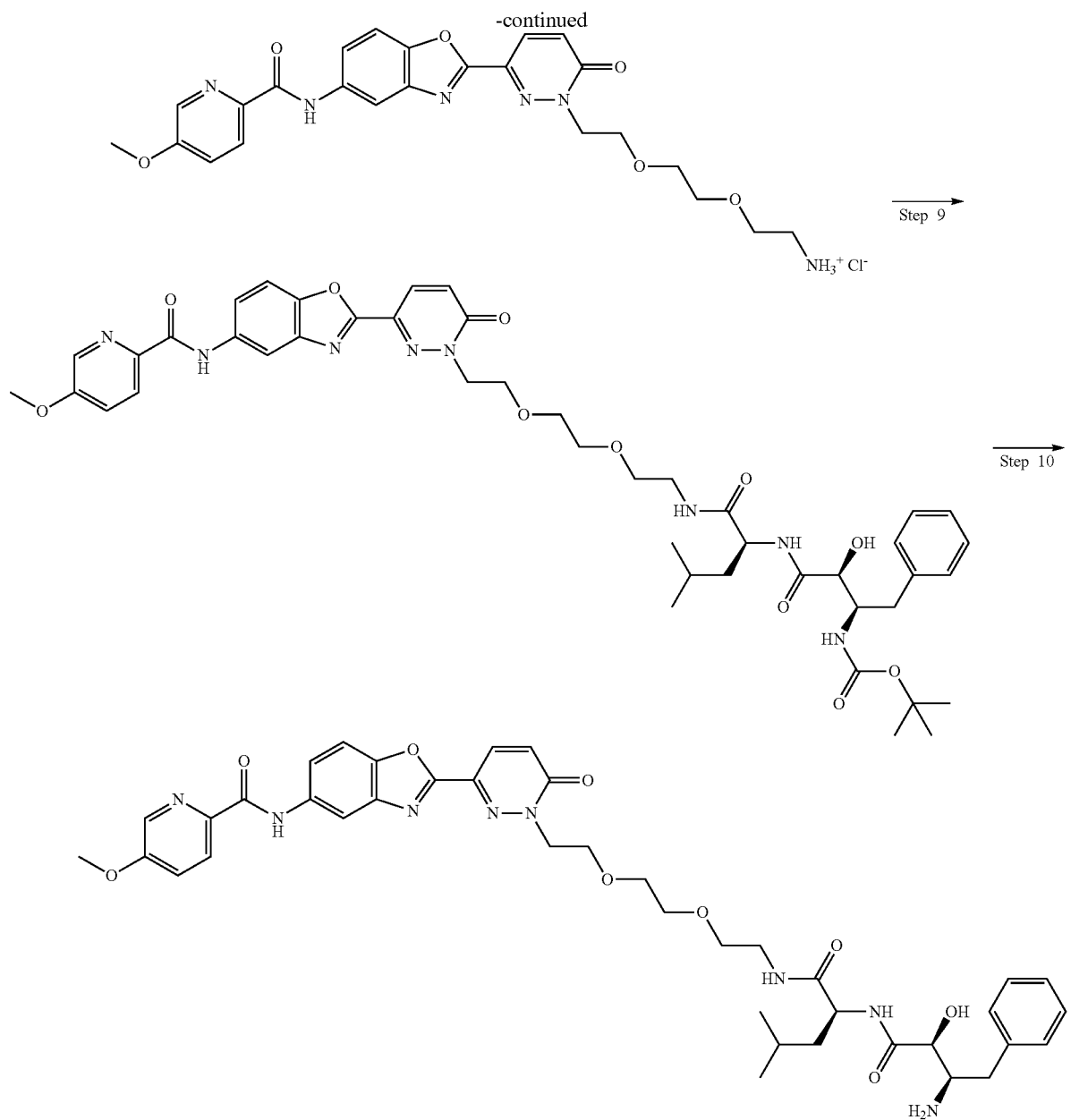

Step 1: 6-Oxo-1-{[2-(trimethylsilyl)ethoxy]methyl}-1,6-dihydropyridazine-3-carboxylic acid Methyl 6-oxo-1,6-dihydropyridazine-3-carboxylate (2.00 g, 12.98 mmol) was dissolved in dry DMF (17.5 mL), cooled to 0° C. and sodium hydride (60% dispersion in mineral oil, 779 mg, 19.46 mmol) was added portion wise. The reaction was stirred at 0° C. for 5 min then [2-(chloromethoxy)ethyl]trimethylsilane (2.76 mL, 15.57 mmol) was added over 5 min and the resulting mixture was stirred at 0° C. for 1 h. The reaction mixture was then poured onto ice cold water and extracted with DCM. The aqueous layer was acidified to ~pH 4 and extracted with DCM (3x). The organic layers from both extractions were combined and evaporated to dryness to give a dark red crude oil, which was dissolved in water:MeOH mixture (1:1, 30 mL) and treated with LiOH.H$_2$O (653 mg, 15.57 mmol). The reaction was stirred at rt for 1 h, then concentrated to a reduced volume and acidified with a 10% solution of citric acid (aq) to pH ~4. The aqueous phase was extracted with DCM and the combined extracts were washed with brine, dried over Na$_2$SO$_4$, filtered and evaporated to dryness to give the title compound. $^1$H NMR (250 MHz, DMSO-d6) δ 7.84 (d, J=9.7 Hz, 1H), 7.03 (d, J=9.7 Hz, 1H), 5.38 (s, 2H), 3.77-3.55 (m, 2H), 0.97-0.81 (m, 2H), −0.04 (s, 9H). Tr(METCR1410)=1.03 min, (ES$^+$) [M+Na]$^+$ 293.

Step 2: N-(2-Hydroxy-5-nitrophenyl)-6-oxo-1-{[2-(trimethylsilyl)ethoxy]methyl}-1,6-dihydropyridazine-3-carboxamide 2-Amino-4-nitrophenol (500 mg, 3.244 mmol) and 1-methyl-6-oxo-1,6-dihydropyridazine-3-carboxylic acid (1.06 g, 13.569 mmol) were combined in pyridine (8 mL)

and stirred until dissolved. EDC-HCl (808 mg, 4.22 mmol) was added in one portion and the reaction stirred overnight. Water was added to the reaction mixture and the solid that precipitated was filtered and washed with water. The crude residue was partitioned between water and EtOAc. The aqueous layer was extracted with EtOAc (3×15 mL) and the combined organic layers were washed with brine, dried over MgSO$_4$, filtered and evaporated to dryness. The solid was further purified by FCC (silica, 0-10% MeOH in DCM) to give the title compound. $^1$H NMR (250 MHz, Chloroform-d) δ 9.34 (s, 1H), 8.41 (d, J=2.7 Hz, 1H), 8.06 (dd, J=9.0, 2.7 Hz, 1H), 8.04 (d, J=9.7 Hz, 1H), 7.10 (d, J=9.8 Hz, 1H), 7.09 (d, J=9.1 Hz, 1H), 5.59 (s, 2H), 3.95-3.64 (m, 2H), 1.13-0.88 (m, 2H), 0.02 (s, 9H). Tr(METCR1410)=1.16 min, no ionization in ES$^+$.

Step 3: 6-(5-Nitro-1,3-benzoxazol-2-yl)-2-{[2-(trimethylsilyl)ethoxy]methyl}-2,3-dihydropyridazin-3-one N-(2-Hydroxy-5-nitrophenyl)-6-oxo-1-{[2-(trimethylsilyl)ethoxy]methyl}-1,6-dihydropyridazine-3-carboxamide (600 mg, 1.476 mmol), triphenylphosphine (774 mg, 2.952 mmol) and hexachloroethane (874 mg, 3.690 mmol) were suspended in DCM (30 mL) at rt. Triethylamine (823 μL, 5.904 mmol) was added and the reaction stirred at rt for 1.5 h. The reaction was diluted with DCM and washed with water and brine. The organic layer was dried over MgSO$_4$, filtered and adsorbed on silica. The crude was purified by FCC (silica, 0-50% EtOAc in Heptane) to give the title compound. $^1$H NMR (250 MHz, Chloroform-d) δ 8.70 (dd, J=2.3, 0.5 Hz, 1H), 8.40 (dd, J=9.0, 2.3 Hz, 1H), 8.15 (d, J=9.8 Hz, 1H), 7.76 (dd, J=9.0, 0.5 Hz, 1H), 7.12 (d, J=9.8 Hz, 1H), 5.63 (s, 2H), 3.89-3.66 (m, 2H), 1.15-0.90 (m, 2H), 0.01 (s, 9H). Tr(METCR1410)=1.34 min, (ES$^+$) [M+Na]$^+$ 411.

Step 4: 6-(5-Nitro-1,3-benzoxazol-2-yl)-2,3-dihydropyridazin-3-one

TFA (1.00 mL, 13.06 mmol) was added dropwise to a solution of 6-(5-nitro-1,3-benzoxazol-2-yl)-2-{[2-(trimethylsilyl)ethoxy]methyl}-2,3-dihydropyridazin-3-one (100 mg, 0.257 mmol) in DCM (10 mL) and the mixture was stirred at rt overnight. The reaction was quenched with a saturated solution of NaHCO$_3$(aq). The organic solvent was removed in vacuo and the yellow solid that precipitated was triturated in the aqueous solution for 5 min then collected by filtration. The solid was then dried at 40° C. under vacuum for 5 h to give the title compound. $^1$H NMR (250 MHz, DMSO-d6) δ 13.80 (s, 1H), 8.72 (d, J=2.3 Hz, 1H), 8.39 (dd, J=9.0, 2.4 Hz, 1H), 8.14 (d, J=9.9 Hz, 1H), 8.08 (d, J=9.0 Hz, 1H), 7.10 (d, J=9.9 Hz, 1H). Tr(METCR1600)=2.38 min, (ES)$^+$ [M+H]$^+$ 259.

Step 5: tert-Butyl N-[2-(2-{2-[3-(5-nitro-1,3-benzoxazol-2-yl)-6-oxo-1,6-dihydropyridazin-1-yl]ethoxy}ethoxy)ethyl]carbamate K$_2$CO$_3$ (33 mg, 0.241 mmol) was added in one portion to a suspension of tert-butyl N-{2-[2-(2-iodoethoxy)ethoxy]ethyl}carbamate (75 mg, 0.209 mmol) and 6-(5-nitro-1,3-benzoxazol-2-yl)-2,3-dihydropyridazin-3-one (41 mg, 0.161 mmol) in DMF (1.5 mL). The reaction mixture was stirred at rt for 22 h and then partitioned between water and EtOAc. The layers were separated and the aqueous phase was extracted with EtOAc (3×15 mL). The combined organic layers were washed with brine, dried over MgSO$_4$, filtered and evaporated to dryness. The crude was purified by FCC (silica, 0-5% MeOH in DCM) to give the title compound. $^1$H NMR (250 MHz, Chloroform-d) δ 8.67 (dd, J=2.3, 0.5 Hz, 1H), 8.37 (dd, J=9.0, 2.3 Hz, 1H), 8.13 (d, J=9.7 Hz, 1H), 7.75 (dd, J=9.0, 0.5 Hz, 1H), 7.09 (d, J=9.8 Hz, 1H), 5.01 (s, 1H), 4.54 (t, J=5.7 Hz, 2H), 3.98 (t, J=5.7 Hz, 2H), 3.68-3.53 (m, 4H), 3.47 (t, J=5.1 Hz, 2H), 3.25 (t, J=6.8 Hz, 2H), 1.41 (s, 9H). Tr(METCR1410)=1.15 min, (ES)$^+$ [M-BOC]$^+$ 390.

Step 6: tert-Butyl N-[2-(2-{2-[3-(5-amino-1,3-benzoxazol-2-yl)-6-oxo-1,6-dihydropyridazin-1-yl]ethoxy}ethoxy)ethyl]carbamate Iron powder (96 mg, 1.716 mmol) was added to a solution of NH$_4$C$_1$ (115 mg, 2.145 mmol) and tert-butyl N-[2-(2-{2-[3-(5-nitro-1,3-benzoxazol-2-yl)-6-oxo-1,6-dihydropyridazin-1-yl]ethoxy}ethoxy)ethyl]carbamate (210 mg, 0.429 mmol) in EtOH (10 mL) and water (1 mL). The mixture was heated to reflux for 3 h, then cooled to rt and filtered through celite. The filtrate was evaporated to dryness and the residue was diluted with EtOAc/water and extracted with EtOAc (3×15 mL). The combined organic layers were dried over MgSO$_4$, filtered and evaporated to dryness to give the title compound. $^1$H NMR (250 MHz, Chloroform-d) δ 8.10 (d, J=9.8 Hz, 1H), 7.40 (d, J=8.7 Hz, 1H), 7.15-6.89 (m, 2H), 6.77 (dd, J=8.7, 2.3 Hz, 1H), 5.05 (s, 1H), 4.53 (t, J=5.8 Hz, 2H), 3.98 (t, J=5.8 Hz, 2H), 3.65-3.43 (m, 6H), 3.27 (q, J=4.5, 3.2 Hz, 2H), 1.43 (s, 9H). Tr(METCR1410)=0.93 min, (ES)$^+$ [M+H]$^+$ 460.

Step 7: tert-Butyl N-{2-[2-(2-{3-[5-(5-methoxypyridine-2-amido)-1,3-benzoxazol-2-yl]-6-oxo-1,6-dihydropyridazin-1-yl}ethoxy)ethoxy]ethyl}carbamate To a stirred solution of DIPEA (197 μL, 1.132 mmol), tert-butyl N-[2-(2-{2-[3-(5-amino-1,3-benzoxazol-2-yl)-6-oxo-1,6-dihydropyridazin-1-yl]ethoxy}ethoxy)ethyl]carbamate (204 mg, 0.377 mmol) and 5-methoxypyridine-2-carboxylic acid (61 mg, 0.377 mmol) in THF (6 mL) at 0° C., was added HATU (172 mg, 0.453 mmol). The mixture was allowed to stir at rt for 6 h. After which time, the reaction was extracted into EtOAc (15 mL) and washed successively with a solution of 10% citric acid (aq), a saturated solution of NaHCO$_3$(aq) and brine. The organic layer was dried over MgSO$_4$, filtered and evaporated to dryness. The crude was purified by FCC (silica, 0-4% MeOH in DCM) to give the title compound. $^1$H NMR (500 MHz, Chloroform-d) δ 9.99 (s, 1H), 8.38-8.23 (m, 3H), 8.16 (d, J=9.7 Hz, 1H), 7.76 (dd, J=8.9, 2.1 Hz, 1H), 7.61 (d, J=8.8 Hz, 1H), 7.36 (dd, J=8.7, 2.9 Hz, 1H), 7.07 (d, J=9.7 Hz, 1H), 5.06 (s, 1H), 4.55 (t, J=5.8 Hz, 2H), 4.00 (t, J=5.9 Hz, 2H), 3.96 (s, 3H), 3.70-3.66 (m, 2H), 3.59 (dd, J=5.8, 3.5 Hz, 2H), 3.50 (t, J=5.2 Hz, 2H), 3.27 (dd, J=8.7, 4.7 Hz, 2H), 1.43 (s, 9H). Tr(METCR1410)=1.18 min, (ES)$^+$ [M+H]$^+$ 595.

Step 8: N-[2-(1-{2-[2-(2-Azaniumylethoxy)ethoxy]ethyl}-6-oxo-1,6-dihydropyridazin-3-yl)-1,3-benzoxazol-5-yl]-5-methoxypyridine-2-carboxamide chloride HCl (4 N in dioxane, 1.50 mL, 6.00 mmol) was added dropwise to a solution of tert-butyl N-{2-[2-(2-{3-[5-(5-methoxypyridine-2-amido)-1,3-benzoxazol-2-yl]-6-oxo-1,6-dihydropyridazin-1-yl}ethoxy)ethoxy]ethyl}carbamate (65 mg, 0.109 mmol) in MeOH (0.5 mL) and stirred at rt for 4 h. After which time, the reaction was evaporated to dryness to give the title compound. ¹H NMR (500 MHz, DMSO-d6) δ 10.74 (s, 1H), 8.47 (d, J=2.0 Hz, 1H), 8.41 (d, J=2.8 Hz, 1H), 8.19 (d, J=9.6 Hz, 1H), 8.17 (d, J=8.7 Hz, 1H), 8.00 (dd, J=8.9, 2.1 Hz, 1H), 7.83 (d, J=8.9 Hz, 1H), 7.80 (s, 3H), 7.64 (dd, J=8.7, 2.9 Hz, 1H), 7.17 (d, J=9.7 Hz, 1H), 4.40 (t, J=5.7 Hz, 2H), 3.95 (s, 3H), 3.87 (t, J=5.7 Hz, 2H), 3.70-3.51 (m, 6H), 2.91 (q, J=5.5 Hz, 2H). Tr(METCR1410) =0.92 min, (ES)⁺ [M+H]⁺ 494.

Step 9: tert-Butyl N-[(1S,2R)-1-hydroxy-1-{[(1S)-1-({2-[2-(2-{3-[5-(5-methoxypyridine-2-amido)-1,3-benzoxazol-2-yl]-6-oxo-1,6-dihydropyridazin-1-yl}ethoxy)ethoxy]ethyl}carbamoyl)-3-methylbutyl]carbamoyl}-3-phenylpropan-2-yl]carbamate DIPEA (160 μL, 0.918 mmol) was added to a suspension of N-[2-(1-{2-[2-(2-azaniumylethoxy)ethoxy]ethyl}-6-oxo-1,6-dihydropyridazin-3-yl)-1,3-benzoxazol-5-yl]-5-methoxypyridine-2-carboxamide chloride (75 mg, 0.141 mmol), (2S)-2-[[(2S,3R)-3-(tert-butoxycarbonylamino)-2-hydroxy-4-phenyl-butanoyl]amino]-4-methyl-pentanoic acid (60 mg, 0.141 mmol), EDC.HCl (108 mg, 0.565 mmol) and HOBT (49 mg, 0.318 mmol) stirred at 0° C. The resulting mixture was stirred at 0° C. then allowed to warm to rt over 2 h. The reaction was partitioned between water and EtOAc. The organic layer was washed successively with a 10% citric acid solution (aq), a saturated solution of NaHCO₃(aq) and brine. The organic phase was dried over MgSO₄, filtered and evaporated to dryness to afford the title compound. ¹H NMR (500 MHz, Chloroform-d) δ 10.00 (s, 1H), 8.33-8.24 (m, 3H), 8.16 (d, J=9.7 Hz, 1H), 7.76 (dd, J=8.8, 2.2 Hz, 1H), 7.61 (d, J=8.7 Hz, 1H), 7.36 (dd, J=8.7, 2.9 Hz, 1H), 7.33 (d, J=8.8 Hz, 1H), 7.25-7.15 (m, 5H), 7.06 (d, J=9.7 Hz, 1H), 6.88 (s, 1H), 5.51 (s, 1H), 5.08 (d, J=8.6 Hz, 1H), 4.61-4.43 (m, 3H), 4.20-4.07 (m, 2H), 4.02-3.92 (m, 5H), 3.61 (d, J=4.4 Hz, 2H), 3.56-3.41 (m, 5H), 3.35-3.25 (m, 1H), 3.12-2.96 (m, 2H), 1.74 (td, J=8.7, 4.4 Hz, 1H), 1.63-1.52 (m, 2H), 1.36 (s, 9H), 0.93 (d, J=6.4 Hz, 3H), 0.90 (s, 3H). Tr(MET-uHPLC-AB-101)=3.79 min, (ES)⁺ [M+H]⁺ 885.

Step 10: N-(2-{1-[2-(2-{2-[(2S)-2-[(2S,3R)-3-Amino-2-hydroxy-4-phenylbutanamido]-4-methyl-pentanamido]ethoxy}ethoxy)ethyl]-6-oxo-1,6-dihydropyridazin-3-yl}-1,3-benzoxazol-5-yl)-5-methoxypyridine-2-carboxamide (Compound 50)

HCl (4 N in dioxane, 2.00 mL, 8.00 mmol) was added dropwise to a stirred suspension of tert-butyl N-[(1S,2R)-1-hydroxy-1-{[(1S)-1-({2-[2-(2-{3-[5-(5-methoxypyridine-2-amido)-1,3-benzoxazol-2-yl]-6-oxo-1,6-dihydropyridazin-1-yl}ethoxy)ethoxy]ethyl}carbamoyl)-3-methylbutyl]carbamoyl}-3-phenylpropan-2-yl]carbamate (98 mg, 0.099 mmol) in MeOH (1.0 mL). The mixture was stirred at rt for 2.5 h. After which time, the reaction was evaporated to dryness and purified by chiral prep HPLC (Methanol with Chiralcel OJ-H 25 cm column at 15 mL/min) to give the title compound. ¹H NMR (500 MHz, Methanol-d4) δ 8.38 (t, J=2.5 Hz, 2H), 8.23 (d, J=9.7 Hz, 1H), 8.19 (d, J=8.7 Hz, 1H), 7.77 (dd, J=8.8, 2.1 Hz, 1H), 7.69 (d, J=8.9 Hz, 1H), 7.55 (dd, J=8.7, 2.9 Hz, 1H), 7.31-7.10 (m, 6H), 4.50 (dd, J=6.2, 4.9 Hz, 2H), 4.40 (dd, J=9.1, 5.5 Hz, 1H), 4.01-3.95 (m, 5H), 3.93 (d, J=3.1 Hz, 1H), 3.69-3.59 (m, 2H), 3.57-3.49 (m, 2H), 3.45 (t, J=5.5 Hz, 2H), 3.28 (td, J=5.4, 2.5 Hz, 3H), 2.89 (dd, J=13.4, 6.9 Hz, 1H), 2.65 (dd, J=13.4, 7.8 Hz, 1H), 1.68-1.51 (m, 3H), 0.93 (d, J=6.1 Hz, 3H), 0.91 (d, J=6.2 Hz, 3H). Tr(METCR1603)=4.20 min, (ES)⁺ [M+H]⁺ 785.

Example 6

Scheme for Example 6

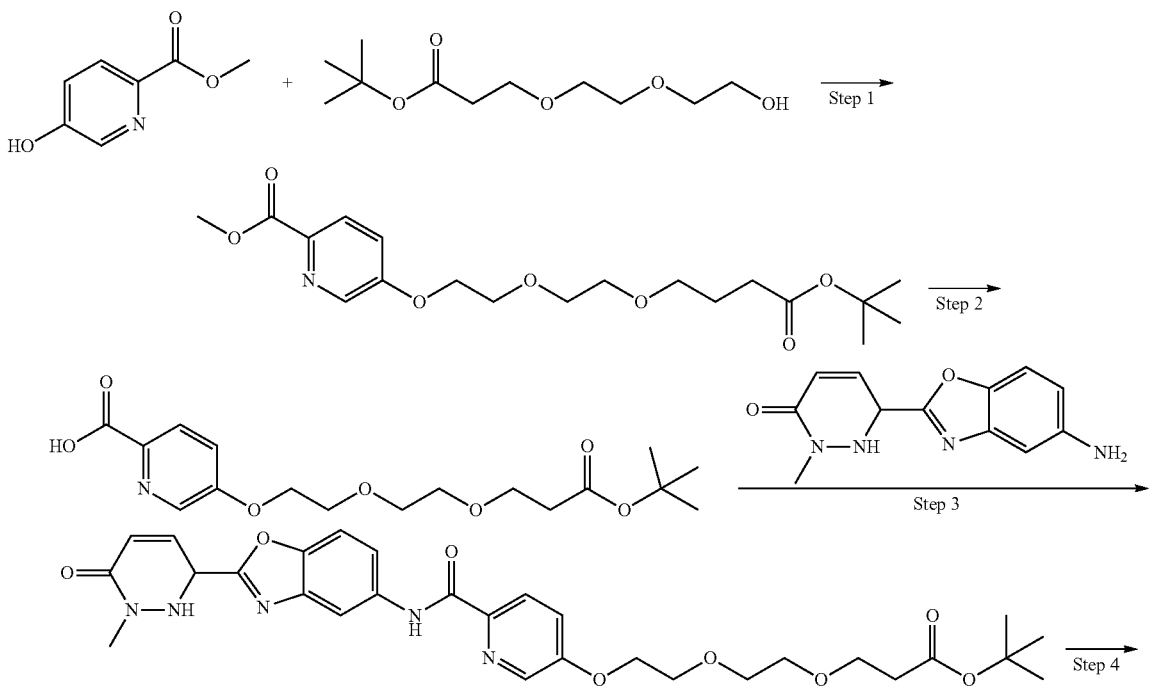

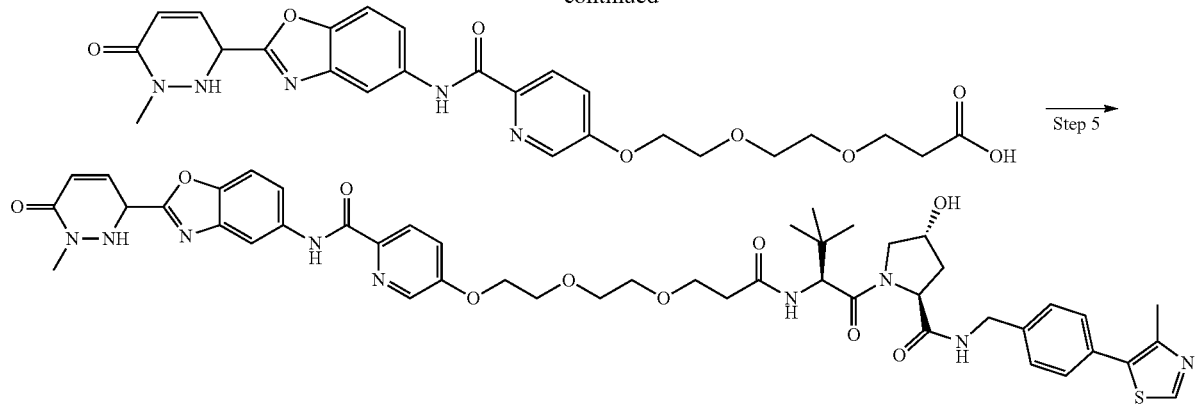

-continued

Step 1: Methyl 5-(2-{2-[3-(tert-butoxy)-3-oxo-propoxy]ethoxy}ethoxy)pyridine-2-carboxylate A solution of methyl 5-hydroxypyridine-2-carboxylate (400 mg, 2.61 mmol), tert-butyl 3-[2-(2-hydroxyethoxy)ethoxy]propanoate (673 mg, 2.87 mmol) in THF (15.0 mL) was cooled to 0° C. and treated with triphenylphosphine (1.03 g, 3.92 mmol). The reaction mixture was stirred for 20 minutes and then treated with DIAD (0.77 mL, 3.92 mmol) dropwise. The mixture was stirred at 0° C. for a further 30 minutes and then at rt overnight. After which time, the reaction mixture was concentrated to dryness and the crude was dissolved in EtOAc (100 mL). The organic layer was washed with water (30 mL) and brine (30 mL), dried over Na$_2$SO$_4$, filtered and evaporated under reduced pressure to give a brown oil, which was purified by FCC (silica, 10-45% EtOAc in heptanes) to give the title compound. $^1$H NMR (500 MHz, Chloroform-d) δ 8.41 (d, J=2.8 Hz, 1H), 8.10 (d, J=8.7 Hz, 1H), 7.28 (dd, J=8.7, 2.9 Hz, 1H), 4.25-4.21 (m, 2H), 3.97 (s, 3H), 3.90-3.87 (m, 2H), 3.73-3.69 (m, 4H), 3.63 (dd, J=5.7, 3.5 Hz, 2H), 2.49 (t, J=6.5 Hz, 2H), 1.44 (s, 9H). Tr (METCR1410)=1.08 min, (ES$^+$) [M+H]$^+$ 370.

Step 2: 5-(2-{2-[3-(tert-Butoxy)-3-oxopropoxy]ethoxy}ethoxy)pyridine-2-carboxylic acid To a solution of 2-(aminomethyl)-5-(4-methylthiazol-5-yl)phenol (400 mg, 0.563 mmol) in THF (3 mL) and MeOH (3 mL) was added 1 M NaOH (1.13 mL, 1.13. mmol) and the reaction was stirred at rt for 2.5 h. The reaction was neutralized with 1 M HCl (1.13 mL) at 0° C., and then the solvent was removed in vacuo. MeCN (2.0 mL) was added, and then crude product was purified by reverse phase chromatography (C-18, 10-100% MeCN/water+0.1% formic acid). The pure fractions were combined and the solvent was removed in vacuo to give the title compound. Tr (METCR1410)=0.96 min, (ES$^+$) [M+H]$^+$ 356.

Step 3: tert-Butyl 3-(2-{2-[(6-{[2-(1-methyl-6-oxo-1,6-dihydropyridazin-3-yl)-1,3-benzoxazol-5-yl]carbamoyl}pyridin-3-yl)oxy]ethoxy}ethoxy)propanoate A stirred solution of 5-(2-{2-[3-(tert-butoxy)-3-oxopropoxy]ethoxy}ethoxy)pyridine-2-carboxylic acid (175 mg, 0.49 mmol), HATU (224 mg, 0.59 mmol) in DMF (5 mL), at 0° C. under nitrogen, was treated with the dropwise addition of DIPEA (0.19 mL, 1.08 mmol). The reaction mixture was stirred at 0° C. for 15 min and then treated with 6-(5-amino-1,3-benzoxazol-2-yl)-2-methyl-pyridazin-3-one (120 mg, 0.49 mmol). The resulting mixture was stirred at 0° C. for 1 h and then at rt over the weekend. After which time, the reaction mixture was concentrated in vacuo and the residue was suspended in water (30 mL), and the suspension was stirred at rt for 30 min. The solid was filtered and washed with water and TBME (10 mL), and then dried in a high vacuum oven at 40° C. overnight to give the title compound. $^1$H NMR (500 MHz, DMSO-d6) δ 10.70 (s, 1H), 8.48-8.37 (m, 2H), 8.19-8.10 (m, 2H), 7.97 (d, J=8.5 Hz, 1H), 7.80 (d, J=8.8 Hz, 1H), 7.63 (d, J=6.4 Hz, 1H), 7.13 (d, J=9.7 Hz, 1H), 4.29 (s, 2H), 3.85-3.77 (m, 5H), 3.63-3.50 (m, 6H), 2.41 (t, J=6.1 Hz, 2H), 1.38 (s, 9H). Tr (METCR1410)=1.19 min, (ES$^+$) [M+H]$^+$ 580.

Step 4: 3-(2-{2-[(6-{[2-(1-Methyl-6-oxo-1,6-dihydropyridazin-3-yl)-1,3-benzoxazol-5-yl]carbamoyl}pyridin-3-yl)oxy]ethoxy}ethoxy)propanoic acid A stirred solution of tert-butyl 3-(2-{2-[(6-{[2-(1-methyl-6-oxo-1,6-dihydropyridazin-3-yl)-1,3-benzoxazol-5-yl]carbamoyl}pyridin-3-yl)oxy]ethoxy}ethoxy)propanoate (215 mg, 0.36 mmol) in DCM (5.0 mL), was treated with TFA (0.14 mL, 1.8 mmol) and the mixture was stirred at rt overnight. The reaction mixture was then re-treated with TFA (0.28 mL, 3.6 mmol) and stirred at rt for a further 24 h. After which time, the reaction mixture was concentrated in vacuo and the residue was diluted with water (10 mL), and neutralized with a saturated solution of NaHCO$_3$(aq) at 0° C. The precipitated solid was collected by filtration, washed with water and then dried in a high vacuum oven at 40° C. for 4 h to give the title compound. $^1$H NMR (500 MHz, DMSO-d6) δ 10.72 (s, 1H), 8.48-8.40 (m, 2H), 8.17 (dd, J=14.1, 9.2 Hz, 2H), 7.99 (d, J=8.7 Hz, 1H), 7.82 (d, J=8.8 Hz, 1H), 7.65 (dd, J=8.6, 2.5 Hz, 1H), 7.15 (d, J=9.7 Hz, 1H), 4.30 (m, 2H), 3.81 (m, 5H), 3.67-3.58 (m, 4H), 3.54 (m, 2H), 2.45 (t, J=6.3 Hz, 2H). Tr (METCR1410 Generic 2 min)=0.97 min, (ES$^+$) [M+H]$^+$ 524.

Step 5: 5-{2-[2-(2-{[(2S)-1-[(2S,4R)-4-Hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}ethoxy)ethoxy]ethoxy}-N-[2-(1-methyl-6-oxo-1,6-dihydropyridazin-3-yl)-1,3-benzoxazol-5-yl]pyridine-2-carboxamide A stirred solution of 3-(2-{2-[(6-{[2-(1-methyl-6-oxo-1,6-dihydropyridazin-3-yl)-1,3-benzoxazol-5-yl]

carbamoyl}pyridin-3-yl)oxy]ethoxy}ethoxy)propanoic acid (80 mg, 0.15 mmol), HATU (87 mg, 0.23 mmol) in DMF (2.5 mL) was stirred at 0° C. under nitrogen and treated with the dropwise addition of DIPEA (0.066 mL, 0.38 mmol). The reaction mixture was stirred at 0° C. for 15 minutes and then treated with (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide (78 mg, 0.17 mmol). The resulting mixture was stirred at 0° C. for 1 h and then at rt over the weekend. After which time, the reaction mixture was directly purified by low pH prep-HPLC. The pure fractions were combined, and the precipitated solid was collected by filtration and further dried in the vacuum oven at 50° C. for several hours to give the title compound. $^1$H NMR (500 MHz, DMSO-d6) 10.73 (s, 1H), 8.98 (s, 1H), 8.55 (t, J=6.1 Hz, 1H), 8.46 (d, J=2.0 Hz, 1H), 8.43 (d, J=2.8 Hz, 1H), 8.19 (d, J=9.7 Hz, 1H), 8.16 (d, J=8.7 Hz, 1H), 7.99 (dd, J=8.9, 2.1 Hz, 1H), 7.91 (d, J=9.4 Hz, 1H), 7.82 (d, J=8.9 Hz, 1H), 7.64 (dd, J=8.8, 2.9 Hz, 1H), 7.44-7.36 (m, 4H), 7.15 (d, J=9.7 Hz, 1H), 5.13 (d, J=3.5 Hz, 1H), 4.56 (d, J=9.4 Hz, 1H), 4.47-4.39 (m, 2H), 4.38-4.34 (m, 1H), 4.32-4.27 (m, 2H), 4.23 (dd, J=15.8, 5.5 Hz, 1H), 3.84-3.78 (m, 5H), 3.70-3.50 (m, 8H), 2.59-2.53 (m, 1H), 2.44 (s, 3H), 2.41-2.33 (m, 1H), 2.08-2.00 (m, 1H), 1.94-1.88 (m, 1H), 0.94 (s, 9H). Tr(METCR1603)=3.87 min, (ES$^+$) (M+H)$^+$ 936.7.

The following compounds were prepared as described above:

| # | Structure | Data |
|---|---|---|
| 22 | 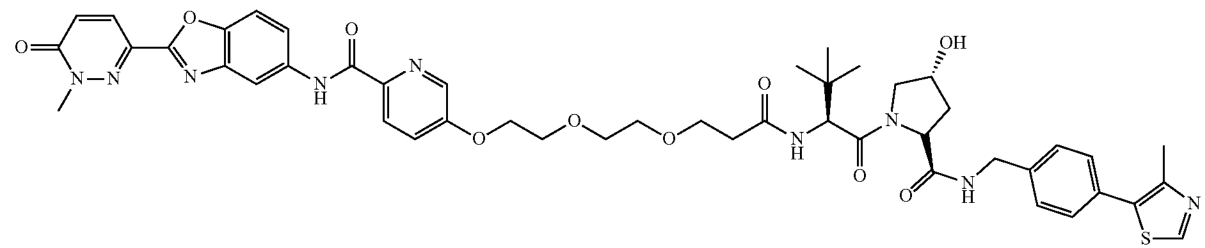 | Tr(METCR1603 High pH 7 min) = 3.87 min, (ES+) (M + H)+ 936.7 |
| 25 | 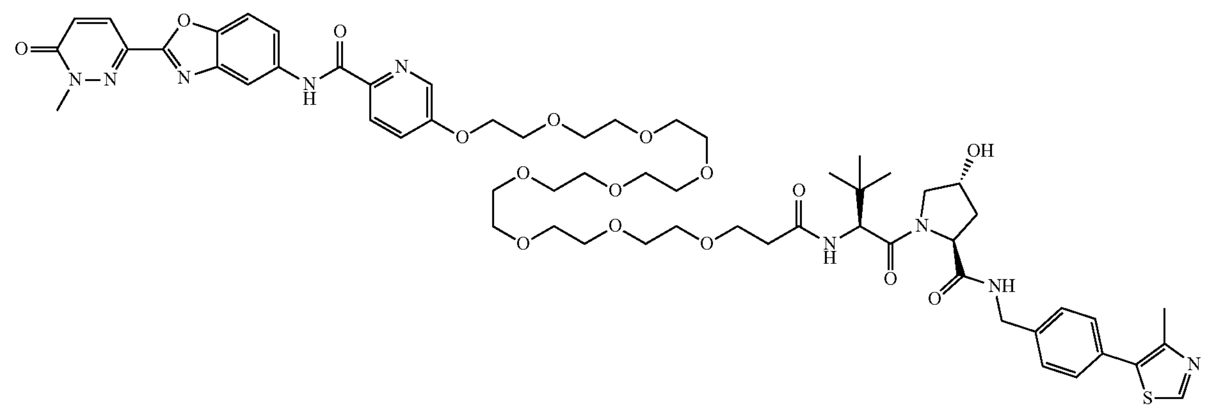 [SMILES: Cc1ncsc1-c1ccc(CNC(=O)[C@@H]2C[C@@H](O)CN2C(=O)[C@@H](NC(=O)CCOCCOCCOCCOCCOCCOCCOCCOCCOc2ccc(C(=O)Nc3ccc4oc(-c5ccc(=O)n(C)n5)nc4c3)nc2)C(C)(C)C)cc1] | Tr(MET-uHPLC-AB-101) = 2.95 min, (ES+) (M + 2H)2+ 601.0 |

| # | Structure | Data |
|---|---|---|
| 26 | 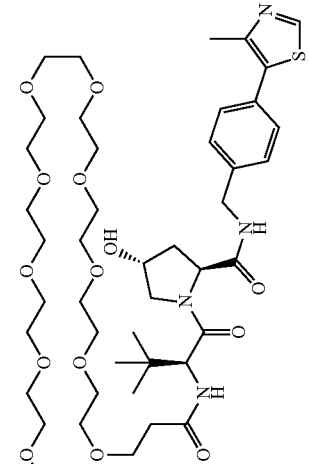 | Tr(MET-uHPLC-AB-101) = 3.0 min, (ES+) (M + H)+ 1377.0 |
| 21 | 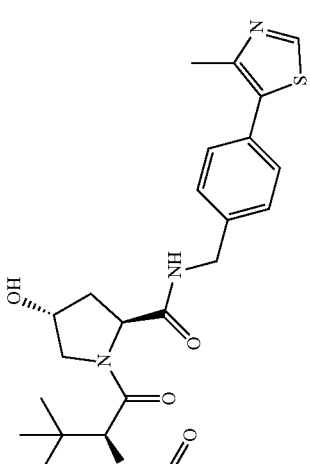 | Tr(MET-uHPLC-AB-101) = 2.84 min, (ES+) (M + H)+ 892.3 |

| # | Structure | Data |
|---|---|---|
| 29 | 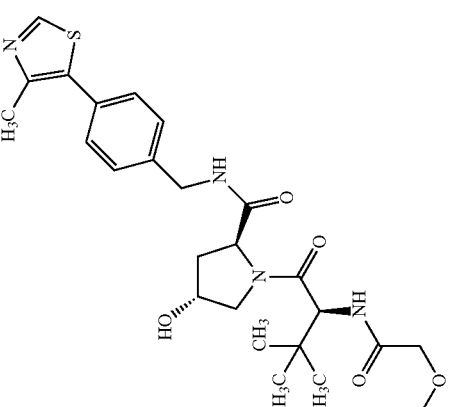 | Tr(MET-uHPLC-AB-101) = 2.87 min, (ES+) (M + H)+ 878.3 |

| # | Structure | Data |
|---|---|---|
| 23 | 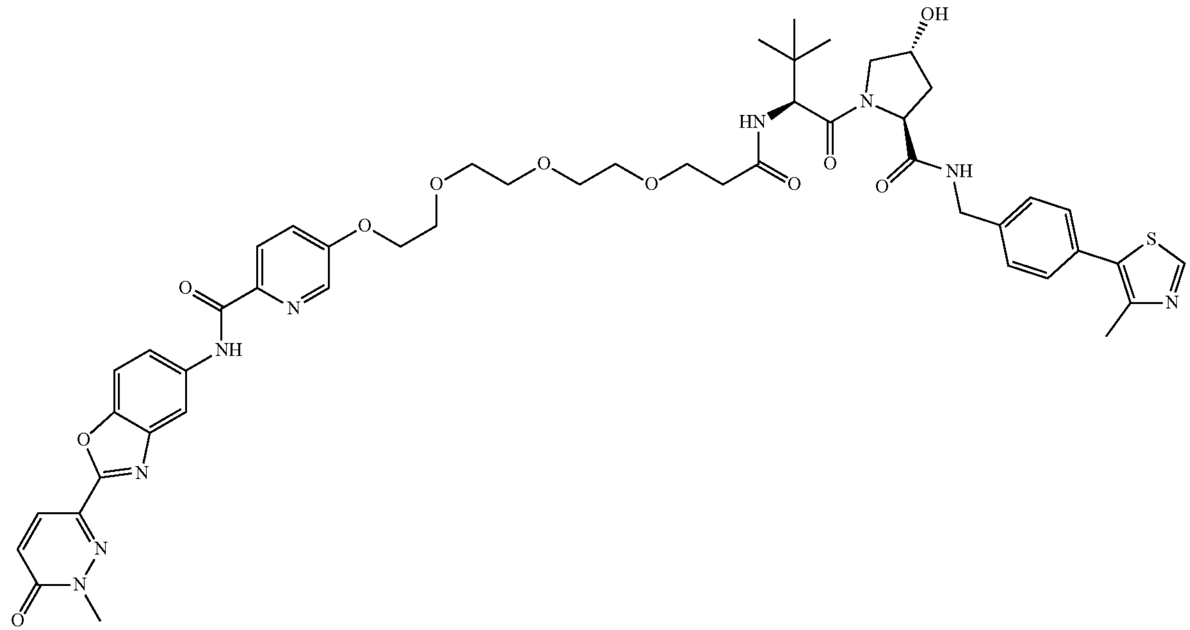 [SMILES: Cc1ncsc1-c1ccc(CNC(=O)[C@@H]2C[C@@H](O)CN2C(=O)[C@@H](NC(=O)CCOCCOCCOCCOc2ccc(C(=O)Nc3ccc4oc(-c5ccc(=O)n(C)n5)nc4c3)nc2)C(C)(C)C)cc1] | Tr(METCRL603 High pH 7 min) = 3.85 min, (ES+) (M + H)+ 980.8 |
| 24 | 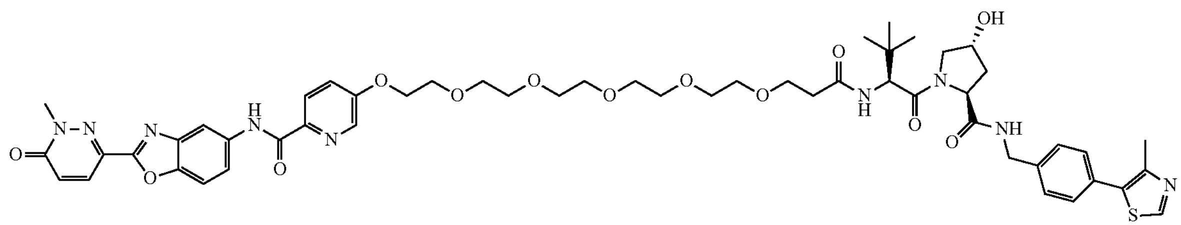 [SMILES: Cc1ncsc1-c1ccc(CNC(=O)[C@@H]2C[C@@H](O)CN2C(=O)[C@@H](NC(=O)CCOCCOCCOCCOCCOCCOc2ccc(C(=O)Nc3ccc4oc(-c5ccc(=O)n(C)n5)nc4c3)nc2)C(C)(C)C)cc1] | Tr(MET-uHPLC-AB-101) = 2.93 min, (ES+) (M + H)+ 535 |

| # | Structure | Data |
|---|---|---|
| 27 | (structure) | Tr(MET-uHPLC-AB-101) = 3.03 min, (ES+) (M + H)+ 1553.8 |
| 28 | (structure) | Tr(MET-uHPLC-AB-101) = 3.0 min, (ES+) (M + H)+ 1376.7 |

| # | Structure | Data |
|---|---|---|
| 41 | 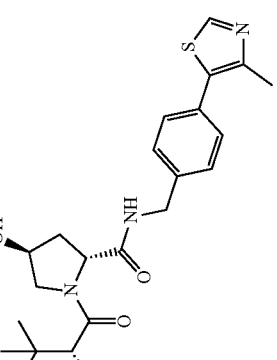 | Tr(MET-uHPLC-AB-101) = 2.95 min, (ES+) (M + H)+ 1069.3 |

Example 7
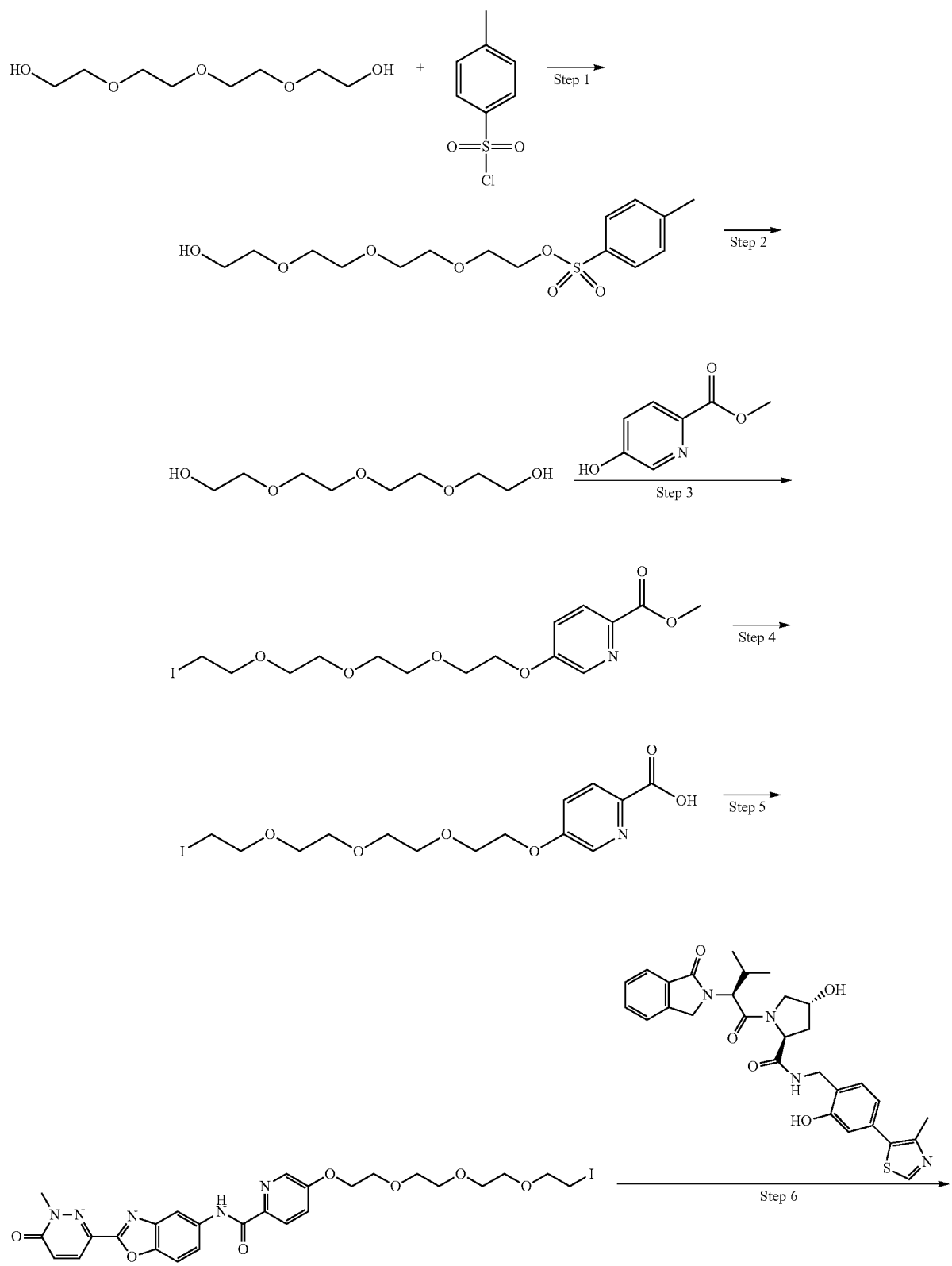

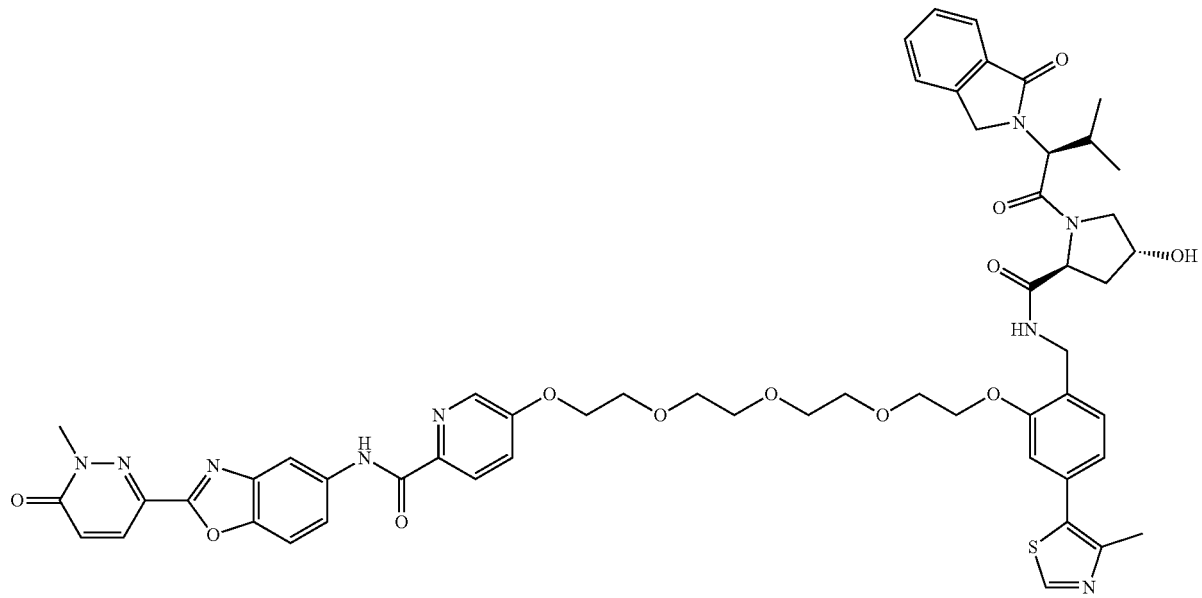

Step 1: 2-[2-[2-(2-Hydroxyethoxy)ethoxy]ethoxy]ethyl 4-methylbenzenesulfonate A stirred solution of 2,2'-[oxybis(ethane-2,1-diyloxy)]diethanol (7.28 g, 37.5 mmol) in THF (2 mL) was cooled to 0° C. (ice/water) and treated with finely crushed sodium hydroxide (0.23 g, 5.72 mmol), followed by a solution of 4-methylbenzenesulfonyl chloride (0.69 g, 3.62 mmol) in THF (20 mL) dropwise over 10 min. The resulting mixture was stirred at 0° C. for 3 h. After which time, the reaction mixture was poured into a mixture of ice/water (75 mL) and the mixture was allowed to melt. The layers were separated and the aqueous phase was extracted with DCM (3×40 mL). The combined organic layers were washed with water (50 mL), brine (2×50 mL), dried over MgSO$_4$, filtered and concentrated in vacuo. The crude material was pre-absorbed onto silica and purified by FCC (silica, 0-100% EtOAc in Heptanes). The clean fractions were combined, concentrated in-vacuo and further dried under high vacuum to give the title compound. $^1$H NMR (500 MHz, DMSO-d6) δ 7.78 (d, J=8.3 Hz, 2H), 7.48 (d, J=8.1 Hz, 2H), 4.55 (t, J=5.1 Hz, 1H), 4.11 (dd, J=5.1, 3.7 Hz, 2H), 3.60-3.54 (m, 2H), 3.52-3.46 (m, 6H), 3.45 (s, 4H), 3.40 (t, J=5.2 Hz, 2H), 2.42 (s, 3H). Tr(METCR1410)=0.97 min, (ES$^+$) (M+H)$^+$ 349.

Step 2: 2-[2-[2-(2-Iodoethoxy)ethoxy]ethoxy]ethanol

A stirred solution of 2-[2-[2-(2-hydroxyethoxy)ethoxy]ethoxy]ethyl 4-methylbenzenesulfonate (447 mg, 1.28 mmol) in acetone (10 mL) was treated with sodium iodide (971 mg, 6.41 mmol) and stirred at 70° C. for 1.5 h. After which time, the reaction mixture was cooled to rt, filtered through Celite and the cake was washed with acetone (10 mL). The filtrate was concentrated in vacuo and the residue was dissolved in DCM (15 mL) and washed with water (10 mL), brine (10 mL), dried over MgSO$_4$, filtered, concentrated in vacuo and further dried under high vacuum to give the title compound. $^1$H NMR (500 MHz, DMSO-d6) δ 4.55 (t, J=5.5 Hz, 1H), 3.66 (t, J=6.4 Hz, 2H), 3.56 (dd, J=5.5, 2.9 Hz, 2H), 3.54-3.51 (m, 6H), 3.49 (q, J=5.1 Hz, 2H), 3.42 (t, J=5.1 Hz, 2H), 3.33 (s, 2H). Tr(METCR1410)=0.81 min, (ES$^+$) (M+H)$^+$ 305.

Step 3: Methyl 5-[2-[2-[2-(2-iodoethoxy)ethoxy]ethoxy]ethoxy]pyridine-2-carboxylate A stirred solution of methyl 5-hydroxypyridine-2-carboxylate (52 mg, 0.34 mmol), 2-[2-[2-(2-iodoethoxy)ethoxy]ethoxy]ethanol (113 mg, 0.37 mmol) in THF (8 mL) was cooled to 0° C. and treated with triphenylphosphine (134 mg, 0.51 mmol). The reaction mixture was stirred for 10 min and then treated with a solution of DIAD (100 μL, 0.51 mmol) in THF (5 mL) dropwise over 10 min. The mixture was stirred at 0° C. for a further 43 min and then at rt overnight. After which time, the reaction mixture was concentrated to dryness to give a product, which is then purified by acidic reverse phase chromatography (C-18, 10-100% MeCN/water+0.1% formic acid) to give the title compound. $^1$H NMR (500 MHz, DMSO-d6) δ 8.39 (d, J=2.9 Hz, 1H), 8.03 (d, J=8.7 Hz, 1H), 7.53 (dd, J=8.7, 2.9 Hz, 1H), 4.31-4.25 (m, 2H), 3.84 (s, 3H), 3.81-3.76 (m, 2H), 3.65 (t, J=6.4 Hz, 2H), 3.60 (dd, J=5.9, 3.2 Hz, 2H), 3.54

(ddq, J=7.5, 5.4, 2.8 Hz, 6H), 3.29 (s, 2H). Tr(METCR1410)=1.04 min, (ES$^+$) (M+H)$^+$ 439.

Step 4: 5-[2-[2-[2-(2-Iodoethoxy)ethoxy]ethoxy]ethoxy]pyridine-2-carboxylic acid A stirred solution of methyl 5-[2-[2-[2-(2-iodoethoxy)ethoxy]ethoxy]ethoxy]pyridine-2-carboxylate (96.4 mg, 0.22 mmol) in THF (2 mL) was treated with a solution of 1 M LiOH (0.98 mL). The mixture was stirred at rt for 4 h. After which time, the reaction mixture was concentrated in vacuo and the remaining aqueous was extracted with ether (3×5 mL). The aqueous phase was then acidified to pH 4 by the addition of a solution of 10% citric acid (1.5 mL). The mixture was extracted with EtOAc (3×15 mL). The combined organic extracts were washed with brine (15 mL), dried over MgSO$_4$, filtered, concentrated in vacuo and then further dried in a high vacuum oven at 50° C. to rt overnight to give the title compound. $^1$H NMR (500 MHz, DMSO-d6) δ 12.71 (s, 1H), 8.38 (d, J=2.9 Hz, 1H), 8.01 (d, J=8.7 Hz, 1H), 7.52 (dd, J=8.7, 2.9 Hz, 1H), 4.30-4.24 (m, 2H), 3.81-3.76 (m, 2H), 3.65 (t, J=6.4 Hz, 2H), 3.60 (dd, J=6.1, 3.4 Hz, 2H), 3.54 (ddq, J=7.4, 5.3, 2.8 Hz, 6H), 3.30 (s, 2H). Tr(METCR1410)=0.93 min, (ES$^+$) (M+H)$^+$ 426.

Step 5: 5-[2-[2-[2-(2-Iodoethoxy)ethoxy]ethoxy]-N-[2-(1-methyl-6-oxo-pyridazin-3-yl)-1,3-benzoxazol-5-yl]pyridine-2-carboxamide A stirred solution of 5-[2-[2-[2-(2-iodoethoxy)ethoxy]ethoxy]ethoxy]pyridine-2-carboxylic acid (74 mg, 0.17 mmol) and N-[(dimethylamino)(3H-[1,2,3]triazolo[4,5-b]pyridin-3-yloxy)methylidene]-N-methylmethanaminium hexafluorophosphate (84 mg, 0.22 mmol) in DMF (2 mL) were cooled to 0° C. and treated with N-ethyl-N-(propan-2-yl)propan-2-amine (70 μL, 0.40 mmol). The resulting mixture was stirred for 8 min and then treated with 6-(5-amino-1,3-benzoxazol-2-yl)-2-methyl-pyridazin-3-one (44 mg, 0.18 mmol). The mixture was stirred at 0° C. for 1 h and then rt overnight. After which time, the reaction mixture was concentrated in vacuo and then partitioned between water (10 mL) and DCM (10 mL). The layers were separated and the aqueous phase was extracted with DCM (3×10 mL). The combined organic phases were washed with a saturated solution of NaHCO$_3$ (10 mL). The layers were separated, and the aqueous phase was extracted with DCM (10 mL). The combined organic phases were washed with brine (10 mL). The layers were separated and the aqueous phase was extracted with DCM (10 mL). The combined organic phases were dried over MgSO$_4$, filtered and concentrated in vacuo. The crude material was purified by FCC (silica, 0-100% EtOAc in Heptanes, followed by a 10% MeOH in DCM flush) followed by acidic reverse phase chromatography (C-18, 10-100% MeCN/Water+0.1% formic acid). The clean fractions were combined, concentrated in vacuo and further dried in a vacuum oven at 50° C. overnight to give the title compound. $^1$H NMR (500 MHz, DMSO-d6) δ 10.74 (s, 1H), 8.46 (d, J=2.0 Hz, 1H), 8.43 (d, J=2.8 Hz, 1H), 8.18 (d, J=9.7 Hz, 1H), 8.15 (d, J=8.7 Hz, 1H), 7.99 (dd, J=8.9, 2.1 Hz, 1H), 7.82 (d, J=8.9 Hz, 1H), 7.65 (dd, J=8.8, 2.9 Hz, 1H), 7.15 (d, J=9.7 Hz, 1H), 4.34-4.28 (m, 2H), 3.81 (s, 5H), 3.66 (t, J=6.4 Hz, 2H), 3.62 (dd, J=6.1, 3.4 Hz, 2H), 3.59-3.56 (m, 2H), 3.55 (dq, J=4.7, 2.7, 1.9 Hz, 4H), 3.30 (s, 2H). Tr(METCR1410)=1.18 min, (ES$^+$) (M+H)$^+$ 650.

Step 6: 5-{2-[2-(2-{2-[2-({[(2S,4R)-4-Hydroxy-1-[(2S)-3-methyl-2-(1-oxo-2,3-dihydro-1H-isoindol-2-yl)butanoyl]pyrrolidin-2-yl]formamido}methyl)-5-(4-methyl-1,3-thiazol-5-yl)phenoxy]ethoxy}ethoxy)ethoxy]ethoxy}-N-[2-(1-methyl-6-oxo-1,6-dihydropyridazin-3-yl)-1,3-benzoxazol-5-yl]pyridine-2-carboxamide A sealed tube was charged with a solution of (4R)-4-hydroxy-N-[[2-hydroxy-4-(4-methylthiazol-5-yl)phenyl]methyl]-1-[3-methyl-2-(1-oxoisoindolin-2-yl)butanoyl]pyrrolidine-2-carboxamide (45.75 mg, 0.08 mmol) in DMF (1 mL) and K$_2$CO$_3$ (19.21 mg, 0.14 mmol) was added. The suspension was stirred at rt for 10 min and then treated with a solution of 5-[2-[2-[2-(2-iodoethoxy)ethoxy]ethoxy]-N-[2-(1-methyl-6-oxo-pyridazin-3-yl)-1,3-benzoxazol-5-yl]pyridine-2-carboxamide (36 mg, 0.06 mmol) in DMF (1.5 mL). The resulting suspension was stirred at 70° C. for 5 h and then allowed to reach rt. The reaction mixture was concentrated in vacuo and the residue was partitioned between water (10 mL) and DCM (10 mL). The layers were separated and the aqueous phase was extracted with DCM (3×10 mL). The combined organics were washed with brine (10 mL). The layers were separated and the aqueous was extracted with DCM (10 mL). The combined organic phases were dried over MgSO$_4$, filtered and concentrated in vacuo. The crude material was purified by acidic reverse phase chromatography (C-18, 10-100% MeCN/Water+0.1% formic acid) and the clean fractions were triturated with ether and then re-purified by acidic reverse phase chromatography (C-18, 10-100% MeCN/Water+0.1% formic acid). The clean fractions were lyophilized overnight to give the title compound. $^1$H NMR (500 MHz, DMSO-d6) 10.72 (s, 1H), 8.97 (s, 1H), 8.45 (d, J=2.0 Hz, 1H), 8.41 (d, J=2.8 Hz, 1H), 8.35 (t, J=5.8 Hz, 1H), 8.18 (d, J=9.7 Hz, 1H), 8.14 (d, J=8.7 Hz, 1H), 7.98 (dd, J=8.9, 2.0 Hz, 1H), 7.81 (d, J=8.9 Hz, 1H), 7.70 (d, J=7.5 Hz, 1H), 7.67-7.57 (m, 3H), 7.49 (t, J=8.0 Hz, 1H), 7.33 (d, J=7.8 Hz, 1H), 7.14 (d, J=9.7 Hz, 1H), 7.04 (d, J=1.4 Hz, 1H), 7.00 (dd, J=7.8, 1.4 Hz, 1H), 5.08 (d, J=3.6 Hz, 1H), 4.71 (d, J=10.8 Hz, 1H), 4.54 (d, J=18.1 Hz, 1H), 4.45 (d, J=18.4 Hz, 1H), 4.41 (t, J=8.0 Hz, 1H), 4.36-4.31 (m, 1H), 4.31-4.20 (m, 4H), 4.21-4.15 (m, 2H), 3.86-3.74 (m, 8H), 3.69 (d, J=9.9 Hz, 1H), 3.66-3.60 (m, 2H), 3.62-3.57 (m, 2H), 3.59-3.54 (m, 4H), 2.46 (s, 3H), 2.36-2.26 (m, 1H), 2.09-2.00 (m, 1H), 1.97-1.87 (m, 1H), 0.96 (d, J=6.5 Hz, 3H), 0.73 (d, J=6.6 Hz, 3H). Tr(MET-uHPLC-AB-101)=3.2 min, (ES$^+$) (M+H)$^+$ 1070.

The following compounds were prepared as described above:

| # | Structure | Data |
|---|---|---|
| 20 | 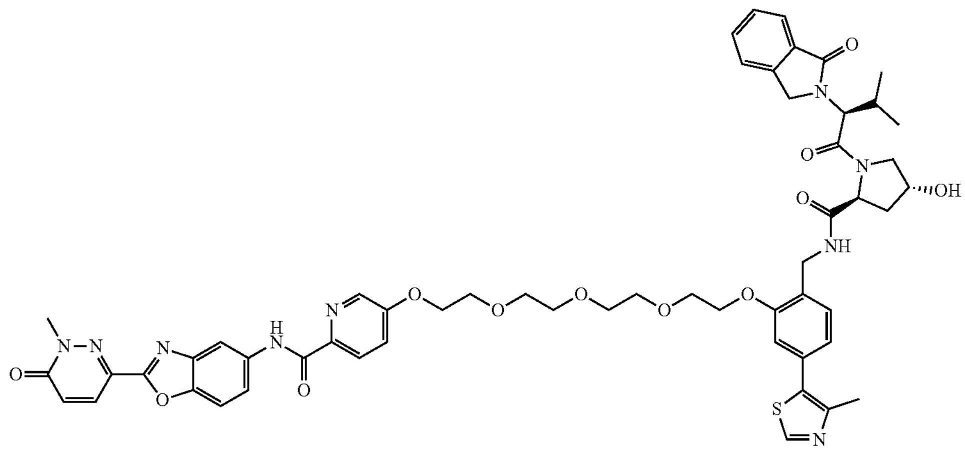 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOCCOc2ccc(C(=O)Nc3ccc4oc(-c5ccc(=O)n(C)n5)nc4c3)nc2)c1] | Tr(MET-uHPLC-AB-101) = 3.2 min, (ES+) (M + H)+ 1070. |
| 11 | 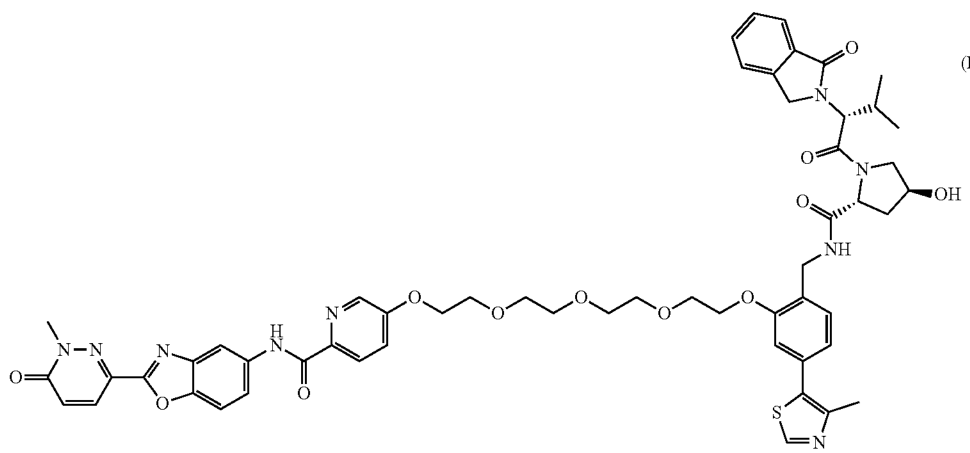 | Tr(METCR1603) = 4.14 min, (ES+) (M + H)+ 1070.6. |
Example 8
40
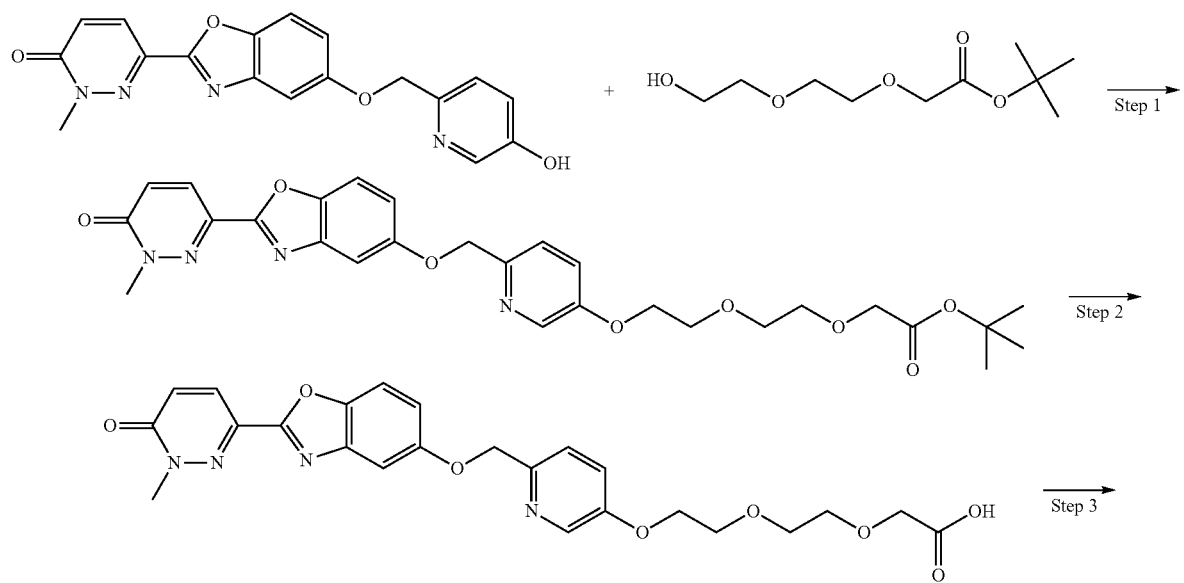
Scheme for Example 8

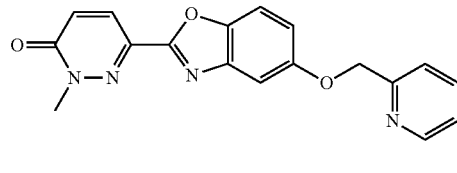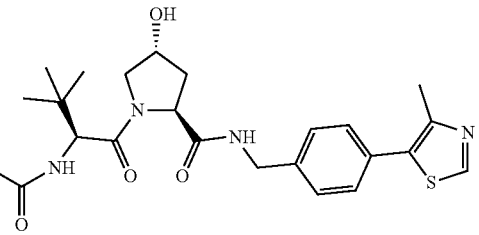

Step 1: tert-Butyl 2-[2-[2-[[6-[[2-(1-methyl-6-oxo-pyridazin-3-yl)-1,3-benzoxazol-5-yl]oxymethyl]-3-pyridyl]oxy]ethoxy]ethoxy]acetate A stirred suspension of 6-[5-[(5-hydroxy-2-pyridyl)methoxy]-1,3-benzoxazol-2-yl]-2-methyl-pyridazin-3-one (160 mg, 0.46 mmol), tert-butyl 2-[2-(2-hydroxyethoxy)ethoxy]acetate (101 mg, 0.46 mmol) in a mixture of THF (10 mL) and DMF (2 mL) was cooled to 0° C. and treated with triphenylphosphine (180 mg, 0.69 mmol). The reaction mixture was stirred for 10 min and then treated with a solution of DIAD (134 μL, 0.69 mmol) in THF (5 mL) dropwise over 10 minutes. The mixture was stirred at 0° C. for a further 16 min and then at rt overnight. After which time, the reaction mixture was concentrated in vacuo and treated with a solution of tert-butyl 2-[2-(2-hydroxyethoxy)ethoxy]acetate (101 mg, 0.46 mmol) in DMF (2 mL), cooled to 0° C. and treated with triphenylphosphine (180 mg, 0.69 mmol). The reaction mixture was stirred for 5 min and then treated with a solution of DIAD (134 μL, 0.69 mmol) in DMF (1 mL) dropwise over 2 min. The mixture was stirred at 0° C. for a further 23 min and then at rt overnight. After which time, the reaction mixture was treated with a solution of tert-butyl 2-[2-(2-hydroxyethoxy)ethoxy]acetate (50 mg, 0.23 mmol) in DMF (1 mL), cooled to 0° C. and treated with triphenylphosphine (90 mg, 0.34 mmol). The reaction mixture was stirred for 10 min and then treated with a solution of DIAD (67 μL, 0.34 mmol) in DMF (1 mL) dropwise over 3 min. The mixture was stirred at 0° C. for a further 15 min and then at rt overnight. After which time, the reaction mixture was concentrated to dryness and the crude material was purified by basic reverse phase chromatography (C-18, 10-100% MeCN/H$_2$O+0.1% NH$_{40}$H) to give the title compound. $^1$H NMR (500 MHz, DMSO-d6) δ 8.31 (d, J=2.8 Hz, 1H), 8.13 (d, J=9.7 Hz, 1H), 7.75 (d, J=8.9 Hz, 1H), 7.51 (d, J=8.6 Hz, 1H), 7.48 (d, J=2.5 Hz, 1H), 7.45 (dd, J=8.6, 2.9 Hz, 1H), 7.16 (dd, J=9.0, 2.5 Hz, 1H), 7.14 (d, J=9.7 Hz, 1H), 5.18 (s, 2H), 4.24-4.15 (m, 2H), 3.99 (s, 2H), 3.80 (s, 3H), 3.78-3.75 (m, 2H), 3.62-3.57 (m, 4H), 1.41 (s, 9H). Tr(METCR1603)=4.28 min, (ES$^+$) (M+H)$^+$ 553.

Step 2: 2-[2-[2-[[6-[[2-(1-Methyl-6-oxo-pyridazin-3-yl)-1,3-benzoxazol-5-yl]oxymethyl]-3-pyridyl]oxy]ethoxy]ethoxy]acetic acid A stirred solution of tert-butyl 2-[2-[2-[[6-[[2-(1-methyl-6-oxo-pyridazin-3-yl)-1,3-benzoxazol-5-yl]oxymethyl]-3-pyridyl]oxy]ethoxy]ethoxy]acetate (111 mg, 0.2 mmol) in DCM (5.0 mL), was treated with TFA (0.08 mL, 1.01 mmol) and the mixture was stirred at rt overnight. The reaction mixture was then re-treated with TFA (0.15 mL, 1.96 mmol) and stirred at rt for a further 6 h, After which time, the reaction mixture was concentrated in vacuo, azeotroped with DCM (2×10 mL) and further dried in a vacuum oven at 50° C. for several hours to give the title compound. $^1$H NMR (500 MHz, DMSO-d6) δ 8.35 (d, J=2.8 Hz, 1H), 8.13 (d, J=9.7 Hz, 1H), 7.75 (d, J=8.9 Hz, 1H), 7.57-7.47 (m, 3H), 7.17 (dd, J=9.0, 2.5 Hz, 1H), 7.14 (d, J=9.7 Hz, 1H), 5.21 (s, 2H), 4.24-4.18 (m, 2H), 4.01 (d, J=8.4 Hz, 2H), 3.80 (s, 3H), 3.78-3.74 (m, 2H), 3.61 (s, 4H). Tr(METCR1410)=0.96 min, (ES$^+$) (M+H)$^+$ 497.

Step 3: (2S,4R)-1-[(2S)-3,3-Dimethyl-2-{2-[2-(2-{[6-({[2-(1-methyl-6-oxo-1,6-dihydropyridazin-3-yl)-1,3-benzoxazol-5-yl]oxy}methyl)pyridin-3-yl]oxy}ethoxy)ethoxy]acetamido}butanoyl]-4-hydroxy-N-{[4-(4-methyl-1,3-thiazol-5-yl)phenyl]methyl}pyrrolidine-2-carboxamide A stirred solution of 2-[2-[2-[[6-[[2-(1-methyl-6-oxo-pyridazin-3-yl)-1,3-benzoxazol-5-yl]oxymethyl]-3-pyridyl]oxy]ethoxy]ethoxy]acetic acid (50 mg, 0.1 mmol) and HATU (46 mg, 0.12 mmol) in DMF (2 mL) was cooled on ice and treated with DIPEA (88 μL, 0.5 mmol). The resulting solution was stirred for 16 min and then treated with (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide hydrochloride (47 mg, 0.1 mmol). The mixture was stirred at 0° C. for 1 h and then at rt overnight. The reaction mixture was concentrated in vacuo and the residue partitioned between water (10 mL) and DCM (10 mL). The layers were separated and the aqueous phase was extracted with DCM (3×10 mL). The combined organic layers were washed with a saturated solution of NaHCO$_3$ (aq) (10 mL) and brine (10 mL), dried over MgSO$_4$, filtered and concentrated in vacuo. The crude material was purified by basic reverse phase chromatography (C-18, 10-100% MeCN/water+0.1% NH$_{40}$H), followed by an ether trituration (5 mL) to give the title compound. $^1$H NMR (500 MHz, DMSO-d6) 8.95 (s, 1H), 8.60 (t, J=6.0 Hz, 1H), 8.29 (d, J=2.9 Hz, 1H), 8.13 (d, J=9.7 Hz, 1H), 7.74 (d, J=8.9 Hz, 1H), 7.50-7.46 (m, 2H), 7.45-7.40 (m, 2H), 7.40-7.34 (m, 4H), 7.18-7.11 (m, 2H), 5.16 (s, 2H), 5.14 (d, J=3.1 Hz, 1H), 4.56 (d, J=9.6 Hz, 1H), 4.44 (t, J=8.2 Hz, 1H), 4.37 (dd, J=15.9, 6.2 Hz, 2H), 4.26 (dd, J=15.7, 5.8 Hz, 1H), 4.20 (t, J=4.6 Hz, 2H), 4.03-3.92 (m, 2H), 3.84-3.75 (m, 5H), 3.71-3.57 (m, 6H), 2.41 (s, 3H), 2.11-2.01 (m, 1H), 1.94-1.86 (m, 1H), 0.90 (s, 9H). Tr(MET-uHPLC-AB-101)=2.85 min, (ES$^+$) (M)$^+$ 909.3; (M+2H)/2$^+$ 455.

The following compounds were prepared as described above:

| # | | Data |
|---|---|---|
| 47 | | Tr(MET-uHPLC-AB-101) = 2.85 min, (ES+) (M)+ 909.3; (M + 2H)/2+ 455. |
| 48 | | Tr(MET-uHPLC-AB-101) = 2.85 min, (ES+) (M)+ 909.3; (M + 2H)/2+ 455. |

147
Example 9
148
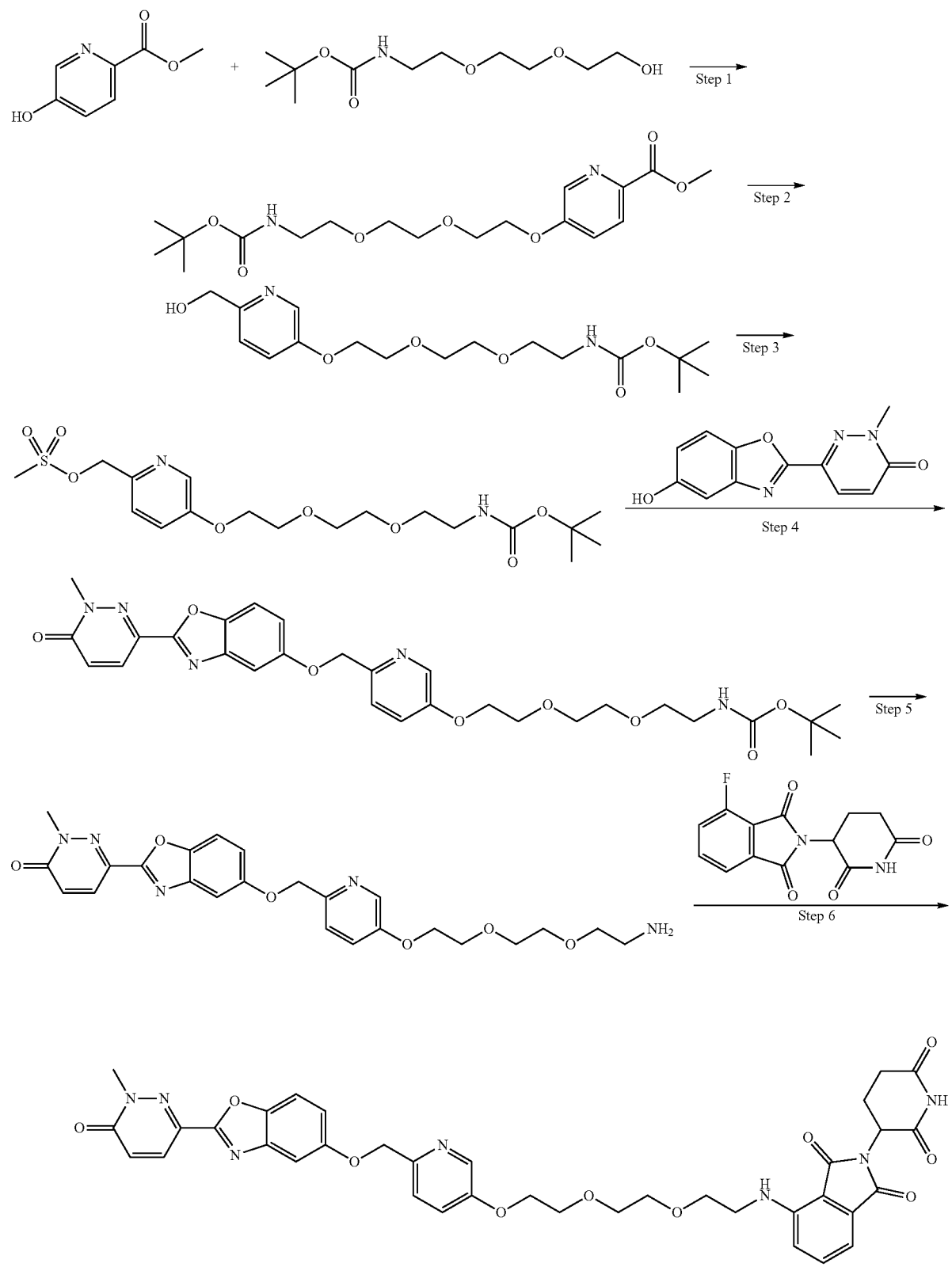
Scheme for Example 9

Step 1: Methyl 5-{2-[2-(2-{[(tert-butoxy)carbonyl]amino}ethoxy)ethoxy]ethoxy}pyridine-2-carboxylate A solution of methyl 5-hydroxypyridine-2-carboxylate (500 mg, 3.26 mmol), tert-butyl N-{2-[2-(2-hydroxyethoxy)ethoxy]ethyl}carbamate (814 mg, 3.26 mmol) in THF (25.0 mL) was cooled to 0° C. and treated with triphenylphosphine (1.28 g, 4.90 mmol). The reaction mixture was stirred for 20 mins and then treated with DIAD (0.96 mL, 4.90 mmol) dropwise over 10 min. The mixture was stirred at 0° C. for a further 30 min and then at rt overnight. After which time, the reaction mixture was re-treated with tert-butyl N-{2-[2-(2-hydroxyethoxy)ethoxy]ethyl}carbamate (407 mg, 1.63 mmol) and cooled to 0° C. PPh$_3$ (0.64 g, 2.45 mmol) was added and the reaction mixture was stirred for 20 mins and then treated with DIAD (0.48 mL, 2.45 mmol). The mixture was stirred at 0° C. for a further 30 min and then at rt for a further 24 h. After which time, the reaction mixture was concentrated to dryness and the crude was dissolved in EtOAc (50 mL). The organic layer was extracted with EtOAc (2×50 mL). The combined organic layers were washed with brine, dried over Na$_2$SO$_4$, filtered and evaporated under reduced pressure to give a crude product, which was purified by FCC (silica, 10-45% EtOAc in heptanes, followed by 1-8% MeOH in DCM) to give the title compound. $^1$H NMR (500 MHz, Chloroform-d) δ 8.42 (d, J=2.8 Hz, 1H), 8.10 (d, J=8.7 Hz, 1H), 7.29 (dd, J=8.7, 2.9 Hz, 1H), 4.95 (s, 1H), 4.28-4.23 (m, 2H), 3.98 (s, 3H), 3.90 (dd, J=5.3, 4.1 Hz, 2H), 3.71 (dd, J=5.7, 3.5 Hz, 2H), 3.64 (dd, J=5.7, 3.5 Hz, 2H), 3.54 (t, J=5.2 Hz, 2H), 3.35-3.27 (m, 2H), 1.43 (s, 9H). Tr(METCR1410)=1.00 min, (ES$^+$) (M+H)$^+$ 385.

Step 2: tert-Butyl N-{2-[2-(2-{[6-(hydroxymethyl)pyridin-3-yl]oxy}ethoxy)ethoxy]ethyl}carbamate To a solution of methyl 5-{2-[2-(2-{[(tert-butoxy)carbonyl]amino}ethoxy)ethoxy]ethoxy}pyridine-2-carboxylate (1.32 g, 3.02 mmol) was added LiAlH$_4$ (1.89 mL, 4.53 mmol) dropwise at −10° C. The reaction was allowed to warm up to rt over 1 h. The reaction was cooled to 0° C., and then quenched with 1 M NaOH until no more gas was produced. A saturated solution of NaHCO$_3$(20 mL) was added. The resulting suspension was filtered through a pad of Celite, the solid was washed with EtOAc and the combined organic layers were washed with brine, dried over Na$_2$SO$_4$, filtered and evaporated under reduced pressure. The crude material was purified by FCC (silica, 10-45% EtOAc in heptanes, followed by 0-100% {10% MeOH in DCM}/DCM) to give the title compound. $^1$H NMR (500 MHz, Chloroform-d) δ 8.29 (s, 1H), 7.26 (m, 1H), 7.18 (d, J=8.5 Hz, 1H), 5.02 (s, 1H), 4.70 (s, 2H), 4.22-4.17 (m, 2H), 3.90-3.84 (m, 2H), 3.71 (dd, J=5.8, 3.3 Hz, 2H), 3.64 (dd, J=5.6, 3.4 Hz, 2H), 3.54 (t, J=5.1 Hz, 2H), 3.37 (s, 1H), 3.31 (d, J=5.0 Hz, 2H), 1.43 (s, 9H). Tr(METCR1410)=0.81 min, (ES$^+$) (M+H)$^+$ 357.

Step 3: tert-Butyl N-(2-{2-[2-({6-[(methanesulfonyloxy)methyl]pyridin-3-yl}oxy)ethoxy]ethoxy}ethyl)carbamate tert-Butyl N-{2-[2-(2-{[6-(hydroxymethyl)pyridin-3-yl]oxy}ethoxy)ethoxy]ethyl}carbamate (350 mg, 0.66 mmol) was dissolved in DCM (8.0 mL) then triethylamine (0.18 mL, 1.32 mmol) was added and the solution was cooled to 0° C. Methanesulfonyl chloride (0.06 mL, 0.79 mmol) was added dropwise and the mixture was stirred at 0° C. for 2 h. Methanesulfonyl chloride (0.06 mL, 0.79 mmol) was added dropwise and the mixture was stirred at 0° C. for further 2 h. Water (20 mL) was added carefully to the cooled solution. The reaction mixture was allowed to warm to room temperature over 30 min, the phases were separated and the aqueous phase was extracted with DCM (2×10 mL). The organic phases were combined, dried over Na$_2$SO$_4$, filtered and concentrated in vacuo to give the title compound, which was used directly in the next step. Tr(METCR1410)=1.04 min, (ES$^+$) (M+H)$^+$ 435.

Step 4: tert-Butyl N-{2-[2-(2-{[6-({[2-(1-methyl-6-oxo-1,6-dihydropyridazin-3-yl)-1,3-benzoxazol-5-yl]oxy}methyl)pyridin-3-yl]oxy}ethoxy)ethoxy]ethyl}carbamate 6-(5-Hydroxy-1,3-benzoxazol-2-yl)-2-methyl-2,3-dihydropyridazin-3-one (150 mg, 0.617 mmol) was dissolved in DMF (6.0 mL) and then Cs$_2$CO$_3$ (508 mg, 1.54 mmol) was added in one portion. The reaction was stirred at rt for 1 h. A solution of tert-butyl N-(2-{2-[2-({6-[(methanesulfonyloxy)methyl]pyridin-3-yl}oxy)ethoxy]ethoxy}ethyl)carbamate (281 mg, 0.65 mmol) in DMF (2.0 mL) was added dropwise, and the reaction mixture was then stirred at rt for 2 h. The reaction mixture was stirred at 45° C. for a further 18 h, and then the solvent was removed in vacuo. The residue was suspended in water (50 mL). The product was extracted with EtOAc (3×20 mL). The combined organic layers were washed with brine, dried over Na$_2$SO$_4$, filtered and evaporated under reduced pressure. The resulting residue was purified by FCC (silica, 0-50% EtOAc in heptane, then 0-10% MeOH in DCM) followed by basic reverse phase chromatography (C-18, 10-100% MeCN/water+0.1% NH$_{40}$H) to give the title compound. $^1$H NMR (500 MHz, DMSO-d$_6$) δ 8.32 (d, J=2.8 Hz, 1H), 8.14 (d, J=9.7 Hz, 1H), 7.75 (d, J=8.9 Hz, 1H), 7.53-7.43 (m, 3H), 7.17 (dd, J=9.0, 2.6 Hz, 1H), 7.14 (d, J=9.7 Hz, 1H), 6.74 (s, 1H), 5.19 (s, 2H), 4.19 (dd, J=5.3, 3.8 Hz, 2H), 3.80 (s, 3H), 3.76 (dd, J=5.3, 3.8 Hz, 2H), 3.59 (dd, J=5.9, 3.5 Hz, 2H), 3.52 (dd, J=5.8, 3.6 Hz, 2H), 3.38 (t, J=6.1 Hz, 2H), 3.06 (q, J=5.9 Hz, 2H), 1.36 (s, 9H). Tr(METCR1410)=1.11 min, (ES$^+$) (M+H)$^+$ 582.

Step 5: 6-{5-[(5-{2-[2-(2-Aminoethoxy)ethoxy]ethoxy}pyridin-2-yl)methoxy]-1,3-benzoxazol-2-yl}-2-methyl-2,3-dihydropyridazin-3-one tert-Butyl N-{2-[2-(2-{[6-({[2-(1-methyl-6-oxo-1,6-dihydropyridazin-3-yl)-1,3-benzoxazol-5-yl]oxy}methyl)pyridin-3-yl]oxy}ethoxy)ethoxy]ethyl}carbamate (185 mg, 0.318 mmol) was dissolved in DCM (5.0 mL), and then TFA (0.06 mL, 0.79 mmol) was added dropwise at 0° C. The reaction was stirred at rt for 2 h. The reaction mixture was quenched with a saturated solution of NaHCO$_3$(aq) at 0° C. The aqueous phases were extracted with DCM (3×20 mL). The combined organic layer was dried over Na$_2$SO$_4$, filtered and evaporated under reduced pressure to give an off-white solid (starting material). The white solid was dissolved in dioxane (4 mL), and then 4 M HCl in dioxane (1.45 mL, 5.80 mmol) was added dropwise and the suspension was stirred at rt for 4 h. The solvent was removed in vacuo, the residue was dissolved in water (20 mL) and basified with a saturated solution of NaHCO$_3$(aq). The aqueous phase was extracted with a solution of DCM:MeOH (5:1, 3×15 mL) and the combined organic layers were dried over Na$_2$SO$_4$, filtered and evaporated under reduced pressure to give the title compound. Tr(METCR1410)=0.88 min, (ES+) (M+H)+ 482.5.

Step 6: 2-(2,6-Dioxopiperidin-3-yl)-4-({2-[2-(2-{[6-({[2-(1-methyl-6-oxo-1,6-dihydropyridazin-3-yl)-1,3-benzoxazol-5-yl]oxy}methyl)pyridin-3-yl]oxy}ethoxy)ethoxy]ethyl}amino)-2,3-dihydro-1H-isoindole-1,3-dione A sealed tube was charged with 6-{5-[(5-{2-[2-(2-aminoethoxy)ethoxy]ethoxy}pyridin-2-yl)methoxy]-1,3-benzoxazol-2-yl}-2-methyl-2,3-dihydropyridazin-3-one (50 mg, 0.104 mmol), 2-(2,6-dioxopiperidin-3-yl)-4-fluoro-2,3-dihydro-1H-isoindole-1,3-dione (29 mg, 0.104 mmol) in DMF (2 mL) and DIPEA (36 µL, 0.208 mmol). The tube was flushed with nitrogen and placed on a pre-heated heating block at 90° C. for 4 h. The reaction mixture was re-treated with 2-(2,6-dioxopiperidin-3-yl)-4-fluoro-2,3-dihydro-1H-isoindole-1,3-dione (29 mg, 0.104 mmol) and DIPEA (36 µL, 0.208 mmol) and stirred at 90° C. for a further 4 h. The reaction was cooled to rt and the product was purified by low pH-prep. The pure fractions were combined and lyophilised overnight to give the title compound. $^1$H NMR (500 MHz, DMSO-d6) δ 11.09 (s, 1H), 8.29 (d, J=2.9 Hz, 1H), 8.14 (d, J=9.7 Hz, 1H), 7.75 (d, J=8.9 Hz, 1H), 7.56 (dd, J=8.4, 7.2 Hz, 1H), 7.52-7.45 (m, 2H), 7.42 (dd, J=8.6, 2.9 Hz, 1H), 7.19-7.10 (m, 3H), 7.03 (d, J=7.0 Hz, 1H), 6.60 (t, J=5.8 Hz, 1H), 5.17 (s, 2H), 5.05 (dd, J=12.8, 5.5 Hz, 1H), 4.20-4.14 (m, 2H), 3.80 (s, 3H), 3.78-3.74 (m, 2H), 3.66-3.56 (m, 6H), 3.46 (q, J=5.5 Hz, 3H), 2.92-2.82 (m, 1H), 2.61-2.55 (m, 1H), 2.05-1.97 (m, 1H). Tr(METCR1603)=4.21 min, (ES+) (M+H)+ 738.4.

The following compounds were prepared as described above:

| # | Structure | Data |
|---|---|---|
| 31 | 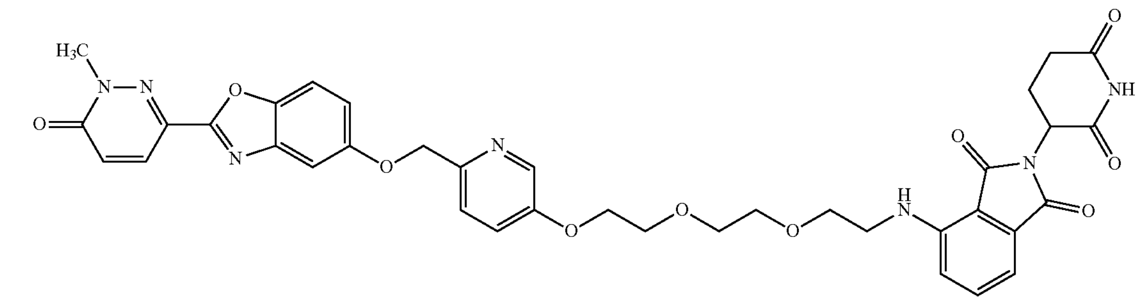 [SMILES: Cn1nc(-c2nc3cc(OCc4ccc(OCCOCCOCCNc5cccc6c5C(=O)N(C5CCC(=O)NC5=O)C6=O)cn4)ccc3o2)ccc1=O] | Tr(METCR1603) = 4.21 min, (ES+) (M + H)+ 738.4. |
| 30 | 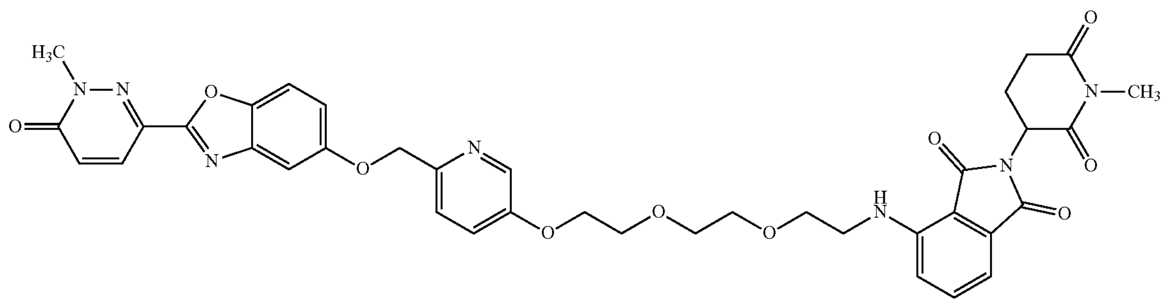 [SMILES: CN1C(=O)CCC(N2C(=O)c3cccc(NCCOCCOCCOc4ccc(COc5ccc6oc(-c7ccc(=O)n(C)n7)nc6c5)nc4)c3C2=O)C1=O] | Tr(METCR1603) = 4.29 min, (ES+) (M + H)+ 752.5. |

Example 10

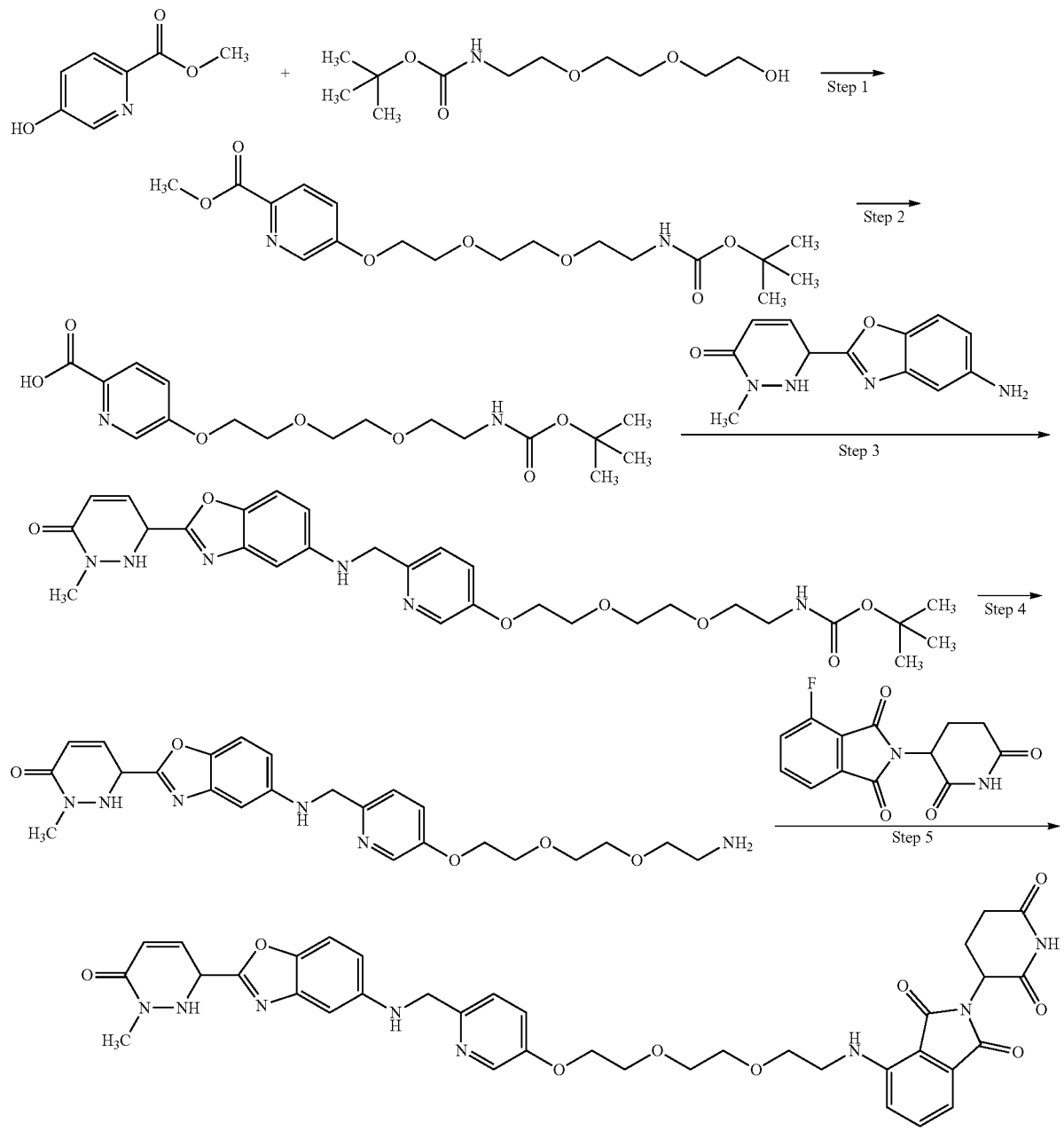

Scheme for Example 10

Step 1: Methyl 5-{2-[2-(2-{[tert-butoxy)carbonyl]amino}ethoxy)ethoxy]ethoxy}pyridine-2-carboxylate A stirred solution of methyl 5-hydroxypyridine-2-carboxylate (500 mg, 3.26 mmol), tert-butyl N-{2-[2-(2-hydroxyethoxy)ethoxy]ethyl}carbamate (895 mg, 3.59 mmol) in THF (20.0 mL) was cooled to 0° C. and treated with triphenylphosphine (1.28 g, 4.90 mmol). The reaction mixture was stirred for 20 min and then treated with DIAD (0.96 mL, 4.90 mmol) dropwise over 10 min. The mixture was stirred at 0° C. for a further 30 min and then at rt o/n. Triphenylphosphine (428 mg, 1.63 mmol) was added and the reaction mixture was stirred for 20 min and then treated with DIAD (0.32 mL, 1.63 mmol) dropwise over 10 min. The mixture was stirred at 0° C. for a further 30 min and then at rt for another 6 h. The reaction mixture was concentrated to dryness and the crude was suspended in water (50 mL). The aqueous was extracted with EtOAc (2×50 mL). The combined organic layer was washed with brine (20 mL), dried over $Na_2SO_4$, filtered and evaporated under reduced pressure to give a brown oil, which was purified by FCC (silica, 10-45% EtOAc in Heptanes, followed by 1-8% MeOH in DCM) to give the title compound. $^1$H NMR (250 MHz, Chloroform-d) δ 8.42 (d, J=2.8 Hz, 1H), 8.10 (d, J=8.7 Hz, 1H), 7.29 (dd, J=8.8, 3.0 Hz, 1H), 4.95 (s, 1H), 4.30-4.21 (m, 2H), 3.98 (s, 3H), 3.94-3.86 (m, 2H), 3.71 (dd, J=5.8, 2.7 Hz, 2H), 3.64 (dd, J=5.9, 2.8 Hz, 2H), 3.54 (t, J=5.2 Hz, 2H), 3.37-3.25 (m, 2H), 1.43 (s, 9H). Tr (METCR1410 Generic 2 min)=1.00 min, (ES$^+$) [M+H]$^+$ 385.

Step 2: 5-{2-[2-(2-{[(tert-Butoxy)carbonyl]amino}ethoxy)ethoxy]ethoxy}pyridine-2-carboxylic acid To a solution of methyl 5-{2-[2-(2-{[(tert-butoxy)carbonyl]amino}ethoxy)ethoxy]ethoxy}pyridine-2-carboxylate (81%, 260 mg, 0.55 mmol) in THF (5 mL) and MeOH (5 mL) was added 1M NaOH (aq) (1.37 ml, 1.37 mmol) at rt and the reaction was stirred for 3 h. The solvent was removed in vacuo, and the aqueous phases were acidified with 1M HCl to adjust the pH to 2-3 at 0° C. The aqueous phase was extracted with DCM (3×15 mL). The combined organic layers were dried over Na$_2$SO$_4$, filtered and evaporated under reduced pressure to give the title compound. Tr (METCR1410 Generic 2 min)=0.92 min, (ES$^+$) [M+H]$^+$ 371.

Step 3: tert-Butyl N-[2-(2-{2-[(6-{[2-(1-methyl-6-oxo-1,6-dihydropyridazin-3-yl)-1,3-benzoxazol-5-yl]carbamoyl}pyridin-3-yl)oxy]ethoxy}ethoxy)ethyl]carbamate A stirred solution of 5-{2-[2-(2-{[(tert-butoxy)carbonyl]amino}ethoxy)ethoxy]ethoxy}pyridine-2-carboxylic acid (90 mg, 0.21 mmol), HATU (94 mg, 0.25 mmol) in DMF (2.5 mL) was stirred at 0° C. under nitrogen and treated with the dropwise addition of DIPEA (0.079 mL, 0.45 mmol). The reaction mixture was stirred at 0° C. for 15 min and then treated with 6-(5-amino-1,3-benzoxazol-2-yl)-2-methyl-2,3-dihydropyridazin-3-one (50 mg, 0.21 mmol). The resulting mixture was stirred at 0° C. for 1 h and then at rt for 4 h. After which time, the reaction mixture was directly submitted to high pH prep HPLC in two batches. The pure fractions were combined and the solvent was removed in vacuo. The obtained solid was dried in a high vacuum oven at 40° C. overnight to give the title compound. $^1$H NMR (500 MHz, DMSO-d$_6$) δ 10.73 (s, 1H), 8.46 (d, J=2.0 Hz, 1H), 8.43 (d, J=2.9 Hz, 1H), 8.18 (d, J=9.7 Hz, 1H), 8.15 (d, J=8.7 Hz, 1H), 7.99 (dd, J=8.9, 2.1 Hz, 1H), 7.82 (d, J=8.9 Hz, 1H), 7.65 (dd, J=8.8, 2.9 Hz, 1H), 7.15 (d, J=9.7 Hz, 1H), 6.75 (s, 1H), 4.33-4.27 (m, 2H), 3.83-3.79 (m, 5H), 3.61 (dd, J=5.9, 3.6 Hz, 2H), 3.53 (dd, J=5.8, 3.6 Hz, 2H), 3.39 (t, J=6.1 Hz, 2H), 3.07 (q, J=5.8 Hz, 2H), 1.36 (s, 9H). Tr (METCR1410 Generic 2 min)=1.13 min, (ES$^+$) [M+H]$^+$ 595.

Step 4: 5-{2-[2-(2-Aminoethoxy)ethoxy]ethoxy}-N-[2-(1-methyl-6-oxo-1,6-dihydropyridazin-3-yl)-1,3-benzoxazol-5-yl]pyridine-2-carboxamide tert-Butyl N-[2-(2-{2-[(6-{[2-(1-methyl-6-oxo-1,6-dihydropyridazin-3-yl)-1,3-benzoxazol-5-yl]carbamoyl}pyridin-3-yl)oxy]ethoxy}ethoxy)ethyl]carbamate (90 mg, 0.15 mmol) was dissolved in dioxane (4.0 mL), and 4M HCl in dioxane (0.38 mL, 1.51 mmol) was added dropwise at rt. The reaction was stirred at rt for 3 h and then left to stand at rt overnight. The solvent was removed in vacuo and the residue was dissolved in water (15 mL), basified with a saturated solution of NaHCO$_3$(aq). The aqueous phase was extracted with a mixture of DCM-MeOH (5:1, 2×15 mL), followed by a solution of IPA-CHCl$_3$ (4:1, 2×10 mL). The combined organic layer was dried over Na$_2$SO$_4$, filtered and evaporated under reduced pressure to give the title compound, which was used in the next step without purification. Tr (METCR1410 Generic 2 min)=0.90 min, (ES$^+$) [M+H]$^+$ 495.

Step 5 (5-{2-[2-(2-{[2-(2,6-Dioxopiperidin-3-yl)-1,3-dioxo-2,3-dihydro-1H-isoindol-4-yl]amino}ethoxy)ethoxy]ethoxy}-N-[2-(1-methyl-6-oxo-1,6-dihydropyridazin-3-yl)-1,3-benzoxazol-5-yl]pyridine-2-carboxamide A sealed tube was charged with 5-{2-[2-(2-aminoethoxy)ethoxy]ethoxy}-N-[2-(1-methyl-6-oxo-1,6-dihydropyridazin-3-yl)-1,3-benzoxazol-5-yl]pyridine-2-carboxamide (70 mg, 0.14 mmol), 2-(2,6-dioxopiperidin-3-yl)-4-fluoro-2,3-dihydro-1H-isoindole-1,3-dione (38.7 mg, 0.14 mmol) in DMF (2 mL) and DIPEA (36 mg, 0.28 mmol). The tube was flushed with nitrogen and placed on a pre-heated heating block at 90° C. for 8 h. The reaction was cooled to rt and the mixture was submitted directly to low pH prep HPLC in two batches. The pure fractions were combined and the solvent was removed by freeze-drying to give the title compound. $^1$H NMR (500 MHz, DMSO-d6) 11.08 (s, 1H), 10.69 (s, 1H), 8.45 (d, J=2.0 Hz, 1H), 8.39 (d, J=2.9 Hz, 1H), 8.18 (d, J=9.7 Hz, 1H), 8.13 (d, J=8.7 Hz, 1H), 7.98 (dd, J=8.9, 2.1 Hz, 1H), 7.82 (d, J=8.9 Hz, 1H), 7.61 (dd, J=8.8, 2.9 Hz, 1H), 7.57 (dd, J=8.5, 7.2 Hz, 1H), 7.17-7.11 (m, 2H), 7.02 (d, J=7.0 Hz, 1H), 6.60 (t, J=5.8 Hz, 1H), 5.05 (dd, J=12.8, 5.4 Hz, 1H), 4.30-4.25 (m, 2H), 3.84-3.79 (m, 5H), 3.67-3.58 (m, 6H), 3.50-3.44 (m, 2H), 2.92-2.82 (m, 1H), 2.60-2.53 (m, 2H), 2.05-1.98 (m, 1H). Tr(METCR1603 High pH 7 min)=3.9 min, (ES$^+$) (M+H)$^+$ 751.

The following compounds were prepared as described above:

| # | Structure | Data |
|---|---|---|
| 33 | 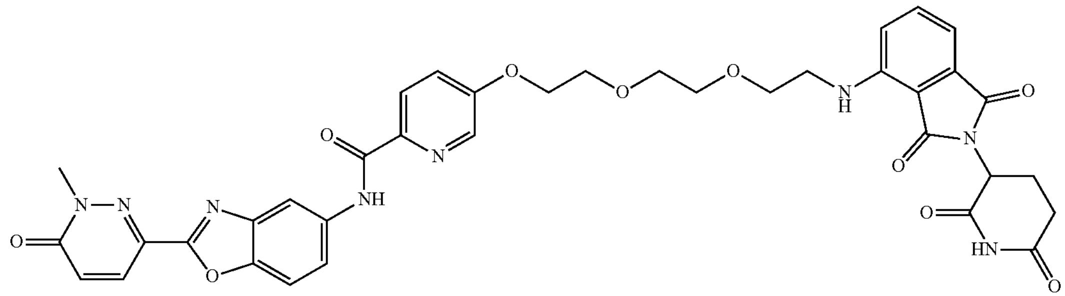 [SMILES: Cn1nc(-c2nc3cc(NC(=O)c4ccc(OCCOCCOCCNc5cccc6c5C(=O)N(C5CCC(=O)NC5=O)C6=O)cn4)ccc3o2)ccc1=O] | Tr(METCR1603 High pH 7 min) 3.9 min, (ES+) (M + H)+ 751. |
| 35 | 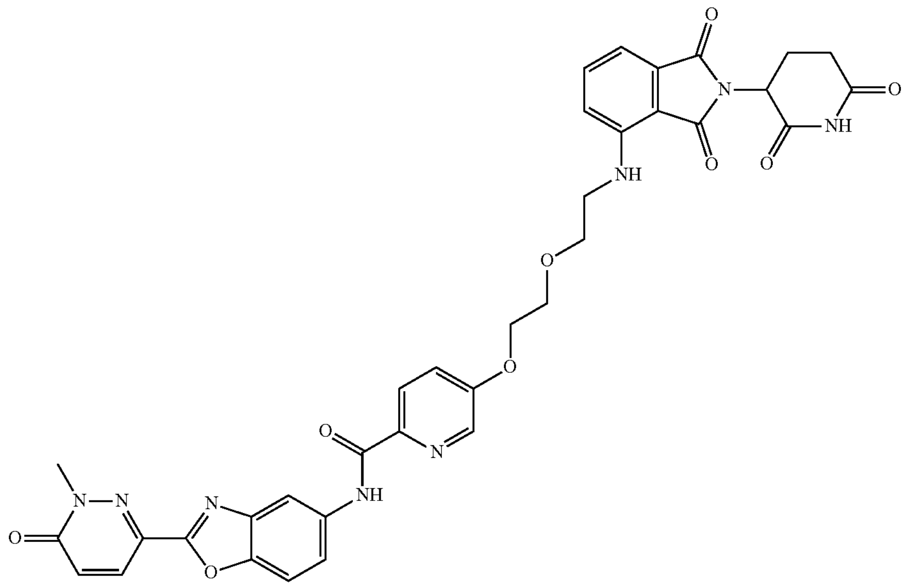 [SMILES: Cn1nc(-c2nc3cc(NC(=O)c4ccc(OCCOCCNc5cccc6c5C(=O)N(C5CCC(=O)NC5=O)C6=O)cn4)ccc3o2)ccc1=O] | Tr(MET-uHPLC-AB-101) = 3.07 min, (ES+) (M + H)+ 707.4. |

| # | Structure | Data |
|---|---|---|
| 36 | *-continued-* | Tr(METCR1603 High pH 7 min) = 3.84 min, (ES+) (M + H)+ 795.4. |

| # | Structure | Data |
|---|---|---|
| 32 | 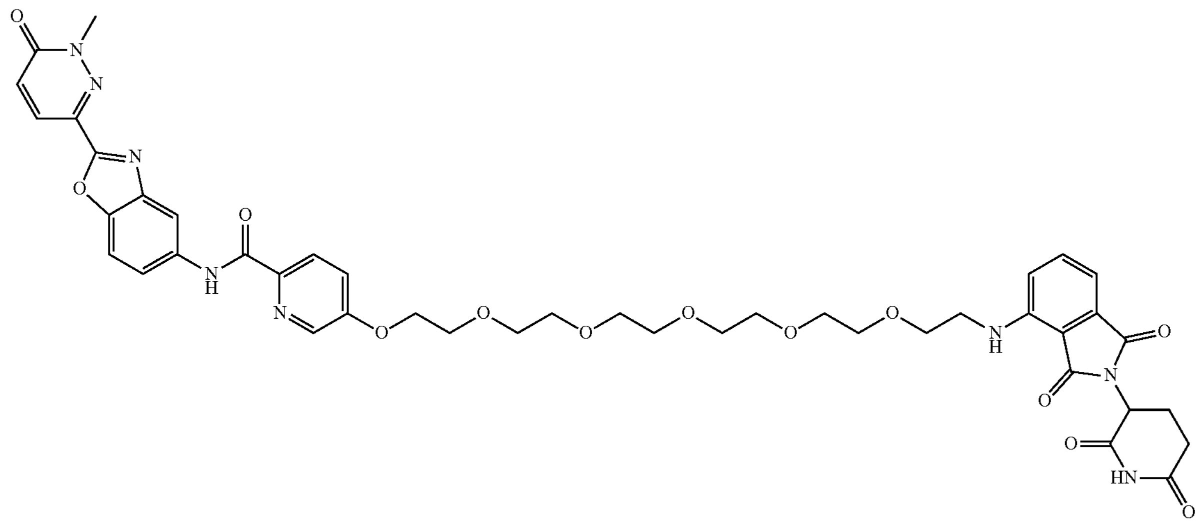 [SMILES: Cn1nc(-c2nc3cc(NC(=O)c4ccc(OCCOCCOCCOCCOCCOCCNc5cccc6c5C(=O)N(C5CCC(=O)NC5=O)C6=O)cn4)ccc3o2)ccc1=O] | Tr(METCRl603 High pH 7 min) = 3.86 min, (ES+) (M + H)+ 883.4. |
| 38 | 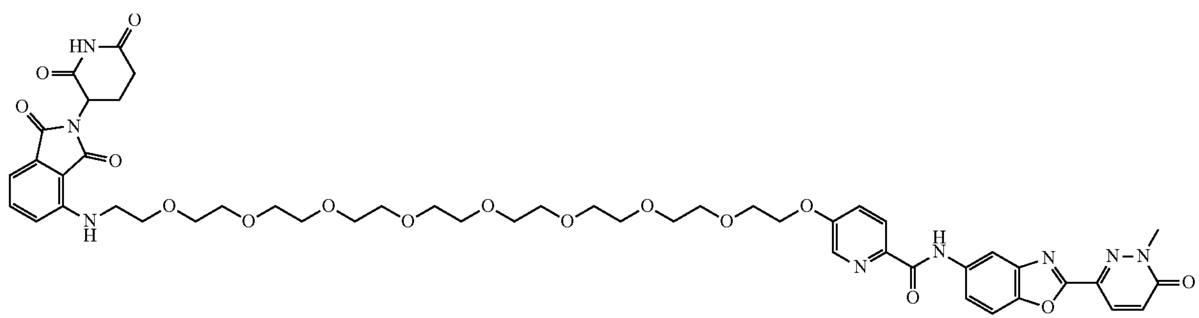 [SMILES: Cn1nc(-c2nc3cc(NC(=O)c4ccc(OCCOCCOCCOCCOCCOCCOCCOCCOCCNc5cccc6c5C(=O)N(C5CCC(=O)NC5=O)C6=O)cn4)ccc3o2)ccc1=O] | Tr(MET-uHPLC-AB-101) = 3.05 min, (ES+) (M + H)+ 1015.5. |

| # | Structure | Data |
|---|---|---|
| 34 | 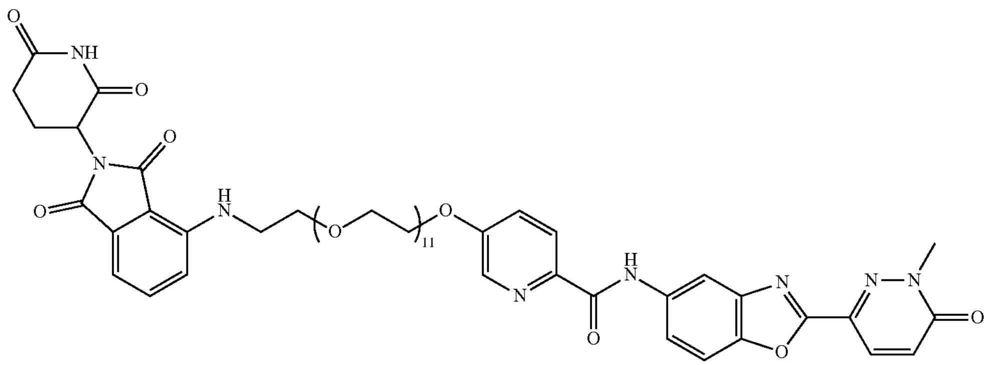 | Tr(MET-uHPLC-AB-101) = 3.07 min, (ES+) (M + H)+ 1147.3. |
| 37 | 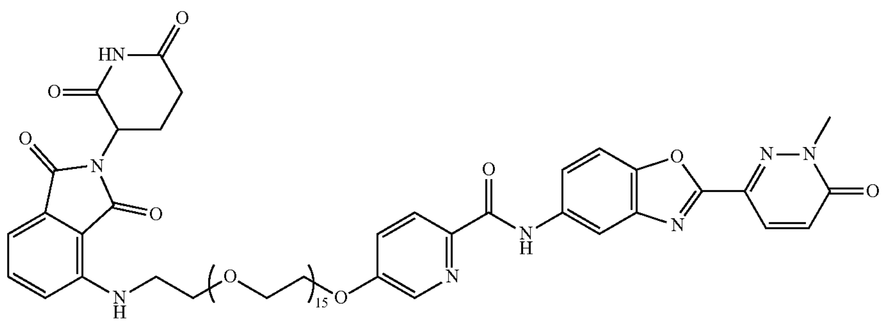 | Tr(MET-uHPLC-AB-101)= 3.1 min, (ES+) (M + H)+ 1323.4. |

| # | Structure | Data |
|---|---|---|
| 39 | 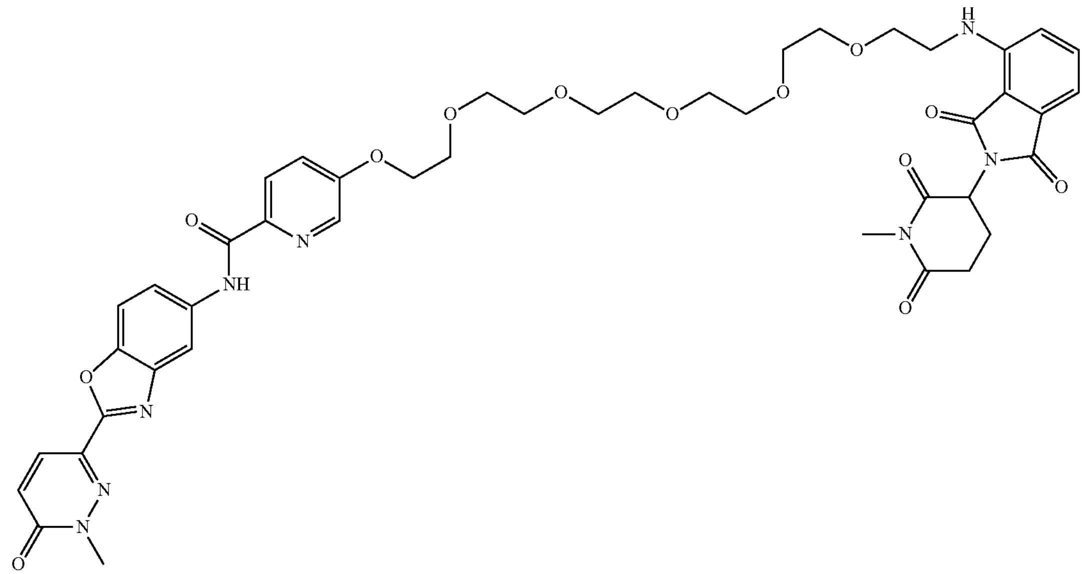 [SMILES: CN1C(=O)CCC(N2C(=O)c3cccc(NCCOCCOCCOCCOCCOCCOc4ccc(C(=O)Nc5ccc6oc(-c7ccc(=O)n(C)n7)nc6c5)nc4)c3C2=O)C1=O] | Tr(METCRl603 High pH 7 min) = 4.08 min, (ES+) (M + H)+ 897.7 |
| 40 | 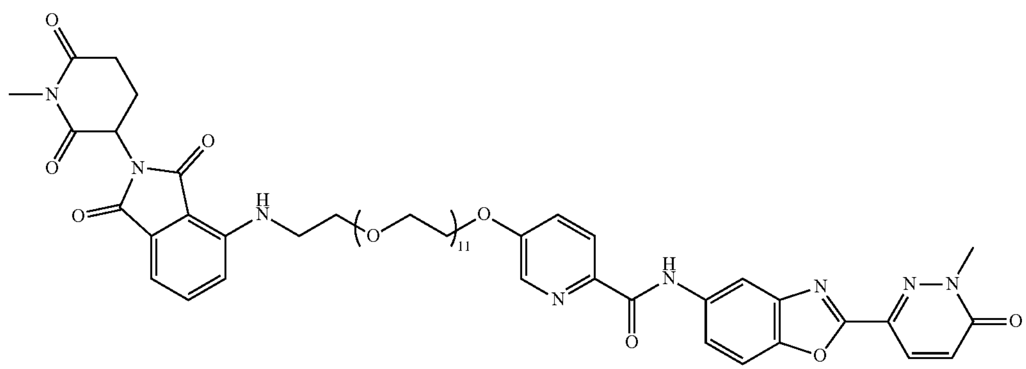 | Tr(MET-uHPLC-AB-101)= 3.28 min, (ES+) (M + H)+ 1161.4 |

-continued
| # | Structure | Data |
|---|---|---|
| 42 | 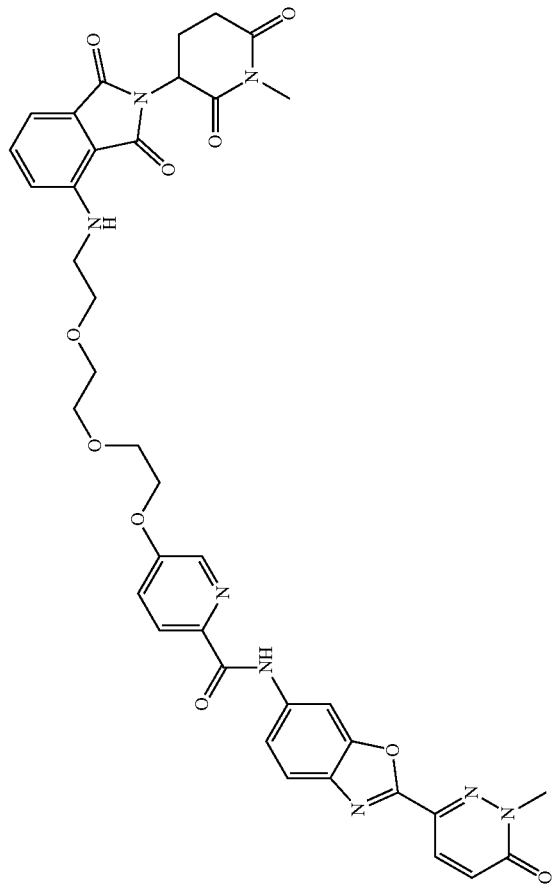 | |
| 70 | 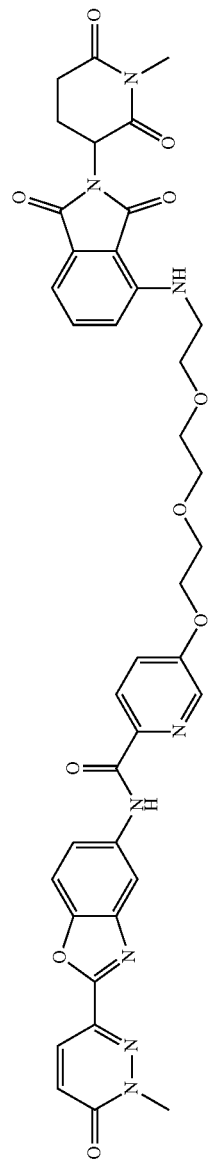 | Tr(MET-uHPLC-AB-101) = 3.41 min<br>m/z (ES+) (M + H)+ 765.3 |

Example 11
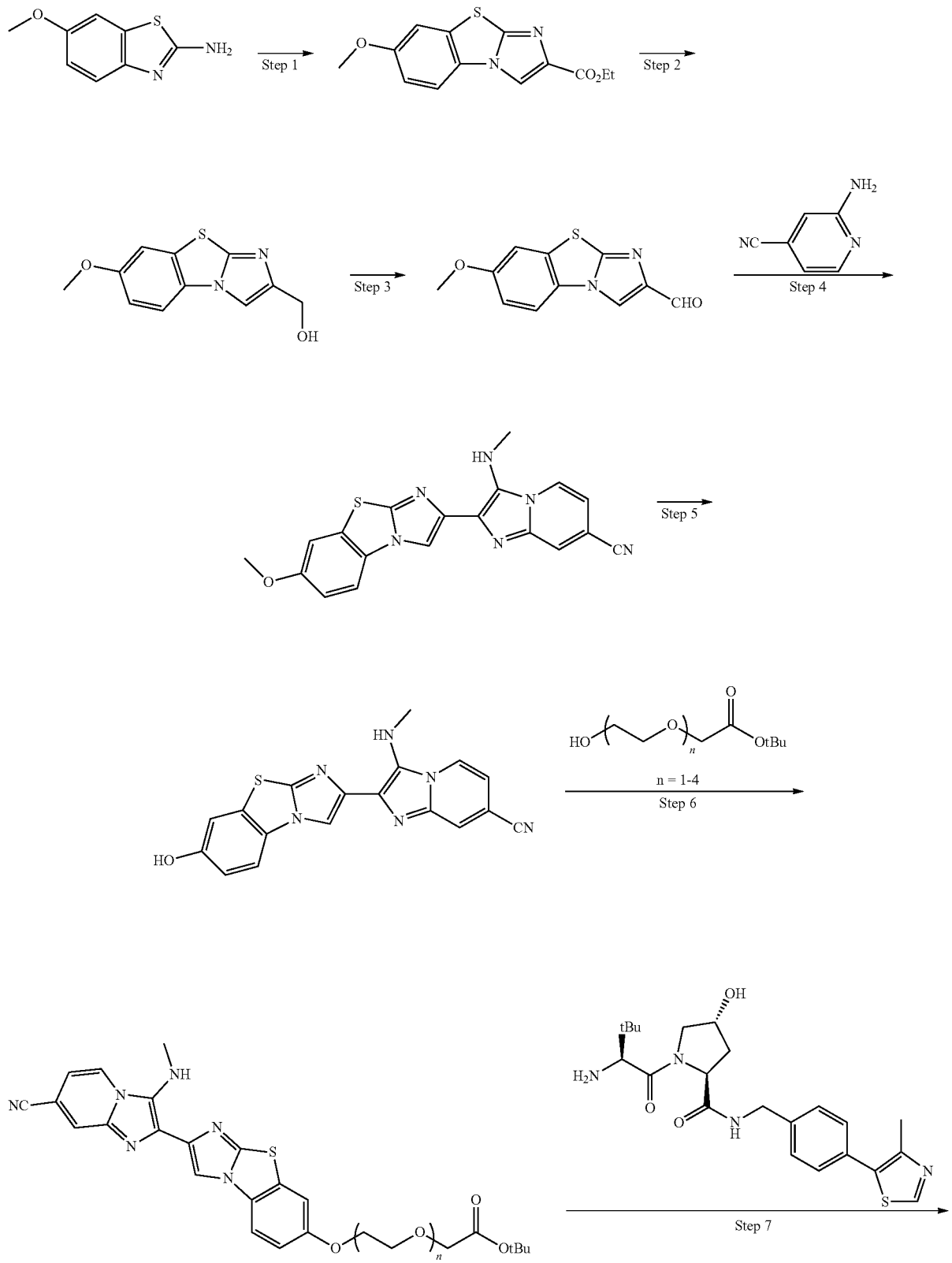

-continued

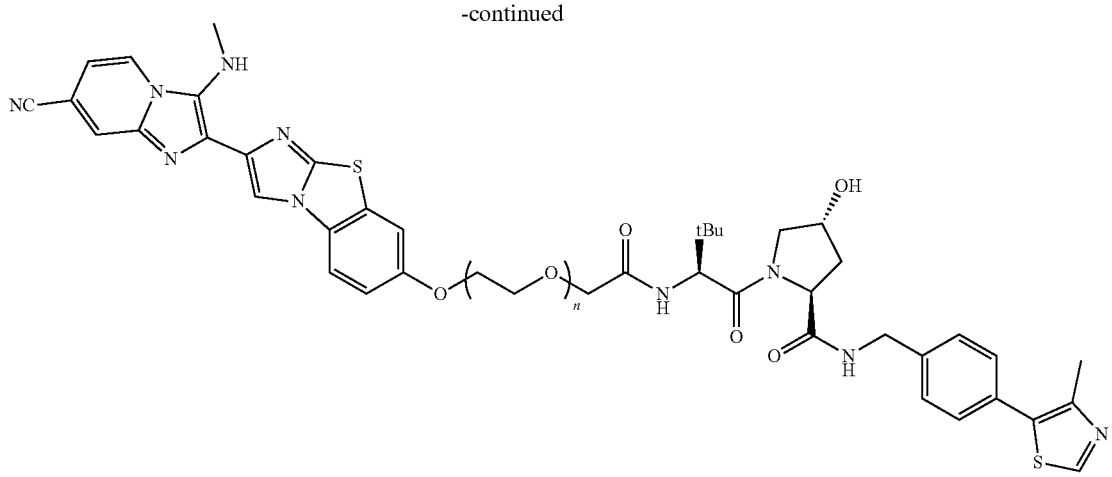

Step 1: Ethyl 7-methoxybenzo[d]imidazo[2,1-b]thiazole-2-carboxylate

A mixture of 6-methoxybenzo[d]thiazol-2-amine (15.00 g, 83.00 mmol) and ethyl 3-bromo-2-oxopropanoate (10.5 mL, 16.3 g, 84.0 mmol) in 1,4-dioxane (150 mL) was heated at 90° C. for 14 h. After this time, another portion of ethyl 3-bromo-2-oxopropanoate (2.5 mL, 3.9 g, 20 mmol) was added, and heating was continued for another 24 h. Volatiles were then removed at reduced pressure, and the residue obtained was treated with saturated sodium bicarbonate (200 mL) and ethyl acetate (300 mL). The mixture was stirred at 50° C. for 1 h, cooled to room temperature, and extracted with ethyl acetate (2×100 mL). The combined organic layers were washed with brine (100 mL), dried over magnesium sulfate and filtered. The resulting ethyl acetate solution was treated with silica gel (100 mL), concentrated at reduced pressure, and purified by chromatography (silica gel; heptane to ethyl acetate; gradient elution) to give two product fractions. The cleaner fraction was triturated with 95:5 heptane/ethyl acetate and filtered to afford product. The less clean fraction was dissolved in ethyl acetate (800 mL), and the solution was washed with 0.1 N HCl (3×100 mL), dried over sodium sulfate, filtered and concentrated at reduced pressure to afford product. $^1$H NMR (500 MHz, DMSO-d$_6$) δ 8.97 (s, 1H), 8.09 (d, J=9.0 Hz, 1H), 7.70 (d, J=2.5 Hz, 1H), 7.16 (dd, J=8.8, 3.0 Hz, 1H), 4.29 (q, J=7.5 Hz, 2H), 3.84 (s, 3H), 1.31 (t, J=7.0 Hz, 3H).

Step 2: (7-methoxybenzo[d]imidazo[2,1-b]thiazol-2-yl)methanol

A 1 M solution of lithium aluminum hydride in THF (6.15 mL, 6.15 mmol) was added dropwise over 10 min to a solution of ethyl 7-methoxybenzo[d]imidazo[2,1-b]thiazole-2-carboxylate (2.00 g, 7.24 mmol) in THF (118 mL) cooled to −78° C. After complete addition, the suspension was allowed to warm. When the mixture reached 0° C., it became clear, and TLC analysis indicated complete consumption of starting material. The solution was carefully poured into saturated ammonium chloride (150 mL) and filtered through diatomaceous earth. The filter cake was rinsed with ethyl acetate (3×75 mL), and the filtrate layers were separated. The aqueous layer was extracted with ethyl acetate (3×35 mL), and the organic layers were combined, dried over sodium sulfate, filtered and concentrated at reduced pressure. The residue obtained was chromatographed (silica gel; ethyl acetate to 95:5 ethyl acetate/methanol; gradient elution) to afford (7-methoxybenzo[d]imidazo[2,1-b]thiazol-2-yl)methanol. $^1$H NMR (500 MHz, DMSO-d$_6$) δ 8.05 (s, 1H), 7.91 (d, J=8.5 Hz, 1H), 7.63 (d, J=2.5 Hz, 1H), 7.10 (dd, J=9.0, 2.5 Hz, 1H), 5.10 (t, J=5.5 Hz, 1H), 4.47 (dd, J=5.8, 1.0 Hz, 2H), 3.82 (s, 3H).

Step 3: (7-Methoxybenzo[d]imidazo[2,1-b]thiazol-2-yl)pentaene-4-carbaldehyde (7-methoxybenzo[d]imidazo[2,1-b]thiazol-2-yl)methanol (80 mg, 0.31 mmol) was dissolved in dichloromethane (5 mL) and treated with Dess-Martin periodinane (156 mg, 0.37 mmol). The mixture was stirred at room temperature for 64 hours. The reaction was then quenched by the addition of saturated aqueous Na$_2$S$_2$O$_3$ (2 mL) and saturated aqueous NaHCO$_3$ (2 mL). The mixture was stirred for 5 minutes, causing most precipitate to dissolve. The mixture was diluted with water (10 mL) and dichloromethane (10 mL). The layers were separated and the aqueous further extracted with dichloromethane (2×10 mL). The combined organic extracts were washed with brine (10 mL), dried (MgSO$_4$), filtered and concentrated to afford the title compound. $^1$H NMR (500 MHz, DMSO-d$_6$) δ 9.83 (s, 1H), 9.06 (s, 1H), 8.08 (d, J=8.9 Hz, 1H), 7.72 (d, J=2.5 Hz, 1H), 7.18 (dd, J=8.9, 2.5 Hz, 1H), 3.85 (s, 3H). Tr(METCR1673)=1.10 min, (ES$^+$) (M+H)$^+$ 233.

Step 4: 2-(7-Methoxybenzo[d]imidazo[2,1-b]thiazol-2-yl)-3-(methyl-amino)imidazo-[1,2-a]pyridine-7-carbonitrile (7-Methoxybenzo[d]imidazo[2,1-b]thiazol-2-yl)pentaene-4-carbaldehyde (65 mg, 0.28 mmol) and 2-aminoisonicotinonitrile (33 mg, 0.28 mmol) were suspended in methanol (5 mL). AcOH (0.5 mL) and methyl isocyanide (22 μl, 0.42 mmol) were added and the mixture stirred at room temperature for 18 hours. The reaction mixture was filtered, and collected solid dried under suction to afford the title compound. $^1$H NMR (500 MHz, DMSO) 8.96 (s, 1H), 8.71 (s, 1H), 8.35 (d, J=7.1 Hz, 1H), 8.15 (s, 1H), 8.05 (d, J=8.9 Hz, 1H), 7.70 (d, J=2.5 Hz, 1H), 7.16 (dd, J=8.9, 2.5 Hz, 1H), 7.11 (dd, J=7.1, 1.6 Hz, 1H), 5.63 (q, J=5.8 Hz, 1H), 3.84 (s, 3H), 2.90 (d, J=5.9 Hz, 3H). Tr(MET-uHPLC-AB-101)=3.12 min, (ES$^+$) (M+H)$^+$ 375.

Step 5: 2-(7-hydroxybenzo[d]imidazo[2,1-b]thiazol-2-yl)-3-(methylamino)-imidazo-[1,2-a]pyridine-7-carbonitrile A 1 M solution of boron tribromide in dichloromethane (8.2 mL, 8.2 mmol) was added dropwise to a suspension of 2-(7-methoxybenzo[d]imidazo[2,1-b]thiazol-2-yl)-3-(methyl-amino)imidazo-[1,2-a]pyridine-7-carbonitrile (0.601 g, 1.63 mmol, prepared from (7-methoxybenzo[d]imidazo[2,1-b]thiazol-2-yl)methanol according to methods known in the art) in dichloromethane (80 mL) cooled to −78° C., and the mixture was allowed to warm to room temperature and stir for 18 h. After this time, the crude product mixture was poured in portions into a vigorously stirred solution of saturated sodium bicarbonate (400 mL). Solid sodium bicarbonate was added periodically to maintain the pH around 8. After complete addition, crude product was collected by filtration as an orange solid. The filtrate was extracted with ethyl acetate (5×100 mL), and the combined organic layers were dried over sodium sulfate, filtered and concentrated at reduced pressure. The residue obtained was combined with the isolated solid product, and the whole was heated at 50° C. in a mixture of methanol (100 mL) and acetonitrile (50 mL). Silica gel (75 mL) was added, and the mixture was concentrated to dryness, dried under high vacuum and chromatographed (silica gel; dichloromethane to 91:9 dichloromethane/methanol; gradient elution) to afford 2-(7-hydroxybenzo[d]imidazo[2,1-b]thiazol-2-yl)-3-(methylamino)imidazo[1,2-a]pyridine-7-carbonitrile. $^1$H NMR (500 MHz, DMSO-d6) δ 9.91 (s, 1H), 8.66 (s, 1H), 8.35 (d, J=7.5 Hz, 1H), 8.14 (s, 1H), 7.93 (d, J=8.5 Hz, 1H), 7.39 (d, J=2.0 Hz, 1H), 7.11 (dd, J=7.0, 1.5 Hz, 1H), 6.96 (dd, J=8.8, 2.5 Hz, 1H), 5.65 (q, J=6.0 Hz, 1H), 2.89 (d, J=6.0 Hz, 3H).

Step 6: tert-butyl 14-((2-(7-cyano-3-(methylamino)imidazo[1,2-a]pyridin-2-yl)benzo[d]imidazo[2,1-b]thiazol-7-yl)oxy)-3,6,9,12-tetraoxatetradecan-1-oate 2-(Tributyl-15-phosphanylidene)acetonitrile (0.290 mL, 0.267 g, 1.11 mmol) was added to a suspension of 2-(7-hydroxybenzo[d]imidazo[2,1-b]thiazol-2-yl)-3-(methylamino)-imidazo[1,2-a]pyridine-7-carbonitrile (0.184 g, 0.511 mmol) and tert-butyl 14-hydroxy-3,6,9,12-tetraoxatetradecan-1-oate (0.317 g, 1.03 mmol) in toluene (10 mL), and the mixture was heated at 100° C. for 6 h. After this time, the mixture was allowed to cool and was concentrated at reduced pressure. The residue obtained was adsorbed onto silica gel and chromatographed (silica gel; ethyl acetate to 98:2 ethyl acetate/methanol; gradient elution). The product fractions were combined and rechromatographed (silica gel; dichloromethane to 96:4 dichloromethane/methanol; gradient elution) to afford tert-butyl 14-((2-(7-cyano-3-(methylamino)imidazo[1,2-a]pyridin-2-yl)benzo[d]imidazo[2,1-b]thiazol-7-yl)oxy)-3,6,9,12-tetraoxatetradecan-1-oate. $^1$H NMR (500 MHz, DMSO-d$_6$) δ 8.73 (s, 1H), 8.35 (dd, J=7.0, 1.0 Hz, 1H), 8.16-8.15 (m, 1H), 8.04 (d, J=8.5 Hz, 1H), 7.70 (d, J=2.5 Hz, 1H), 7.18 (dd, J=8.5, 2.5 Hz, 1H), 7.12 (dd, J=7.3, 2.0 Hz, 1H), 5.64 (q, J=6.0 Hz, 1H), 4.19-4.17 (m, 2H), 3.97 (s, 2H), 3.80-3.78 (m, 2H), 3.62-3.60 (m, 2H), 3.57-3.52 (m, 10H), 2.90 (d, J=5.5 Hz, 3H), 1.40 (s, 9H); MS (ESI) m/z 651 [M+H]$^+$.

Step 7: (2S,4R)-1-((S)-2-(tert-butyl)-17-((2-(7-cyano-3-(methylamino)-imidazo[1,2-a]pyridin-2-yl)benzo[d]imidazo[2,1-b]thiazol-7-yl)oxy)-4-oxo-6,9,12,15-tetraoxa-3-azaheptadecan-1-oyl)-4-hydroxy-N-(4-(4-methylthiazol-5-yl)benzyl)-pyrrolidine-2-carboxamide Trifluoroacetic acid (0.50 mL, 0.75 g, 35 mmol) was added dropwise to a solution of tert-butyl 14-((2-(7-cyano-3-(methylamino)imidazo[1,2-a]pyridin-2-yl)benzo[d]imidazo[2,1-b]thiazol-7-yl)oxy)-3,6,9,12-tetraoxatetradecan-1-oate (0.120 g, 0.184 mmol) in dichloromethane (8 mL), and the mixture was stirred at room temperature. After 4 h, TLC analysis indicated incomplete reaction, so an additional portion of trifluoroacetic acid (0.50 mL, 0.75 g, 35 mmol) was added, and the reaction was continued for another 2 h. After this time, the volatiles were removed at reduced pressure. The residue obtained was azeotroped with dichloromethane (2×20 mL), then with toluene (2×20 mL) and again with dichloromethane (2×20 mL) to afford crude 14-((2-(7-cyano-3-(methylamino)imidazo[1,2-a]pyridin-2-yl)benzo[d]imidazo[2,1-b]thiazol-7-yl)oxy)-3,6,9,12-tetraoxatetradecan-1-oic acid.

To a solution of crude 14-((2-(7-cyano-3-(methylamino)imidazo[1,2-a]pyridin-2-yl)benzo-[d]imidazo[2,1-b]thiazol-7-yl)oxy)-3,6,9,12-tetraoxatetradecan-1-oic acid (0.184 mmol) and (2S,4R)-1-((S)-2-amino-3,3-dimethylbutanoyl)-4-hydroxy-N-(4-(4-methyl-thiazol-5-yl)benzyl)pyrrolidine-2-carboxamide (0.0840 g, 0.195 mmol, see, Galdeano et al, J. Med. Chem. 2014, 57, 8657-8663) in N,N-dimethylformamide (8 mL) was added N,N-diisopropyl-ethylamine (0.128 mL, 0.0950 g, 0.733 mmol), and the mixture was stirred at room temperature for 5 min. HATU (0.084 g, 0.23 mmol) was then added, and the mixture was stirred at room temperature for 30 min. After this time, water (15 mL) was added, and the aqueous layer was saturated with sodium chloride and extracted with ethyl acetate (6×50 mL). The organic layers were combined, washed with brine (4×30 mL), dried over sodium sulfate, filtered and concentrated at reduced pressure. The residue obtained was chromatographed (silica gel; dichloromethane to 92:8 dichloromethane/methanol; gradient elution) to afford the title compound. This material was dissolved in dichloromethane (3 mL) and precipitated by addition to heptane (25 mL). The resulting solid was collected by filtration and lyophilized from 50:50 acetonitrile/water (9 mL) to afford the title compound. $^1$H NMR (500 MHz, DMSO-d$_6$, observed as a 94:6 mixture of rotational isomers; chemical shifts given for the major isomer) δ 8.97 (s, 1H), 8.72 (s, 1H), 8.60 (t, J=6.0 Hz, 1H), 8.35 (dd, J=7.0, 0.5 Hz, 1H), 8.15 (br s, 1H), 8.03 (d, J=8.5 Hz, 1H), 7.69 (d, J=2.5 Hz, 1H), 7.42-7.37 (m, 5H), 7.16 (dd, J=9.0, 2.5 Hz, 1H), 7.11 (dd, J=7.0, 1.5 Hz, 1H), 5.64 (q, J=5.5 Hz, 1H), 5.15 (d, J=3.6 Hz, 1H), 4.56 (d, J=9.5 Hz, 1H), 4.46-4.35 (m, 3H), 4.24 (dd, J=16.0, 5.5 Hz, 1H), 4.17-4.15 (m, 2H), 3.96 (s, 2H), 3.77-3.75 (m, 2H), 3.67 (dd, J=10.5, 3.5 Hz, 1H), 3.61-3.52 (m, 13H), 2.89 (d, J=6.0 Hz, 3H), 2.43 (s, 3H), 2.07-2.04 (m, 1H), 1.93-1.87 (m, 1H), 0.94 (s, 9H); MS (ESI) m/z 1007 [M+H]$^+$; HPLC: Method 1, t$_R$=6.01 min.

The following compounds were prepared as described above:

| # | Structure | Data |
|---|---|---|
| 4 | 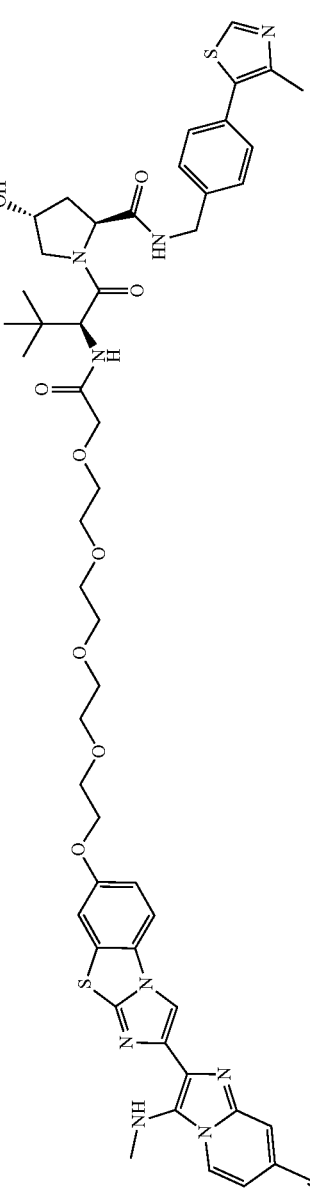 | MS (ESI) m/z 1007 [M + H]+; HPLC: t$_R$ = 6.01 min |
| 5 | 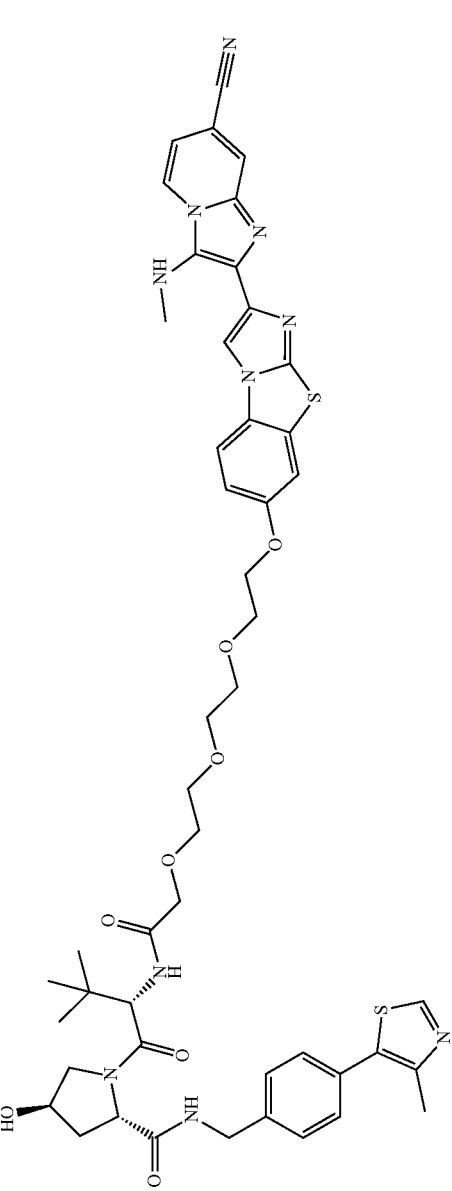 | MS (ESI) m/z 963 [M + H]+; HPLC: t$_R$ = 6.03 min |

-continued
| # | Structure | Data |
|---|---|---|
| 2 | 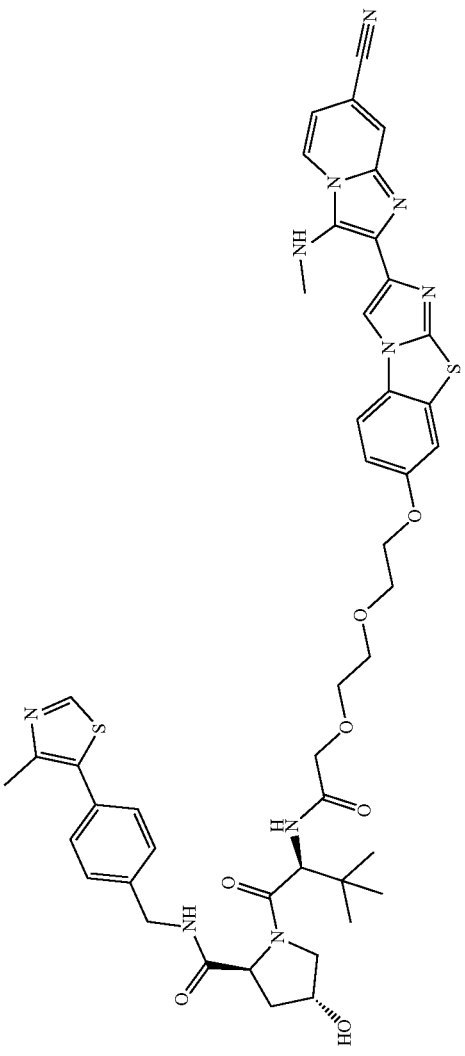 | MS (ESI) m/z 919 [M + H]+; HPLC: $t_R$ = 5.94 min |
| 1 | 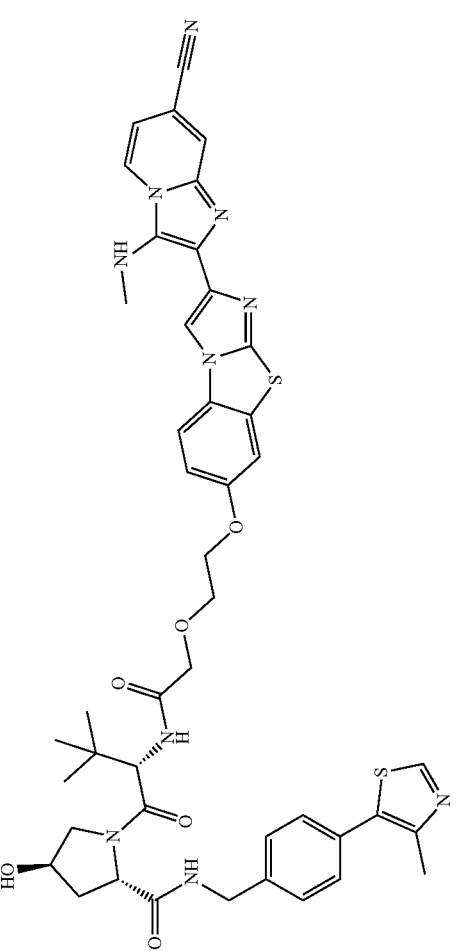 | MS (ESI) m/z 875 [M + H]+; HPLC: $t_R$ = 5.94 min |

| # | Structure | Data |
|---|---|---|
| 10 | 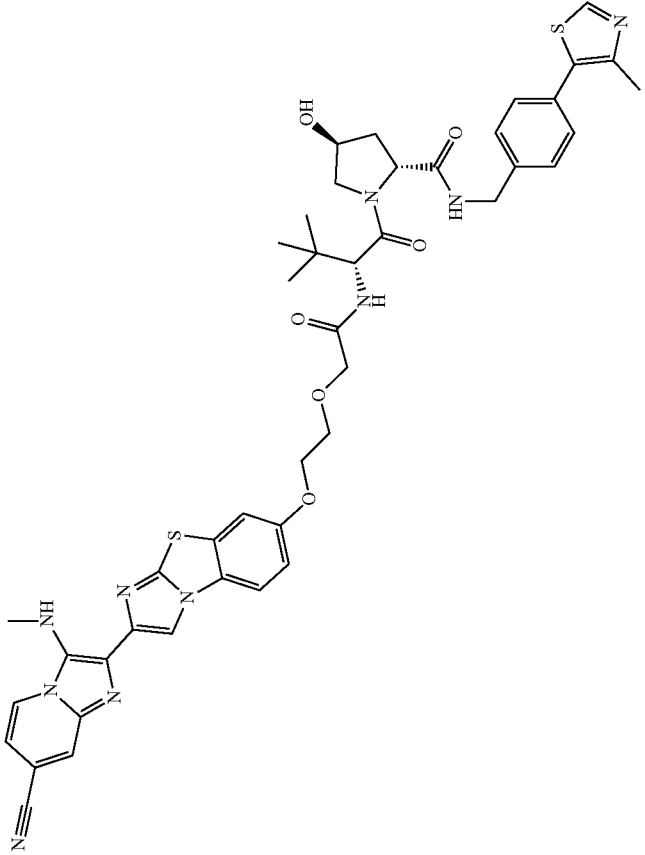 | Tr(METCRl603 High pH 7 min) = 4.07 min<br>m/z (ES+) (M + H)+ 875.5 |

Example 12
Scheme for Example 12
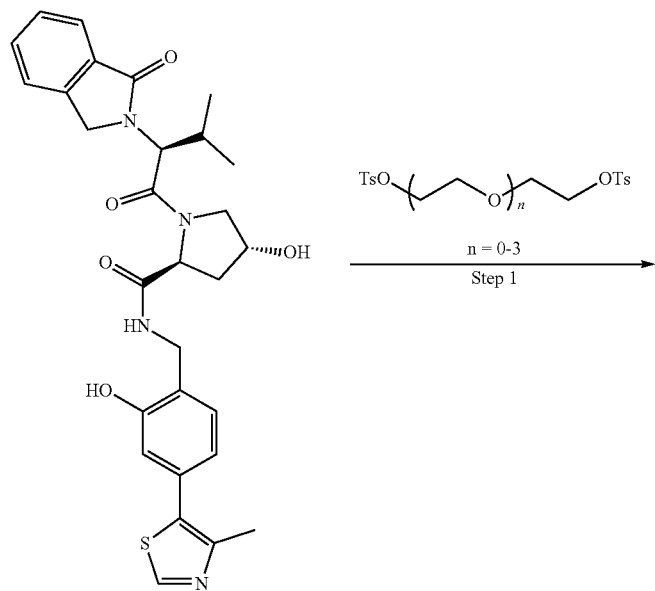
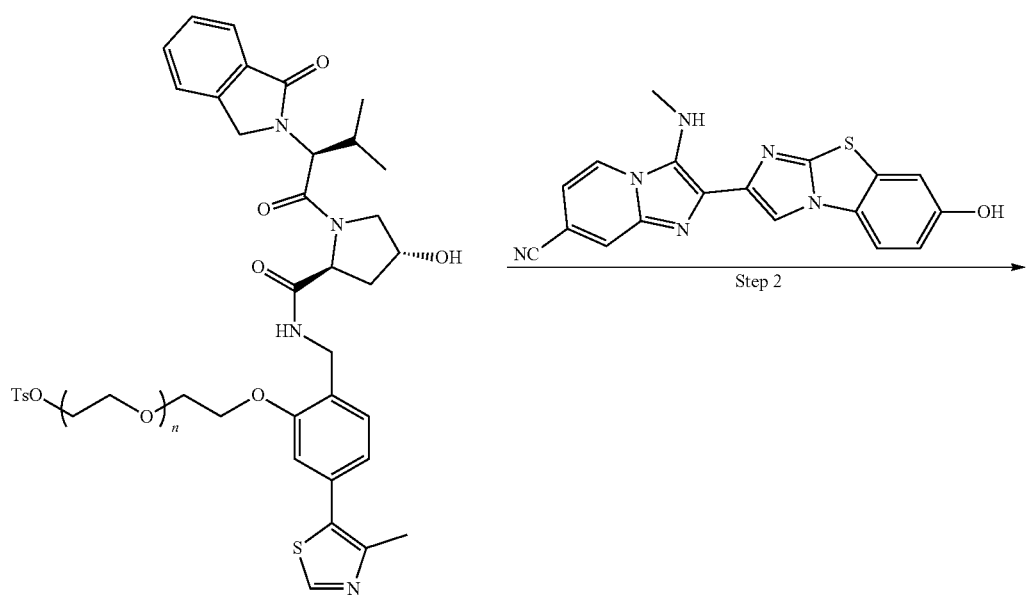

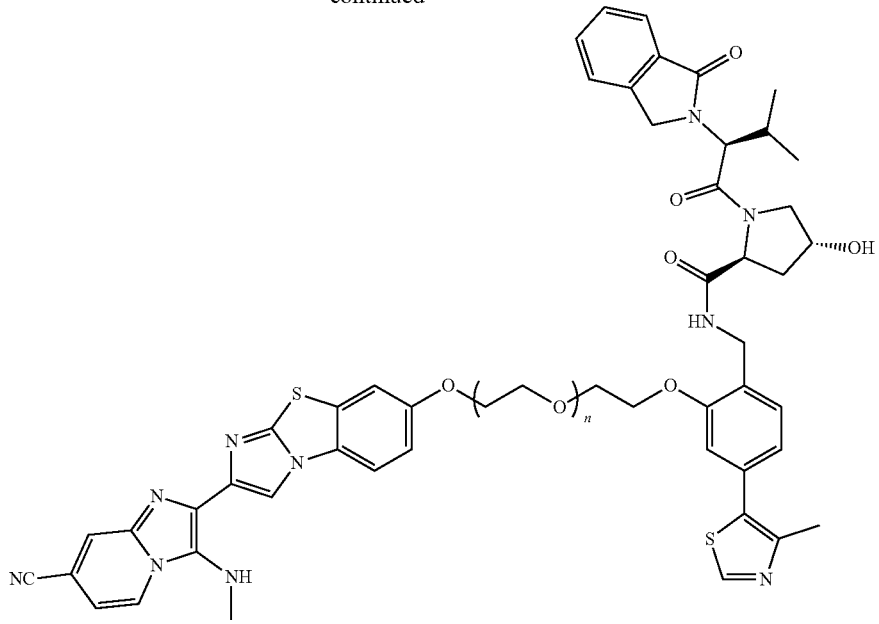

Step 1: 2-(2-(((2S,4R)-4-hydroxy-1-((S)-3-methyl-2-(1-oxoisoindolin-2-yl)butanoyl)pyrrolidine-2-carboxamido)methyl)-5-(4-methylthiazol-5-yl)phenoxy)-ethyl 4-methyl-benzenesulfonate A mixture of (2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide (0.150 g, 0.273 mmol), ethane-1,2-diyl bis(4-methyl-benzenesulfonate) (0.506 g, 1.37 mmol) and cesium carbonate (0.136 g, 0.417 mmol) in acetonitrile (10 mL) was heated at 60° C. for 2 h. After this time, the mixture was allowed to cool to room temperature and was filtered through a glass frit. The filter cake was rinsed with dichloromethane (3×5 mL) and ethyl acetate (3×5 mL), and the filtrate was concentrated at reduced pressure. The residue obtained was chromatographed (silica gel; dichloromethane to 95:5 dichloromethane/methanol; gradient elution) to afford the title compound. $^1$H NMR (500 MHz, DMSO-$d_6$, mixture of rotational isomers, chemical shifts of the major rotamer are reported): δ 8.98 (s, 1H), 8.36 (t, J=6.0 Hz, 1H), 7.82-7.80 (m, 2H), 7.72 (d, J=7.5 Hz, 1H), 7.64-7.60 (m, 2H), 7.51 (ddd, J=7.7, 5.8, 2.5 Hz, 1H), 7.46-7.44 (m, 2H), 7.32 (d, J=8.0 Hz, 1H), 7.00 (dd, J=8.0, 1.5 Hz, 1H), 6.93 (d, J=1.5 Hz, 1H), 5.09 (d, J=4.0 Hz, 1H), 4.72 (d, J=11.0 Hz, 1H), 4.56 (d, J=18.0 Hz, 1H), 4.47 (d, J=18.0 Hz, 1H), 4.42 (t, J=8.0 Hz, 1H), 4.39-4.34 (m, 3H), 4.27-4.25 (m, 2H), 4.14-4.05 (m, 2H), 3.79 (dd, J=10.8, 4.5 Hz, 1H), 3.70 (d, J=10.5 Hz, 1H), 2.44 (s, 3H), 2.36 (s, 3H), 2.34-2.32 (m, 1H), 2.09-2.05 (m, 1H), 1.95 (ddd, J=12.8, 8.0, 5.0 Hz, 1H), 0.97 (d, J=6.5 Hz, 3H), 0.74 (d, J=6.5 Hz, 3H); MS (ESI) m/z 769 [M+Na]$^+$, 747 [M+H]$^+$.

Step 2: (2S,4R)—N-(2-(2-((2-(7-cyano-3-(methylamino)imidazo[1,2-a]pyridin-2-yl)benzo[d]imidazo[2,1-b]thiazol-7-yl)oxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide A mixture of 2-(2-(((2S,4R)-4-hydroxy-1-((S)-3-methyl-2-(1-oxoisoindolin-2-yl)butanoyl)-pyrrolidine-2-carboxamido)methyl)-5-(4-methylthiazol-5-yl)phenoxy)ethyl 4-methylben-zenesulfonate (0.112 g, 0.150 mmol), 2-(7-hydroxybenzo[d]imidazo[2,1-b]thiazol-2-yl)-3-(methylamino)imidazo[1,2-a]pyridine-7-carbonitrile (0.056 g, 0.16 mmol) and cesium carbonate (0.099 g, 0.30 mmol) in N,N-dimethylformamide (8 mL) was heated at 60° C. for 2 h. After this time, the mixture was cooled to room temperature, and ethyl acetate (15 mL), water (15 mL) and brine (15 mL) were added. An orange-brown precipitate that formed was removed by filtration, and the filtrate layers were separated. The aqueous layer was extracted with ethyl acetate (4×20 mL), and the organic layers were combined, washed with brine (4×20 mL), dried over sodium sulfate and filtered. The solid collected prior to extraction was dissolved in dichloromethane/methanol and added to the ethyl acetate extracts before the whole was concentrated at reduced pressure. The residue obtained was adsorbed onto silica gel and chromatographed (silica gel; dichloromethane to 93:7 dichloromethane/methanol; gradient elution) to afford the title compound. The product obtained was dissolved in a mixture of methylene chloride and methanol (92:8, 4.0 mL), and the solution was added dropwise to a stirring mixture of heptane and ethyl acetate (95:5, 20 mL). The suspension was stirred at room temperature for approximately 30 min and filtered. The filter cake was washed with a mixture of heptane and ethyl acetate (95:5, 2×3 mL), dried under reduced pressure, lyophilized from 2:1 acetonitrile/water (10 mL), and dried in vacuo at 55° C. for 2 h to afford the title compound. $^1$H NMR (500 MHz, DMSO-$d_6$, mixture of rotational isomers, chemical shifts of the major rotamer are reported) δ 8.99 (s, 1H), 8.72 (s, 1H), 8.37-8.34 (m, 2H), 8.14 (s, 1H), 8.05 (d, J=9.0 Hz, 1H), 7.78 (d, J=2.5 Hz, 1H), 7.70 (d, J=7.5 Hz, 1H), 7.60 (d, J=4.0 Hz, 2H), 7.50-7.47 (m, 1H), 7.35 (d, J=7.5 Hz, 1H), 7.24 (dd, J=9.0, 2.5 Hz, 1H), 7.12-7.10 (m, 2H), 7.04 (dd, J=8.0, 1.5 Hz, 1H), 5.64 (q, J=6.0 Hz, 1H), 5.06 (d, J=4.0 Hz, 1H), 4.70 (d, J=11.0 Hz, 1H), 4.55-4.38 (m, 7H), 4.31-4.21 (m, 3H), 3.77 (dd, J=10.5, 4.5 Hz, 1H), 3.67 (d, J=11.0 Hz, 1H), 2.90 (d, J=3.0 Hz, 3H), 2.48 (s, 3H), 2.34-2.26 (m, 1H), 2.04-2.00 (m, 1H), 1.92-1.87 (m, 1H), 0.94 (d, J=6.5 Hz, 3H), 0.71 (d, J=6.5 Hz, 3H); MS (ESI) m/z 957 [M+Na]$^+$; HPLC $t_R$=6.41 min.

The following compounds were prepared as described above:

| # | Structure | Data |
|---|---|---|
| 5 | 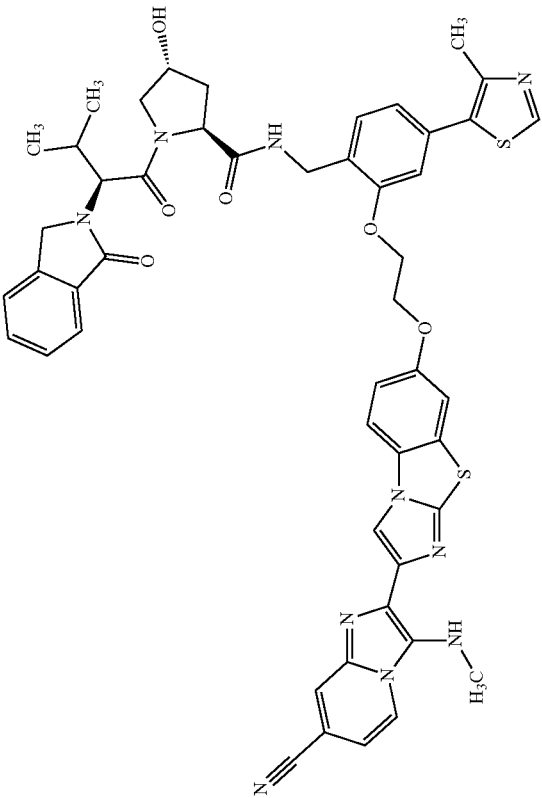 | MS (ESI) m/z 957 [M + Na]+; HPLC t$_R$ = 6.41 min |

| # | Structure | Data |
|---|---|---|
| 6 | 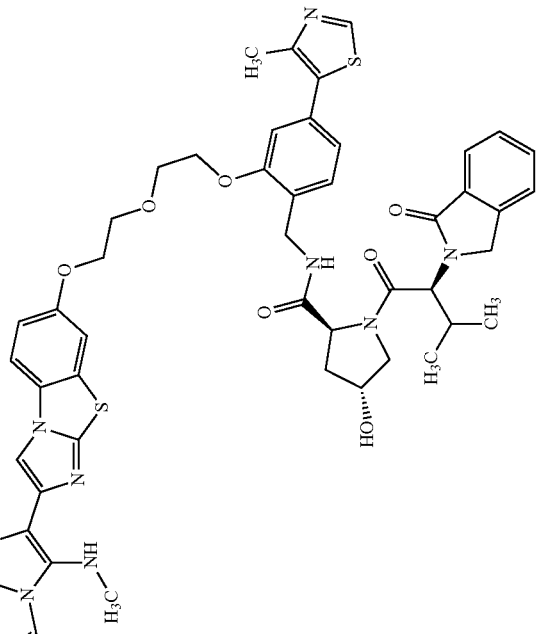 | MS (ESI) m/z 1001 [M + Na]$^+$; HPLC: $t_R$ = 6.30 min |

-continued

| # | Structure | Data |
|---|---|---|
| 7 | 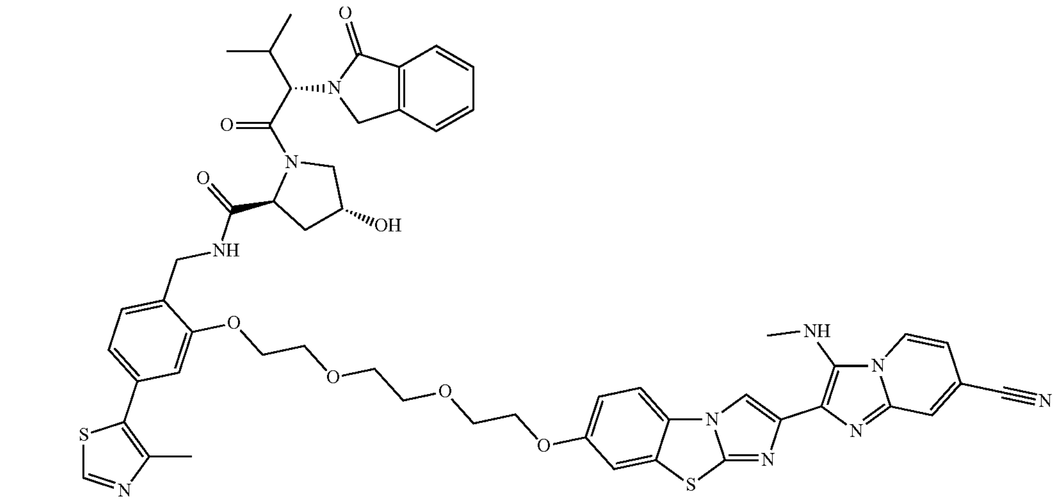 [SMILES: CNc1c(-c2cn3c(n2)sc2cc(OCCOCCOCCOc4cc(-c5scnc5C)ccc4CNC(=O)[C@@H]4C[C@@H](O)CN4C(=O)[C@H](C(C)C)N4Cc5ccccc5C4=O)ccc23)nc2cc(C#N)ccn12] | MS (ESI) m/z 1023 [M + H]⁺; HPLC: t_R = 6.35 min |
| 8 | 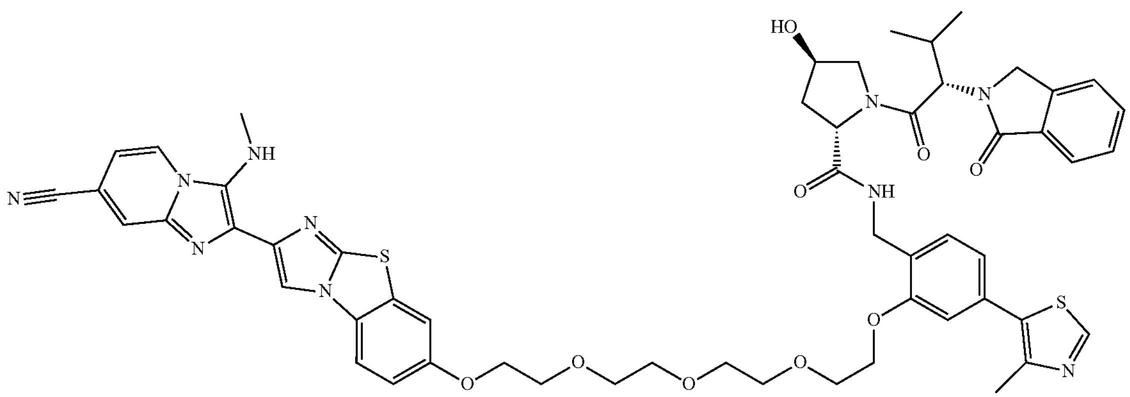 [SMILES: CNc1c(-c2cn3c(n2)sc2cc(OCCOCCOCCOCCOc4cc(-c5scnc5C)ccc4CNC(=O)[C@@H]4C[C@@H](O)CN4C(=O)[C@H](C(C)C)N4Cc5ccccc5C4=O)ccc23)nc2cc(C#N)ccn12] | MS (ESI) m/z 1089 [M+Na]⁺; HPLC: t_R = 6.28 min |

Example 13
Scheme for Example 13
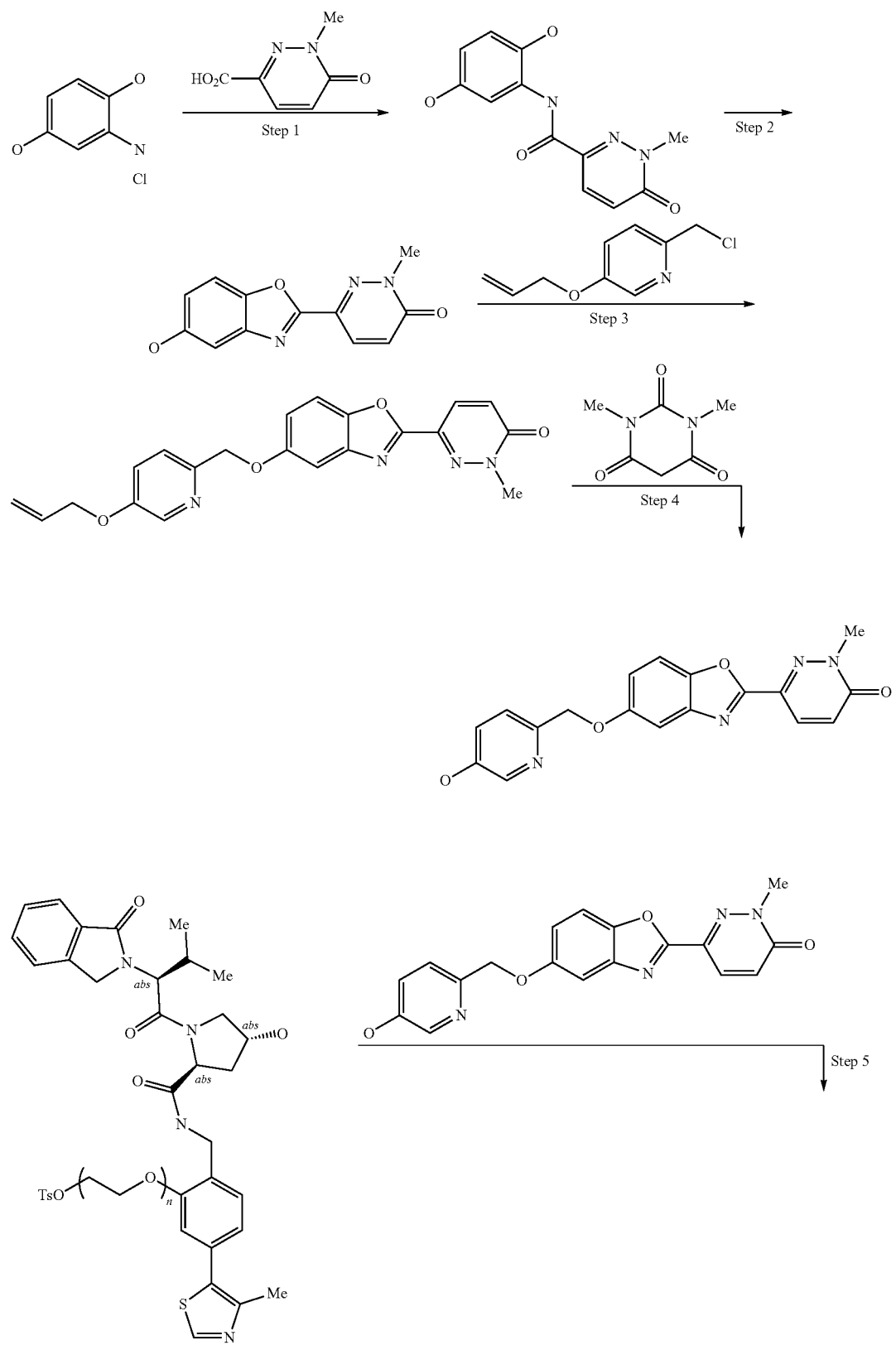

-continued

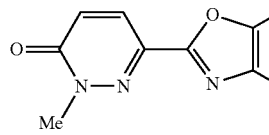 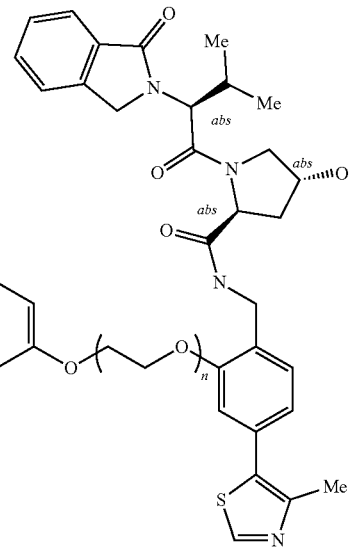

Step 1: N-(2,5-dihydroxyphenyl)-1-methyl-6-oxo-1,6-dihydropyridazine-3-carboxamide EDC (0.774 g, 4.03 mmol) was added to a mixture of 2-aminobenzene-1,4-diol hydro-chloride (0.500 g, 3.09 mmol) and 1-methyl-6-oxo-1,6-dihydropyridazine-3-carboxylic acid (0.526 g, 3.41 mmol) in anhydrous pyridine (4 mL), and the reaction mixture was stirred at room temperature for 16 h. After this time, the solvent was removed under reduced pressure, and the residue obtained was triturated with a 2:2:1 methylene chloride/ethyl acetate/methanol mixture (20 mL). The solid product was collected by filtration and rinsed with cold methanol (3×5 mL) to afford the title compound. $^1$H NMR (500 MHz, DMSO-$d_6$) δ 9.49 (s, 1H), 9.46 (s, 1H), 8.85 (s, 1H), 7.97 (d, J 9.5 Hz, 1H), 7.74 (d, J 3.0 Hz, 1H), 7.09 (d, J=9.5 Hz, 1H), 6.72 (d, J 9.0 Hz, 1H), 6.38 (dd, J 8.5, 3.0 Hz, 1H), 3.76 (s, 3H); MS (ESI) m/z 262 [M+H]$^+$.

Step 2: 6-(5-hydroxybenzo[d]oxazol-2-yl)-2-methylpyridazin-3(2H)-one

A suspension of N-(2,5-dihydroxyphenyl)-1-methyl-6-oxo-1,6-dihydropyridazine-3-carboxamide (0.150 g, 0.574 mmol) in glacial acetic acid (2.5 mL) was heated at 200° C. for 3.5 h under microwave irradiation. After this time, the solvent was removed under reduced pressure, and the residue obtained was triturated with a 2:2:1 methylene chloride/ethyl acetate/methanol mixture (10 mL) to afford the title compound. $^1$H NMR (500 MHz, DMSO-$d_6$) δ 9.63 (s, 1H), 8.12 (d, J=10.0 Hz, 1H), 7.62 (d, J=9.0 Hz, 1H), 7.14-7.12 (m, 2H), 6.92 (dd, J=9.0, 2.5 Hz, 1H), 3.79 (s, 3H); MS (ESI) m/z 244 [M+H]$^+$.

Step 3: 6-(5-((5-(allyloxy)pyridin-2-yl)methoxy)benzo[d]oxazol-2-yl)-2-methyl-pyridazin-3(2H)-one Sodium hydride (60% dispersion in mineral oil, 0.280 g, 6.99 mmol) was added to a mixture of 6-(5-hydroxybenzo[d]oxazol-2-yl)-2-methylpyridazin-3(2H)-one (0.567 g, 2.33 mmol), 5-(allyloxy)-2-(chloromethyl)pyridine (0.856 g, 4.66 mmol), and potassium iodide (0.387 g, 2.33 mmol) in anhydrous N,N-dimethylacetamide (16 mL). The resulting reaction mixture was stirred at room temperature for 10 min before heating at 80° C. for 2 h. After this time, the reaction mixture was cooled to room temperature and quenched with water (100 mL). The product was extracted with methylene chloride (2×100 mL), and the combined organic layers were dried over sodium sulfate, filtered, and the filtrate concentrated under reduced pressure. The residue obtained was purified by chromatography (silica gel; methylene chloride to 95:5 methylene chloride/methanol; gradient elution). The product obtained was again purified by chromatography (silica gel; methylene chloride to ethyl acetate; gradient elution) to afford the title compound. $^1$H NMR (500 MHz, CDCl$_3$) δ 8.32 (d, J 2.8 Hz, 1H), 8.12 (d, J 9.7 Hz, 1H), 7.55-7.46 (m, 2H), 7.35-7.29 (m, 2H), 7.14 (dd, J 8.9, 2.5 Hz, 1H), 7.07 (d, J 9.7 Hz, 1H), 6.11-5.97 (m, 1H), 5.48-5.33 (m, 2H), 5.25 (s, 2H), 4.61 (d, J 5.3 Hz, 2H), 3.96 (s, 3H).

Step 4: 6-(5-((5-hydroxypyridin-2-yl)methoxy)benzo[d]oxazol-2-yl)-2-methylpyridazin-3(2H)-one A mixture of 6-(5-((5-(allyloxy)pyridin-2-yl)methoxy)benzo[d]oxazol-2-yl)-2-methyl-pyridazin-3(2H)-one (0.295 g, 0.756 mmol) and 1,3-dimethylpyrimidine-2,4,6(1H,3H,5H)-trione (0.118 g, 0.756 mmol) in anhydrous methanol (30 mL) was purged with nitrogen for 5 min. Tetrakis(triphenylphosphine)palladium(0) (0.021 g, 0.019 mmol) was added, and the mixture was purged with nitrogen for an additional 5 min, and then heated at 50° C. for 2 h. After this time, the solid product was collected by filtration, rinsed with methanol, adsorbed onto silica gel and purified by chromatography (silica gel; methylene chloride to 90:10 methylene chloride/methanol; gradient elution) to afford 6-(5-((5-hydroxypyridin-2-yl)methoxy)benzo[d]oxazol-2-yl)-2-methylpyridazin-3(2H)-one. The isolated product was recrystallized from DMSO and lyophilized to afford clean product. $^1$H NMR (500 MHz, DMSO-$d_6$) δ 9.96 (s, 1H), 8.14-8.12 (m, 2H), 7.74 (d, J 8.9 Hz, 1H), 7.47 (d, J 2.5 Hz, 1H), 7.39 (d, J=8.4 Hz, 1H), 7.20 (dd, J 8.4, 2.9 Hz, 1H), 7.16-7.12 (m, 2H), 5.12 (s, 2H), 3.80 (s, 3H); MS (ESI) m/z 351 [M+H]$^+$; HPLC: $t_R$=7.84 min.

Step 5: (2S,4R)-4-hydroxy-1-((S)-3-methyl-2-(1-oxoisoindolin-2-yl)butan-oyl)-N-(2-(2-((6-(((2-(1-methyl-6-oxo-1,6-dihydropyridazin-3-yl)benzo[d]oxazol-5-yl)oxy)methyl)pyridin-3-yl)oxy)ethoxy)-4-(4-methylthiazol-5-yl)benzyl)pyrrolidine-2-carboxamide Cesium carbonate (0.086 g, 0.27 mmol) was added to a suspension of 2-(2-(((2S,4R)-4-hydroxy-1-((S)-3-methyl-2-(1-oxoisoindolin-2-yl)butanoyl)pyrrolidine-2-carboxamido)-methyl)-5-(4-methylthiazol-5-yl)phenoxy)ethyl 4-methylbenzenesulfonate (0.099 g, 0.13 mmol) and 6-(5-((5-hydroxypyridin-2-yl)methoxy)benzo[d]oxazol-2-yl)-2-methyl-pyridazin-3(2H)-one (0.056 g, 0.16 mmol) in N,N-dimethylformamide (15 mL) in a microwave reaction tube. The tube was sealed, placed in a preheated aluminum block, and the mixture was stirred at 60° C. for 4.5 h. After this time, the reaction mixture was cooled to room temperature and concentrated under reduced pressure. The residue obtained was absorbed onto silica gel and purified by column chromatography (silica gel; dichloromethane to 86:14 dichloromethane/methanol; gradient elution) to afford (2S,4R)-4-hydroxy-1-((S)-3-methyl-2-(1-oxoisoindolin-2-yl)butanoyl)-N-(2-(2-((6-(((2-(1-methyl-6-oxo-1,6-dihydro-pyridazin-3-yl)benzo[d]oxazol-5-yl)oxy)methyl)pyridin-3-yl)oxy)ethoxy)-4-(4-methylthiazol-5-yl)benzyl)pyrrolidine-2-carboxamide. This material was combined with another lot and purified by column chromatography (silica gel; dichloro-methane to 86:14 dichloromethane/methanol; gradient elution). The product obtained was dissolved in a solution of 96:4 dichloromethane/methanol (1 mL) and added to a stirring solution of 88:12 heptane/ethyl acetate (13 mL). The suspension was stirred for 5 min, let stand for 20 min, and filtered. The filter cake was washed with 88:12 heptane/ethyl acetate (2×5 mL), and then dissolved in a solution of 1:1 acetonitrile/water (17 mL) and lyophilized to afford the title compound. $^1$H NMR (500 MHz, DMSO-$d_6$; mixture of rotational isomers, data are reported for the major isomer) δ 9.00 (s, 1H), 8.38 (t, J=1.5 Hz, 1H), 8.35 (t, J=6.0 Hz, 1H), 8.13 (d, J=9.5 Hz, 1H), 7.75 (d, J=9.0 Hz, 1H), 7.70 (d, J=7.5 Hz, 1H), 7.62-7.60 (m, 2H), 7.54-7.53 (m, 2H), 7.51-7.48 (m, 2H), 7.35 (d, J=7.5 Hz, 1H), 7.17 (dd, J=9.0, 2.5 Hz, 1H), 7.14 (d, J=9.5 Hz, 1H), 7.12 (d, J=1.5 Hz, 1H), 7.03 (dd, J=7.5, 1.5 Hz, 1H), 5.20 (s, 2H), 5.07 (d, J=4.0 Hz, 1H), 4.70 (d, J=11.0 Hz, 1H), 4.54 (d, J=18.0 Hz, 1H), 4.50-4.48 (m, 2H), 4.46-4.41 (m, 3H), 4.39 (d, J=8.0 Hz, 1H), 4.32-4.19 (m, 3H), 3.79 (s, 3H), 3.75 (dd, J=10.5, 4.5 Hz, 1H), 3.68 (d, J=11.0 Hz, 1H), 2.48 (s, 3H), 2.34-2.26 (m, 1H), 2.04-2.00 (m, 1H), 1.92-1.87 (m, 1H), 0.94 (d, J=6.5 Hz, 3H), 0.71 (d, J=6.5 Hz, 3H); MS (ESI) m/z 947 [M+Na]$^+$; HPLC: Method 1, $t_R$=5.71 min.

The following compounds were prepared as described above:

| # | Structure | Data |
|---|---|---|
| 43 | 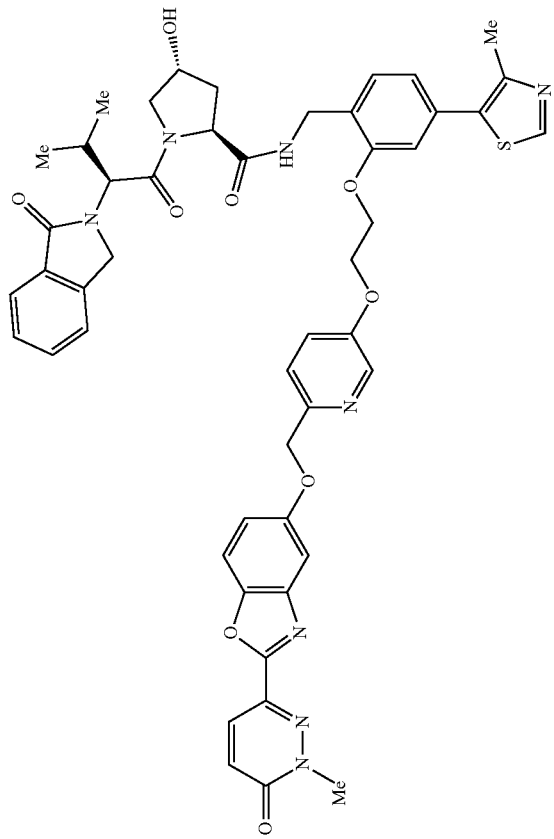 | MS (ESI) m/z 947 [M + Na]+; HPLC: $t_R$ = 5.71 min |

| # | Structure | Data |
|---|---|---|
| 44 | 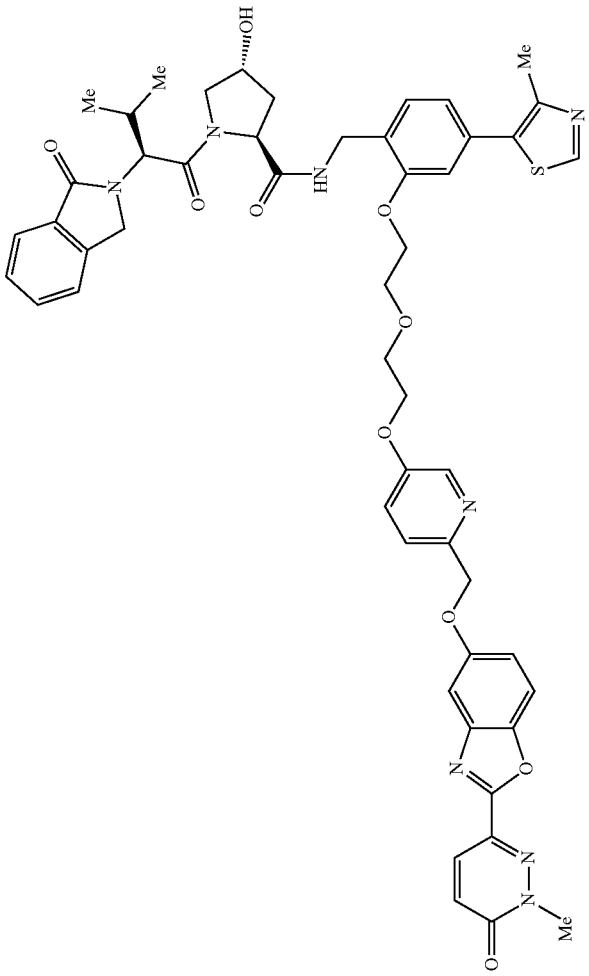 | MS (ESI) m/z 991 [M + Na]+; HPLC: $t_R$ = 5.74 min |

-continued
| # | Structure | Data |
|---|---|---|
| 45 | 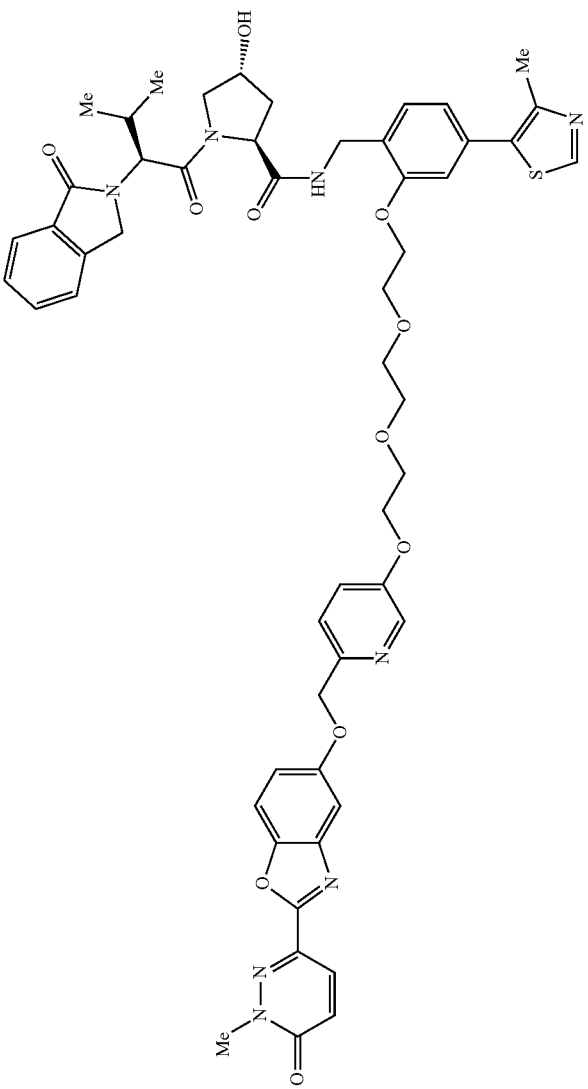 | MS (ESI) m/z 1035 [M + Na]$^+$; HPLC: $t_R$ = 5.75 min |

-continued
| # | Structure | Data |
|---|---|---|
| 46 | 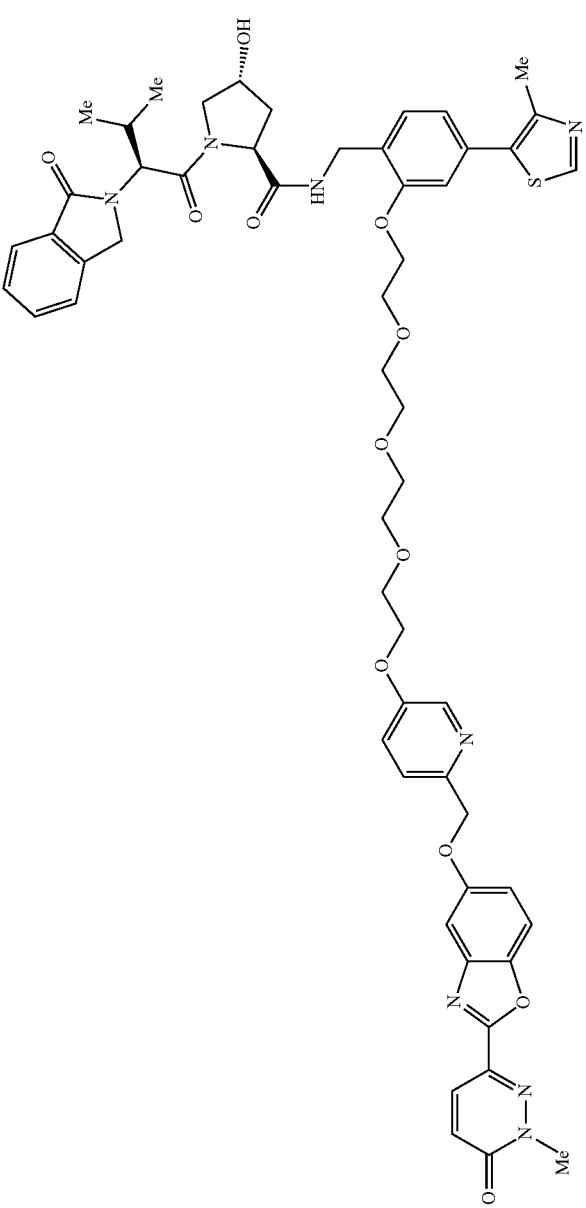 | MS (ESI) m/z 1079 [M + Na]⁺; HPLC: Method 1, $t_R$ = 5.72 min |

Example 14
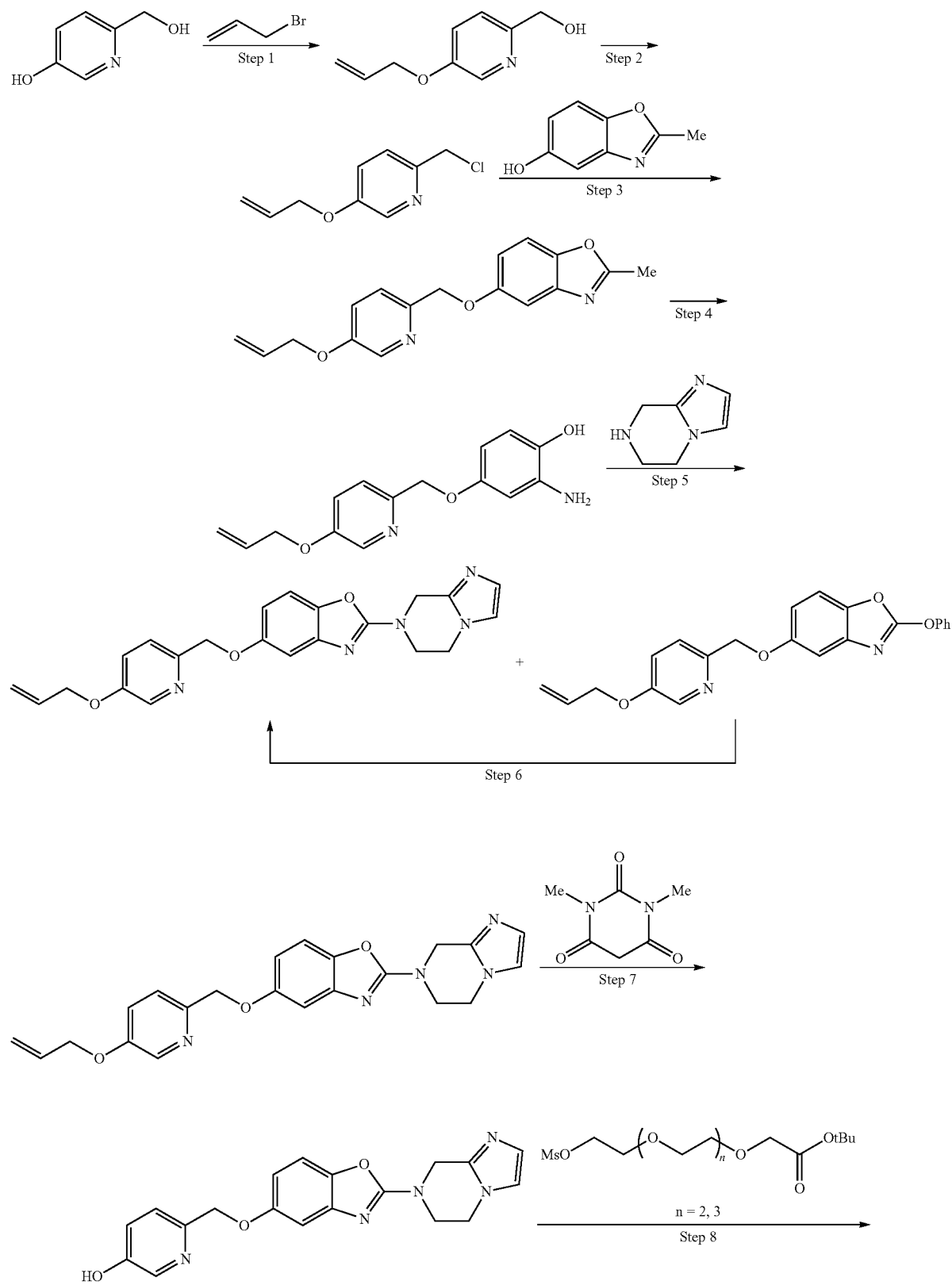
Scheme for Example 14

-continued

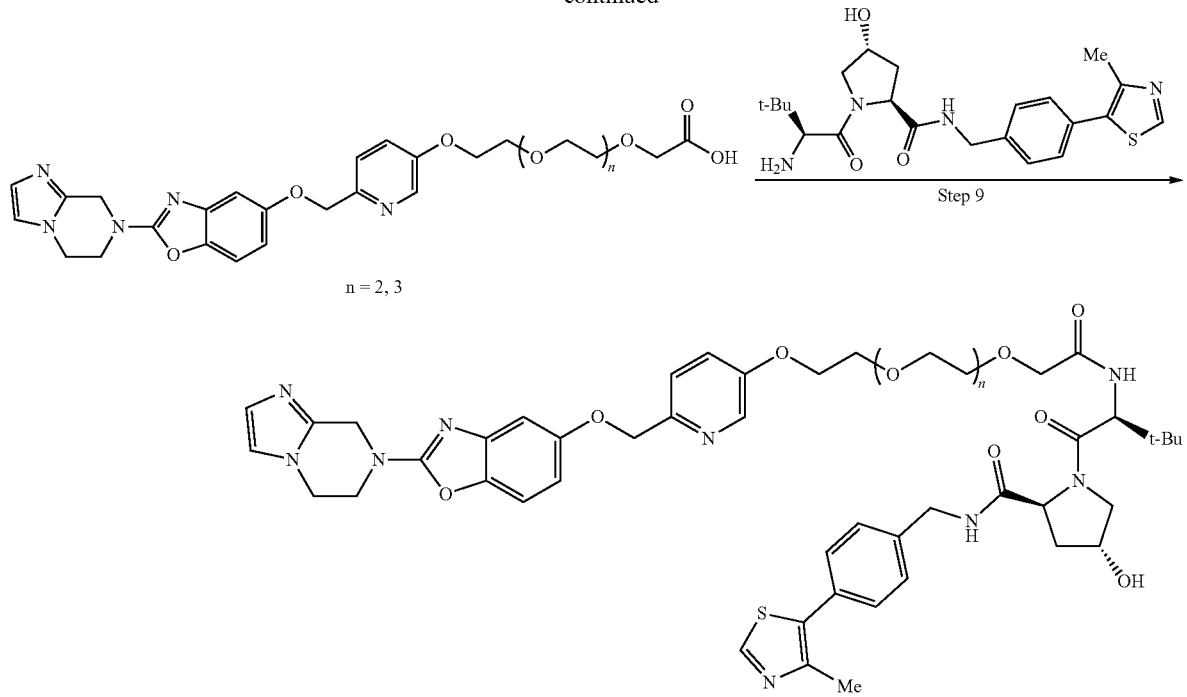

n = 2, 3

Step 1: (5-(Allyloxy)pyridin-2-yl)methanol

A solution of potassium carbonate (1.65 g, 11.9 mmol) in water (4 mL) was added dropwise over 15 min to a mixture of 6-(hydroxymethyl)pyridin-3-ol (1.00 g, 7.99 mmol) and allyl bromide (0.80 mL, 9.3 mmol) in anhydrous acetone (10 mL), and the reaction mixture was heated at 60° C. for 2 h in a sealed tube. After this time, the mixture was cooled to room temperature, and the product was extracted with MTBE (3×100 mL). The organic layers were combined, dried over sodium sulfate, filtered, and the filtrate concentrated under reduced pressure to afford the title compound that was used in the next step without further purification. $^1$H NMR (500 MHz, DMSO-$d_6$) δ 8.19 (dd, J=2.5, 0.5 Hz, 1H), 7.49-7.35 (m, 2H), 6.07-5.99 (m, 1H), 5.40 (dq, J 17.5, 1.5 Hz, 1H), 5.29-5.25 (m, 2H), 4.63 (dt, J 5.0, 1.5 Hz, 2H), 4.48 (d, J 5.5 Hz, 2H).

Step 2: 5-(Allyloxy)-2-(chloromethyl)pyridine

Thionyl chloride (1.27 mL, 17.6 mmol) was added dropwise at 0° C. to a solution of (5-(allyloxy)pyridin-2-yl)methanol (1.45 g, 8.78 mmol) in anhydrous methylene chloride (30 mL). The resulting mixture was stirred at 0° C. for 30 min and at room temperature for 2 h. After this time, the mixture was concentrated under reduced pressure. The residue obtained was dissolved in methylene chloride (100 mL) and washed with saturated aqueous sodium bicarbonate (75 mL). The organic layer was dried over sodium sulfate and filtered, and the filtrate concentrated under reduced pressure to afford the title compound. $^1$H NMR (500 MHz, DMSO-$d_6$) δ 8.27 (d, J 2.7 Hz, 1H), 7.50-7.40 (m, 2H), 6.11-5.98 (m, 1H), 5.41 (dq, J 17.1, 2.5 Hz, 1H), 5.29 (dq, J 17.5, 2.5 Hz, 1H), 4.73 (s, 2H), 4.67 (dt, J 9.0, 2.5 Hz, 2H).

Step 3: 5-((5-(allyloxy)pyridin-2-yl)methoxy)-2-methylbenzo[d]oxazole

Sodium hydride (60% dispersion in mineral oil, 0.263 g, 6.57 mmol) was added to a solution of 5-(allyloxy)-2-(chloromethyl)pyridine (1.06 g, 4.73 mmol), 2-methylbenzo[d]-oxazol-5-ol (0.700 g, 4.69 mmol) and potassium iodide (0.156 g, 0.939 mmol) in N,N-dimethylacetamide (60 mL), and the mixture was stirred at room temperature for 7.75 h. After this time, the reaction mixture was cooled to 0° C. in an ice/water bath and slowly treated with water (150 mL). The resulting mixture was poured into stirring water (500 mL), diluted to a total volume of 1 L with water and stirred for 5 min. The resulting suspension was placed in an ice/water bath, let stand 30 min and filtered. The filter cake was washed with water (2×20 mL) and dried under vacuum to afford the title compound. The filtrate from above was extracted with ethyl acetate (4×100 mL), and the combined organic layers were washed with water (2×100 mL) and brine (50 mL), dried over sodium sulfate, filtered and the filtrate concentrated under reduced pressure. The residue obtained was purified by column chromatography (silica gel; heptane to 60:40 heptane/ethyl acetate; gradient elution) to give additional title compound. $^1$H NMR (500 MHz, DMSO-$d_6$) δ 8.30 (d, J=3.0 Hz, 1H), 7.54 (d, J=9.0 Hz, 1H), 7.48 (d, J=8.5 Hz, 1H), 7.43 (dd, J=8.5, 3.0 Hz, 1H), 7.29 (d, J=2.5 Hz, 1H), 6.99 (dd, J=9.0, 2.5 Hz, 1H), 6.08-6.01 (m, 1H), 5.41 (dq, J=17.5, 1.5 Hz, 1H), 5.29 (dq, J=10.5, 1.5 Hz, 1H), 5.13 (s, 2H), 4.66 (t, J=1.5 Hz, 1H), 4.65 (t, J=1.5 Hz, 1H), 2.57 (s, 3H).

Step 4: 4-((5-(allyloxy)pyridin-2-yl)methoxy)-2-aminophenol

2 M Hydrochloric acid (5.5 mL, 11 mmol) was added to a stirring solution of 5-((5-(allyl-oxy)pyridin-2-yl)methoxy)-2-methylbenzo[d]oxazole (0.538 g, 1.82 mmol) in ethanol (11 mL) at room temperature, and the resulting suspension was placed in a preheated aluminum block and stirred at 105° C. for 6 h. After this time, the reaction mixture was cooled to room temperature, and ethanol was removed under reduced pressure. The residue obtained was partitioned between saturated aqueous sodium bicarbonate (100 mL) and dichloromethane (50 mL). The layers were separated, and the aqueous layer was extracted with dichloromethane (2×50 mL). The combined organic layers were dried over sodium sulfate and filtered, and the filtrate concentrated under reduced pressure to afford the title compound. $^1$H NMR (500 MHz, DMSO-$d_6$) δ 8.48 (s, 1H), 8.26 (dd, J=2.5, 1.0 Hz, 1H), 7.41 (dd, J=8.5, 2.5 Hz, 1H), 7.38 (dd, J=8.5, 1.0 Hz, 1H), 6.50 (d, J=8.5 Hz, 1H), 6.27 (d, J=3.0 Hz, 1H), 6.09-6.00 (m, 2H), 5.41 (dq, J=17.5, 1.5 Hz, 1H), 5.28 (dq, J=10.5, 1.5 Hz, 1H), 4.90 (s, 2H), 4.65 (t, J=1.5 Hz, 1H), 4.62 (t, J=1.5 Hz, 1H), 4.54 (br s, 2H).

Step 5: 5-((5-(allyloxy)pyridin-2-yl)methoxy)-2-(5,6-dihydroimidazo[1,2-a]pyrazin-7(8H)-yl)benzo[d]oxazole Dichlorodiphenoxymethane (0.3 g, 1.0 mmol) was added to a solution of 4-((5-(allyloxy)-pyridin-2-yl)methoxy)-2-aminophenol (0.27 g, 0.98 mmol), 5,6,7,8-tetrahydroimidazo-[1,2-a]pyrazine (0.1 g, 1.0 mmol) and triethylamine (0.1 mL, 1.0 mmol) in toluene (7.0 mL) and 1,2-dichloroethane (1.0 mL), and the resulting reaction mixture was heated at 80° C. for 24 h. After this time, the mixture was slowly cooled to room temperature, diluted with dichloromethane (15 mL) and quenched with saturated sodium bicarbonate (15 mL). The mixture was stirred vigorously for 5 min, the phases were separated, and the aqueous phase was extracted with dichloromethane (3×20 mL). The combined organic phases were dried over sodium sulfate, filtered and concentrated in vacuo. The residue obtained was purified by column chromatography (silica gel; dichloromethane to 90:10 dichloromethane/methanol; gradient elution) to the title compound. $^1$H NMR (500 MHz, DMSO-$d_6$) δ 8.29 (d, J=3.0 Hz, 1H), 7.46 (d, J=8.5 Hz, 1H), 7.42 (dd, J=8.5, 3.0 Hz, 1H), 7.34 (d, J=9.0 Hz, 1H), 7.15 (d, J=1.5 Hz, 1H), 7.01 (d, J=2.5 Hz, 1H), 6.91 (d, J=1.0 Hz, 1H), 6.70 (dd, J=9.0, 1.0 Hz, 1H), 6.08-6.00 (m, 1H), 5.41 (dq, J=17.5, 1.5 Hz, 1H), 5.28 (dq, J=11.0, 2.0 Hz, 1H), 5.08 (s, 2H), 4.79 (s, 2H), 4.65 (dt, J=5.5, 1.5 Hz, 2H), 4.15 (t, J=5.5 Hz, 2H), 4.05 (t, J=5.5 Hz, 2H). Also isolated from chromatography was 5-((5-(allyloxy)pyridin-2-yl)methoxy)-2-phenoxybenzo[d]oxazole. $^1$H NMR (500 MHz, DMSO-$d_6$) δ 8.29 (dd, J=2.0, 0.5 Hz, 1H), 7.53-7.46 (m, 6H), 7.41 (dd, J=8.5, 2.5 Hz, 1H), 7.38-7.35 (m, 1H), 7.18 (d, J=2.5 Hz, 1H), 6.93 (dd, J=8.5, 2.5 Hz, 1H), 6.07-6.00 (m, 1H), 5.41 (dq, J=17.5, 1.5 Hz, 1H), 5.28 (dq, J=11.0, 2.0 Hz, 1H), 5.10 (s, 2H), 4.65 (dt, J=5.5, 1.5 Hz, 2H).

Step 6: 5-((5-(allyloxy)pyridin-2-yl)methoxy)-2-(5,6-dihydroimidazo[1,2-a]pyrazin-7(8H)-yl)benzo[d]oxazole Cesium carbonate (0.305 g, 0.935 mmol) was added to a solution of 5-((5-(allyloxy)-pyridin-2-yl)methoxy)-2-phenoxybenzo[d]oxazole (0.14 g, 0.37 mmol) and 5,6,7,8-tetrahydroimidazo[1,2-a]pyrazine (0.115 g, 0.935 mmol) in N,N-dimethylformamide (15 mL), and the reaction mixture was heated at 50° C. for 24 h. After this time, the mixture was cooled to room temperature, quenched with water (30 mL) and extracted with ethyl acetate (3×50 mL). The combined organic phase was washed with brine (3×50 mL), dried over sodium sulfate, filtered and concentrated in vacuo. The residue obtained was purified by column chromatography (silica gel; dichloromethane to 90:10 dichloro-methane/methanol; gradient elution) to afford the title compound. $^1$H NMR (500 MHz, DMSO-$d_6$) δ 8.29 (d, J=3.0 Hz, 1H), 7.46 (d, J=8.5 Hz, 1H), 7.42 (dd, J=8.5, 3.0 Hz, 1H), 7.34 (d, J=9.0 Hz, 1H), 7.15 (d, J=1.5 Hz, 1H), 7.01 (d, J=2.5 Hz, 1H), 6.91 (d, J=1.0 Hz, 1H), 6.70 (dd, J=9.0, 1.0 Hz, 1H), 6.08-6.00 (m, 1H), 5.41 (dq, J=17.5, 1.5 Hz, 1H), 5.28 (dq, J=11.0, 2.0 Hz, 1H), 5.08 (s, 2H), 4.79 (s, 2H), 4.65 (dt, J=5.5, 1.5 Hz, 2H), 4.15 (t, J=5.5 Hz, 2H), 4.05 (t, J=5.5 Hz, 2H).

Step 7: 6-(((2-(5,6-dihydroimidazo[1,2-a]pyrazin-7(8H)-yl)benzo[d]oxazol-5-yl)oxy)methyl)pyridin-3-ol A mixture of 5-((5-(allyloxy)pyridin-2-yl)methoxy)-2-(5,6-dihydroimidazo[1,2-a]pyrazin-7(8H)-yl)benzo[d]oxazole (0.97 g, 2.4 mmol) and 1,3-dimethylbarbituric acid (0.45 g, 2.9 mmol) in anhydrous methanol (96 mL) was purged with argon for 30 min. Tetrakis-(triphenylphosphine)palladium (0) (0.14 g, 0.12 mmol) was added, and the mixture was stirred at 50° C. for 1 h. After this time, the mixture was cooled to room temperature, diluted with water (100 mL) and extracted with dichloromethane (3×100 mL). The combined organic phase was washed with brine (100 mL), dried over sodium sulfate, filtered and concentrated in vacuo. The residue obtained was purified by column chromatography (silica gel; dichloromethane to 90:10 dichloromethane/methanol; gradient elution) to afford the title compound. $^1$H NMR (500 MHz, DMSO-$d_6$) δ 9.94 (s, 1H), 8.11 (d, J=2.0 Hz, 1H), 7.36-7.33 (m, 2H), 7.19-7.15 (m, 2H), 7.01 (d, J=3.5 Hz, 1H), 6.91 (d, J=1.0 Hz, 1H), 6.69 (dd, J=8.5, 2.5 Hz, 1H), 5.02 (s, 2H), 4.79 (s, 2H), 4.15 (t, J=5.5 Hz, 2H), 4.05 (t, J=5.5 Hz, 2H).

Step 8: 2-(2-(2-(2-((6-(((2-(5,6-dihydroimidazo[1,2-a]pyrazin-7(8H)-yl)benzo-[d]oxazol-5-yl)oxy)methyl)pyridin-3-yl)oxy)ethoxy)ethoxy)ethoxy)acetic acid Sodium hydride (60% dispersion in mineral oil, 0.040 g, 1.1 mmol) was added to a solution of 6-(((2-(5,6-dihydro-imidazo[1,2-a]pyrazin-7(8H)-yl)benzo[d]oxazol-5-yl)oxy)-methyl)pyridin-3-ol (0.2 g, 0.5 mmol) and tert-butyl 2-(2-(2-(2-((methylsulfonyl)oxy)-ethoxy)ethoxy)ethoxy)acetate (0.23 g, 0.66 mmol) in N,N-dimethylacetamide (9 mL) at 0° C. After 10 min, the mixture was heated at 50° C. for 4.5 h. After this time, the mixture was quenched with water (20 mL) and extracted with ethyl acetate (2×50 mL). The aqueous phase was concentrated in vacuo, and the residue obtained was adsorbed onto diatomaceous earth and purified by reverse phase chromatography (C18; 95:5 water/acetonitrile to acetonitrile; gradient elution) to afford the title compound. $^1$H NMR (500 MHz, CDCl$_3$) δ 8.25 (d, J=2.5 Hz, 1H), 7.36 (d, J=8.5 Hz, 1H), 7.19 (dd, J=8.5, 3.0 Hz, 1H), 7.34 (d, J=9.0 Hz, 1H), 7.05 (d, J=1.0 Hz, 1H), 6.98 (d, J=2.5 Hz, 1H), 6.87 (d, J=1.0 Hz, 1H), 6.68 (dd, J=8.5, 2.5 Hz, 1H), 5.07 (s, 2H), 4.91 (s, 2H), 4.15-4.09 (m, 6H), 3.81 (br s, 4H), 3.68-3.53 (m, 8H).

Step 9: (2S,4R)-1-((S)-2-(tert-butyl)-14-((6-(((2-(5,6-dihydroimidazo[1,2-a]pyrazin-7(8H)-yl)benzo[d]oxazol-5-yl)oxy)methyl)pyridin-3-yl)oxy)-4-oxo-6,9,12-trioxa-3-azatetra-decan-1-oyl)-4-hydroxy-N-(4-(4-methylthiazol-5-yl)benzyl)-pyrrolidine-2-carboxamide HATU (0.058 g, 0.15 mmol) was added to a solution of 2-(2-(2-(2-((6-(((2-(5,6-dihydro-imidazo[1,2-a]pyrazin-7(8H)-yl)benzo[d]oxazol-5-yl)oxy)methyl)pyridin-3-yl)oxy)

ethoxy)-ethoxy)ethoxy)acetic acid (0.085 g, 0.15 mmol), (2S,4R)-1-((S)-2-amino-3,3-dimethyl-butanoyl)-4-hydroxy-N-(4-(4-methylthiazol-5-yl)benzyl)pyrrolidine-2-carboxamide (0.060 g, 0.14 mmol) and N,N-diisopropylethylamine (0.146 mL, 0.836 mmol) in N,N-dimethylformamide, and the mixture was stirred at room temperature for 30 min. After this time, saturated sodium bicarbonate (20 mL) was added, and the mixture was extracted with ethyl acetate (3×40 mL). The combined organic phase was washed with brine (3×30 mL), dried over sodium sulfate, filtered and concentrated in vacuo. The residue obtained was purified by column chromatography (silica gel; dichloro-methane to 90:10 dichloromethane//9:1 methanol/ammonium hydroxide; gradient elution), and the product obtained was lyophilized from 1:1 water/acetonitrile to afford the title compound. $^1$H NMR (500 MHz, DMSO-d6) δ 8.96 (s, 1H), 8.59 (t, J=6.0 Hz, 1H), 8.26 (d, J=8.0 Hz, 1H), 7.44-7.33 (m, 8H), 7.15 (d, J=1.0 Hz, 1H), 7.01 (d, J=2.5 Hz, 1H), 6.91 (d, J=1.0 Hz, 1H), 6.69 (dd, J=8.5, 2.5 Hz, 1H), 5.15 (d, J=4.0 Hz, 1H), 5.07 (s, 2H), 4.79 (s, 2H), 4.56 (d, J=9.5 Hz, 1H), 4.45-4.34 (m, 3H), 4.24 (dd, J=16.0, 3.0 Hz, 1H), 4.16-4.14 (m, 4H), 4.04 (t, J=5.5 Hz, 2H), 3.96 (s, 2H), 3.73-3.71 (m, 2H), 3.67-3.55 (m, 10H), 2.43 (s, 3H), 2.08-2.03 (m, 1H), 1.92-1.87 (m, 1H), 0.93 (s, 9H); MS (ESI) m z 966 [M+H]$^+$; HPLC: Method 2, $t_R$=4.80 min.

The following compounds were prepared as described above:

| # | Structure | Data |
|---|---|---|
| 58 | 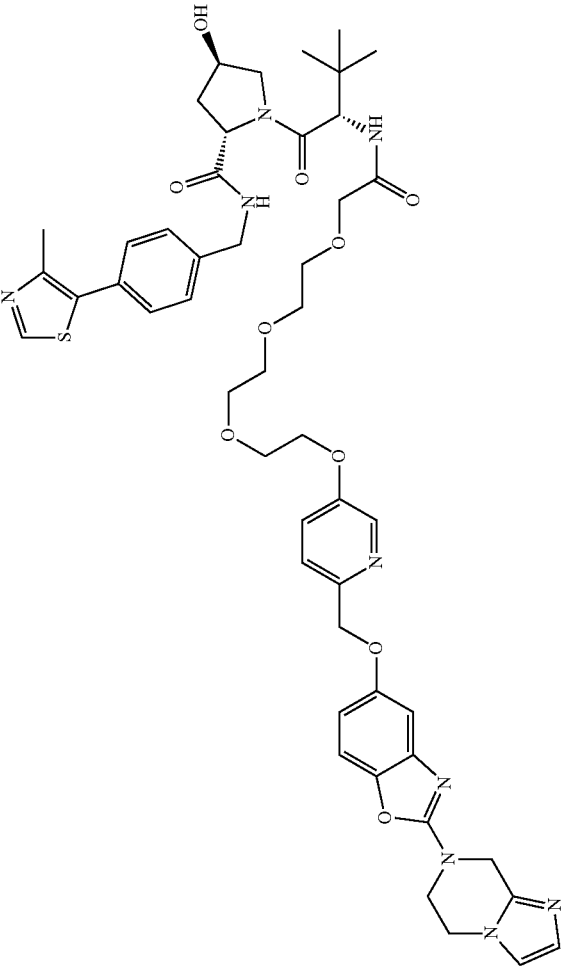 | MS (ESI) m/z 966 [M + H]+; HPLC: Method 2, $t_R$ = 4.80 min |
| 57 | 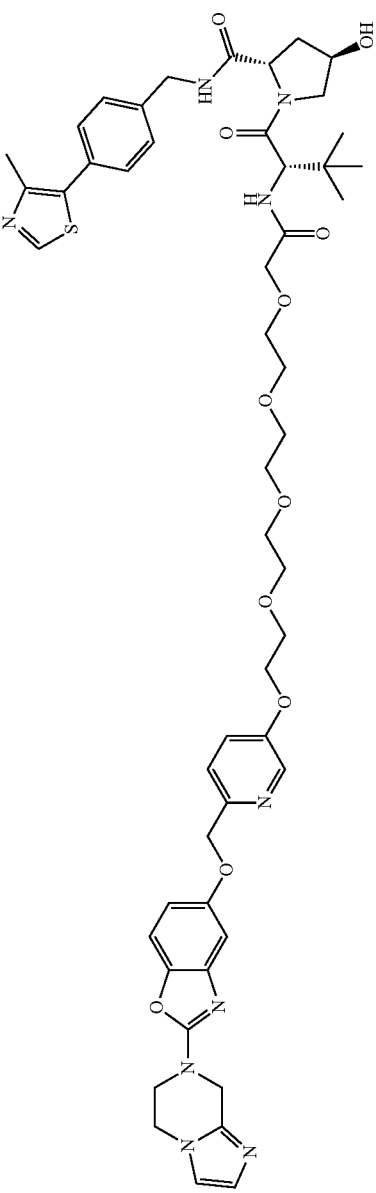 | MS (ESI) m/z 1010 [M + H]+, $t_R$ = 4.83 min |

Example 15
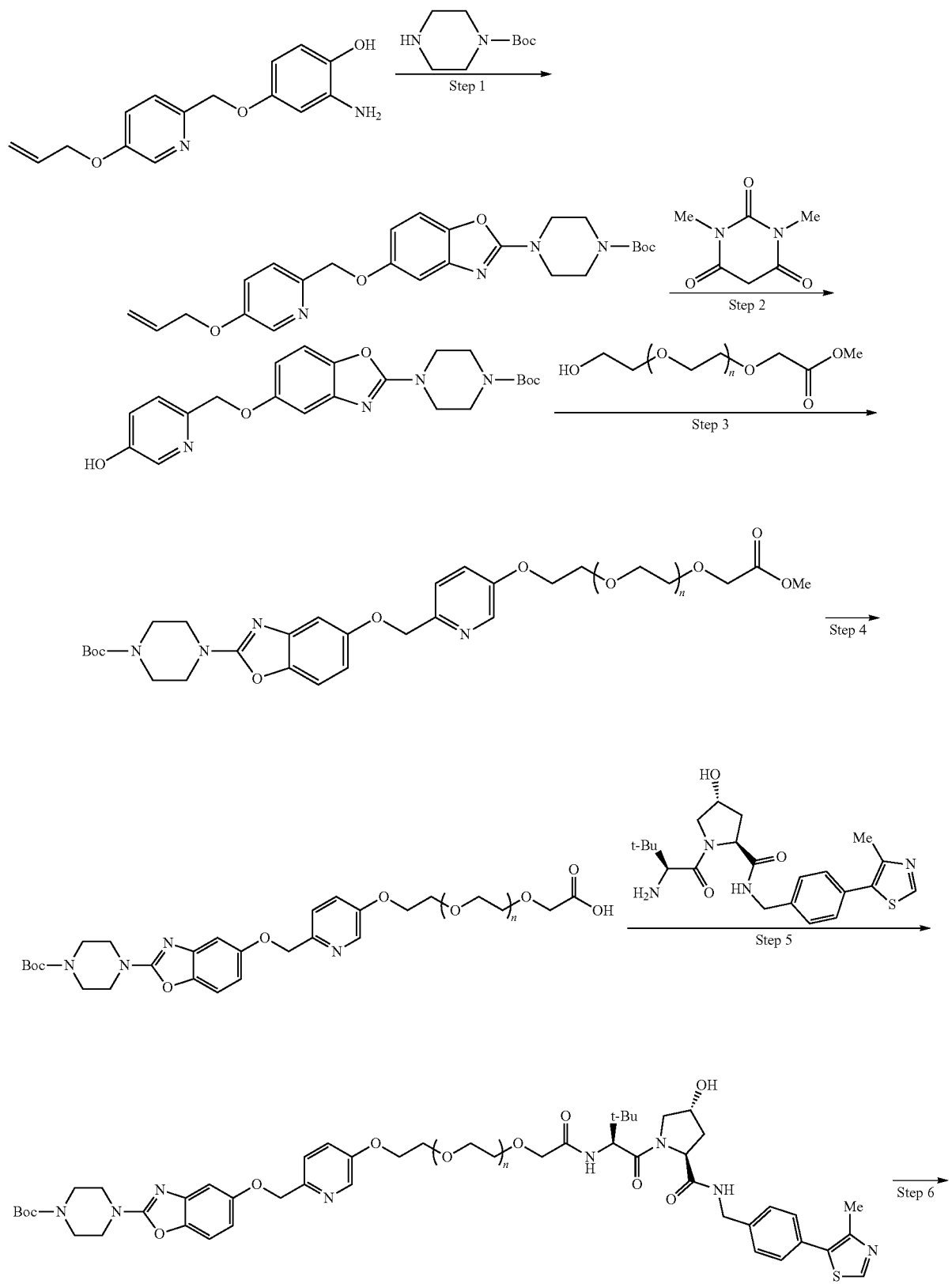

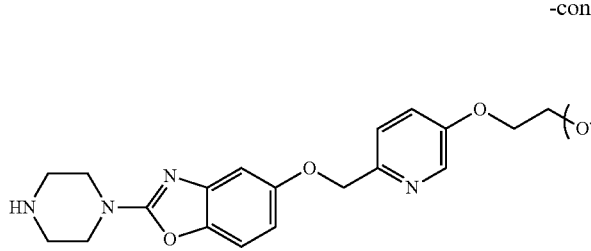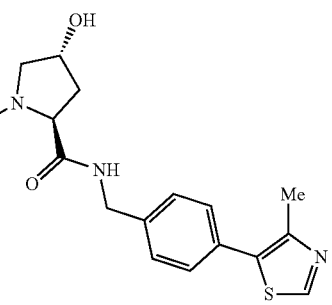

Step 1: tert-butyl 4-(5-((5-(allyloxy)pyridin-2-yl)methoxy)benzo[d]oxazol-2-yl)piperazine-1-carboxylate Tetramethoxymethane (0.42 mL, 3.2 mmol) was added to a solution of 4-((5-(allyloxy)-pyridin-2-yl)methoxy)-2-aminophenol (0.426 g, 1.56 mmol), tert-butyl piperazine-1-carboxylate (0.584 g, 3.14 mmol) and acetic acid (0.36 mL, 6.3 mmol) in chloroform (9 mL), and the mixture was stirred at 60° C. for 20 h. After this time, the reaction mixture was cooled to room temperature and diluted with chloroform (100 mL). The organic phase was washed with water (40 mL), 1 M aqueous sodium hydroxide (40 mL) and brine (40 mL) then dried over sodium sulfate, filtered and the filtrated concentrated under reduced pressure. The residue obtained was purified by column chromatography (silica gel; heptane to ethyl acetate; gradient elution) to afford the title compound. $^1$H NMR (500 MHz, DMSO-$d_6$) δ 8.29 (dd, J=3.0, 0.5 Hz, 1H), 7.46 (dd, J=8.5, 0.5 Hz, 1H), 7.42 (dd, J=8.5, 3.0 Hz, 1H), 7.29 (d, J=8.5 Hz, 1H), 6.96 (d, J=2.5 Hz, 1H), 6.66 (dd, J=8.5, 2.5 Hz, 1H), 6.08-6.00 (m, 1H), 5.41 (dq, J=17.5, 1.5 Hz, 1H), 5.29 (dq, J=10.5, 1.5 Hz, 1H), 5.07 (s, 2H), 4.66 (t, J=1.5 Hz, 1H), 4.65 (t, J=1.5 Hz, 1H), 3.57-3.55 (m, 4H), 3.47-3.45 (m, 4H), 1.42 (s, 9H); MS (ESI) m/z 467 [M+H]$^+$.

Step 2: tert-butyl 4-(5-((5-hydroxypyridin-2-yl)methoxy)benzo[d]oxazol-2-yl)piperazine-1-carboxylate A mixture of tert-butyl 4-(5-((5-(allyloxy)pyridin-2-yl)methoxy)benzo[d]oxazol-2-yl)pipera-zine-1-carboxylate (0.347 g, 0.744 mmol) and 1,3-dimethylbarbituric acid (0.139 g, 0.893 mmol) in anhydrous N,N-dimethylformamide (30 mL) was purged with argon for 30 min. Tetrakis(triphenylphosphine)palladium(0) (0.043 g, 0.037 mmol) was added, and the mixture was stirred at room temperature for 6 h under argon. After this time, the reaction mixture was diluted with water (150 mL) and extracted with ethyl acetate (3×60 mL). The combined organic layers were washed with brine (40 mL), dried over sodium sulfate, and filtered, and the filtrate concentrated under reduced pressure. The residue obtained was purified by column chromatography (silica gel; dichloromethane to 95:5 dichloromethane/methanol; gradient elution) to afford the title compound. $^1$H NMR (500 MHz, CDCl$_3$) δ 8.20 (d, J=3.0 Hz, 1H), 7.39-7.34 (m, 2H), 7.17 (d, J=8.5, 3.0 Hz, 1H), 7.13 (d, J=8.5 Hz, 1H), 6.95 (d, J=2.5 Hz, 1H), 6.70 (dd, J=8.5, 2.5 Hz, 1H), 5.13 (s, 2H), 3.65-3.63 (m, 4H), 3.56-3.54 (m, 4H), 1.48 (s, 9H); MS (ESI) m/z 427 [M+H]$^+$.

Step 3: tert-butyl 4-(5-((5-((3-oxo-2,5,8,11-tetraoxatridecan-13-yl)oxy)-pyridin-2-yl)methoxy)benzo[d]oxazol-2-yl)piperazine-1-carboxylate A solution of tert-butyl 4-(5-((5-hydroxypyridin-2-yl)methoxy)benzo[d]oxazol-2-yl)pipera-zine-1-carboxylate (0.197 g, 0.462 mmol), methyl 2-(2-(2-(2-hydroxyethoxy)ethoxy)-ethoxy)acetate (0.226 g, 1.02 mmol) and 2-(tributyl-15-phosphanylidene)acetonitrile (0.260 g, 1.08 mmol) in toluene (15 mL) was stirred at 100° C. for 15 h. After this time, the reaction mixture was cooled to room temperature and concentrated under reduced pressure. The residue obtained was purified by column chromatography (silica gel; ethyl acetate to 94:6 ethyl acetate/methanol; gradient elution) to afford the title compound. $^1$H NMR (500 MHz, CDCl$_3$) δ 8.30 (d, J=2.5 Hz, 1H), 7.43 (d, J=8.5 Hz, 1H), 7.24 (dd, J=8.5, 2.5 Hz, 1H), 7.13 (d, J=8.5 Hz, 1H), 6.99 (d, J=2.5 Hz, 1H), 6.69 (dd, J=8.5, 2.5 Hz, 1H), 5.13 (s, 2H), 4.19-4.17 (m, 2H), 4.16 (s, 2H), 3.88-3.87 (m, 2H), 3.74 (s, 3H), 3.73-3.68 (m, 8H), 3.66-3.64 (m, 4H), 3.56-3.54 (m, 4H), 1.49 (s, 9H); MS (DUIS) m/z 631 [M+H]$^+$.

Step 4: 2-(2-(2-(2-((6-(((2-(4-(tert-butoxycarbonyl)piperazin-1-yl)benzo[d]-oxazol-5-yl)oxy)methyl)pyridin-3yl)oxy)ethoxy)ethoxy)ethoxy)acetic acid A solution of lithium hydroxide (0.031 g, 1.3 mmol) in water (10 mL) was added to a solution of tert-butyl 4-(5-((5-((3-oxo-2,5,8,11-tetraoxatridecan-13-yl)oxy)pyridin-2-yl)methoxy)benzo[d]oxazol-2-yl)piperazine-1-carboxylate (0.175 g, 0.277 mmol) in methanol (40 mL), and the mixture was stirred at room temperature for 5.5 h. After this time, the reaction mixture was concentrated under reduced pressure, and the residue obtained was purified by reverse phase chromatography (C18; 95:5 water/acetonitrile to acetonitrile; gradient elution) to afford the title compound. $^1$H NMR (500 MHz, DMSO-$d_6$) δ 12.58 (br s, 1H), 8.29 (dd, J=2.5, 1.0 Hz, 1H), 7.46 (dd, J=8.5, 1.0 Hz, 1H), 7.42 (dd, J=8.5, 2.5 Hz, 1H), 7.29 (d, J=8.5 Hz, 1H), 6.96 (d, J=2.5 Hz, 1H), 6.66 (dd, J=8.5, 2.5 Hz, 1H), 5.07 (s, 2H), 4.19-4.17 (m, 2H), 4.00-3.99 (m, 2H), 3.77-3.75 (m, 2H), 3.60-3.52 (m, 12H), 3.47-3.45 (m, 4H), 1.43 (s, 9H); MS (DUIS) m/z 617 [M+H]$^+$.

Step 5: tert-butyl 4-(5-((5-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)oxy)pyridin-2-yl)methoxy)benzo[d]oxazol-2-yl)piperazine-1-carboxylate HATU (0.090 g, 0.24 mmol) was added to a suspension of 2-(2-(2-(2-((6-(((2-(4-(tert-butoxycarbonyl)piperazin-1-yl)

benzo[d]oxazol-5-yl)oxy)methyl)pyridin-3-yl)oxy)ethoxy)-ethoxy)acetic acid (0.145 g, 0.235 mmol), (2S,4R)-1-((S)-2-amino-3,3-dimethyl-butanoyl)-4-hydroxy-N-(4-(4-methylthiazol-5-yl)benzyl)pyrrolidine-2-carboxamide (0.101 g, 0.235 mmol) and N,N-diisopropylethylamine (0.15 mL, 0.86 mmol) in N,N-dimethylformamide (6.5 mL), and the mixture was stirred at room temperature for 30 min. After this time, the reaction mixture was diluted with saturated aqueous sodium bicarbonate (60 mL) and brine (20 mL), and extracted with ethyl acetate (3×50 mL). The combined organic layers were washed with brine (20 mL), dried over sodium sulfate, and filtered, and the filtrate concentrated under reduced pressure. The residue obtained was purified by column chromatography (silica gel; dichloromethane to 90:10 dichloromethane/methanol; gradient elution) to afford the title compound. $^1$H NMR (500 MHz, DMSO-$d_6$, mixture of rotational isomers, chemical shifts of the major rotamer are reported) δ 8.97 (s, 1H), 8.60 (t, J=6.0 Hz, 1H), 8.26 (d, J=2.5 Hz, 1H), 7.45-7.37 (m, 7H), 7.28 (d, J=8.5 Hz, 1H), 6.96 (d, J=2.5 Hz, 1H), 6.66 (dd, J=8.5, 2.5 Hz, 1H), 5.15 (d, J=3.5 Hz, 1H), 5.06 (s, 2H), 4.56 (d, J=9.5 Hz, 1H), 4.46-4.42 (m, 1H), 4.41-4.35 (m, 2H), 4.25 (dd, J=16.0, 5.5 Hz, 1H), 4.16-4.14 (m, 2H), 3.96 (s, 2H), 3.73-3.72 (m, 2H), 3.67 (dd, J=10.5, 3.5 Hz, 1H), 3.62-3.55 (m, 13H), 3.46-3.44 (m, 4H), 2.43 (s, 3H), 2.08-2.03 (m, 1H), 1.93-1.87 (m, 1H), 1.42 (s, 9H), 0.94 (s, 9H); MS (DUIS) m/z 1029 [M+H]$^+$.

Step 6: (2S,4R)-1-((S)-2-(tert-butyl)-4-oxo-14-((6-(((2-(piperazin-1-yl)benzo-[d]oxazol-5-yl)oxy)methyl)pyridin-3-yl)oxy)-6,9,12-trioxa-3-azatetradecanoyl)-4-hydroxy-N-(4-(4-methylthiazol-5-yl)benzyl)pyrrolidine-2-carboxamide Trifluoroacetic acid (4.0 mL, 52 mmol) was added to a solution of tert-butyl 4-(5-((5-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)oxy)pyridin-2-yl)methoxy)benzo[d]oxazol-2-yl)piperazine-1-carboxylate (0.113 g, 0.110 mmol) in dichloromethane (4.0 mL) at 0° C., and the mixture was stirred at 0° C. for 1 h and at room temperature for 1 h. After this time, the reaction mixture was concentrated under reduced pressure, and the residue obtained was purified by reverse phase chromatography (C18; 95:5 water/acetonitrile to acetonitrile; 0.1% trifluoroacetic acid additive; gradient elution). The product fractions were added to saturated aqueous sodium bicarbonate (75 mL) and extracted with dichloromethane (3×100 mL). The combined organic layers were washed with brine (50 mL), dried over sodium sulfate, filtered and the filtrate concentrated under reduced pressure. The residue obtained was further purified by reverse phase chromatography (C18; 95:5 water/acetonitrile to acetonitrile; no additive; loaded in 1:1 tetrahydrofuran/water; gradient elution). The product fractions were lyophilized to afford the title compound. $^1$H NMR (500 MHz, DMSO-$d_6$, mixture of rotational isomers, chemical shifts of the major rotamer are reported) δ 8.97 (s, 1H), 8.60 (t, J=6.0 Hz, 1H), 8.26 (d, J=2.5 Hz, 1H), 7.45-7.37 (m, 7H), 7.25 (d, J=8.5 Hz, 1H), 6.92 (d, J=2.5 Hz, 1H), 6.63 (dd, J=8.5, 2.5 Hz, 1H), 5.15 (d, J=3.5 Hz, 1H), 5.06 (s, 2H), 4.56 (d, J=9.5 Hz, 1H), 4.46-4.43 (m, 1H), 4.41-4.35 (m, 2H), 4.25 (dd, J=16.0, 6.0 Hz, 1H), 4.16-4.14 (m, 2H), 3.96 (s, 2H), 3.74-3.72 (m, 2H), 3.67 (dd, J=11.0, 4.0 Hz, 1H), 3.62-3.56 (m, 9H), 3.49-3.47 (m, 4H), 2.78-2.76 (m, 4H), 2.43 (s, 3H), 2.08-2.04 (m, 1H), 1.93-1.87 (m, 1H), 0.94 (s, 9H); MS (ESI) m/z 929 [M+H]$^+$; HPLC: Method 1, $t_R$=4.66 min.

The following compounds were prepared as described above:

| # | Structure | Data |
|---|---|---|
| 53 | 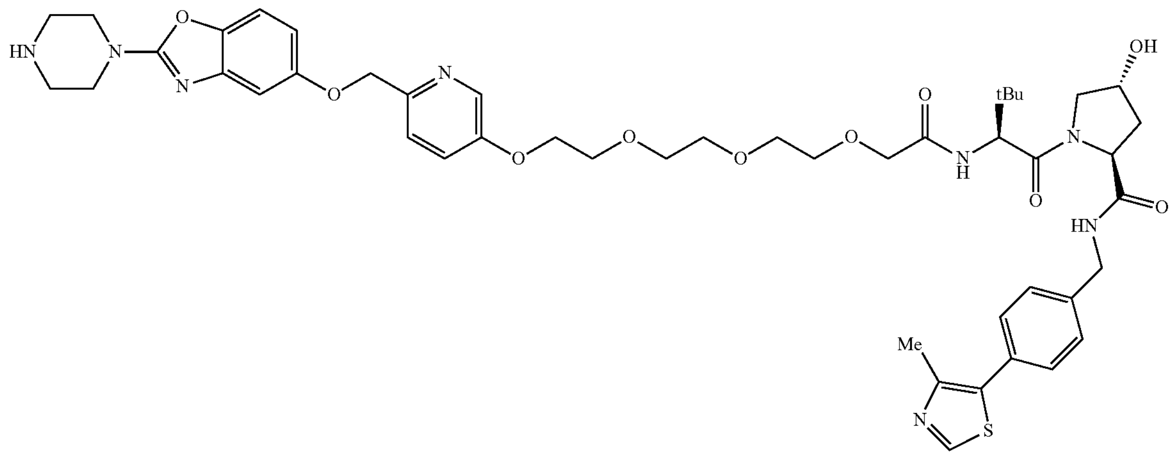 [SMILES: Cc1ncsc1-c1ccc(CNC(=O)[C@@H]2C[C@@H](O)CN2C(=O)[C@@H](NC(=O)COCCOCCOCCOc2ccc(COc3ccc4oc(N5CCNCC5)nc4c3)nc2)C(C)(C)C)cc1] | MS (ESI) m/z 929 [M + H]⁺; HPLC: Method 1, $t_R$ = 4.66 min |
| 54 | 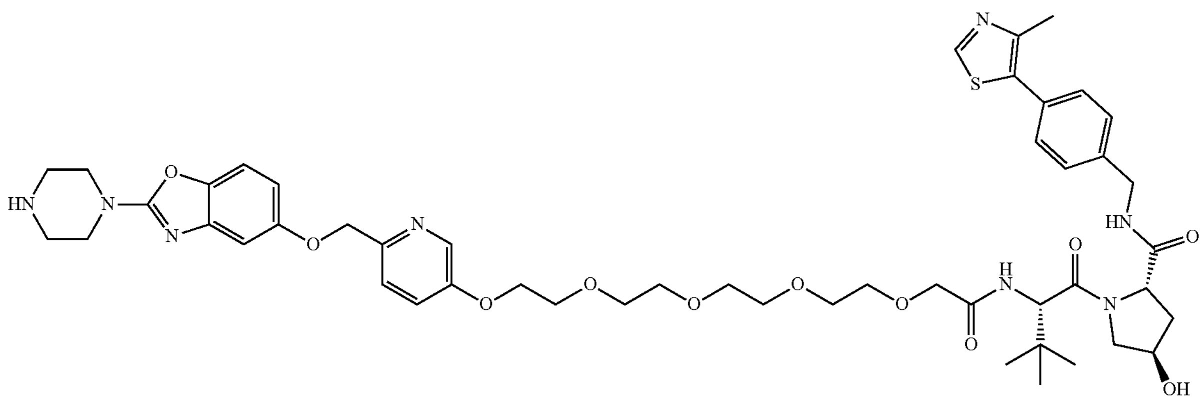 [SMILES: Cc1ncsc1-c1ccc(CNC(=O)[C@@H]2C[C@@H](O)CN2C(=O)[C@@H](NC(=O)COCCOCCOCCOCCOc2ccc(COc3ccc4oc(N5CCNCC5)nc4c3)nc2)C(C)(C)C)cc1] | MS (ESI) m/z 995 [M + Na]⁺; HPLC: Method 1, $t_R$ = 6.16 min |

Example 16
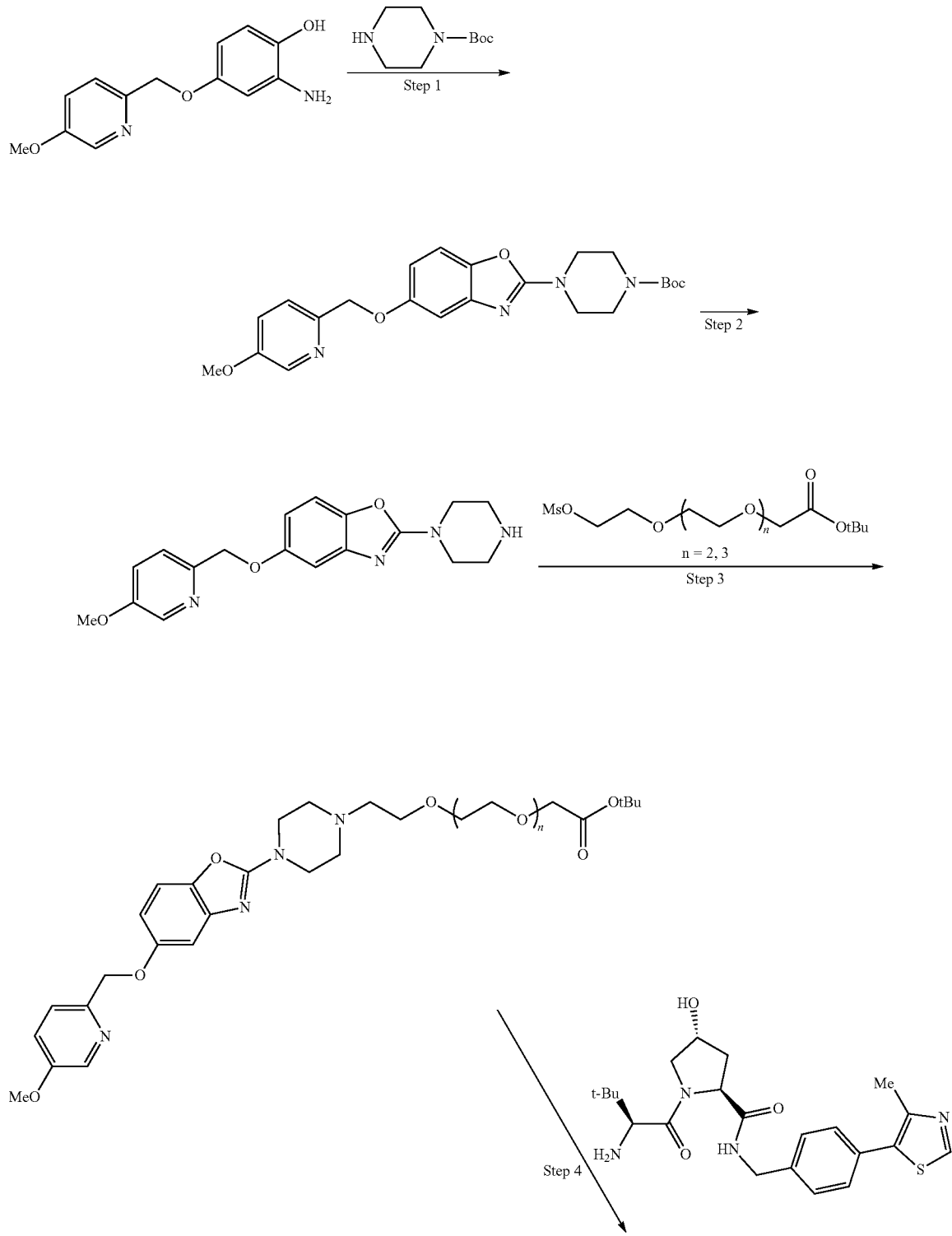

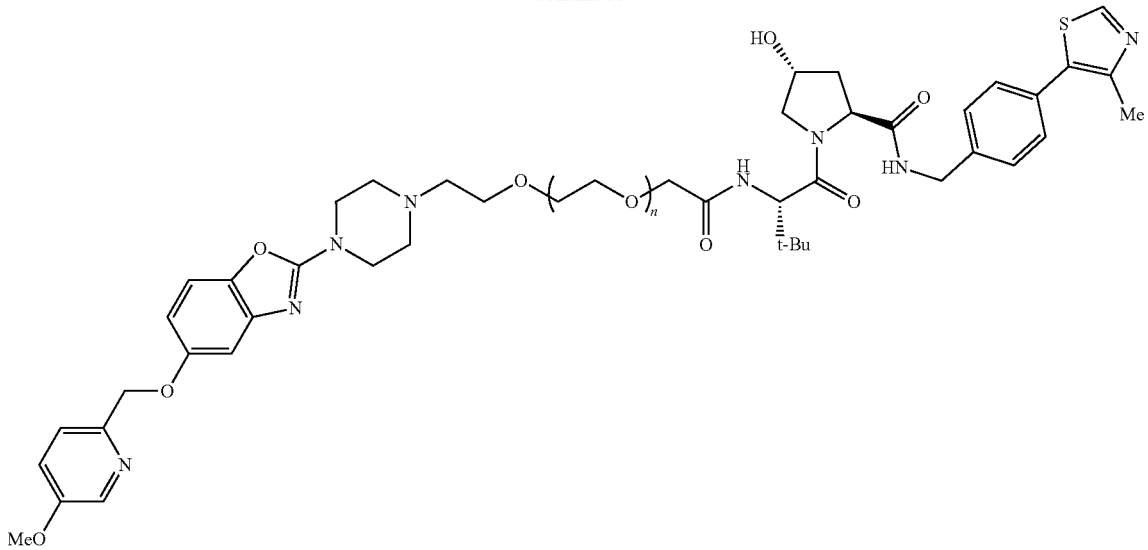

Step 1: tert-butyl 4-(5-((5-methoxypyridin-2-yl)methoxy)benzo[d]oxazol-2-yl)piperazine-1-carboxylate To a solution of 2-amino-4-((5-methoxypyridin-2-yl)methoxy)phenol (0.466 g, 1.89 mmol) in chloroform (15 mL) was added tert-butyl piperazine-1-carboxylate (0.705 g, 3.78 mmol), acetic acid (0.433 mL, 7.57 mmol) and tetramethoxymethane (0.504 mL, 3.78 mmol), and the mixture was heated at 60° C. overnight. After this time, the reaction mixture was cooled to room temperature, diluted with dichloromethane (30 mL) and washed with water (30 mL), 1 M aqueous sodium hydroxide (20 mL) and brine (30 mL). The organic phase was dried over sodium sulfate, filtered and the filtrate concentrated under reduced pressure. The residue obtained was purified by column chromatography (silica gel; dichloromethane to ethyl acetate; gradient elution) to afford the title compound. $^1$H NMR (500 MHz, DMSO-$d_6$) δ 8.28 (dd, J=2.5, 0.5 Hz, 1H), 7.47 (d, J=8.5 Hz, 1H), 7.41 (dd, J=8.5, 2.5 Hz, 1H), 7.29 (d, J=8.5 Hz, 1H), 6.96 (d, J=2.5 Hz, 1H), 6.66 (dd, J=8.5, 2.5 Hz, 1H), 5.08 (s, 2H), 3.83 (s, 3H), 3.57-3.55 (m, 4H), 3.47-3.44 (m, 4H), 1.43 (s, 9H).

Step 2: 5-((5-methoxypyridin-2-yl)methoxy)-2-(piperazin-1-yl)benzo[d]-oxazole To a solution of tert-butyl 4-(5-((5-methoxypyridin-2-yl)methoxy)benzo[d]oxazol-2-yl)piperazine-1-carboxylate (0.060 g, 0.14 mmol) in 1,4-dioxane (4 mL) was added 4 M hydrogen chloride in 1,4-dioxane (0.25 mL, 1.0 mmol), and the mixture was stirred at room temperature overnight. After this time, the reaction mixture was concentrated under reduced pressure, and the residue obtained was partitioned between dichloromethane (10 mL) and 10% aqueous sodium bicarbonate (10 mL). The layers were separated, and the aqueous layer was extracted with dichloromethane (2×10 mL). The combined organic layers were dried over sodium sulfate, filtered, and the filtrate concentrated under reduced pressure to afford the title compound. $^1$H NMR (500 MHz, DMSO-$d_6$) δ 8.28 (dd, J=3.0, 0.5 Hz, 1H), 7.46 (d, J=8.5 Hz, 1H), 7.41 (dd, J=8.5, 2.5 Hz, 1H), 7.26 (d, J=8.5 Hz, 1H), 6.92 (d, J=2.5 Hz, 1H), 6.63 (dd, J=8.5, 3.0 Hz, 1H), 5.07 (s, 2H), 3.83 (s, 3H), 3.50-3.48 (m, 4H), 2.78-2.76 (m, 4H).

Step 3: tert-butyl 2-(2-(2-(2-(4-(5-((5-methoxypyridin-2-yl)methoxy)benzo-[d]oxazol-2-yl)piperazin-1-yl)ethoxy)ethoxy)ethoxy)acetate N,N-Diisopropylethylamiine (0.21 mL, 1.2 mmol) was added to a solution of 5-((5-methoxypyridin-2-yl)methoxy)-2-(piperazin-1-yl)benzo[d]oxazole (0.150 g, 0.410 mmol) and tert-butyl 2-(2-(2-(2-((methylsulfonyl)oxy)ethoxy)ethoxy)ethoxy)acetate (0.178 g, 0.520 mmol) in acetonitrile (3.5 mL), and the mixture was stirred at reflux for 18 h. After this time, the reaction mixture was cooled to room temperature and concentrated under reduced pressure. The residue obtained was purified by column chromatography (silica gel; dichloromethane to 80:20 dichloromethane/methanol; gradient elution) to afford the title compound. $^1$H NMR (500 MHz, CDCl$_3$) δ 8.29 (d, J=2.5 Hz, 1H), 7.44 (d, J=8.5 Hz, 1H), 7.20 (dd, J=8.5, 2.5 Hz, 1H), 7.11 (d, J=8.5 Hz, 1H), 6.97 (d, J=2.5 Hz, 1H), 6.67 (dd, J=8.5, 2.5 Hz, 1H), 5.14 (s, 2H), 4.02 (s, 2H), 3.86 (s, 3H), 3.73-3.63 (m, 14H), 2.65 (t, J=5.5 Hz, 2H), 2.63-2.61 (m, 4H), 1.47 (s, 9H); MS (DUIS) m/z 587 [M+H]$^+$.

Step 4: (2S,4R)-1-((S)-2-(tert-butyl)-14-(4-(5-((5-methoxypyridin-2-yl)meth-oxy)benzo[d]oxazol-2-yl)piperazin-1-yl)-4-oxo-6,9,12-trioxa-3-azatetradecanoyl)-4-hydroxy-N-(4-(4-methylthiazol-5-yl)benzyl)pyrrolidine-2-carboxamide Trifluoroacetic acid (1.0 mL, 13 mmol) was added to a solution of tert-butyl 2-(2-(2-(2-(4-(5-((5-methoxypyridin-2-yl)methoxy)benzo[d]oxazol-2-yl)piperazin-1-yl)ethoxy)ethoxy)-ethoxy)acetate (0.156 g, 0.266 mmol) in dichloromethane (1.5 mL), and the mixture was stirred at room temperature for 80 min. After this time, the reaction mixture was concentrated to dryness and solvent exchanged with dichloromethane (2×25 mL) to afford crude 2-(2-(2-(2-(4-(5-((5-methoxypyridin-2-yl)methoxy)benzo[d]oxazol-2-yl)piperazin-1-yl)ethoxy)ethoxy)ethoxy)acetic acid, trifluoroacetic acid salt. MS (DUIS) m/z 531 [M+H]$^+$.

The crude 2-(2-(2-(2-(4-(5-((5-methoxypyridin-2-yl)methoxy)benzo[d]oxazol-2-yl)piperazin-1-yl)ethoxy)ethoxy)ethoxy)acetic acid, trifluoroacetic acid salt (0.266 mmol) was dissolved in N,N-dimethylformamide (3.5 mL), treated with (2S,4R)-1-((S)-2-amino-3,3-dimethylbutanoyl)-4-hydroxy-N-(4-(4-methylthiazol-5-yl)benzyl)pyrrolidine-2-carbox-amide (0.115 g, 0.266 mmol), N,N-diisopropylethylaminie (0.24 mL, 1.4 mmol) and HATU (0.111 g, 0.293 mmol), and the mixture was stirred at room temperature for 30 min. After this time, the reaction mixture was diluted with 1:1 water/saturated aqueous sodium bicarbonate (80 mL), and extracted with ethyl acetate (3×50 mL). The combined organic layers were washed with brine (2×30 mL), dried over sodium sulfate, filtered and the filtrate concentrated under reduced pressure. The residue obtained was purified by column chromatography (silica gel; dichloromethane to 80:20 dichloromethane/methanol; gradient elution). The product fractions were concentrated under reduced pressure and lyophilized from 2:1 acetonitrile/water (7 mL) to afford the title compound. $^1$H NMR (500 MHz, MeOD; mixture of rotational isomers, chemical shifts of the major rotamer are reported) δ 8.86 (s, 1H), 8.21 (d, J=2.5 Hz, 1H), 7.52 (d, J=8.5 Hz, 1H), 7.45-7.39 (m, 5H), 7.19 (d, J=8.5 Hz, 1H), 6.90 (d, J=2.5 Hz, 1H), 6.70 (dd, J=8.5, 2.5 Hz, 1H), 5.09 (s, 2H), 4.69 (s, 1H), 4.58-4.49 (m, 3H), 4.34 (d, J=15.5 Hz, 1H), 4.08-4.01 (m, 2H), 3.88-3.85 (m, 4H), 3.79 (dd, J=11.0, 4.0 Hz, 1H), 3.72-3.62 (m, 14H), 2.68-2.62 (m, 6H), 2.46 (s, 3H), 2.24-2.19 (m, 1H), 2.11-2.05 (m, 1H), 1.04 (s, 9H); MS (ESI) m/z 943 [M+H]$^+$; HPLC: Method 1, $t_R$=5.17 min.

The following compounds were prepared as described above:

| # | Structure | Data |
|---|---|---|
| 55 | 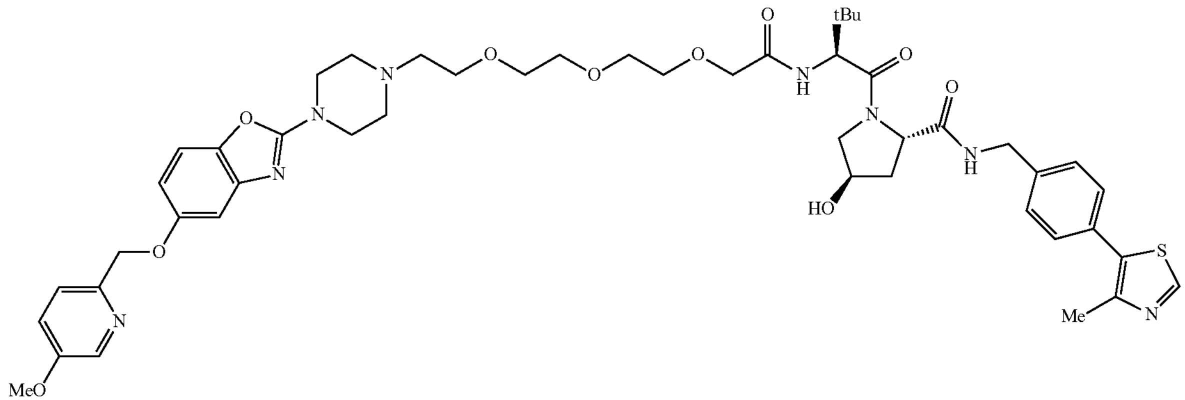 [SMILES: COc1ccc(COc2ccc3oc(N4CCN(CCOCCOCCOCC(=O)N[C@H](C(=O)N5C[C@H](O)C[C@H]5C(=O)NCc5ccc(-c6scnc6C)cc5)C(C)(C)C)CC4)nc3c2)nc1] | MS (ESI) m/z 943 [M + H]⁺; HPLC: Method 1, $t_R$ = 5.17 min |
| 56 | 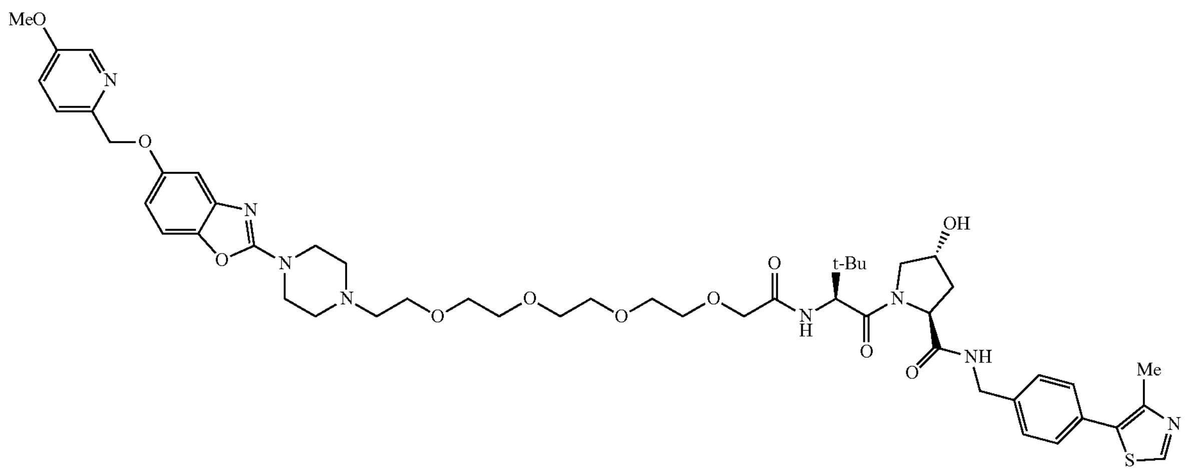 [SMILES: COc1ccc(COc2ccc3oc(N4CCN(CCOCCOCCOCCOCC(=O)N[C@H](C(=O)N5C[C@H](O)C[C@H]5C(=O)NCc5ccc(-c6scnc6C)cc5)C(C)(C)C)CC4)nc3c2)nc1] | MS (ESI) m/z 987 [M + H]⁺; HPLC: Method 1, $t_R$ = 4.77 min |

233 234
Example 17
Scheme for Example 17
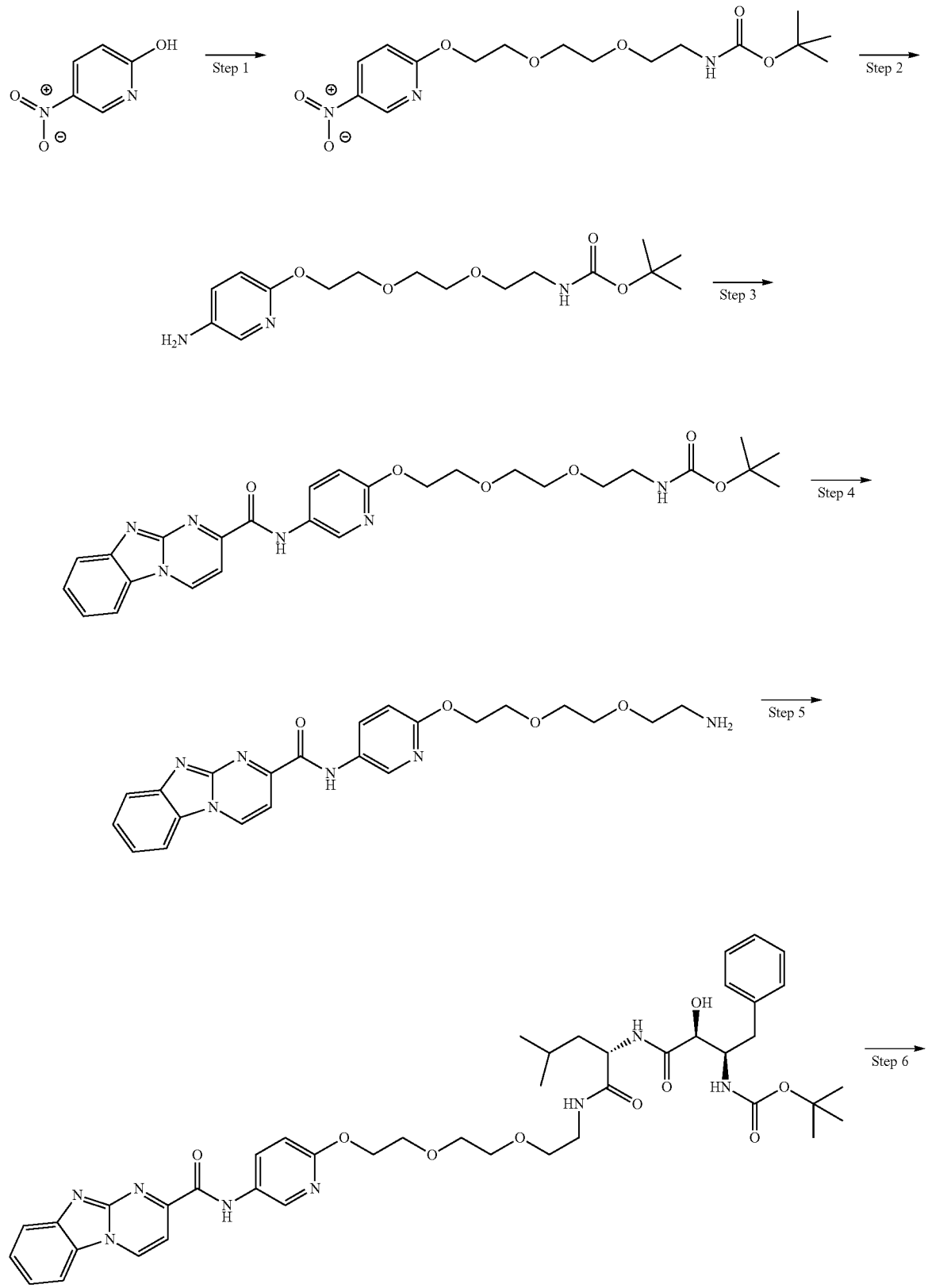

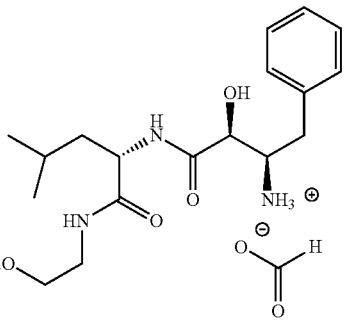

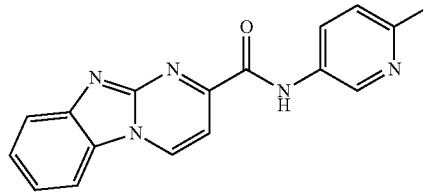

Step 1: tert-Butyl N-[2-(2-{2-[(5-nitropyridin-2-yl)oxy]ethoxy}ethoxy)ethyl]carbamate A suspension of 2-chloro-5-nitropyridine (100 mg, 0.63 mmol), tert-butyl N-{2-[2-(2-hydroxyethoxy)ethoxy]ethyl}carbamate (173 mg, 0.69 mmol) and potassium tert-butoxide (85 mg, 0.76 mmol) in DMF (1 mL) was stirred at ambient temperature for 3 h. The mixture was partitioned between water and EtOAc and extracted 3 times. Combined organic layers were washed with brine, dried over MgSO$_4$, filtered and evaporated to dryness. The crude was adsorbed on silica and purified by FCC (silica, 20-100% EtOAc in heptane) to give the title compound. $^1$H NMR (500 MHz, Chloroform-d) δ 9.06 (d, J=2.8 Hz, 1H), 8.35 (dd, J=9.1, 2.8 Hz, 1H), 6.88 (d, J=9.1 Hz, 1H), 4.97 (s, 1H), 4.65-4.56 (m, 2H), 3.93-3.85 (m, 2H), 3.74-3.67 (m, 2H), 3.67-3.60 (m, 2H), 3.55 (t, J=5.2 Hz, 2H), 3.36-3.26 (m, 2H), 1.44 (s, 9H). Tr(METCR1410)=1.12 min (ES$^+$) [M+Na]$^+$ 394.

Step 2: tert-Butyl N-[2-(2-{2-[(5-aminopyridin-2-yl)oxy]ethoxy}ethoxy)ethyl]carbamate Iron powder (120 mg, 2.15 mmol) was added to a solution of NH$_4$C$_1$ (144 mg, 2.69 mmol) and tert-butyl N-[2-(2-{2-[(5-nitropyridin-2-yl)oxy]ethoxy}ethoxy)ethyl]carbamate (200 mg, 0.54 mmol) in EtOH (10 mL) and water (1 mL). The mixture was heated to reflux for 90 min then cooled to rt and filtered through Celite. The filtrate was evaporated to dryness and partitioned between water and EtOAc. The aqueous layer was extracted once more with EtOAc. Combined layers were washed with brine, dried over MgSO$_4$, filtered and evaporated to dryness to give the title compound. $^1$H NMR (250 MHz, Chloroform-d) δ 7.62 (dd, J=3.0, 0.7 Hz, 1H), 7.02 (dd, J=8.7, 3.0 Hz, 1H), 6.64 (dd, J=8.7, 0.7 Hz, 1H), 5.04 (s, 1H), 4.43-4.36 (m, 2H), 3.86-3.79 (m, 2H), 3.74-3.60 (m, 4H), 3.54 (t, J=5.1 Hz, 2H), 3.47-3.24 (m, 4H), 1.43 (s, 9H). Tr(METCR1410)=0.87 min, (ES$^+$) [M+H]$^+$ 342.

Step 3: tert-Butyl N-[2-(2-{2-[(5-{1,8,10-triazatricyclo[7.4.0.0$^{2,7}$]trideca-2,4,6,8,10,12-hexaene-11-amido}pyridin-2-yl)oxy]ethoxy}ethoxy)ethyl]carbamate 1,8,10-Triazatricyclo[7.4.0.0$^{2,7}$]trideca-2(7),3,5,8,10,12-hexaene-11-carboxylic acid (108 mg, 0.51 mmol) and HATU (212 mg, 0.56 mmol) were dissolved in DMF (4 mL). DIPEA (206 μL, 1.18 mmol) was added and the mixture was stirred at rt for 5 min. A solution of tert-butyl N-[2-(2-{2-[(5-aminopyridin-2-yl)oxy]ethoxy}ethoxy)ethyl]carbamate (173 mg, 0.51 mmol) in DMF (1 mL) was added and the solution stirred at rt under N$_2$ for 3 h then diluted with water (5 mL). The thick yellow solid that precipitated from the mixture was triturated for 5 min, collected by filtration and washed with water. The solid was dried in the vacuum oven at 40° C. overnight to give the title compound. $^1$H NMR (250 MHz, Chloroform-d) δ 9.89 (s, 1H), 8.99 (d, J=7.0 Hz, 1H), 8.51 (d, J=2.7 Hz, 1H), 8.15 (dd, J=8.9, 2.7 Hz, 1H), 8.08 (dd, J=8.3, 1.0 Hz, 1H), 7.99 (dd, J=8.2, 1.0 Hz, 1H), 7.91 (d, J=7.0 Hz, 1H), 7.68 (ddd, J=8.3, 7.2, 1.0 Hz, 1H), 7.53 (ddd, J=8.2, 7.2, 1.0 Hz, 1H), 6.87 (d, J=8.9 Hz, 1H), 5.04 (s, 1H), 4.65-4.40 (m, 2H), 3.95-3.84 (m, 2H), 3.77-3.62 (m, 4H), 3.56 (d, J=5.2 Hz, 2H), 3.32 (d, J=5.2 Hz, 2H), 1.44 (s, 9H). Tr(METCR1410)=1.09 min, (ES$^+$) [M+H]$^+$ 537.

Step 4: N-(6-{2-[2-(2-Aminoethoxy)ethoxy]ethoxy}pyridin-3-yl)-1,8,10-triazatricyclo[7.4.0.0$^{2,7}$]trideca-2,4,6,8,10,12-hexaene-11-carboxamide TFA (1 mL) was added dropwise to a solution of tert-butyl N-[2-(2-{2-[(5-{1,8,10-triazatricyclo[7.4.0.0$^2$,7]trideca-2,4,6,8,10,12-hexaene-11-amido}pyridin-2-yl)oxy]ethoxy}ethoxy)ethyl]carbamate (200 mg, 0.373 mmol) in DCM (10 mL) cooled to 0° C. The mixture was allowed to warm to rt over 2 h then it was partitioned between sat NaHCO$_3$(aq) and DCM. The aqueous layer was separated and extracted 3 times with DCM and once with 5% MeOH in DCM. Combined organic layers were washed with brine, dried over MgSO$_4$, filtered and evaporated to dryness to give the title compound. $^1$H NMR (500 MHz, DMSO-d6) δ 11.05 (s, 1H), 9.77 (d, J=7.0 Hz, 1H), 8.69 (d, J=2.7 Hz, 1H), 8.43 (d, J=8.2 Hz, 1H), 8.22 (dd, J=8.9, 2.7 Hz, 1H), 7.96 (d, J=8.2 Hz, 1H), 7.76 (d, J=7.0 Hz, 1H), 7.64 (dd, J=8.2, 7.9 Hz, 1H), 7.52 (dd, J=8.2, 7.9 Hz, 1H), 6.90 (d, J=8.9 Hz, 1H), 4.47-4.32 (m, 2H), 3.82-3.67 (m, 2H), 3.65-3.52 (m, 4H), 3.43 (t, J=5.5 Hz, 2H), 2.74 (t, J=5.5 Hz, 2H). Tr(METCR1410)=0.82 min, (ES$^+$) [M+H]$^+$ 437.

237

Step 5: tert-Butyl N-[(1S,2R)-1-hydroxy-1-{[(1S)-3-methyl-1-{[2-(2-{2-[(5-{1,8,10-triazatricyclo[7.4.0.0²,⁷]trideca-2,4,6,8,10,12-hexaene-11-amido}pyridin-2-yl)oxy]ethoxy}ethoxy)ethyl]carbamoyl}butyl]carbamoyl}-3-phenylpropan-2-yl]carbamate To a mixture of N-(6-{2-[2-(2-aminoethoxy)ethoxy]ethoxy}pyridin-3-yl)-1,8,10-triazatricyclo[7.4.0.0²,⁷]trideca-2,4,6,8,10,12-hexaene-11-carboxamide (36 mg, 0.081 mmol), (2S)-2-[[(2S,3R)-3-(tert-butoxycarbonylamino)-2-hydroxy-4-phenyl-butanoyl]amino]-4-methyl-pentanoic acid (36 mg, 0.081 mmol), HOBT (28 mg, 0.182 mmol) and DIPEA (63 µL, 0.364 mmol) in DMF (1 mL) was added EDC.HCl (62 mg, 0.323 mmol) at 0° C. The reaction mixture was stirred at rt for 16 h. The mixture was partitioned between water (10 mL) and EtOAc (10 mL). The phases were separated and the aqueous layer was extracted with more EtOAc (3×10 mL). Combined organic layers were washed with 10% citric acid (aq) (10 mL), sat NaHCO₃ (aq) (2×10 mL), brine (1×10 mL), dried over MgSO₄, filtered and evaporated to dryness. The crude was purified by FCC (silica, 0-6% MeOH in DCM) to afford the title compound. ¹H NMR (500 MHz, Methanol-d₄) δ 9.50 (d, J=7.0 Hz, 1H), 8.62 (d, J=2.7 Hz, 1H), 8.24 (dd, J=8.2, 1.0 Hz, 1H), 8.15 (dd, J=8.9, 2.7 Hz, 1H), 7.92 (dd, J=8.3, 1.0 Hz, 1H), 7.83 (d, J=7.0 Hz, 1H), 7.66 (ddd, J=8.3, 7.1, 1.0 Hz, 1H), 7.53 (td, J=8.2, 7.1, 1.0 Hz, 1H), 7.29-7.11 (m, 5H), 6.86 (d, J=8.9 Hz, 1H), 4.52-4.40 (m, 3H), 4.15 (td, J=7.7, 2.3 Hz, 1H), 4.07-3.96 (m, 1H), 3.90-3.80 (m, 2H), 3.68 (dd, J=5.9, 3.3 Hz, 2H), 3.65-3.59 (m, 2H), 3.53 (t, J=5.5 Hz, 2H), 3.42-3.34 (m, 2H), 2.94-2.79 (m, 2H), 1.77-1.50 (m, 2H), 1.33 (s, 9H), 0.99-0.81 (m, 6H). Tr(MET-uPLC-AB-101)=3.46 min, (ES⁺) [M+H]⁺ 827.

238

Step 6: N-{6-[2-(2-{2-[(2S)-2-[(2S,3R)-3-amino-2-hydroxy-4-phenylbutanamido]-4-methylpentanamido]ethoxy}ethoxy)ethoxy]pyridin-3-yl}-1,8,10-triazatricyclo[7.4.0.0²,⁷]trideca-2,4,6,8,10,12-hexaene-11-carboxamide A mixture of tert-butyl N-[(1S,2R)-1-hydroxy-1-{[(1S)-3-methyl-1-{[2-(2-{2-[(5-{1,8,10-triazatricyclo[7.4.0.0²,⁷]trideca-2,4,6,8,10,12-hexaene-11-amido}pyridin-2-yl)oxy]ethoxy}ethoxy)ethyl]carbamoyl}butyl]carbamoyl}-3-phenylpropan-2-yl]carbamate (47.6 mg, 0.57 mmol) in HCl in dioxane (4N, 1.00 ml, 4.00 mmol) was stirred at rt. The mixture was sonicated at rt for 10 min then stirred at rt for 4 h. The reaction was diluted with MeOH and then evaporated to dryness. The crude was partitioned between sat NaHCO₃ (25 mL and DCM (25 mL). The phases were separated and the aqueous layer was extracted with more DCM (4×15 mL). Combined organic layers were washed with brine, dried over MgSO₄, filtered and evaporated to dryness. The crude was adsorbed on silica and purified by FCC (silica, 0-20% MeOH in DCM). Combined fractions were evaporated to dryness to afford the title compound. ¹H NMR (500 MHz, Methanol-d₄) δ 9.50 (d, J=7.0 Hz, 1H), 8.62 (d, J=2.7 Hz, 1H), 8.25 (dd, J=8.4, 1.0 Hz, 1H), 8.15 (dd, J=8.8, 2.7 Hz, 1H), 7.93 (d, J=8.2 Hz, 1H), 7.83 (d, J=7.0 Hz, 1H), 7.67 (ddd, J=8.3, 7.1, 1.1 Hz, 1H), 7.54 (ddd, J=8.2, 7.1, 1.0 Hz, 1H), 7.34-7.10 (m, 5H), 6.86 (d, J=8.8 Hz, 1H), 4.50-4.37 (m, 3H), 3.95 (d, J=3.1 Hz, 1H), 3.87-3.78 (m, 2H), 3.71-3.64 (m, 2H), 3.63-3.58 (m, 2H), 3.52 (t, J=5.5 Hz, 2H), 3.39-3.32 (m, 3H), 2.90 (dd, J=13.4, 6.9 Hz, 1H), 2.66 (dd, J=13.4, 7.8 Hz, 1H), 1.69-1.59 (m, 3H), 0.95 (d, J=6.1 Hz, 3H), 0.93 (d, J=6.2 Hz, 3H). Tr(METCR1603)=4.00 min, (ES)⁺ [M+H]⁺ 727.

The following compound was prepared as described above:

| # | Structure | Data |
|---|-----------|------|
| 59 | 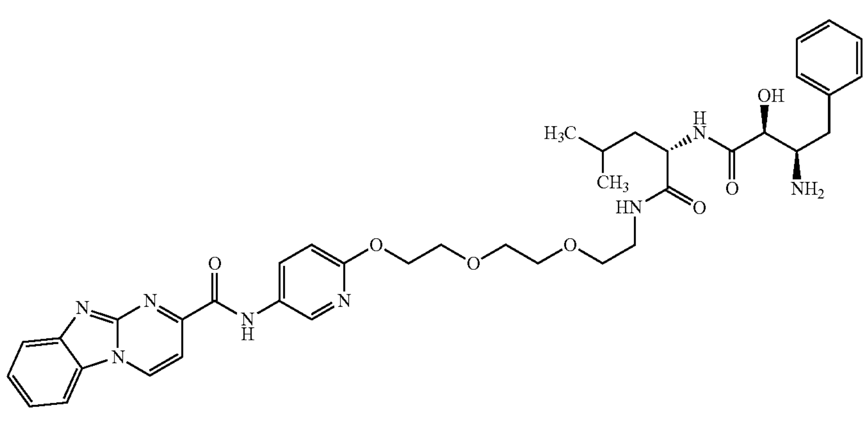 [SMILES: CC(C)C[C@H](NC(=O)[C@@H](O)[C@H](N)Cc1ccccc1)C(=O)NCCOCCOCCOc1ccc(NC(=O)c2ccn3c(n2)nc2ccccc23)cn1] | Tr(METCR1603) = 4.00 min, (ES)⁺ [M + H]⁺ 727 |

Example 18
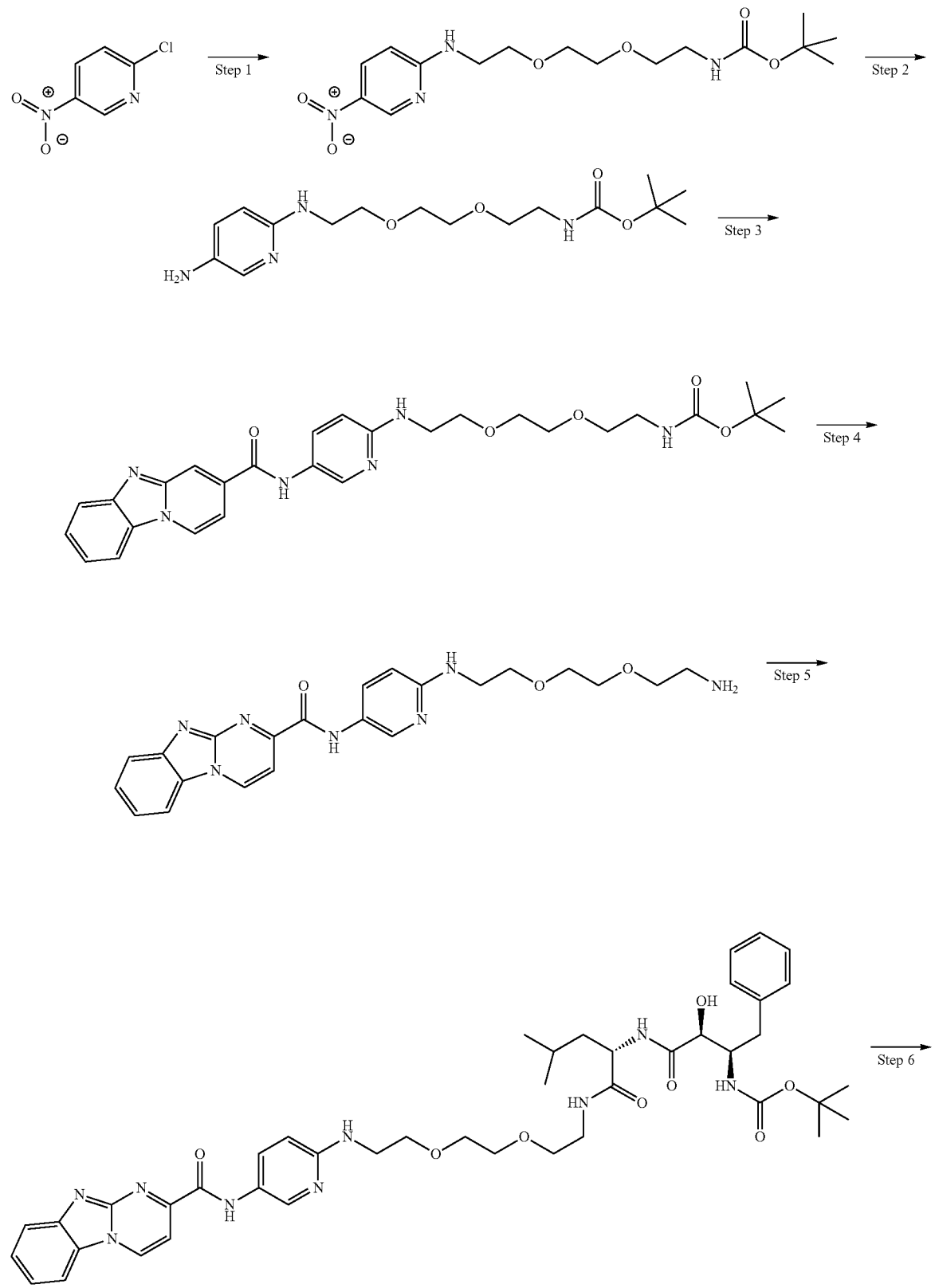
Scheme for 18

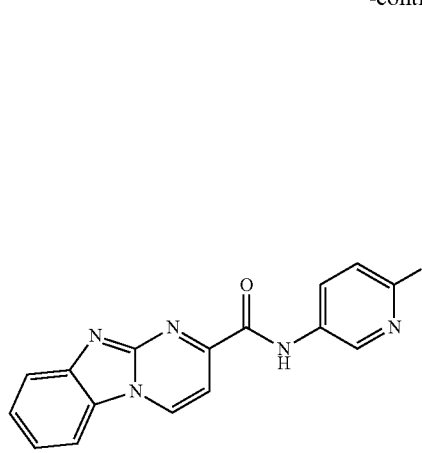
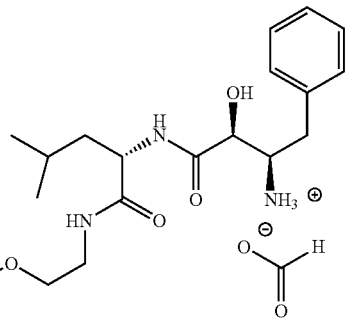

Step 1: tert-Butyl N-[2-(2-{2-[(5-nitropyridin-2-yl)amino]ethoxy}ethoxy)ethyl]carbamate Triethylamine (198 µl, 1.42 mmol) was added dropwise to a solution of 2-chloro-5-nitropyridine (150 mg, 0.95 mmol) and tert-butyl N-{2-[2-(2-aminoethoxy)ethoxy]ethyl}carbamate (282 mg, 1.14 mmol) in MeCN (1.5 mL). The mixture was stirred in a sealed tube at reflux for 4 h then cooled to rt and partitioned between EtOAc and water. The aq layer was extracted twice. Combined organic layers were washed with brine, dried over MgSO$_4$, filtered and evaporated to dryness. The crude was adsorbed on silica and purified by FCC (silica, 25-100% EtOAc in heptane) to give the title compound. $^1$H NMR (500 MHz, Chloroform-d) δ 9.02 (d, J=2.6 Hz, 1H), 8.16 (s, 1H), 6.57-6.36 (m, 1H), 6.08 (s, 1H), 5.52 (s, 1H), 3.74-3.49 (m, 10H), 3.35 (d, J=6.6 Hz, 2H), 1.45 (s, 9H). Tr(METCR1410)=1.09 min, (ES$^+$) [M+H]$^+$ 371.

Step 2: tert-Butyl N-[2-(2-{2-[(5-aminopyridin-2-yl)amino]ethoxy}ethoxy)ethyl]carbamate Iron powder (175 mg, 0.79 mmol) was added to a solution of NH$_4$C$_1$ (210 mg, 3.93 mmol) and tert-butyl N-[2-(2-{2-[(5-nitropyridin-2-yl)amino]ethoxy}ethoxy)ethyl]carbamate (291 mg, 0.54 mmol) in EtOH (10 mL) and water (1 mL). The mixture was heated to reflux for 2 h. More NH$_4$C$_1$ (100 mg) and iron powder (50 mg) were added and the reaction was stirred at reflux for 1 h. The reaction was cooled to rt and filtered through Celite, washing with EtOH. The filtrate was evaporated to dryness and then purified by FCC (silica, 0-20% MeOH in DCM) to give the title compound. $^1$H NMR (500 MHz, Chloroform-d) δ 9.02 (d, J=2.6 Hz, 1H), 8.16 (s, 1H), 6.57-6.36 (m, 1H), 6.08 (s, 1H), 5.52 (s, 1H), 3.74-3.49 (m, 10H), 3.35 (d, J=6.6 Hz, 2H), 1.45 (s, 9H). Tr(METCR1410)=0.80 min, (ES)+[M+H]$^+$ 341.

Step 3: tert-Butyl N-[2-(2-{2-[(5-{1,8,10-triazatricyclo[7.4.0.0$^{2,7}$]trideca-2,4,6,8,10,12-hexaene-11-amido}pyridin-2-yl)amino]ethoxy}ethoxy)ethyl]carbamate 1,8,10-Triazatricyclo[7.4.0.0$^{2,7}$]trideca-2(7),3,5,8,10,12-hexaene-11-carboxylic acid (137 mg, 0.64 mmol) and HATU (270 mg, 0.71 mmol) were dissolved in DMF (4 mL). DIPEA (262 µL, 1.51 mmol) was added and the reaction was stirred for 5 min. A solution of tert-butyl N-[2-(2-{2-[(5-aminopyridin-2-yl)amino]ethoxy}ethoxy)ethyl]carbamate (220 mg, 0.64 mmol) in DMF (1 mL) was added and the solution stirred for 18 h at rt under N$_2$. Water (10 mL) was added to the mixture to induce precipitation of the product. The resulting suspension was stirred at rt for 10 min, collected by filtration and washed with more water. The solid was dried in the vacuum oven overnight at 40° C. to the title compound. $^1$H NMR (500 MHz, Chloroform-d) δ 9.84 (s, 1H), 8.99 (d, J=7.0 Hz, 1H), 8.55 (s, 1H), 8.07 (d, J=8.3 Hz, 1H), 8.00-7.98 (m, 2H), 7.90 (d, J=7.0 Hz, 1H), 7.68 (ddd, J=8.3, 7.1, 1.1 Hz, 1H), 7.54 (td, J=8.2, 7.1, 1.1 Hz, 1H), 6.67 (s, 1H), 5.78 (s, 1H), 5.28 (s, 1H), 3.75 (t, J=5.0 Hz, 2H), 3.69-3.63 (m, 4H), 3.61-3.56 (m, 4H), 3.35 (s, 2H), 1.44 (s, 9H). Tr(METCR1410)=0.94 min, (ES$^+$) [M+H]$^+$ 536.

Step 4: 2-(2-{2-[(5-{1,8,10-Triazatricyclo[7.4.0.0$^2$,7]trideca-2,4,6,8,10,12-hexaene-11-amido}pyridin-2-yl)amino]ethoxy}ethoxy)ethan-1-aminium chloride tert-Butyl N-[2-(2-{2-[(5-{1,8,10-triazatricyclo[7.4.0.0$^2$,7]trideca-2,4,6,8,10,12-hexaene-11-amido}pyridin-2-yl)amino]ethoxy}ethoxy)ethyl]carbamate (250 mg, 0.45 mmol) was dissolved in HCl (4N in dioxane, 5 mL, 20 mmol) and the resulting mixture was stirred at rt for 4 h. The reaction was evaporated to dryness to give the title compound. $^1$H NMR (500 MHz, DMSO-d$_6$) δ 11.38 (s, 1H), 9.90 (d, J=7.0 Hz, 1H), 9.02 (s, 1H), 8.63 (d, J=2.5 Hz, 1H), 8.51 (d, J=8.3 Hz, 1H), 8.37 (dd, J=9.7, 2.5 Hz, 1H), 8.06-7.95 (m, 4H), 7.89 (d, J=6.9 Hz, 1H), 7.70 (t, J=7.7 Hz, 1H), 7.59 (t, J=7.7 Hz, 1H), 7.27 (d, J=9.7 Hz, 1H), 3.69-3.53 (m, 10H), 2.96 (q, J=5.6 Hz, 2H). Tr(METCR1410)=0.78 min, (ES$^+$) [M+H]$^+$ 436.

Step 5: tert-Butyl N-[(1S,2R)-1-hydroxy-1-{[(1S)-3-methyl-1-{[2-(2-{2-[(5-{1,8,10-triazatricyclo[7.4.0.0$^2$,7]trideca-2,4,6,8,10,12-hexaene-11-amido}pyridin-2-yl)amino]ethoxy}ethoxy)ethyl]carbamoyl}butyl]carbamoyl}-3-phenylpropan-2-yl]carbamate To a mixture of 2-(2-{2-[(5-{1,8,10-triazatricyclo[7.4.0.0$^2$,7]trideca-2,4,6,8,10,12-hexaene-11-- amido}pyridin-2-yl)amino]ethoxy}ethoxy)ethan-1-aminium chloride (100 mg, 0.21 mmol), (2S)-2-[[(2S,3R)-3-(tert-butoxycarbonylamino)-2-hydroxy-4-phenyl-butanoyl]amino]-4-methyl-pentanoic acid (94 mg, 0.21 mmol), HOBT (73 mg, 0.48 m mol) and DIPEA (240 µL, 1.38 mmol) in DMF (2 mL) was added EDC.HCl (162 mg, 0.85 mmol) at 0° C. The reaction mixture was stirred at rt for 7 h. The reaction was partitioned between water (50 mL) and EtOAc (50 mL). The phases were separated and the aq layer was extracted with more EtOAc (2×15 mL). Combined org layers were washed with 10% citric acid (1×30 mL), sat. NaHCO$_3$(2×30 mL) and brine (30 mL). The organic layer was dried over Na$_2$SO$_4$, filtered and evaporated to dryness. The crude was purified by FCC (silica, 0-10% MeOH in DCM) to give the title compound. $^1$H NMR (500 MHz, Methanol-d$_4$) δ 9.42 (d, J=7.0 Hz, 1H), 8.45 (d, J=2.6 Hz, 1H), 8.19 (d, J=8.3 Hz, 1H), 7.90-7.84 (m, 2H), 7.77 (d, J=7.0 Hz, 1H), 7.62 (ddd, J=8.3, 7.1, 1.1 Hz, 1H), 7.49 (ddd, J=8.2, 7.1, 1.0 Hz, 1H), 7.28-7.12 (m, 5H), 6.58 (d, J=8.9 Hz, 1H), 6.25 (d, J=9.6 Hz, 1H), 4.48 (dd, J=9.3, 5.5 Hz, 1H), 4.23-4.09 (m, 1H), 4.09-3.93 (m, 1H), 3.70-3.57 (m, 6H), 3.53 (t, J=5.4 Hz, 2H), 3.45 (t, J=5.4 Hz, 2H), 3.41-3.32 (m, 2H), 2.87 (dd, J=13.4, 7.7 Hz, 1H), 2.82 (dd, J=13.4, 7.7 Hz, 1H), 1.71-1.52 (m, 3H), 1.33 (s, 9H), 0.93 (d, J=6.4 Hz, 3H), 0.90 (d, J=6.4 Hz, 3H). Tr(MET-uPLC-AB-101)=2.51 min, (ES$^+$) [M+H]$^+$ 826.

Step 6: N-(6-{[2-(2-{2-[(2S)-2-[(2S,3R)-3-azaniumyl-2-hydroxy-4-phenylbutanamido]-4-methylpentanamido]ethoxy}ethoxy)ethyl]amino}pyridin-3-yl)-1,8,10-triazatricyclo[7.4.0.0$^{2,7}$]trideca-2,4,6,8,10,12-hexaene-11-carboxamide formate A mixture of tert-butyl N-[(1S,2R)-1-hydroxy-1-{[(1S)-3-methyl-1-{[2-(2-{2-[(5-{1,8,10-triazatricyclo[7.4.0.0$^{2,7}$]trideca-2,4,6,8,10,12-hexaene-11-amido}pyridin-2-yl)amino]ethoxy}ethoxy)ethyl]carbamoyl}butyl]carbamoyl}-3-phenylpropan-2-yl]carbamate (96 mg, 0.116 mmol) in HCl in dioxane (4N, 1.00 mL, 4.068 mmol) was stirred at rt for 4 h. The mixture was concentrated in vacuo and partitioned between DCM (25 mL) and sat NaHCO$_3$(50 mL). The aqueous layer was extracted with DCM (4×25 mL) and the combined extracts were washed with brine, dried over MgSO$_4$, filtered and evaporated to dryness. The crude was purified by FCC (silica, 0-15% MeOH in DCM) and by acidic reverse phase chromatography (C-18, 0-100% MeCN/Water+0.1% formic acid) to give the title compound. $^1$H NMR (500 MHz, Methanol-d$_4$) δ 9.50 (d, J=7.0 Hz, 1H), 8.47 (d, J=2.6 Hz, 1H), 8.38 (s, 1H), 8.25 (d, J=8.2 Hz, 1H), 7.94-7.88 (m, 2H), 7.82 (d, J=7.0 Hz, 1H), 7.67 (ddd, J=8.3, 7.1, 1.1 Hz, 1H), 7.54 (ddd, J=8.2, 7.0, 1.0 Hz, 1H), 7.32-7.22 (m, 5H), 6.64 (d, J=9.0 Hz, 1H), 4.39 (dd, J=8.6, 6.3 Hz, 1H), 4.17 (d, J=3.1 Hz, 1H), 3.81 (td, J=7.5, 3.1 Hz, 1H), 3.68 (t, J=5.5 Hz, 2H), 3.64-3.58 (m, 4H), 3.53 (t, J=5.5 Hz, 2H), 3.48 (t, J=5.4 Hz, 2H), 3.42-3.33 (m, 2H), 3.11 (dd, J=13.9, 7.9 Hz, 1H), 2.92 (dd, J=13.9, 7.0 Hz, 1H), 1.82-1.54 (m, 3H), 0.93 (s, 6H). Tr(MET-uHPLC-AB-101)=1.53 min, (ES)+[M+H]$^+$ 726.

The following compounds were prepared as described above:

| # | Structure | Data |
|---|---|---|
| 60 | 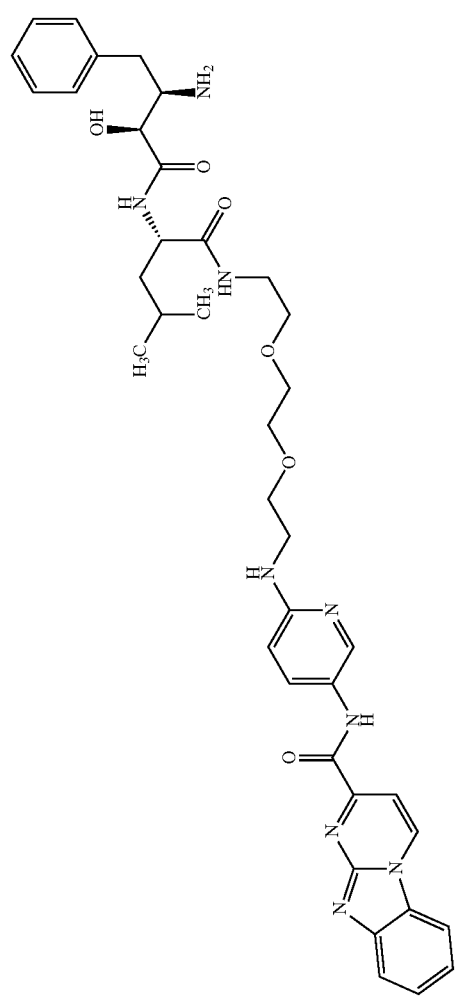 | Tr(MET-uHPLC-AB-101) = 1.53 min, (ES+) (M + H)+ 726 |

| # | Structure | Data |
|---|---|---|
| 9 | 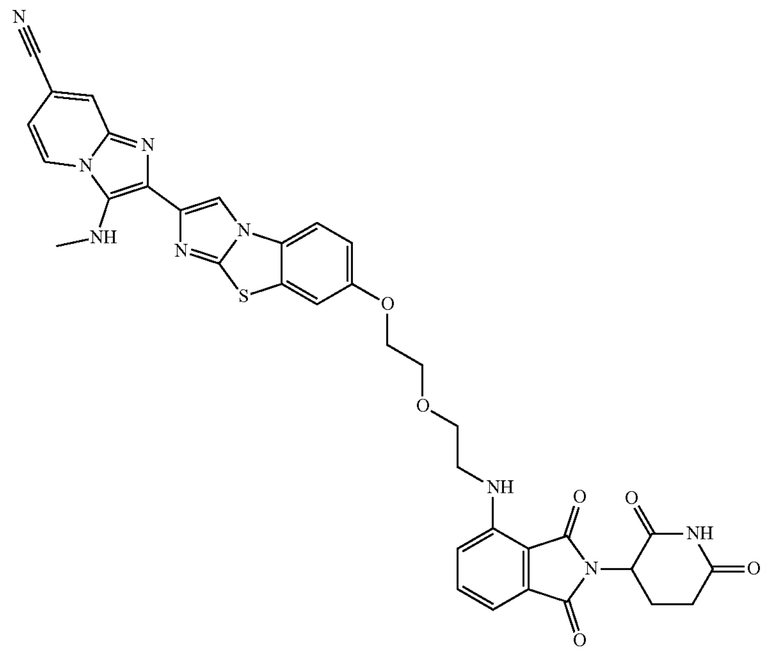 [SMILES: CNc1c(-c2cn3c(n2)sc2cc(OCCOCCNc4cccc5c4C(=O)N(C4CCC(=O)NC4=O)C5=O)ccc23)nc2cc(C#N)ccn12] | Tr(MET-uHPLC-AB-101) = 3.36 min<br>m/z (ES+) (M + H)+ 704.3. |

Example 19

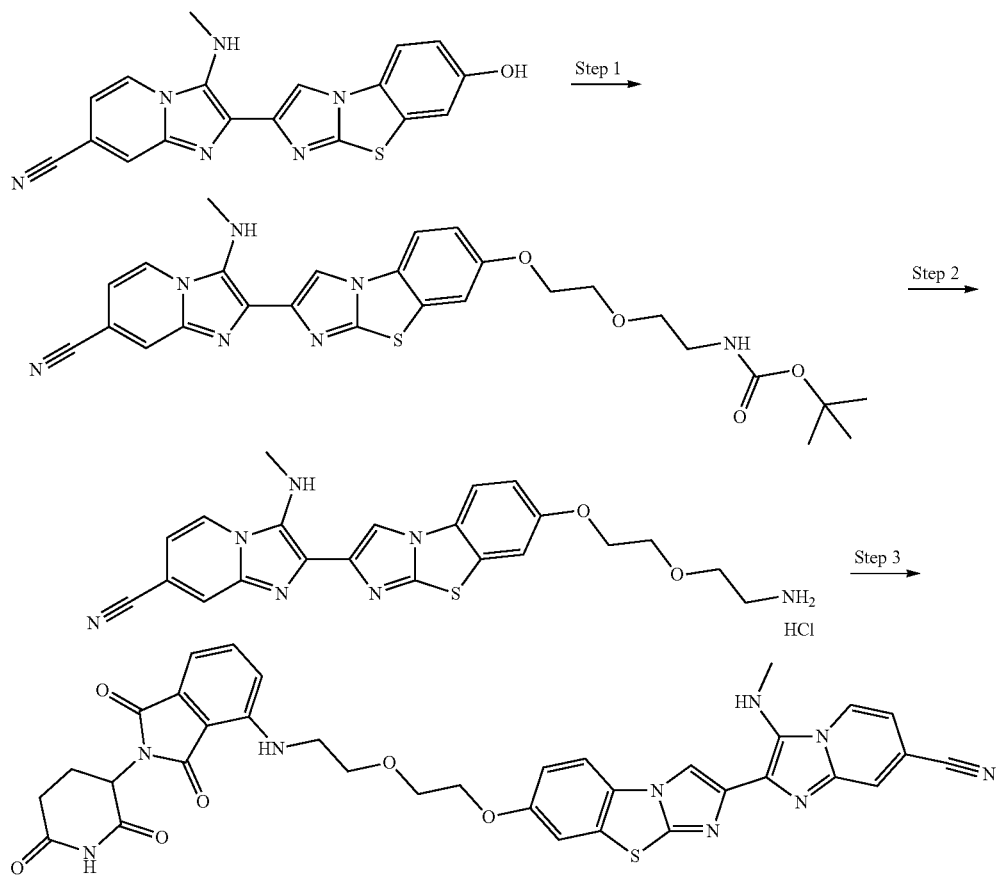

Scheme from Method 19

Step 1: tert-Butyl N-[2-[2-[2-[7-cyano-3-(methyl-amino)imidazo[1,2-a]pyridin-2-yl]imidazo[2,1-b][1,3]benzothiazol-6-yl]oxyethoxy]ethyl]carbamate CMBP (0.33 mL, 1.23 mmol) was added to a suspension of 2-(6-hydroxyimidazo[2,1-b][1,3]benzothiazol-2-yl)-3-(methylamino)imidazo[1,2-a]pyridine-7-carbonitrile (192 mg, 0.533 mmol) and tert-butyl N-[2-(2-hydroxyethoxy)ethyl]carbamate (219 mg, 1.07 mmol) in toluene (5 mL). The reaction was stirred at 100° C. for 2 hr. The reaction was then cooled to rt and the precipitate formed was filtered and washed with toluene to give the title compound. $^1$H NMR (500 MHz, DMSO-$d_6$) δ 8.70 (s, 1H), 8.34 (dd, J=7.1, 0.7 Hz, 1H), 8.14 (d, J=0.9 Hz, 1H), 8.03 (d, J=8.9 Hz, 1H), 7.69 (d, J=2.5 Hz, 1H), 7.17 (dd, J=8.9, 2.4 Hz, 1H), 7.11 (dd, J=7.1, 1.6 Hz, 1H), 6.79 (s, 1H), 5.63 (q, J=5.8 Hz, 1H), 4.29-4.09 (m, 2H), 3.80-3.68 (m, 2H), 3.47 (t, J=6.1 Hz, 2H), 3.11 (q, J=5.9 Hz, 2H), 2.89 (d, J=5.9 Hz, 3H), 1.37 (s, 9H). Tr(METCR1410)=1.20 min, (ES$^+$) (M+H)$^+$ 548.

Step 2: 2-[6-[2-(2-aminoethoxy)ethoxy]imidazo[2,1-b][1,3]benzothiazol-2-yl]-3-(methylamino)imidazo[1,2-a]pyridine-7-carbonitrile hydrochloride 4 M HCl in Dioxane (0.83 mL, 3.33 mmol) was added dropwise to a solution of tert-butyl N-[2-[2-[2-[7-cyano-3-(methylamino)imidazo[1,2-a]pyridin-2-yl]imidazo[2,1-b][1,3]benzothiazol-6-yl]oxyethoxy]ethyl]carbamate (198 mg, 0.333 mmol) in 1,4-dioxane (5 mL) and MeOH (2.5 ml). The mixture was stirred at rt for 24 hr after which time more 4N HCl in dioxane (0.20 ml) was added and the mixture was stirred at rt for another 24 hr. The reaction was evaporated to dryness to afford the title compound. $^1$H NMR (400 MHz, DMSO-$d_6$) δ 8.78 (s, 1H), 8.46 (s, 1H), 8.20 (s, 1H), 8.07 (d, J=8.9 Hz, 1H), 7.88 (s, 3H), 7.72 (s, 1H), 7.40-7.12 (m, 2H), 4.26-4.18 (m, 2H), 3.90-3.80 (m, 2H), 3.69 (t, J=5.2 Hz, 2H), 3.02 (q, J=5.5 Hz, 2H), 2.90 (s, 3H). Tr(METCR1410)=0.87 min, (ES$^+$) (M+H)$^+$ 448.

Step 3: 2-[6-[2-[2-[[2-(2,6-dioxo-3-piperidyl)-1,3-dioxo-isoindolin-4-yl]amino]ethoxy]ethoxy]imidazo[2,1-b][1,3]benzothiazol-2-yl]-3-(methylamino)imidazo[1,2-a]pyridine-7-carbonitrile (Compound 9)

DIPEA (0.072 mL, 0.413 mmol) was added to a suspension of 2-(2,6-dioxo-3-piperidyl)-4-fluoro-isoindoline-1,3-dione (57 mg, 0.207 mmol) and 2-[6-[2-(2-aminoethoxy)ethoxy]imidazo[2,1-b][1,3]benzothiazol-2-yl]-3-(methylamino)imidazo[1,2-a]pyridine-7-carbonitrile; hydrochloride (100 mg, 0.207 mmol) in DMF (2.5 mL). The solution was heated at 90° C. for 48 hr. The reaction was evaporated to dryness and purified by low pH prep HPLC to give the title compound. $^1$H NMR (500 MHz, DMSO-$d_6$) δ 11.10 (s, 1H), 8.68 (s, 1H), 8.35 (d, J=7.1 Hz, 1H), 8.14 (s, 1H), 7.99 (d, J=8.9 Hz, 1H), 7.65 (d, J=2.4 Hz, 1H), 7.60-7.54 (m, 1H), 7.18-7.13 (m, 2H), 7.11 (dd, J=7.1, 1.6 Hz, 1H), 7.02 (d, J=7.0 Hz, 1H), 6.64 (t, J=5.7 Hz, 1H), 5.63 (q, J=5.8 Hz, 1H), 5.04 (dd, J=12.8, 5.4 Hz, 1H), 4.29-4.07 (m, 2H), 3.95-3.76 (m, 2H), 3.72 (t, J=5.4 Hz, 2H), 3.51 (q, J=5.4 Hz, 2H), 2.95-2.81 (m, 4H), 2.71-2.54 (m, 1H), 2.53-2.51 (m, 1H), 2.08-1.95 (m, 1H). Tr(MET-uHPLC-AB-101)=3.36 min m/z (ES$^+$) (M+H)$^+$ 704.3.
Example 20
Scheme for Example 20
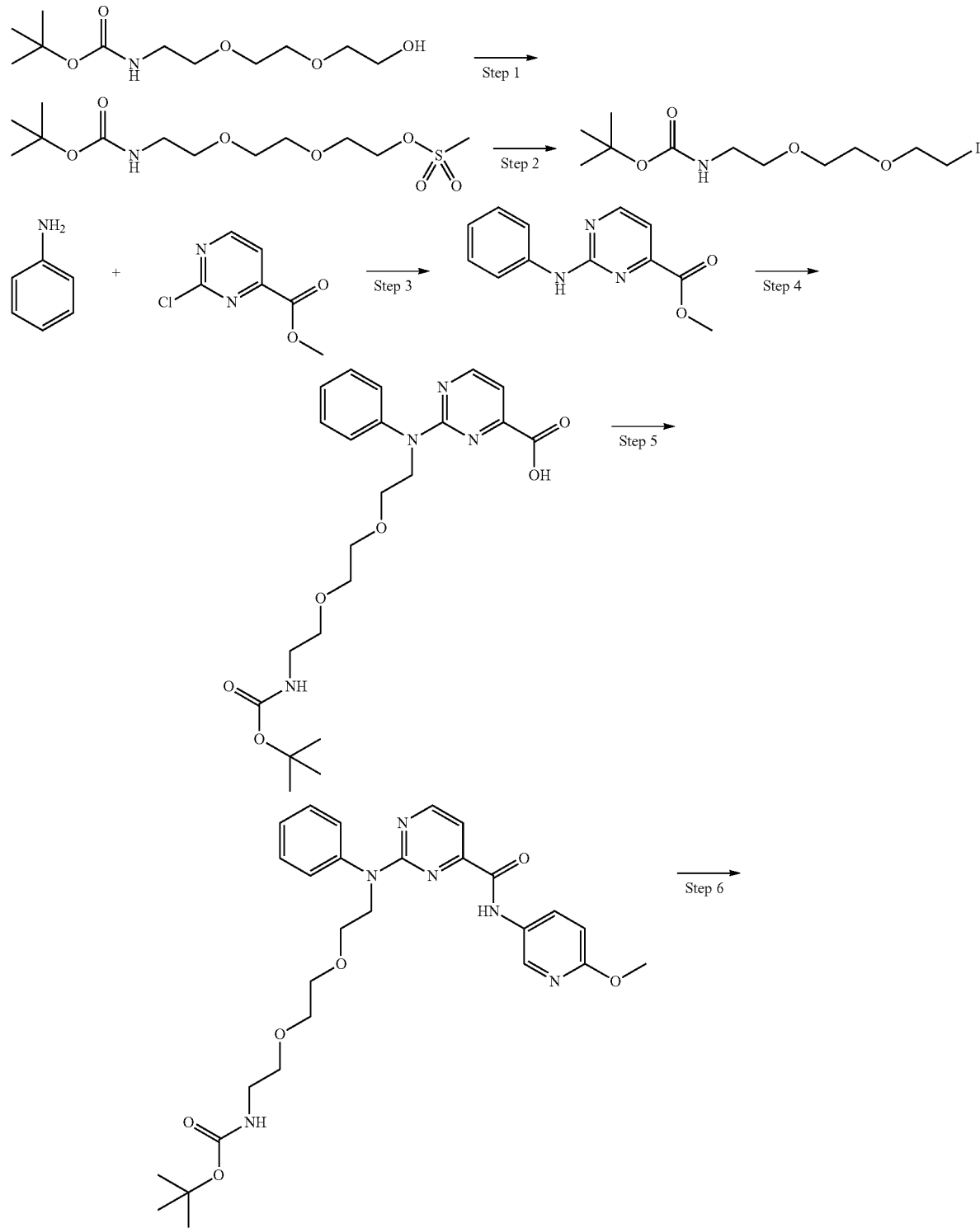

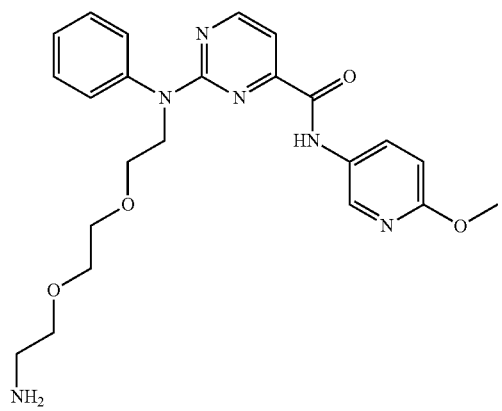

+ 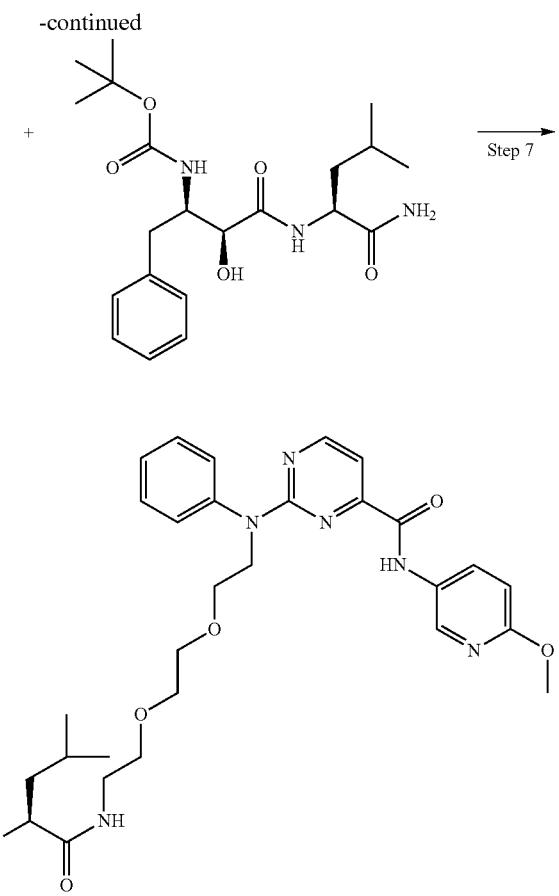

Step 7 →

Step 1: 2-[2-[2-(tert-Butoxycarbonylamino)ethoxy]ethoxy]ethyl methanesulfonate A stirred solution of tert-butyl N-{2-[2-(2-hydroxyethoxy)ethoxy]ethyl}carbamate (250 mg, 1.00 mmol) and NEt₃ (181 μL, 1.3 mmol) in DCM (5 mL) at 0° C. was treated with the dropwise addition of MsCl (93 μL, 1.2 mmol). After the addition, the mixture was stirred at 0° C. for 1.5 h and then at rt for 3 h. The reaction mixture was diluted with DCM (10 mL) and washed with a solution of saturated NaHCO₃(15 mL) and brine (15 mL). The organic layer was dried over MgSO₄, filtered, concentrated in vacuo and further dried on a high vac line for 2 h to give the title compound. ¹H NMR (500 MHz, DMSO-d6) δ 6.78-6.70 (m, 1H), 4.35-4.25 (m, 2H), 3.70-3.65 (m, 2H), 3.55 (dd, J=5.9, 3.2 Hz, 2H), 3.51 (dd, J=5.9, 3.3 Hz, 2H), 3.38 (t, J=6.1 Hz, 2H), 3.17 (s, 3H), 3.06 (q, J=6.0 Hz, 2H), 1.37 (s, 9H). Tr (METCR1410)=0.97 min, (ES⁺) [MH-Boc]⁺ 228.

Step 2: tert-Butyl N-[2-[2-(2-iodoethoxy)ethoxy]ethyl]carbamate

To a stirred solution of tert-butyl N-(2-{2-[2-(methanesulfonyloxy)ethoxy]ethoxy}ethyl)carbamate (333 mg, 1.02 mmol) in dry acetone (8 mL), was added KI (675 mg, 4.06 mmol). The resulting suspension was stirred at 50° C. overnight. After which time, the reaction mixture was allowed to cool to rt, diluted with dry acetone (10 mL) and treated with KI (675 mg, 4.06 mmol). The reaction mixture was stirred at 50° C. overnight. After which time, the reaction mixture was treated with KI (300 mg, 1.81 mmol) and heating was continued for 3 h. After which time, the reaction mixture was cooled to rt, and partitioned between water (10 mL) and EtOAc (10 mL). The layers were separated and the aqueous phase was extracted with EtOAc (4×15 mL). The combined organic phase was washed with a solution of sat. Na₂S₂O₃ (aq) (20 mL) and brine (20 mL), dried over MgSO₄, filtered and concentrated in-vacuo to give crude product. The crude product pre-absorbed onto silica and purified by FCC (silica, 0-100% EtOAc in heptanes). The pure fractions were combined, concentrated in vacuo and further dried on a high vacuum line for 2 h to give the title compound. ¹H NMR (500 MHz, DMSO-d6) δ 6.72 (t, J=5.1 Hz, 1H), 3.66 (t, J=6.4 Hz, 2H), 3.55 (dd, J=5.8, 3.2 Hz, 2H), 3.51 (dd, J=5.8, 3.3 Hz, 2H), 3.39 (t, J=6.1 Hz, 2H), 3.35-3.31 (m, 2H), 3.06 (q, J=6.0 Hz, 2H), 1.37 (s, 9H). Tr (METCR1410)=1.13 min, (ES⁺) [MH-Boc]⁺ 260.0

Step 3: Methyl 2-anilinopyrimidine-4-carboxylate

In a sealed tube was placed methyl 2-chloropyrimidine-4-carboxylate (250 mg, 1.45 mmol) in dioxane (2 mL), followed by aniline (135 μL, 1.45 mmol) and acetic acid (158 μL, 2.9 mmol). The tube was flushed with nitrogen, placed on a pre-heated heating block set at 100° C. and stirred for 1 h and then at rt overnight. The reaction mixture was heated at 100° C. for a further 5 h and then left to stand at rt over the weekend. The reaction mixture was heated for a further 6 h and then left to reach room temperature. The red solution was then diluted with a solution of saturated NaHCO₃(8 mL) and the resulting mixture was extracted with EtOAc (4×15 mL). The combined organics were washed with brine (15 mL), dried over MgSO$_4$, filtered and concentrated in vacuo to give crude product. The crude material was pre-absorbed onto silica and purified by FCC (0-100% EtOAc in Heptanes) to give the title compound. $^1$H NMR (500 MHz, DMSO-d6) δ 10.03 (s, 1H), 8.73 (d, J=4.9 Hz, 1H), 7.81 (d, J=7.7 Hz, 2H), 7.32 (d, J=4.9 Hz, 1H), 7.31-7.26 (m, 2H), 6.98 (t, J=7.3 Hz, 1H), 3.91 (s, 3H). Tr (METCR1603)=3.93 min, (ES$^+$) [M+H]$^+$ 230.1.

Step 4: 2-[N-[2-[2-[2-(tert-Butoxycarbonylamino) ethoxy]ethoxy]ethyl]anilino]pyrimidine-4-carboxylic acid A sealed tube was charged with methyl 2-(phenylamino) pyrimidine-4-carboxylate (103 mg, 0.45 mmol) in DMF (2 mL) and cooled to 0° C. (ice/water). Sodium hydride (60%, 20 mg, 0.49 mmol) was added in one portion and the mixture was stirred for 15 min. A solution of tert-butyl N-[2-[2-(2-iodoethoxy)ethoxy]ethyl]carbamate (241 mg, 0.67 mmol) in DMF (2 mL) was then added over 2 min and the mixture was stirred for a further 10 min at 0° C., 1.5 h at rt, 50° C. for 4 h and overnight at 80° C. After which time, the reaction mixture was cooled to rt and concentrated in vacuo to give a product. The product was suspended in THF (2 mL) and treated with 1 M LiOH (1 mL). The mixture was briefly sonicated and stirred at room temperature for 2.5 h. After which time, the reaction mixture was concentrated in vacuo and the remaining aqueous was extracted with ether (3×5 mL). The aqueous phase was then acidified to pH 4 by the addition of a solution of 10% citric acid (aq) (2 mL). The mixture was extracted with EtOAc (3×15 mL). The combined organic extracts were washed with brine (15 mL), dried over MgSO$_4$, filtered, concentrated in vacuo and further dried in the vacuum oven to give crude product. The crude residue was purified by acidic reverse phase Biotage (C-18, 0-100% MeCN/water+0.1% formic acid) to give the title compound. $^1$H NMR (500 MHz, DMSO-d6) δ 8.50 (d, J=4.8 Hz, 1H), 7.40 (t, J=7.8 Hz, 2H), 7.33 (dd, J=8.4, 1.2 Hz, 2H), 7.25 (t, J=7.3 Hz, 1H), 7.15 (d, J=4.8 Hz, 1H), 6.70 (t, J=4.9 Hz, 1H), 4.12 (t, J=6.1 Hz, 2H), 3.62 (t, J=6.1 Hz, 2H), 3.47 (dd, J=5.8, 3.3 Hz, 2H), 3.43 (dd, J=5.7, 3.2 Hz, 2H), 3.34 (s, 2H), 3.02 (q, J=5.9 Hz, 2H), 1.35 (s, 9H). Tr(METCR1410)=1.12 min, (ES$^+$) [M+H]$^+$ 447.2.

Step 5: tert-Butyl N-[2-[2-[2-(N-[4-[(6-methoxy-3-pyridyl)carbamoyl]pyrimidin-2-yl]anilino)ethoxy] ethoxy]ethyl]carbamate A stirred solution of 2-[N-[2-[2-[2-(tert-butoxycarbonylamino)ethoxy]ethoxy]ethyl]anilino]pyrimidine-4-carboxylic acid (57 mg, 0.1 mmol), N-[(dimethylamino)(3H-[1,2,3]triazolo[4,5-b]pyridin-3-yloxy)methylidene]-N-methylmethanaminium hexafluorophosphate (58 mg, 0.15 mmol) in DMF (2 mL) was stirred at 0° C. under nitrogen and treated with the dropwise addition of N-ethyl-N-(propan-2-yl)propan-2-amine (24 µL, 0.14 mmol). The reaction mixture was stirred at 0° C. for 10 min and then treated with a solution of 6-methoxypyridin-3-amine (15.79 mg, 0.13 mmol) in DMF (1 mL). The resulting mixture was stirred at 0° C. for 2 h and then at room temperature overnight. After which time, the reaction mixture was concentrated in vacuo and the residue was partitioned between DCM (10 mL) and water (10 mL). The layers were separated and the aqueous phase was extracted with DCM (3×10 mL). The combined organics were washed with brine (15 mL). The layers were separated and the aqueous phase was extracted with DCM (10 mL). The combined organic phases were dried over MgSO$_4$, filtered and concentrated in vacuo to give a crude residue. The crude residue was pre-absorbed onto silica and purified by FCC (silica, 0-100% EtOAc in heptane) to give the title compound. $^1$H NMR (500 MHz, DMSO-d6) δ 10.11 (s, 1H), 8.56 (d, J=4.8 Hz, 1H), 8.45 (d, J=2.5 Hz, 1H), 8.00 (dd, J=8.9, 2.7 Hz, 1H), 7.47-7.42 (m, 2H), 7.42-7.36 (m, 2H), 7.32-7.25 (m, 2H), 6.88 (d, J=8.8 Hz, 1H), 6.68 (t, J=5.4 Hz, 1H), 4.29 (t, J=5.8 Hz, 2H), 3.85 (s, 3H), 3.66 (t, J=5.8 Hz, 2H), 3.49 (dd, J=5.8, 3.7 Hz, 2H), 3.42 (dd, J=5.8, 3.7 Hz, 2H), 3.30 (s, 2H), 3.01 (q, J=6.0 Hz, 2H), 1.34 (s, 9H). Tr(METCR1410)=1.31 min, (ES$^+$) [M+H]$^+$ 553.

Step 6: 2-[N-[2-[2-(2-Aminoethoxy)ethoxy]ethyl] anilino]-N-(6-methoxy-3-pyridyl)pyrimidine-4-carboxamide hydrochloride tert-Butyl N-[2-[2-[2-(N-[4-[(6-methoxy-3-pyridyl)carbamoyl]pyrimidin-2-yl]anilino)ethoxy]ethoxy]ethyl]carbamate (59.5 mg, 0.11 mmol) was treated with 4 M HCl in dioxane (1.12 mL), diluted with MeOH (2 mL) and the resulting solution was stirred at rt for 5 h. After which time the reaction mixture was concentrated in vacuo and further dried in a vacuum oven at 50° C. to give the title compound. Obtained as a 1:1 mixture of the title compound and the O-demethylated product. Tr(METCR1410)=0.95 min, (ES$^+$) [M+H]$^+$ 453.1.

Step 7: 2-[N-[2-[2-[2-[[(2S)-2-[[(2S,3R)-3-Amino-2-hydroxy-4-phenyl-butanoyl]amino]-4-methyl-pentanoyl]amino]ethoxy]ethoxy]ethyl]anilino]-N-(6-methoxy-3-pyridyl)pyrimidine-4-carboxamide A mixture of 2-[N-[2-[2-(2-aminoethoxy)ethoxy]ethyl]anilino]-N-(6-methoxy-3-pyridyl)pyrimidine-4-carboxamide;hydrochloride (46%, 61 mg, 0.06 mmol), (2S)-2-[[(2S,3R)-3-(tert-butoxycarbonylamino)-2-hydroxy-4-phenyl-butanoyl]amino]-4-methyl-pentanoic acid (51 mg, 0.12 mmol) and 1H-benzotriazol-1-ol hydrate (1:1) (42 mg, 0.27 mmol) in DMF (2 mL) was briefly sonicated and then cooled on ice and treated with DIPEA (65 µL, 0.37 mmol), followed by EDC HCl (49 mg, 0.26 mmol). The mixture was stirred at 0° C. for 12 min and then at rt over the weekend. After which time, the reaction mixture was concentrated in vacuo and the resulting oily residue was partitioned between EtOAc (10 mL) and water (5 mL). The layers were separated and the aqueous phase was extracted with EtOAc (3×10 mL). The combined organic extracts were washed successively with a solution of 10% citric acid (aq) (10 mL), a solution of sat. NaHCO$_3$(aq) (10 mL), brine (10 mL), dried over MgSO$_4$, filtered, concentrated in vacuo to give product. The crude product was re-dissolved in MeOH (2 mL) and treated with 4 M HCl in dioxane (373 µL) and stirred at rt for 2 h. The mixture was re-treated with 4 M HCl in dioxane (373 µL) and stirred at rt for a further 1.5 h. After which time, the reaction mixture was concentrated in vacuo and the residue was dissolved in water (5 mL), treated with solid NaHCO$_3$(720 mg) and extracted with DCM (3×15 mL). The combined organic extracts were washed with brine (15 mL), dried over MgSO$_4$, filtered and concentrated in vacuo to give crude product. The crude product was purified by basic reverse phase chromatography (C-18, 0-100% MeCN/water+0.1% NH$_{40}$H). The clean fractions were combined, concentrated in vacuo and lyophilised overnight to give the title compound. $^1$H NMR (500 MHz, DMSO-d6) δ 10.11 (s, 1H), 8.56 (d, J=4.8 Hz, 1H), 8.45 (d, J=2.5 Hz, 1H), 8.18 (t, J=5.6 Hz, 1H), 8.00 (dd, J=8.9, 2.7 Hz, 1H), 7.69 (d, J=8.6 Hz, 1H), 7.44 (t, J=7.7 Hz, 2H), 7.41-7.35 (m, 2H), 7.32-

7.23 (m, 4H), 7.20 (d, J=6.9 Hz, 2H), 7.19-7.15 (m, 1H), 6.88 (d, J=8.8 Hz, 1H), 5.47 (d, J=5.6 Hz, 1H), 4.28 (q, J=8.9, 7.3 Hz, 3H), 3.85 (s, 3H), 3.74 (s, 1H), 3.65 (t, J=5.8 Hz, 2H), 3.46 (dd, J=5.9, 3.7 Hz, 2H), 3.39 (dd, J=5.8, 3.6 Hz, 2H), 3.33-3.31 (m, 2H), 3.19-3.07 (m, 3H), 2.76 (dd, J=13.2, 6.5 Hz, 1H), 2.52 (s, 1H), 1.64-1.52 (m, 1H), 1.46 (dtt, J=22.1, 8.3, 4.2 Hz, 2H), 1.36 (d, J=35.5 Hz, 2H), 0.84 (d, J=6.6 Hz, 3H), 0.81 (d, J=6.5 Hz, 3H). Tr(MET-uHPLC-AB-101)=2.53 min, (ES$^+$) [M+H]$^+$ 743.2.

Biological Assays

Example 21: Q46_RBA Assay

Binding of W to mHTT. A radioligand binding assay was developed to screen for compounds which can efficiently displace a radioligand detailed elsewhere (see, e.g., U.S. Patent Publication No. from US 2017/0292150) pre-formed polyQ46 or Exon1-polyQ46 aggregates (Q46_RBA).

Aggregation of polyQ peptides is initiated by cleavage of the tag from a GST-polyQ46 or from a MBP-Exon1-polyQ46 fusion protein. The pre-formed aggregates are then incubated with compounds which compete with the [$^3$H]-radiolabelled ligand for binding to the aggregates. The readout is a scintillation based MicroBeta measurement of radioligand bound to aggregates. The activity was indicated as: +++, <100 nM; ++, 100-500 nM; +, >500 nM.

TABLE 3

| # | Q46_RBA IC50 (nM) |
|---|---|
| 1 | +++ |
| 2 | +++ |
| 3 | +++ |
| 4 | ++ |
| 5 | ++ |
| 6 | ++ |
| 7 | ++ |
| 8 | ++ |
| 9 | +++ |
| 10 | +++ |
| 11 | +++ |
| 12 | +++ |
| 13 | +++ |
| 14 | +++ |
| 15 | +++ |
| 16 | +++ |
| 17 | +++ |
| 18 | +++ |
| 19 | ++ |
| 20 | +++ |
| 21 | +++ |
| 22 | +++ |
| 23 | +++ |
| 24 | +++ |
| 25 | ++ |
| 26 | ++ |
| 27 | ++ |
| 28 | +++ |
| 29 | +++ |
| 30 | +++ |
| 31 | +++ |
| 32 | +++ |
| 33 | +++ |
| 34 | +++ |
| 35 | +++ |
| 36 | +++ |
| 37 | +++ |
| 38 | +++ |
| 39 | +++ |
| 40 | +++ |
| 41 | +++ |
| 43 | +++ |
| 44 | ++ |
| 45 | ++ |
| 46 | 101 |
| 47 | +++ |
| 48 | +++ |
| 49 | +++ |
| 50 | +++ |
| 51 | +++ |
| 52 | +++ |
| 53 | + |
| 54 | + |
| 55 | ++ |
| 56 | + |
| 57 | +++ |
| 58 | ++ |
| 59 | +++ |
| 60 | +++ |
| 61 | +++ |
| 62 | +++ |
| 63 | +++ |
| 64 | + |
| 65 | ++ |
| 66 | ++ |
| 67 | ++ |
| 68 | ++ |
| 69 | + |
| 70 | +++ |

Example 22: SPR Assay

Surface Plasmon Resonance (SPR) assays have been developed to test the affinity (KD) of VHL or CRBN-based compounds to respective recombinant ligase complex/domain.

The assays are based on surface plasmon resonance (SPR), which enables to measure the changes of the local refractive index due to changes of molecular mass on a gold chip surface in the case of a binding event and in a flowing system. To detect binding between both partners, the respective E3 ligase is immobilized to the chip surface, while the test compounds are flown over the chip surface at a steady velocity. The detected changes in the RU response are indicative of the binding event and are concentration dependent.

For the SPR experiments, either a commercially available VHL complex (Merck, 23-044; composed of 5 units: VHL, Elongin B, Elongin C, Cul2, and Rbx1) exhibiting a his-tag at the Cul2 subunit or an internally produced biotin-tagged mouse CRBN thalidomide binding domain (mCRBN-TBD) was used. These tags provide the anchor for the capturing process to either an NTA or Streptavidin coated chip surface (immobilization level of 3,000-5,000 RU). Because of the rather complex structure of the VHL complex, it was additionally coupled to the chip surface by amino coupling to prevent any protein loss by disruption of the complex in the flowing system.

To detect binding of compounds and extract dissociation constants $K_D$ for the tested compounds to the immobilized E3 ligase, concentration response curves of the compounds were recorded. Compounds were usually tested in 10-pt dilutions up to 20 µM final concentration in assay buffer and were flown over the chip at 30 µL/min. The contact time for each cycle includes 90 s for association and 200 s for dissociation of compounds. Every test cycle was read out as a sensorgram that was referenced to the sensor surface that does not present the target protein.

In the following tables, the $K_d$ values are indicated as: +++, <100 nM; ++, 100-500 nM; +, >500 nM.

TABLE 4

| # | VHL SPR $K_d$ (nM) |
|---|---|
| 1 | ++ |
| 2 | ++ |
| 3 | ++ |
| 11 | + |
| 20 | ++ |
| 21 | ++ |
| 22 | +++ |
| 23 | +++ |
| 24 | +++ |
| 25 | ++ |
| 26 | +++ |
| 43 | + |
| 44 | + |
| 45 | + |
| 46 | + |
| 47 | ++ |
| 48 | + |
| 53 | ++ |
| 54 | + |
| 55 | ++ |
| 56 | ++ |
| 57 | ++ |
| 58 | + |

TABLE 5

| # | CRBN SPR $K_d$ (nM) |
|---|---|
| 30 | + |
| 31 | ++ |
| 32 | ++ |
| 33 | ++ |
| 34 | + |
| 36 | ++ |
| 37 | ++ |
| 38 | ++ |
| 39 | + |
| 40 | + |
| 70 | + |

Example 23: HTT Degradation Assay

Compounds described herein were tested for efficacy in HTT-lowering in human HeLa cells transiently overexpressing HTT-Exon1-polyQ$_n$ proteins. For HTT degradation experiments HeLa cells were transiently transfected with pcDNA3.1(+)-hHTT-E1mixQn-EGFP plasmids for transient expression of HTT-Exon1 proteins of different polyQ length (HTT-exon1-Q23/73/145-EGFP). Two hours after transfection the cells were treated with test compounds at 7 concentrations from 0.01 μM to 10 μM (final assay concentration)+DMSO control. After a 22 hr incubation with test compounds the cells were washed with 1×PBS and lysed in MSD lysis buffer (150 mM NaCl; 20 mM Tris ph 7.5; 1 mM EDTA, 1 mM EGTA; 1% Triton X-100, 1×Phosphatase Inh. Cocktail 2, 1× Phosphatase Inh. Cocktail 3, 1×Protease Inh. Cocktail, 10 mM NaF, 1 mM PMSF) for 30 min on ice.

For analysis of HTT protein levels by Meso Scale Discovery (MSD) assays, MSD 384-well plates were coated overnight at 4° C. with 10 μL of the respective coating antibody (soluble mHTT-assay 6: 2B7 (5 μg/mL); aggregated HTT-assay-45: MW8; 4 μg/mL)) in carbonate-bicarbonate coating buffer (15 mM Na$_2$CO$_3$, 35 mM NaHCO$_3$, pH 9.6) per well. Plates were then washed three times with 35 μL of washing buffer (0.2% Tween-20 in PBS) per well and blocked with 35 μL of blocking buffer (2% probumin, 0.2% Tween-20 in PBS) per well for 1 h at RT with rotational shaking.

For the mHTT aggregate-specific MSD assay cell lysates were diluted to a final concentration of 1 mg/ml total protein in blocking buffer. For the soluble mHTT MSD assay cell lysates were first diluted in lysis buffer to a concentration of 0.2 mg/ml total protein and then further diluted to 0.1 mg/ml total protein in blocking buffer.

After an additional washing step, 10 μL per sample were transferred to each well of the antibody-coated MSD plate and incubated with shaking for 1 h at RT. After disposal of samples and three wash cycles with 35 μL of washing buffer each, 10 μL of the primary SULFO-TAG (ST) labeled detection antibody (soluble HTT: MW1 (5 μg/mL); aggregated HTT: 4C$_9$ (1 μg/mL)) were added to each well and incubated with shaking for 1 h at RT. After washing three times with washing buffer, 35 μL of read buffer T with surfactant (Meso Scale Discovery) were added to each well. Plate were imaged on a Sector Imager 6000 (Meso Scale Discovery) according to manufacturer's instructions and settings recommended for 384-well plates. The obtained readout is the MSD signal intensity for each well. Background values were subtracted from each sample. Relative mHTT levels were normalized to DMSO-only control samples containing the highest mHTT protein load.

Figure 1B:
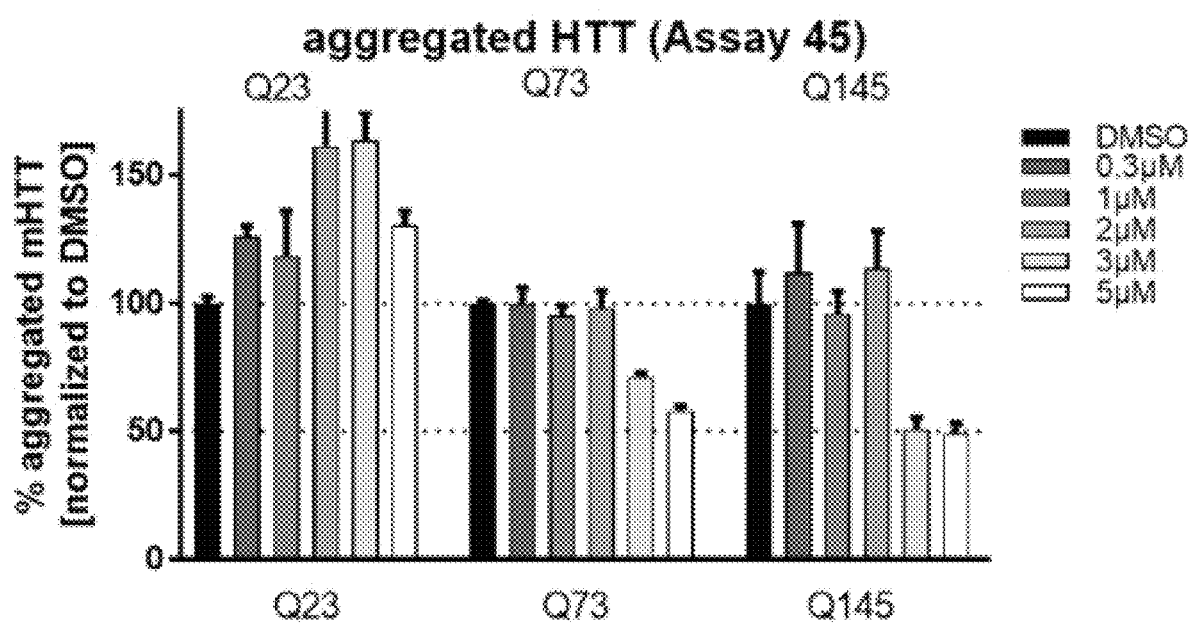
Figure 2:
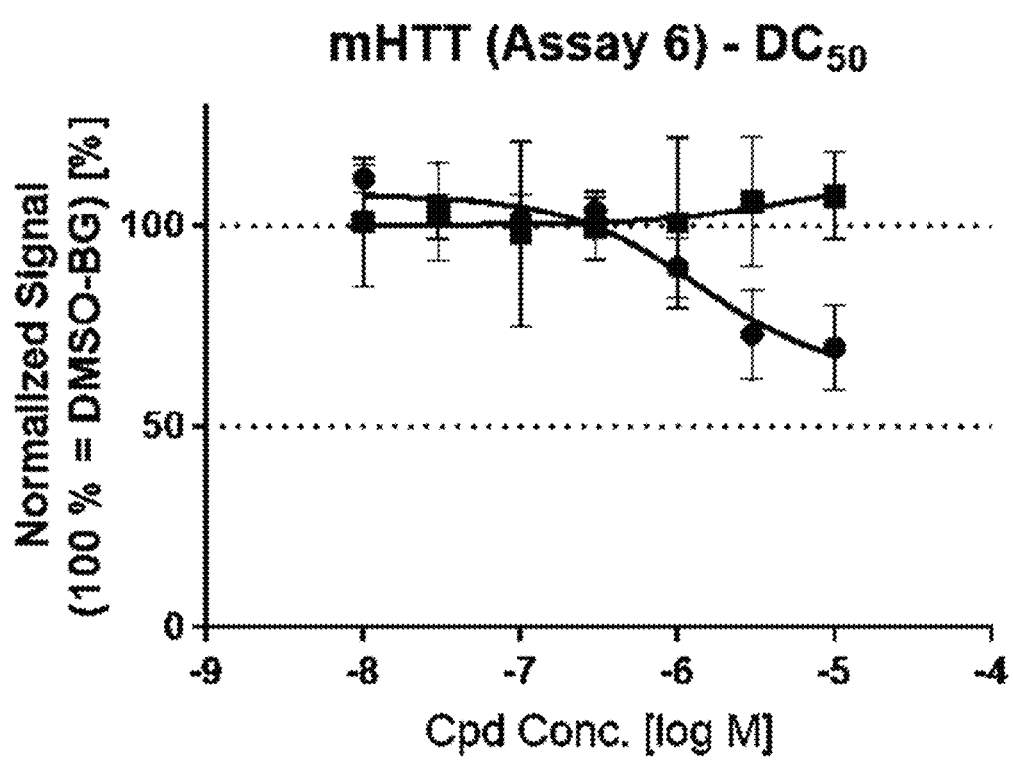
FIG. 2 depicts HTT degradation using compound 1 and compound 10 in HeLa cells transfected with Exon1-Q73-EGFP. Analysis by mHTT MSD assay. Blue circles refer to compound 1 and squares refer to compound 10; n=6(3) independent experiments. Mean+/−SEM; BG=background.

Reduction of soluble and aggregated mHTT Exon1-Q73 levels by compound 1 was confirmed by MSD assays (FIGS. 1A, 1B, and 2). Compound 10 having an inactive enantiomeric liganse binding domain was found to be less active.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

All publications, patent applications, patents, and other references mentioned herein are expressly incorporated by reference in their entirety, to the same extent as if each were incorporated by reference individually. In case of conflict, the present specification, including definitions, will control.

The invention claimed is:

1. A compound of formula (I):

W-L-ULM  (I)

or a pharmaceutically acceptable salt, a stereoisomer, a mixture of stereoisomers, or isotopically enriched analog thereof, wherein:

W is a compound of formula (B), formula (C), formula (D), formula (E), or formula (F):

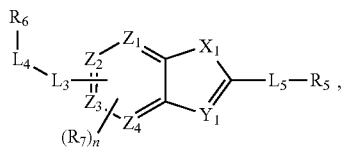

(B)

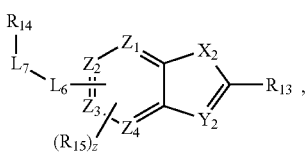
(C)

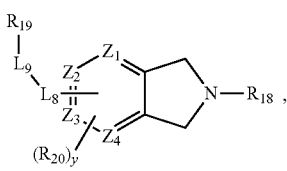
(D)

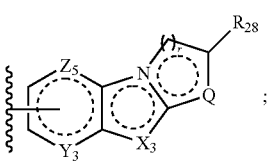
(E)

(F)

wherein:
the point of attachment of W to L-ULM is at any substitutable atom of formula (B), or at any substitutable atom of formula (C), at any substitutable atom of formula (D), or at any substitutable atom of formula (E); and
the wavy line of formula (F) indicates the point of attachment of W to L of L-ULM;

$Z_1$, $Z_2$, $Z_3$, and $Z_4$ are independently selected from CH and N, provided that at least two of $Z_1$, $Z_2$, $Z_3$, and $Z_4$ are CH;

$R_5$ is heteroaryl, heterocycloalkenyl, or heterocycloalkyl, each of which is optionally substituted with one or two groups independently selected from cyano, halo, lower alkyl optionally substituted with amino, alkylamino, or di(alkyl)amino, lower alkoxy optionally substituted with lower alkoxy, optionally substituted amino, haloalkyl, di(alkyl)aminocarbonyl, alkylaminocarbonyl, and aminocarbonyl,
or
$R_5$ is phenyl optionally substituted with one or two groups independently selected from cyano, heteroaryl, halo, phenoxy, benzyloxy, heteroaryl, lower alkyl optionally substituted with amino, (alkyl)amino, or di(alkyl) amino, lower alkoxy, optionally substituted amino, di(alkyl)aminocarbonyl, alkylaminocarbonyl, and aminocarbonyl;

$L_3$ is —O— and $L_4$ is —(CR$_8$R$_9$)$_p$— or —(CR$_8$R$_9$)$_p$O—; or
$L_3$ is —NR$_{10}$— and $L_4$ is —C(O)— or —(R$_8$R$_9$)$_p$—; or
$L_3$ is —NR$_{10}$— and $L_4$ is —C(O)(O)(R$_8$R$_9$)$_p$—; or
$L_3$ is —NR$_{10}$— and $L_4$ is —C(O)(R$_8$R$_9$)$_p$(O)—; or
$L_3$ is —NR$_{10}$— and $L_4$ is —C(O)(R$_8$R$_9$)$_p$—; or
$L_3$ is —NR$_{10}$— and $L_4$ is —C(O)CR$_8$=CR$_9$—; or
$L_3$ is —C(O)— and $L_4$ is NR$_{10}$—; or
$L_3$ is —(R$_8$R$_9$)$_p$— and $L_4$ is —NR$_{10}$—, —C(O)— or —O—; or
$L_3$ is absent and $L_4$ is absent; or
$L_3$ taken together with $L_4$ is —CH=CH—, —C≡C—, or heterocyclylene;

$L_5$ is —CH=CH—, or $L_5$ is absent;

$R_6$ is selected from heterocycloalkyl, aryl, and heteroaryl, each of which is optionally substituted with one or two groups selected from
—OC(O)—R$_{11}$,
—C(O)O—R$_{11}$,
amino,
halo,
haloalkyl,
phenyl,
heteroaryl,
cyano,
(lower alkyl)thio,
phenoxy,
phenoxymethyl,
heteroaryloxy,
heteroaryloxy substituted with lower alkyl,
hydroxyl,
lower alkenyloxy,
lower alkoxy,
lower alkoxy substituted with lower alkoxy, amino, (alkyl)amino, (dialkyl)amino, heterocycloalkyl, heteroaryl, or halo,
lower alkyl, and
lower alkyl substituted with amino, (alkyl)amino, (dialkyl)amino, hydroxyl or lower alkoxy;

$X_1$ is NR$_{12}$, O, or S;
$Y_1$ is CR$_{12}$ or N;
$R_{10}$ is hydrogen or lower alkyl;
$R_{12}$ is hydrogen, halo, cyano, or lower alkyl;
each $R_7$ is independently selected from lower alkyl, lower alkoxy, and halo;
$R_{11}$ is lower alkyl;
each $R_8$ is independently selected from hydrogen, hydroxyl, trifluoromethyl, and lower alkyl;
each $R_9$ is independently selected from hydrogen and lower alkyl;
n is 0 or 1;
p is 0, 1, or 2;
$X_2$ is (CR$_{16}$=CR$_{16}$), O, NH, or S;
$Y_2$ is CR$_{16}$ or N;
each $R_{16}$ is independently selected from hydrogen, halo, cyano, and lower alkyl;
$R_{13}$ is aryl, heteroaryl, or heterocycloalkyl, each of which is optionally substituted with one or two groups independently selected from alkynyl, heteroaryl, cyano, optionally substituted amino, halo, and lower alkyl optionally substituted with optionally substituted amino;
$L_6$ is absent, C(O)O, O, or NR$_{17}$,
$R_{17}$ is hydrogen or lower alkyl;
$L_7$ is (CH$_2$)$_q$;
$R_{14}$ is hydrogen, hydroxyl, lower alkyl, lower haloalkyl, halo, or lower alkoxy,
each $R_{15}$ is independently selected from lower alkyl, lower alkoxy, and halo; or $R_{14}$ and $R_{15}$, taken together with any intervening atoms forms a 5- to 7-membered heterocycloalkyl ring;

z is 0 or 1;

q is 0, 1, or 2;

$R_{18}$ is aryl, heteroaryl, or heterocycloalkenyl, each of which is optionally substituted with one or two groups independently selected from alkynyl, heteroaryl, cyano, optionally substituted amino, halo, lower alkyl, and lower alkyl substituted with optionally substituted amino;

$L_8$ is O or $NR_{21}$;

$R_{21}$ is hydrogen or lower alkyl;

$L_9$ is $(CH_2)_x$;

$R_{19}$ is hydrogen, aryl, aryl substituted with hydroxyl or lower alkoxy, heteroaryl, and heteroaryl substituted with hydroxyl or lower alkoxy;

each $R_{20}$ is independently selected from lower alkyl, lower alkoxy, halo, and oxo (as a substituent on the heterocycloalkyl ring);

x is 0, 1, or 2;

y is 0 or 1;

J is C(=O) or —$CH_2$—;

$X_3$ is S or N;

$Y_3$ is CH or N;

$Z_5$ is CH or N;

Q is N or S;

for each occurrence, $R_{23}$ is independently selected from halo, lower alkoxy, hydroxy, aryl, heteroaryl, cycloalkoxy, and lower alkyl, wherein the lower alkoxy, cycloalkoxy, lower alkyl, aryl, or heteroaryl are each optionally substituted with one, two, or three groups independently selected from lower alkoxy, alkenyl, —$NR_{24}R_{25}$, halo, and heteroaryl optionally substituted with one to three lower alkoxy;

$R_{21}$ is hydrogen or lower alkyl; and $R_{22}$ is alkyl, aryl, aralkyl, heterocycloalkyl, heterocycloalkenyl, heteroaryl, or heteroaralkyl, each of which is optionally substituted with one, two, or three groups independently selected from hydroxy, lower alkoxy optionally substituted with lower alkoxy or halo, lower alkyl optionally substituted with halo, halo, heteroaryl, —$(CH_2)NR_{24}R_{25}$, oxo, cyano, and —C(O)—$NR_{24}R_{25}$, or $R_{21}$ and $R_{22}$ taken together with the nitrogen to which they are bound form a heterocycloalkyl ring, optionally substituted with one, two, or three groups independently selected from hydroxy, lower alkoxy, lower alkyl, halo, and —C(O)—$NR_{24}R_{25}$;

t is 0, 1, or 2;

each $R_{24}$ is independently selected from hydrogen and lower alkyl;

each $R_{25}$ is independently selected from hydrogen and lower alkyl; or $R_{24}$ and $R_{25}$ taken together with the nitrogen to which they are bound form a heterocycloalkyl ring, optionally substituted with one, two, or three groups independently selected from hydroxy, lower alkoxy, lower alkyl, halo, and —C(O)—$NR_{26}R_{27}$;

each $R_{26}$ is independently hydrogen or lower alkyl;

each $R_{27}$ is independently hydrogen or lower alkyl;

s is 0, 1, or 2;

r is 1 or 2;

$R_{28}$ is heteroaryl optionally substituted with one, two, or three groups independently selected from cyano, lower alkoxy, lower alkenyl, —$NR_{24}R_{25}$, halo, and heteroaryl optionally substituted with one to three lower alkoxy;

L is a bond or

-$G_1$-(($CH_2$)$_a$-$G_2$)$_c$-($CH_2$)$_b$-$G_3$- wherein:

each of $G_1$, $G_2$, and $G_3$ are independently a bond, —$NR_{28}$—, —O—, —$S(O)_{0-2}$—, —$NR_{28}C(O)$—, —$C(O)NR_{28}$—, —$NR_{28}S(O)_2$—, —$S(O)_2NR_{28}$—, —$CR_{29}$=N—$NR_{28}$—, —$NR_{28}$—N=$CR_{29}$—, or —C(O)—, alkylene, heteroalkylene, alkenylene, heteroalkenylene, alkynylene, heteroalkynylene, arylene, heteroarylene, cycloalkylene, or heterocycloalkylene;

wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl;

each $R_{28}$ is independently hydrogen, $C_{1-4}$ alkyl, $C_{1-4}$ haloalkyl, aryl, heteroaryl, cycloalkyl, or heterocyclyl;

$R_{29}$ is $C_{1-4}$ alkyl, $C_{1-4}$ haloalkyl, aryl, heteroaryl, cycloalkyl, or heterocyclyl;

a and b are each independently 0, 1, 2, 3, 4, 5, 6, 7, or 8;

c is an integer between 0-20; and

ULM selected from:

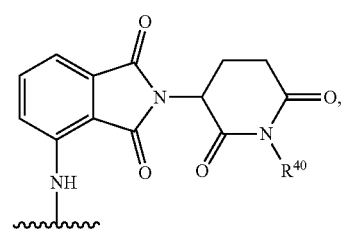

(II)

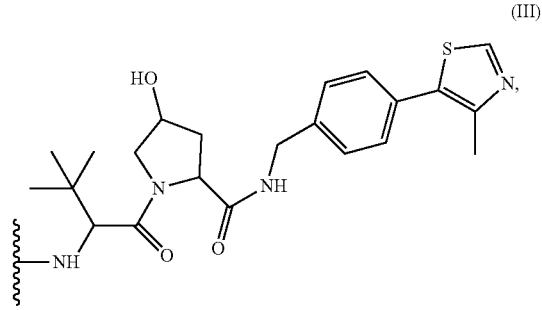

(III)

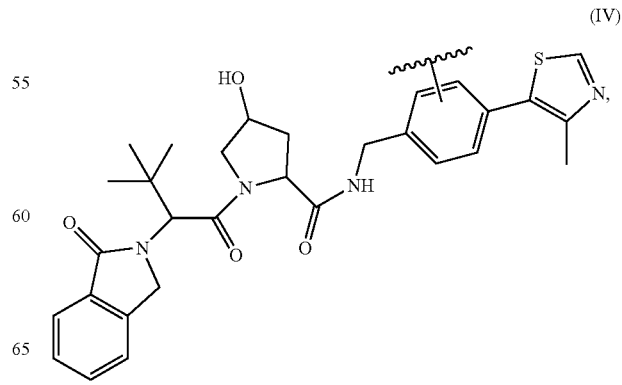

(IV)

-continued
(V)
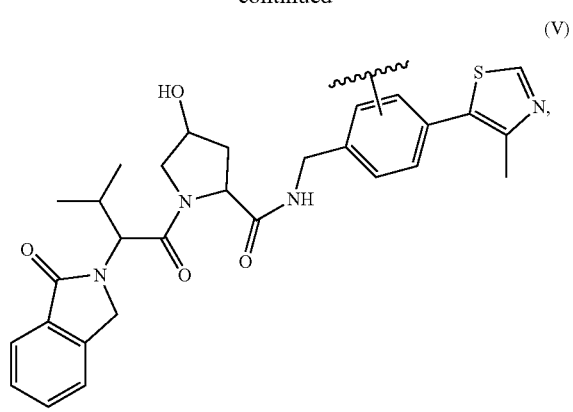
(VI)
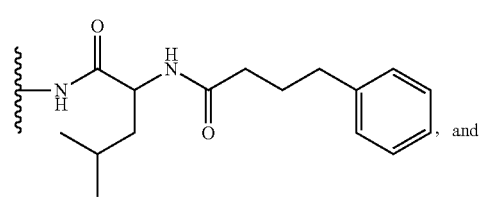
, and
(VII)
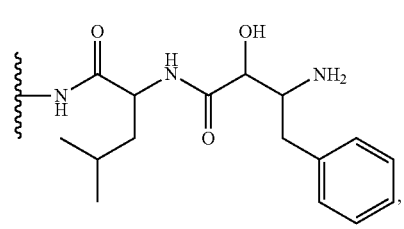
,
wherein R⁴⁰ is hydrogen or $C_{1-6}$ alkyl;
provided that the compound is not:
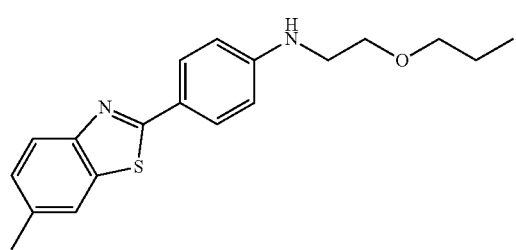
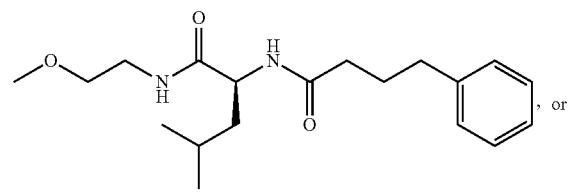
, or
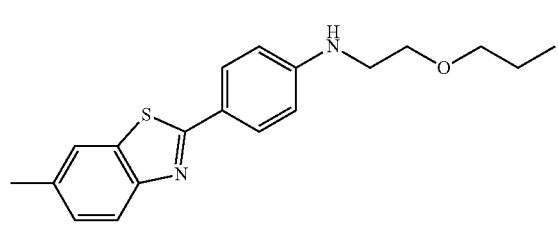
-continued
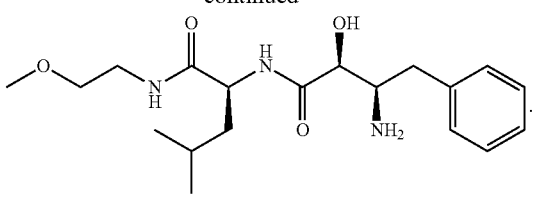
.
2. The compound of claim 1, wherein ULM is:
(II)(i)
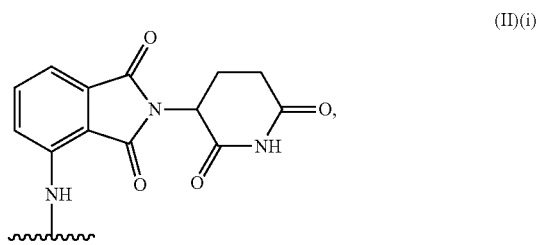
,
(III)(i)
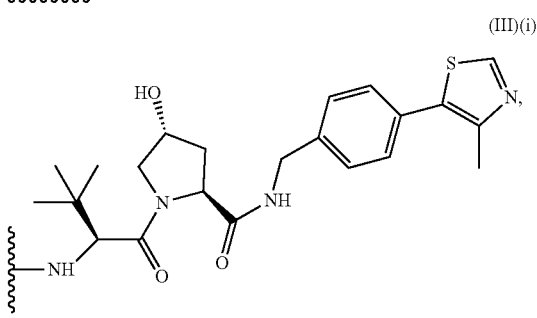
,
(IV)(i)
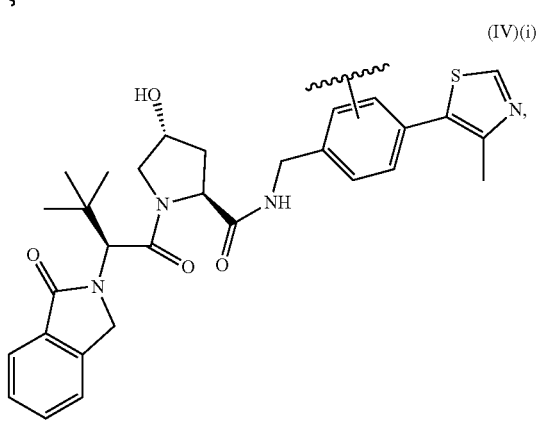
,
(V)(i)
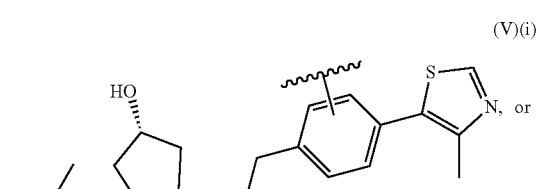
, or
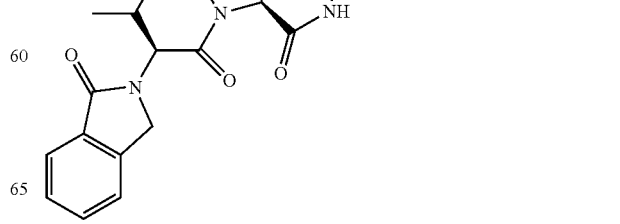

(VII)(i)

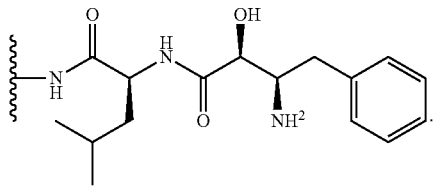

3. The compound of claim 1, wherein W is a compound of formula (B)(i):

(B)(i)

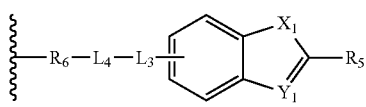

wherein the wavy line indicates the point of attachment to L of L-ULM.

4. The compound of claim 1, wherein W is a compound of formula (B)(i)(a):

(B)(i)(a)

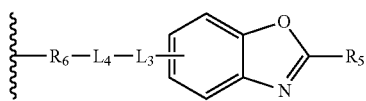

wherein the wavy line indicates the point of attachment to L of L-ULM.

5. The compound of claim 1, wherein W is a compound of formula (B)(ii):

(B)(ii)

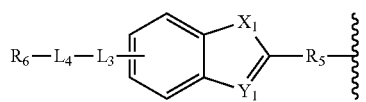

wherein the wavy line indicates the point of attachment to L of L-ULM.

6. The compound of claim 1, wherein W is a compound of formula (B)(ii)(a):

(B)(ii)(a)

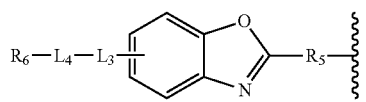

wherein the wavy line indicates the point of attachment to L of L-ULM.

7. The compound of claim 1, wherein $R_5$ is heteroaryl optionally substituted with one or two groups independently selected from cyano, halo, lower alkyl optionally substituted with amino, alkylamino, or di(alkyl)amino, lower alkoxy optionally substituted with lower alkoxy, optionally substituted amino, haloalkyl, di(alkyl)aminocarbonyl, alkylaminocarbonyl, and aminocarbonyl.

8. The compound of claim 1, wherein $R_5$ is heterocycloalkenyl optionally substituted with one or two groups independently selected from cyano, halo, lower alkyl optionally substituted with amino, alkylamino, or di(alkyl)amino, lower alkoxy optionally substituted with lower alkoxy, optionally substituted amino, haloalkyl, di(alkyl)aminocarbonyl, alkylaminocarbonyl, and aminocarbonyl.

9. The compound of claim 1, wherein $R_5$ is heterocycloalkyl optionally substituted with one or two groups independently selected from cyano, halo, lower alkyl optionally substituted with amino, alkylamino, or di(alkyl)amino, lower alkoxy optionally substituted with lower alkoxy, optionally substituted amino, haloalkyl, di(alkyl)aminocarbonyl, alkylaminocarbonyl, and aminocarbonyl.

10. The compound of claim 1, wherein $R_6$ is 5-6 membered heteroaryl, each of which is optionally substituted with one or two groups selected from: halo; lower alkoxy; lower alkoxy substituted with lower alkoxy, amino, (alkyl)amino, (dialkyl)amino, heterocycloalkyl, heteroaryl, or halo; lower alkyl, and lower alkyl substituted with amino, (alkyl)amino, (dialkyl)amino, hydroxyl or lower alkoxy.

11. The compound of claim 1, wherein W is a compound of formula (C).

12. The compound of claim 1, wherein W is a compound of formula (D).

13. The compound of claim 1, wherein W is a compound of formula (E).

14. The compound of claim 1, wherein W is a compound of formula (F).

15. A pharmaceutical composition comprising a compound of claim 1, and a pharmaceutically acceptable excipient or carrier.

16. A method for inducing degradation of mHTT comprising administering a therapeutically effective amount of a compound of claim 1.

17. A method for treating Huntington's disease comprising administering a therapeutically effective amount of a compound of claim 1.

* * * * *

UNITED STATES PATENT AND TRADEMARK OFFICE
CERTIFICATE OF CORRECTION

PATENT NO. : 12,083,108 B2  
APPLICATION NO. : 17/752683  
DATED : September 10, 2024  
INVENTOR(S) : Celia Dominguez et al.

Page 1 of 2

It is certified that error appears in the above-identified patent and that said Letters Patent is hereby corrected as shown below:

In the Claims

In Claim 1, Column 267, Line 42, please replace "(C), at" with -- (C), or at --.

In Claim 1, Column 268, Line 6, please replace "is $NR_{10}$—;" with -- is —$NR_{10}$—; --.

In Claim 1, Column 269, Line 43, please replace "—$(CH_2)NR_{24}R_{25}$," with -- —$(CH_2)_t NR_{24}R_{25}$, --.

In Claim 1, Column 271, Lines 40-58, please replace " 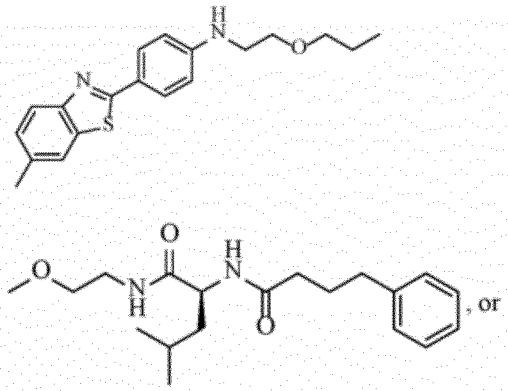 "

with -- 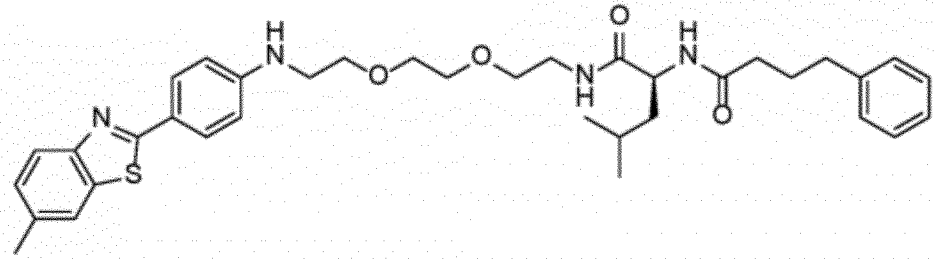 --.

In Claim 1, Column 271, Line 59 to Column 272, Line 10, please replace

Signed and Sealed this  
Twenty-fifth Day of February, 2025

Coke Morgan Stewart  
*Acting Director of the United States Patent and Trademark Office*

CERTIFICATE OF CORRECTION (continued)
U.S. Pat. No. 12,083,108 B2

"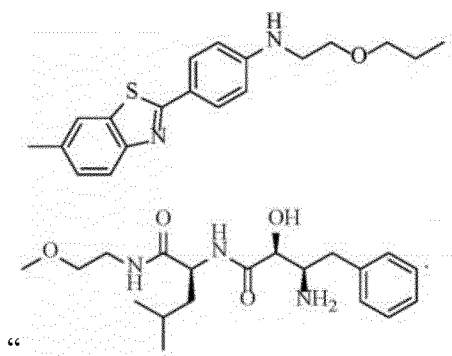" with

--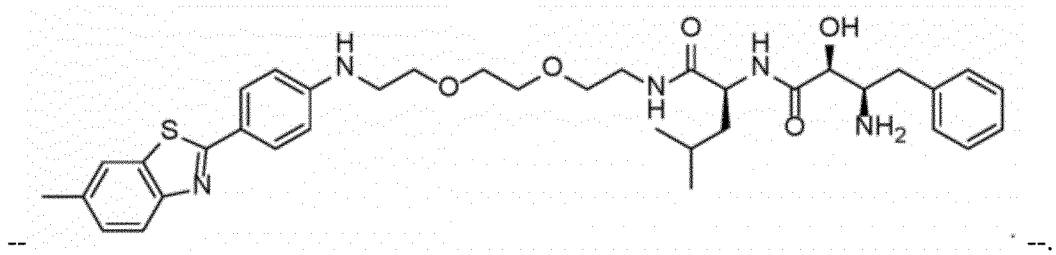--.

(VII)(i)

In Claim 2, Column 273, Lines 2 to 10, please replace "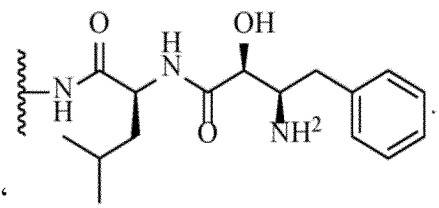"

with --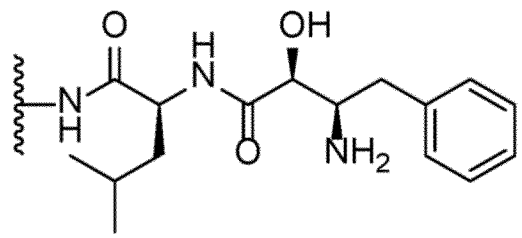 (VII)(i). --.

SEQUENCE LISTING

<160> NUMBER OF SEQ ID NOS: 13

<210> SEQ ID NO 1
<211> LENGTH: 19

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Phe Phe Tyr Gly Gly Ser Arg Gly Lys Arg Asn Asn Phe Lys Thr
1               5                   10                  15

Glu Glu Tyr

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Glu Glu Leu Arg Val Arg Leu Ala Ser His Leu Arg Lys Leu Arg
1               5                   10                  15

Lys Arg Leu Leu Arg Asp Ala
            20

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Arg Lys Leu Arg Lys Arg Leu Leu Arg Lys Leu Arg Lys Arg
1               5                   10                  15

Leu Leu

<210> SEQ ID NO 4
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ser Val Ile Asp Ala Leu Gln Tyr Lys Leu Glu Gly Thr Thr Arg Leu
1               5                   10                  15

Thr Arg Lys Arg Gly Leu Lys Leu Ala Thr Ala Leu Ser Leu Ser Asn
            20                  25                  30

Lys Phe Val Glu Gly Ser
            35

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr His Arg Pro Pro Met Trp Ser Pro Val Trp Pro
1               5                   10
```

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Met Pro Arg Leu Arg Gly Cys
1               5

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Trp Pro Lys His Phe Asp Lys His Thr Phe Tyr Ser Ile Leu Lys
1               5                   10                  15

Leu Gly Lys His
            20

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Gly Asn Tyr Lys Ala Leu His Pro His Asn Gly
1               5                   10

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Tyr Gln Gln Ile Leu Thr Ser Met Pro Ser Arg Asn Val Ile Gln Ile
1               5                   10                  15

Ser Asn Asp Leu Glu Asn Leu Arg Asp Leu Leu His Val Leu
            20                  25                  30

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 10

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly
                20                  25

<210> SEQ ID NO 11
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Val Ala Leu Asp Pro Ile Asp Ile Ser Ile Val Leu Asn Lys Ile Lys
1               5                   10                  15

Ser Asp Leu Glu Glu Ser Lys Glu Trp Ile Arg Arg Ser Asn Lys Ile
                20                  25                  30

Leu Asp Ser Ile
            35

<210> SEQ ID NO 12
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Val Asn Lys Lys Ile Glu Glu Ile Asp Lys Lys Ile Glu Glu Leu Asn
1               5                   10                  15

Lys Lys Leu Glu Glu Leu Glu Lys Lys Leu Glu Glu Val Asn Lys Lys
                20                  25                  30

<210> SEQ ID NO 13
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Pro Pro Ile Ser Leu Glu Arg Leu Asp Val Gly Thr Asn Leu Gly Asn
1               5                   10                  15

Ala Ile Ala Lys Leu Glu Asp Ala Lys Glu Leu Leu Glu Ser Ser Asp
                20                  25                  30

Gln Ile Leu Arg
            35
```